(12) United States Patent
Heal et al.

(10) Patent No.: US 8,748,182 B2
(45) Date of Patent: Jun. 10, 2014

(54) MUTANT PROTEINS AND METHODS FOR PRODUCING THEM

(75) Inventors: Jonathan Richard Heal, Cambridge (GB); Richard Henderson, Cambridge (GB); Christopher Gordon Tate, Cambridge (GB); Malcolm Peter Weir, Welwyn Garden City (GB)

(73) Assignee: Heptares Therapeutics Limited, Hertfordshire (GB)

( * ) Notice: Subject to any disclaimer, the term of this patent is extended or adjusted under 35 U.S.C. 154(b) by 194 days.

(21) Appl. No.: 12/746,674

(22) PCT Filed: Dec. 8, 2008

(86) PCT No.: PCT/GB2008/004032
§ 371 (c)(1),
(2), (4) Date: Oct. 13, 2010

(87) PCT Pub. No.: WO2009/071914
PCT Pub. Date: Jun. 11, 2009

(65) Prior Publication Data
US 2011/0028700 A1  Feb. 3, 2011

(30) Foreign Application Priority Data
Dec. 8, 2007 (GB) .................................. 0724051.8

(51) Int. Cl.
*C12N 15/11* (2006.01)
*C07K 14/705* (2006.01)

(52) U.S. Cl.
USPC ............ 435/440; 435/7.2; 435/69.1; 436/501

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner et al. | |
| 5,223,409 A | 6/1993 | Ladner et al. | |
| 5,290,681 A | 3/1994 | Kuroda et al. | |
| 5,585,277 A | 12/1996 | Bowie et al. | |
| 5,834,250 A | 11/1998 | Wells et al. | |
| 5,925,549 A | 7/1999 | Hsueh et al. | |
| 6,153,410 A | 11/2000 | Arnold et al. | |
| 6,448,377 B1 | 9/2002 | Kobilka et al. | |
| 6,537,749 B2 | 3/2003 | Kuimelis et al. | |
| 7,094,593 B1 | 8/2006 | Pausch et al. | |
| 7,115,377 B2 | 10/2006 | Yao et al. | |
| 7,462,457 B2 | 12/2008 | Beachy et al. | |
| 2002/0028443 A1 | 3/2002 | Short | |
| 2002/0147170 A1* | 10/2002 | Kopin et al. | 514/44 |
| 2003/0036092 A1 | 2/2003 | Iverson et al. | |
| 2003/0096297 A1* | 5/2003 | Gilchrist et al. | 435/7.1 |
| 2003/0129649 A1 | 7/2003 | Kobilka et al. | |
| 2004/0157268 A1 | 8/2004 | Kobilka et al. | |
| 2005/0136392 A1 | 6/2005 | Torres et al. | |
| 2005/0143402 A1 | 6/2005 | Cheetham et al. | |
| 2005/0287565 A1* | 12/2005 | Merchiers et al. | 435/6 |
| 2007/0154947 A1 | 7/2007 | Broach et al. | |
| 2007/0196389 A1 | 8/2007 | Caligiuri et al. | |
| 2010/0190188 A1 | 7/2010 | Henderson et al. | |
| 2011/0027910 A1 | 2/2011 | Weir et al. | |
| 2011/0046351 A1 | 2/2011 | Weir et al. | |
| 2011/0112037 A1 | 5/2011 | Warne et al. | |
| 2012/0165507 A1 | 6/2012 | Jazayeri-Dezfuly et al. | |
| 2012/0270230 A1 | 10/2012 | Henderson et al. | |
| 2013/0224238 A1 | 8/2013 | Hutchings et al. | |

FOREIGN PATENT DOCUMENTS

| | | |
|---|---|---|
| EP | 0 184 187 A2 | 6/1986 |
| EP | 0 239 400 A2 | 9/1987 |
| EP | 0 397 834 B1 | 2/2000 |
| EP | 1 376 132 A1 | 1/2004 |
| EP | 1 505 074 A1 | 2/2005 |
| GB | 2 188 638 | 10/1987 |
| WO | WO 91/17271 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 95/32425 A1 | 11/1995 |
| WO | WO 97/35881 A2 | 10/1997 |
| WO | WO 00/22129 A1 | 4/2000 |
| WO | WO 01/36471 A2 | 5/2001 |
| WO | WO 02/059346 A2 | 8/2002 |
| WO | WO 02/068600 A2 | 9/2002 |
| WO | WO 03/035693 A2 | 5/2003 |
| WO | WO 2005/121755 A1 | 12/2005 |
| WO | WO 2006/023248 A2 | 3/2006 |
| WO | WO 2008/068534 A2 | 6/2008 |
| WO | WO 2008/114020 A2 | 9/2008 |
| WO | WO 2009/071914 A2 | 6/2009 |
| WO | WO 2009/081136 A2 | 7/2009 |

OTHER PUBLICATIONS

U.S. Appl. No. 60/080686, filed Apr. 3, 1998, Kuimelis et al.
International Search Report and Written Opinion for PCT/GB2008/000986 mailed Jan. 19, 2009.
International Preliminary Report on Patentability for PCT/GB2008/000986 mailed Jul. 6, 2009.
International Search Report and Written Opinion for PCT/GB2008/004032 mailed Aug. 19, 2009.
International Preliminary Report on Patentability for PCT/GB2008/004032 issued Jun. 8, 2010.
International Search Report and Written Opinion for PCT/GB2008/004223 mailed Aug. 19, 2009.
International Preliminary Report on Patentability for PCT/GB2008/004223 issued Jun. 22, 2010.
International Search Report and Written Opinion for PCT/GB2009/000310 mailed Jun. 23, 2009.

(Continued)

*Primary Examiner* — John Ulm
(74) *Attorney, Agent, or Firm* — Wolf, Greenfield & Sacks, P.C.

(57) ABSTRACT

Aspects of the invention relate to methods of producing a mutant GPCR with increased stability relative to its parent GPCR.

16 Claims, 68 Drawing Sheets

(56) References Cited

OTHER PUBLICATIONS

International Preliminary Report on Patentability for PCT/GB2009/000310 mailed Aug. 26, 2010.
International Search Report and Written Opinion for PCT/GB2008/000740 mailed Jul. 28, 2008.
International Preliminary Report on Patentability for PCT/GB2008/000740 issued Sep. 7, 2010.
International Search Report and Written Opinion for PCT/GB2010/001227 mailed Jun. 20, 2011.
International Preliminary Report on Patentability for PCT/GB2010/001227 mailed Jan. 12, 2012.
Office Action mailed Feb. 14, 2012 for U.S. Appl. No. 12/450,358.
[No author listed] Uniprot Database Accession No. P08482. 1988. Muscarinic acetylcholine receptor M1.
[No author listed] http://blanco.biomol.uci.edu. Stephen White Laboratory at UC Irvine. Downloaded May 1, 2012.
[No author listed] IUPHAR database. G protein-coupled receptors. http://www.iuphar-db.org/GPCR/ReceptorFamiliesForward. Downloaded May 1, 2012.
[No author listed] The CCP4 suite: programs for protein crystallography. Collaborative Computational Project, No. 4. Acta Crystallogr. 1994. D50:760-763.
Abagyan & Totrov. High-throughput docking for lead generation. Curr. Opin. Chem. Biol. 2001. 5:375-382.
Abagyan et al., ICM—a new method for protein modelling and design. Applications to docking and structure prediction from the distorted native conformation. J. Comput. Chem. 1994. 15:488-506.
Adams et al., PHENIX: building new software for automated crystallographic structure determination. Acta Crystallogr. 2002. D58:1948-1954.
Afonine et al., The Phenix refinement framework. CCP Newsletter. 2005. Contribution 8.
Alexandrov et al., Microscale Fluorescent Thermal Stability Assay for Membrane Proteins; Structure; 2008;16:351-359.
Ali & Caffrey. Membrane Protein Crystallization in Lipidic Mesophases: Detergent Effects. Biophys. J. 2000.79:394-405.
Alkhatib et al., HIV coreceptors: from discovery and designation to new paradigms and promise. Eur. J. Med. Res. 2007 12(9):375-384.
Altschul & Gish. Local alignment statistics. Methods in Enzymology. 1996. 266:460-480.
Altschul et al., Basic local alignment search tool. J. Mol. Biol. 1990. 215:403-410.
Altschul et al., Gapped BLAST and PSI-BLAST: a new generation of protein database search programs. Nucl Acids Res. 1997 25:3389-3402.
Alves et al., Plasmon Resonance Methods in GPCR Signaling and Other Membrane Events. Curr. Prot. & Peptide Sci. 2005 6:293-312.
Artymiuk et al., Graph theoretic methods for the analysis of structural relationships in biological macromolecules. J Amer. Soc. Info. Sci Tech. 2005 56(5):518-528.
Avlani et al., Critical role for the second extracellular loop in the binding of both orthosteric and allosteric G protein-coupled receptor ligands. J Biol Chem. 2007. 282:25677-25686.
Babcook et al., A novel strategy for generating monoclonal antibodies from single, isolated lymphocytes producing antibodies of defined specificities. PNAS. 1996 93:7843-7848.
Baker. The selectivity of β-adrenoceptor antagonists at the human β1, β2 and β3 adrenoceptors. British J. Pharmacol. 2005. 144:317-322.
Bakker et al., Constitutively Active Mutants of the Histamine H1 Receptor Suggest a Conserved Hydrophobic Asparagine-Cage That Constrains the Activation of Class A G Protein-Coupled Receptors. Mol. Pharmacol. 2008. 73:94-103.
Balbes et al., A Perspective of Modem Methods in Computer-Aided Drug Design. Reviews in Computational Chemistry. 1994. 5:337-380.
Baldwin et al., An alpha-carbon template for the transmembrane helices in the rhodopsin family of G-proteincoupled receptors. J. Mol. Biol. 1997. 272:144-164.

Ballesteros & Weinstein. Integrated methods for the construction of three-dimensional models and computational probing of structure-function relations in G-protein coupled receptors. Methods in Neurosciences. 1995 Sealfon, S.C.and Conn, P.M. (eds.). Academic Press San Diego, CA 366-428.
Ballesteros et al., Activation of the beta 2-adrenergic receptor involves disruption of an ionic lock between the cytoplasmic ends of transmembrane segments 3 and 6. J. Biol. Chem. 2001. 276:29171-29177.
Ballesteros et al., Structural mimicry in GPCR: Implications of the high-resolution structure of rhodopsin for structure-function analysis of rhodopsin-like receptors. Mol. Pharmacology 60, 1-19, 2001.
Bamber et al., Yeast mitochondrial ADP ATP carriers are monomeric in detergents. PNAS. 2006 103:16224-16229.
Baneres et al., Molecular Characterization of a Purified 5-HT4 Receptor. J. Biol. Chem. 2005. 208:20253-20260.
Baranski et al., C5a Receptor Activation. J. Biol. Chem. 1999. 274(22):15757-15765.
Barbas et al., Assembly of combinatorial antibody libraries on phage surfaces: The gene III site. PNAS. 1991 88:7978-7982.
Baroni et al., A Common Reference Framework for Analyzing/Comparing Proteins and Ligands. Fingerprints for Ligands and Proteins (FLAP): Theory and Application. J. Chem Inf. Mod. 2007. 47:279-294.
Barroso S. et al., 2000, Identification of Residues Involved in Neurotensin Binding and Modeling of the Agonist Binding Site in Neurotensin Receptor 1, Journal of Biological Chemistry, 275(1):328-336.
Barroso S. et al., 2002, Constitutive activation of the neurotensin receptor 1 by mutation of Phe358 in Helix seven, British Journal of Pharmacology, 135:997-1002.
Barry et al., Quantitative protein profiling using antibody arrays. Proteomics. 2004 4:3717-3726.
Bartlett et al., CAVEAT: A Program to Facilitate the Structure-Derived Design of Biologically Active Molecules. Molecular Recognition: Chemical and Biological Problems, 1989. S. M. Roberts, Editor, Royal Society of Chemistry. 78:182-196.
Bee et al., 2007, Functional analysis of transmembrane domain 2 of the M1 muscarinic acetylocholine receptor, J. Biol. Chem. 282(44):32471-32479.
Behr et al., Novel mutants of the human β1-adrenergic receptor reveal amino acids relevant for receptor activation. J. Biol. Chem. 2006. 281(26):18120-18125.
Berchiche et al., Direct Assessment of CXCR4 Mutant Conformations Reveals Complex Link between Receptor Structure and G(alpha)(i) Activation. J. Biol. Chem. 2007. 282(8):5111-5115.
Besenicar et al., Surface plasmon resonance in protein-membrane interactions. Chem. Phys. Lipids. 2006 141:169-178.
Black. Drugs from Emasculated Hormones: The Principle of Syntopic Antagonism (Nobel Lecture). Angew Chem. Int. Edit. 1989. 28:886-894.
Blundell et al., Knowledge-based prediction of protein structures and the design of novel molecules. Nature. 1987. 326:347-352.
Blundell et al., Knowledge-based protein modelling and design; 18th Sir Hans Krebs Lecture Eur. J. Biochem. 1988. 173:513-520.
Bockaert and Pin. Molecular tinkering of G piotein-coupled receptors: an evolutionary success. EMBO J. 1999. 18:1723-1729.
Bockaert et al., GPCR-GIP networks: a first step in the discovery of new therapeutic drugs? Curr Opin Drug Discov and Dev. 2004. 7:649-657.
Bohm. The computer program LUDI: a new method for the de novo design of enzyme inhibitors. J. Comput. Aided Mol. Des. 1992. 6:61-78.
Bommarius et al., High-throughput screening for enhanced protein stability. Curr Opin Biotechnol. 2006. 17(6):606-610. Epub Oct 17, 2006.
Bonner et al., Identification of a family of muscarinic acetylcholine receptor genes. Science. 1987. 237:527-532.
Boucard et al., Constitutive Activation of the Angiotensin II Type 1 Receptor Alters the Spatial Proximity of Transmembrane 7 to the Ligand-binding Pocket. J. Biol. Chem. 2003. 278(38):36628-36636. Epub Jul. 3, 2003.

(56) References Cited

OTHER PUBLICATIONS

Bowie. Stabilizing membrane proteins. Curr. Opin. Struct. Biol. 2001. 11(4):397-402.

Brenner & Lerner. Encoded combinatorial chemistry. PNAS. 1992. 89:5381-5383.

Brodeur et al., Mouse-Human Myeloma Partners for the Production of Heterohybridomas. Mono. Antib. Prod. Tech. Apps. 1987. 51-63.

Brunger et al., Recent developments for the efficient crystallographic refinement of macromolecular structures. Curr. Opin. Struct. Biol. 1998. 8(5):606-611.

Bruns et al., Human glutathione transferase A4-4 crystal structures and mutagenesis reveal the basis of high catalytic efficiency with toxic lipid peroxidation products. J Mol Biol. 1999. 288:427-439.

Burstein et al., The second intracellular loop of the m5 muscarinic receptor is the switch which enables G-protein coupling. J Biol Chem. 1998. 273:24322-24327.

Caron et al., Affinity chromatography of the beta-adrenergic receptor. J. Biol. Chem.1979. 254:2923-2927.

Carrillo H. & Lipman D.J. The multiple sequence alignment problem in biology. SIAM J. Appl. Math. 1988; 48:1073-1082.

Carson. Ribbons 2.0. Appl. Crystallogr. 1991. 24:958-961.

Chan et al., Allosteric modulation of the muscarinic M4 receptor as an approach to treating schizophrenia. PNAS. 2008. 105:10978-10983.

Chapple et al., Multiplexed expression and screening for recombinant protein production in mammalian cells. BMC Biotechnol. 2006. 22:6-49.

Cherezov et al., A robotic system for crystallizing membrane and soluble proteins in lipidic mesophases. Acta. Crystallogr. D. Biol. Crystallogr. 2004. 60(Pt 10):1795-1807. Epub Sep. 23, 2004.

Cherezov et al., Crystallization Screens: Compatibility with the Lipidic Cubic Phase for in Meso Crystallization of Membrane Proteins. Biophys. J. 2001. 81:225-242.

Cherezov et al., High Resolution Crystal Structure of an Engineered Human β2-Adrenergic G protein-Coupled Receptor. Science. 2007. 318(5854):1258-1265. Epub Oct. 25, 2007.

Cherezov et al., Room to Move: Crystallizing Membrane Proteins in Swollen Lipidic Mesophases. J. Mol. Biol. 2006. 357:1605-1618.

Christopoulos. Allosteric binding sites on cell-surface receptors: Novel targets for drug discovery. Nat. Rev. Drug Discov. 2002. 1:198-210.

Clackson et al., Making antibody fragments using phage display libraries. Nature: 1991. 352:624-628.

Claeysen et al., A single mutation in the 5-HT4 receptor (5-HT4-R D100(3.32)A) generates a Gs-coupled receptor activated exclusively by synthetic ligands (RASSL).J Biol Chem. Jan. 10, 2003;278(2):699-702. Epub Nov. 18, 2002.

Cohen et al., Molecular modeling software and methods for medicinal chemistry. J. Med. Chem. 1990.33:883-894.

Conklin et al., Engineering GPCR signaling pathways with RASSLs. Nat Methods. 2008 Aug;5(8):673-8.

Cooper. Advances in membrane receptor screening and analysis. J. Mol. Recognit. 2004. 17(4):286-315.

Cooper. Non-optical screening platforms: the next wave in label-free screening? Drug Discov. Today. 2006. 11(23-24):1068-1074. Epub Oct. 20, 2006.

Cornell et al., A Second Generation Force Field for the Simulation of Proteins, Nucleic Acids, and Organic Molecules. JACS. 1995. 117(19):5179-5197.

D'Antona et al., A cannabinoid receptor 1 mutation proximal to the DRY motif results in constitutive activty and reveals intramolecular interactions involved in receptor activation. Brain Research. 2006 1108(1):1-11.

D'Antona et al., Mutations of CB1 T210 Produce Active and Inactive Receptor Forms: Correlations with Ligand Affinity, Receptor Stability, and Cellular Localization. Biochemistry. 2006. 45:5606-5617.

Day et al., A monoclonal antibody for G protein-coupled receptor crystallography. Nat Methods. 2007.4(11):927-929.

Degrip. Thermal Stability of Rhodopsin and Opsin in Some Novel Detergents. Methods in Enzymology. 1982. 81:256-265.

Devereux et al., A comprehensive set of sequence analysis programs for the VAX; Nucl. Acids Rec. 12:387-395, 1984.

Dignam. Preparation of extracts from higher eukaryotes. Methods in Enzymology. 1990. 182:194-203.

Domazet et al., The second transmembrane domain of the human type 1 angiotensin II receptor participates in the formation of the ligand binding pocket and undergoes integral pivoting movement during the process of receptor activation. J Biol Chem. May 1, 2009;284(18):11922-9. Epub Mar 9, 2009.

Dupriez et al. Aequorin-based functional assays for G-protein-coupled receptors, ion channels and tyrosine kinase receptors. Receptors Channels. 2002. 8(5-6):319-330.

Duthey et al., A Single Subunit (GB2) is Required for G-protein Activation by the Heterodimeric GABAB Receptor: J. Biol.Chem 277(5):3236-3241.

Dyson et al., Identification of soluble protein fragments by gene fragmentation and genetic selection. Nucl. Acid Research. 2008. 36:e51.

Dyson et al., Production of soluble mammalian proteins in Escherichia coli: identification of protein features that correlate with successful expression. BMC Biotechnology. 2004. 4:32.

Eddy et al., Maximum Discrimination Hidden Markov Models of Sequence Consensus. J. Comput Biol. 1995. 2(1):9-23.

Eglen. Functional G protein-coupled receptor assays for primary and secondary screening. Comb. Chem. High Throughput Screen. 2005. 8(4):311-318.

Eisen et al., HOOK: a program for finding novel molecular architectures that satisfy the chemical and steric requirements of a macromolecule binding site. Proteins:Structure, Function and Genetics. 1994.19(3):199-221.

Eldridge et al., Empirical scoring functions: I. the development of a fast empirical scoring function to estimate the binding affinity of ligands in receptor complexes. J. Comp. Aided Mol. Des. 1997. 11(5):425-445.

Ernst et al., Intrinsic biophysical monitors of transducin activation: fluorescence, UV-visible spectroscopy, light scattering, and evanescent field techniques. Meth. Enzymol. 2000. 315:471-489.

Evans & McCoy. An introduction to molecular replacement. Acta Crystallogr. 2008. D64:1-10.

Faham et al., Side-chain contributions to membrane protein structure and stability. J. Mol. Biol. 2004. 335:297-305.

Fanelli. Theoretical study on mutation-induced activation of the luteinizing hormone receptor. J. Mol. Biol. 2000. 296(5):1333-1351.

Fang et al., G protein-coupled receptor microarrays for drug discovery. Drug Discovery Today. 2003. 8:755-761.

Felix et al., Immunoadsorption as a new therapeutic principle for treatment of dilated cardiomyopathy. Eur. Heart J. Supplements. 2002. 4:163-168.

Ferracci et al., Real time analysis of intact organelles using surface plasmon resonance. Anal. Biochem. 2004. 334:367-375.

Ferro & Hermans. A different best rigid body molecular fit routine. Acta Cryst. 1977. A33:345-347.

Fetrow & Bryant. New programs for protein tertiary structure prediction. Biotechnology. 1993. 11(4):479-484.

Folkertsma et al., A family-based approach reveals the function of residues in the nuclear receptor ligand-binding domain. J. Mol. Biol. 2004. 341(2):321-335.

Foord et al., International Union of Pharmacology. XLVI. G Protein-Coupled Receptor List. Pharmacol. Rev. 2005. 57:279-288.

Foord S.M. & Marshall F.H. RAMPs: accessory proteins for seven transmembrane domain receptors, Trends Pharmacol Sci. 20(5):184-187 1999.

Frändberg et al., Cysteine Residues Are Involved in Structure and Function of Melanocortin 1 Receptor: Substitution of a Cysteine Residue in Transmembrane Segment Two Converts an Agonist to Antagonist. Biochem. Biophys. Res. Commun. 2001. 281(4):851-857.

Frielle et al., Cloning of the cDNA for the human-β-adrenergic receptor. PNAS. 1987. 84:7920-7924.

Fuchs et al., Targeting recombinant antibodies to the surface of *escherichia coli*: fusion to a peptidglycan associated lipoprotein. Biotechnology. 1991. 9:1369-1372.

(56) References Cited

OTHER PUBLICATIONS

Gales et al., Real-time monitoring of receptor and G-protein interactions in living cells, Nat. Methods. 2(3):177-184 (2005).
Garcia-Lopez et al., Strategies for design of non peptide CCK1R agonist/antagonist ligands. Curr. Top. Med. Chem. 2007. 7(12):1180-1194.
Gardella et al., Transmembrane residues of the parathyroid hormone (PTH)/PTH-related peptide receptor that specifically affect binding and signaling by agonist ligands. J Biol Chem. 1996 May 31;271(22):12820-5.
Garrard et al., Fab assembly and enrichment in a monovalent phage display system. Biotechnology. 1991. 9:1373-1377.
Gerber et al., An Activation Switch in the Ligand Binding Pocket of the C5a Receptor. J. Biol. Chem. 2001. 276(5):3394-3400.
Gether et al., Structural Instability of a Constitutively Active G Protein-coupled Receptor Agonist-Independent Activation Due to Conformational Flexibility. J. Biol. Chem. 1997. 272:2587-2590.
Gether. Uncovering Molecular Mechanisms Involved in Activation of G Protein-Coupled Receptors. Endocr. Rev. 2000. 21:90-113.
Gillet et al., SROUT—a program for structure generation. J. Comput. Aided Mol. Des.1993. 7:127-153.
Ginalski, Comparative modeling for protein structure prediction. Curr. Op. Struct. Biol. 2006. 16(2):172-177.
Gish & States. Identification of protein coding regions by database similarity search. Nature Genetics. 1993. 3:266-272.
Goding. Production of Monoclonal Antibodies: Principles and Practice. Academic Press. 1986. 59-103.
Goodford. A Computational Procedure for Determining Energetically Favorable Binding Sites on Biologically Important Macromolecules. J. Med. Chem. 1985. 28:849-857.
Goodsell et al., Automated docking of substrates to proteins by simulated annealing. Proteins: Structure, Function and Genetics. 1990. 8:195-202.
Gram et al., In vitro selection and affinity maturation of antibodies from a naïve combinatorial immunoglobulin library. PNAS. 1992. 89:3576-3580.
Graneli et al., Characterization of a proton pumping transmembrane protein incorporated into a supported three-dimensional matrix of proteoliposomes. Anal. Biochem. 2007. 367:87-94.
Graneli et al., Utilizing adsorbed proteoliposomes trapped in a non-ruptured state on SiO2 for amplified detection of membrane proteins. Biosens. Bioelectron. 2004. 20:498-504.
Gray et al., Identification of Two Serine Residues Essential for Agonist-Induced 5-HT2a Receptor Desensitization. Biochemistry. 2003. 42(36):10853-10862.
Gray. High-resolution protein-protein docking. Curr. Opin. Struct. Biol. 2006. 16:183-193.
Greer et al., Application of the Three-Dimensional Structures of Protein Target Molecules in Structure-Based Drug Design. J. Med. Chem. 1994. 37:1035-1054.
Greer. Comparative modeling of homologous proteins. Methods in Enzymology. 1991. 202:239-252.
Greer. Model structure for the inflammatory protein C5a. Science. 1985. 228:1055-1060.
Griffiths et al. Human anti-self antibodies with high specificity from phage display libraries. EMBO J. 1993. 12:725-734.
Grindley et al., Identification of Tertiary Structure Resemblance in Proteins Using a Maximal Common Subgraph Isomorphism Algorithm. J. Mol. Biol. 1993. 229:707-721.
Grisshamer et al. Expression of a rat neurotensin receptor in Escherichia coli. Biochem J. 1993. 295(2):571-576.
Grisshammer & Tate. Overexpression of integral membrane proteins for structural studies. Q. Rev. Biophys. 1995. 28:315-422.
Groves & Dustin. Supported planar bilayers in studies on immune cell adhesion and communication. Immunol. Meth. 2003. 278:19-32.
Groves. Membrane array technology for drug discovery. Curr. Op. Drug Discov. Develop. 2002. 5:606-612.
Gschwend & Kuntz. Orientational sampling and rigid-body minimization in molecular docking revisited: on-the-fly optimization and degeneracy removal. J. Comput. Aided Mol. Des. 1996. 10:123-132.
Guida. Software for structure-based drug design. Curr. Opin. Struct. Biol. 1994. 4:777-781.
Gupta & Devi. The use of receptor-specific antibodies to study G-protein-coupled receptors. Mt. Sinai J. Med. 2006. 73(4):673-681.
Gupta et al., Conformation State-sensitive Antibodies to G-protein-coupled Receptors. J. Biol. Chem. 2007. 282(8): 5116-5124.
Halperin et al., Principles of docking: An overview of search algorithms and a guide to scoring functions. Proteins. 2002. 47:409-443.
Hamuro et al., Hydrogen/deuterium-exchange (H/D-Ex) of PPARyLBD in the presence of various modulators. Protein Science. 2006. 15(8):1883-1892.
Han et al., Constitutive activation of opsin by mutation of methionine 257 on transmembrane helix 6. Biochemistry. Jun. 2, 1998;37(22):8253-61.
Harding et al., Direct analysis of a GPCR-agonist interaction by surface plasmon resonance. Eur. Biophys. J. Biophys. Let. 2006. 35:709-712.
Harding. Metal-ligand geometry relevant to proteins and in proteins: sodium and potassium. Acta Crystallogr. 2002. D58:872-874.
Hawkins et al., Selection of phage antibodies by binding affinity: mimicking affinity maturation. J. Mol. Biol. 1992. 226:889-896.
Hay et al., Bacteriophage Cloning and *Escherichia coli* Expression of a Human IgM Fab. Hum. Antibod. Hybridomas. 1992. 3:81-85.
Hendrickson. Transformations to optimize the superposition of similar structures. Acta Crystallogr. 1979. A35:158-163.
Henikoff & Henikoff. Amino acid substitution matrices from protein blocks. Proc Natl Acad Sci U.S.A. Nov. 15, 1992; 89(22)10915-10919.
Hoffmann et al., a FlAsH-based FRET approach to determine G protein-coupled receptor activation in living cells. Nat Methods. 2005 Mar;2(3):171-6. Epub Feb. 17, 2005.
Holm & Sander. Dali/FSSP classification of three-dimensional protein folds. Nucl. Acids Res. 1997. 25:231-234.
Holm & Sander. Mapping the Protein Universe. Science. 1996. 273:595-603.
Hoogenboom et al., Multi-subunit proteins on the surface of filamentous phage: methodologies for displaying antibody (Fab) heavy and light chains. Nuc. Acid Res. 1991. 19:4133-4137.
Hopkins & Groom. The druggable genome. Nature Rev. Drug Discovery. 2002. 1:727-730.
Hoppe & Schomburg. Prediction of protein thermostability with a direction- and distance-dependent knowledge-based potential. Protein Science. 2005. 14:2682-2692.
Huang et al., A probabilistic method to correlate ion pairs with protein thermostability. Applied Bioinformics. 2004. 3(1):21-29.
Hubbell et al., Rhodopsin structure, dynamics, and activation: a perspective from crystallography, site-directed spin labeling, sulfhydryl reactivity, and disulfide cross-linking. Adv. Protein Chem. 2003. 63:243-290.
Hudson et al., High content screening of known G protein-coupled receptors by arrestin translocation. Methods Enzymol. 414:63-78.
Hulme & Curtis. Purification of recombinant M1 muscarinic acetylcholine receptor. Biochemical Society Transactions. 1998. 26:S361.
Hunte et al., Structure at 2.3 Åresolution of the cytochrome bcl complex from the yeast Saccharomyces cerevisiae co-crystallized with an antibody Fv fragment. Structure. 2000. 8:669-684.
Hus et al. Assignment strategy of proteins with known structure. J. Magn. Reson. 2002. 157(1):119-123.
Huse et al., Generation of a large combinatorial library of the immunoglobulin repertoire in phage lambda. Science. 1989. 246:1275-1281.
Ikuta et al., Crystallographic Approach to Identification of Cyclin-dependent Kinase 4 (CDK4)-specific Inhibitors by Using CDK4 Mimic CDK2 Protein. J. Biol. Chem. 2001. 276:27548-27554.
Isogaya et al., Binding pockets of the β1 and β2 adrenergic receptors for subtype-selective agonists. Mol. Pharmacol. 1999. 56(5):875-885.
Isogaya et al., Identification of a Key Amino Acid of the β2-Adrenergic Receptor for High Affinity Binding of Salmeterol. Mol. Pharmacol. 1998. 54:616-622.
Jaakola et al., The 2.6 Å Crystal Structure of a Human A2A Adenosine Receptor Bound to an Antagonist. Science. 2008. 322:1211-1217.

(56) References Cited

OTHER PUBLICATIONS

Jaenicke & Bohm. The stability of proteins in extreme environments. Current Opinion in Structural Biology. 1998. 8:738-748.
Jahns et al., Direct evidence for a β1-adrenergic receptor—directed autoimmune attack as a cause of idiopathic dilated cardiomyopathy. J. Clinical Investigation. 2004. 113(10):1419-1429.
Jahns et al., Modulation of Beta1-Adrenoceptor Activity by Domain-Specific Antibodies and Heart Failure—Associated Autoantibodies. J. Am. Coll. Cardiol. 2000. 36(4):1280-1287.
Jameson et al., Real-time Detection of Basal and Stimulated G Protein GTPase Activity Using Fluorescent GTP Analogues. J. Biol. Chem. 2005. 280(9):7712-7719.
Jane-wit D. et al., β1-Adrenergic Receptor Autoantibodies Mediate Dilated Cardiomyopathy by Agonistically Inducing Cardiomyocyte Apoptosis. Circulation. 2007. 116(4):399-410. Epub Jul. 9, 2007.
Jap et al., 2D crystallization: from art to science; Ultramicroscopy. 1992. 46(1-4):45-84.
Jerne & Nordin. Plaque formation in agar in single antibody-producing cells. Science. 1963. 140:405.
Johnson & Chriswell. Human antibody engineering. Curr. Op. Structural Biol. 1993. 3:564-571.
Johnson et al., A 1,536-well 35S GTPgarnmaS scintillation proximity binging assay for ultra-high-throughput screening of an orphan galphai-coupled GPCR. Assay Drug Dev Technol 6, 327-337 (2008).
Johnson et al., Knowledge-based protein modeling. Crit Rev Biochem Mol Biol. 1994. 29:1-68.
Jones et al., Development and validation of a genetic algorithm for flexible docking. J Mol. Biol. 1997. 267:727-748.
Jones et al., Docking small-molecule ligands into active sites. Curr. Opin. Biotech. 1995. 6:652-656.
Jones et al., Improved methods for building protein models in electron density maps and the location of errors in these models. Acta Crystallogr. 1991. A47:110-119.
Jones et al., Molecular Recognition of Receptor Sites Using a Genetic Algorithm with a Description of Desolvation. J Mol Biol. 1995. 245:43-53.
Kabsch, A discussion of the solution for the best rotation to relate two sets of vectors. Acta Crystallogr. 1978. A34:827-828.
Kabsch., A solution of the best rotation to relate two sets of vectors. Acta Crystallogr. 1976. A32:922-23.
Karlin & Altschul. Applications and statistics for multiple high-scoring segments in molecular sequences. PNAS. 1993. 90:5873-5877.
Karlsson & Lofas. Flow-Mediated On-Surface Reconstitution of G-Protein Coupled Receptors for Applications in Surface Plasmon Resonance Biosensors. Anal. Biochem. 2002. 300(2):132-138.
Kearsley. On the orthogonal transformation used for structural comparisons. Acta Crystallogr. 1989. A45:208-210.
Kenakin et al., Protean agonists. Keys to active receptor states? Ann. N. Y. Acad. Sci. 1997. 812:116-125.
Kenakin. Inverse, protean, and ligand-selective agonism: matters of receptor conformation. FASEB J. 2001. 15(3):598-611.
Kent et al., Development of a Generic Dual-Reporter Gene Assay for Screening G-Protein-Coupled Receptors. J. Biomol. Screen. 2005. 10(5):437-446.
Kent et al., G-protein-coupled receptor heterodimerization: assay technologies to clinical significance. Curr. Opin. Drug Discov. Devel. 2007. 10(5):580-589.
Kerr et al., Encoded combinational peptide libraries containing non-natural amino acids. JACS. 1993. 115:2529-2531.
Kikkawa et al., The Role of the Seventh Transmembrane Region in High Affinity Binding of a b2-Selective Agonist TA-2005. Mol. Pharmacol. 1998. 53:128-134.
Klco et al., Essential role for the second extracellular loop in C5a receptor activation. Nat Struct Mol Biol. 2005. 12:320-326.
Kleywegt & Jones. A super position. CCP4/ESF-EACBM Newsletter on Protein Crystallography. 1994. 31:9-14.
Kobilka & Deupi. Conformation complexity of G-protein coupled receptors. Trends in Pharmacological Sciences. 2007. 28(8):397-406.
Kobilka & Schertler. New G-protein-coupled receptor crystal structures: insights and limitations. Trends Pharm. Sci. 2008. 29(2):79-83.
Köhler & Milstein. Continuous cultures of fused cells secreting antibody of predefined specificity. Nature. 1975. 256:495-497.
Komolov et al., Surface Plasmon Resonance Study of G Protein/Receptor Coupling in a Lipid Bilayer-Free System. Anal. Chem. 2006. 78:1228-1234.
Kozbor et al., A human hybrid myeloma for production of human monoclonal antibodies. J. Immunol. 1984. 133:3001-3005.
Kristiansen. Molecular mechanisms of ligand binding, signalling, and regulation within the superfamily of G-protein-coupled receptors: molecular modelling and mutagenesis approaches to receptor structure and function. Pharmacology and therapeutics. 2004. 103:21-80.
Kuhlbrandt. Three-dimensional crystallization of membrane proteins. Q. Rev. Biophys. 1988. 21:429-477.
Kuhlbrandt. Two-dimensional crystallization of membrane proteins. Q. Rev. Biophys. 1992. 25(1):1-49.
Kukkonen et al., Muscarinic Toxin 7 Selectivity Is Dictated by Extracellular Receptor Loops. J. Biol. Chem. 2004. 279:50923-50929.
Kuntz et al., A Geometric Approach to Macromolecule-Ligand Interactions. J. Mol. Biol. 1982. 161:269-288.
Kuroda et al., Systems for the detection and analysis of protein-protein interactions. Appl. Microbiol. Biotechnol. 2006. 71(2):127-136.
Kyte & Doolittle. A Simple Method for Displaying the Hydropathic Character of a Protein. J. Mol. Biol. 1982. 157:105-132.
Labbé-JulliéC. et al., 1998, Mutagenesis and Modeling of the Neurotensin Receptor NTR1, Journal of Biological Chemistry, 273(26):16351-16357.
Lamb et al., Modulation of the ligand binding properties of the transcription repressor NmrA by GATA-containing DNA and site-directed mutagenesis. Prot. Sci. 2004. 13(12):3127-3138.
Landau & Rosenbusch. Lipidic cubic phases: A novel concept for the crystallization of membrane proteins. PNAS USA. 1996. 93:14532-14535.
Lane et al., Protean agonism at the dopamine D2 receptor: (S)-3-(3-hydroxyphenyl)-N-propylpiperidine is an agonist for activation of Go1 but an antigonist/inverse agonist for Gi1, Gi2, and Gi3. Mil Pharmacol. 2007 71(5):1349-1359. Epub Feb. 7, 2007.
Lang et al., Structure-activity relationship studies: Methods and ligand design for g-protein coupled peptide receptors. Curr. Prot. Peptide Sci. 2006. 7:335-353.
Latronico et al., Gonadotropin-Independent Precocious Puberty Due to Luteinizing Hormone Receptor Mutations in Brazilian Boys: A Novel Constitutively Activating Mutation in the First Transmembrane Helix. J. Clin. Endocrinol. Metabl. 2000. 85(12):4799-4805.
Lattion et al., Constitutively active mutants of the β31-adrenergic receptor. FEBS Letters 1999 457(3):302-306.
Lattman. Use of Rotation and Translation Functions. Meth. Enzymol. 1985. 115:55-77.
Lau et al., Changing single side chains can greatly enhance the resistance of a membrane protein to irreversible inactivation. J. Mol. Biol. 1999. 290:559-564.
Lauri & Bartlett. CAVEAT: A Program to Facilitate the Design of Organic Molecules. J. Comp. Aided Mol. Design. 1994. 8:51-66.
Lee et al., Alanine scanning mutagenesis of conserved arginine/lysine-arginine/lysine-x-xarginie/lysine G protein/activating motifs on M1 muscarinic acetylcholine receptors. Molecular Pharmacology. 1996 50(1):140-148.
Lee et al., D2 Dopamine receptor homodimerization is mediated by multiple sites of interaction, including an intermolecular interaction involving transmembrane domain 4. Biochemistry. 2003. 42(37):11023-31.
Lee et al., State of the art in studying protein folding and protein structure predictio using molecular dynamics methods. J. Mol. Graph & Modelling. 2001. 19(1):146-149.
Lefèvre et al., Alanine-stretch scanning mutagenesis: a simple and efficient method to probe protein structure and function. Nucl. Acids Res. 1997. 25(2):447-448.

(56) References Cited

OTHER PUBLICATIONS

Lehmann et al., The consensus concept for thermostability engineering of proteins: further proof of concept. Protein Engineering. 2002. 15(5):403-411.
Leifert et al., G-Protein-Coupled Receptors in Drug Discovery: Nanosizing Using Cell-Free Technologies and Molecular Biology Approaches. J. Biomol. Screening. 2005. 10:765-779.
Leroy et al., G Protein-coupled receptor-mediated ERK 1/2 phosphorylation: towards a generic sensor of GPCR activation. J. Recept. Signal. Transduct. Res. 2007. 27(1):83-97.
Lewis & Lofthouse. Adverse reactions with beta-adrenoceptor blocking drugs: an update. Drug Safety. 1993. 9:272-279.
Li et al., Distinct Structural Changes in a G Protein-coupled Receptor Caused by Different Classes of Agonist Ligands. J. Biol. Chem. 2007. 282(36):26284-26293.
Li et al., Random Mutagenesis of the M3 Muscarinic Acetylcholine Receptor Expressed in Yeast. J. Biol. Chem. 2005. 280:5664-5675.
Li et al., Structure of Bovine Rhodopsin in a Trigonal Crystal Form. J. Mol. Biol. 2004. 343:1409-1438.
Liu & Wu. Analysis of the coupling of G12/13 to G protein-coupled receptors using a luciferase reporter assay. Methods Mol. Biol. 2004. 237:145-149.
Lohse et al. Kinetic analysis of G protein-coupled receptor signaling using fluorescence resonance energy transfer in living cells. Adv Protein Chem 2007 74:167-188.
Luecke et al., Structure of bacteriorhodopsin at 1.55 A resolution. J. Mol. Biol. 1999. 291(4):899-911.
Maclean et al., Encoded combinatorial chemistry: Synthesis and screening of a library of highly functionalized pyrrolidines. PNAS. 1997. 94:2805-2810.
Madabushi et al., Evolutionary Trace of G Protein-coupled Receptors Reveals Clusters of Residues That Determine Global and Class-specific Functions; J Biol Chem 2004 279(9):8126-8132.
Magnani et al., Co-evolving stability and conformational homogeneity of the human adenosine A2a receptor. PNAS. 2008. 105(31):10744-10749.
Makino et al., Automated flexible ligand docking method and its application for database search. J Comput. Chem. 1997. 18:1812-1825.
Marshall. Heterodimerization of G-protein-coupled receptors in the CNS. Curr. Opin. Pharmacol. 2001. 1(1):40-44.
Martin et al., A simple vector system to improve performance and utilisation of recombinant antibodies. BMC Biotechnology. 2006. 6:46.
Martin et al., Apolipoprotein A-I Assumes a "Looped Belt" Conformation on Reconstituted High Density Lipoprotein. J. Biol. Chem. 2006. 281(29):20418-20426.
Martin. 3D Database searching in drug design. J. Med. Chem. 1992. 35:2145-2154.
Martin-Garcia et al., Interaction with CD4 and Antibodies to CD4-Induced Epitopes of the Envelope gp120 from a Microglial Cell-Adapted Human Immunodeficiency Virus Type 1 Isolate. J. Virology. 2005. 79:6703-6713.
Mathews & Rossmann. Comparison of Protein Structures. Methods of Enzymology. 1985. 115:397-420.
Matsui et al., Specific removal of β1-adrenoceptor autoantibodies by immunoabsorption in rabbits with autoimmune cardiomyopathy improved cardiac structure and function. J. Mol. Cell Cardiol. 2006. 41(1):78-85. epub Jun. 14, 2006.
McCafferty et al., Phage antibodies: filamentous phage displaying antibody variable domains. Nature. 1990. 348:552-553.
McCoy. Phaser' crystallographic software. Acta Crystallogr. 2007. 40:658-674.
McCoy. Solving Structures of protein complexes by molecular replacement with Phaser. Acta Crystallogr. 2007. D63:32-42.
McLachlan. Gene duplications in the structural evolution of chymotrypsin. J. Mol. Biol. 1979. 128, 49-79.
Mehler et al., Ab initio computational modelling of loops in G-protein-coupled receptors: Lessons from the crystal structure of rhodopsin. Proteins Structures Function and Bioinformatics. 2006. 64(3):673-690.
Meng et al., Automated docking with grid-based energy evaluation. J. Comp. Chem. 1992. 13:505-524.
Mezzasalma et al., Enhancing recombinant protein quality and yield by protein stability profiling. J. Biolmol. Screening. 2007. 12(3):418-428.
Michaelson et al., Antibodies to muscarinic acetylcholine receptors in myasthenia gravis. Biochem. Biophys. Res. Commun. 1982. 104(1):52-57.
Milligan & White. Protein—protein interactions at G-protein-coupled receptors. Trends Pharmacol. Sci. 2001. 22:513-518.
Milligan. G protein-coupled receptor dimerisation: Molecular basis and relevance to function. Biochim. Biophys Acta. 2007. 1768(4):825-835.
Milstein & Cuello. Hybrid hybridomas and their use in immunohistochemistry. Nature. 1983. 305:537-540.
Minic et al., Immobilization of native membrane-bound rhodopsin on biosensor surfaces. Biochim. Biophys. Acta-General Subjects. 2005. 1924:324-332.
Minneman et al., A Comparison of the Beta-Adrenergic Receptor of the Turkey Erythrocyte with Mammalian Beta1 and Beta2 Receptors. Mol. Pharmacol. 1980. 17:1-7.
Miranker et al., Functionality Maps of Binding Sites: A Multiple Copy Simultaneous Search Method Proteins: Structure, Function and Genetics. 1991. 11:29-34.
Misquitta et al. Membrane Protein Crystallization in Lipidic Mesophases with Tailored Bilayers. Structure. 2004. 12:2113-2124.
Moran et al., Radio frequency tag encoded combinatorial library method for the discovery of tripeptide-substituted cinnamic acid inhibitors of the protein tyrosine phosphatase PTB1B. JACS. 1995. 117:10787-10788.
Morris et al., Automated docking using a Lamarckian genetic algorithm and an empirical binding free energy function. J. Comput. Chem 1998. 19:1639-1662.
Morrison. Success in specification. Nature. 1994. 368:812-813.
Mozsolits et al., Surface plasmon resonance spectroscopy in the study of membrane-mediated cell signalling. J. Peptide Sci. 2003. 9:77-89.
Munson & Rodbard. Ligand: a versatile computerized approach for characterization of ligand-binding systems. Anal. Biochem. 1980. 107:220-239.
Murakami et al., Crystal structure of squid rhodopsin. Nature. 2008 May 15;453(7193):363-7.
Myburgh et al., A single amino acid substitution in transmembrane helix VI results in overexpression of the human GnRH receptor. Eur. J. Endocrinol. 1998.139(4):438-447.
Navarro et al., Receptor-Dependent G-Protein activation in Lipidic Cubic phase. Biopolymers. 2002. 67:167-177.
Navaza. AMoRe: an Automated Package for Molecular Replacement. Acta Cryst. 1994. D50:157-163.
Navia & Murko. Use of structural information in drug design. Curr Opin Struc Biol. 1992. 2:202-210.
Navratilova et al., Analyzing ligand and small molecule binding activity of solubilized GPCRs using biosensor technology. Anal. Biochem. 2006. 355:132-139.
Nawaratne et al., New insights into the function of M4 muscarinic acetylcholine receptors gained using a novel allosteric modulator and a DREADD (designer receptor exclusively activated by a designer drug). Mol Pharmacol. Oct. 2008;74(4):1119-31. Epub Jul. 15, 2008.
Needleman SB & Wunsch C.D. A general method applicable to the search for similarities in the amino acid sequence of two proteins. J Mol Biol 1970 Mar; 48(3):443-453.
Neubig et al., International Union of Pharmacology Committee on Receptor Nomenclature and Drug Classification. XXXVIII. Update on Terms and Symbols in Quantitative Pharmacology. Pharmacol. Rev. 2003. 55:597-606.
Newman-Tancredi et al., Agonist and inverse agonist efficacy at human recombinant serotonin 5-HT1A receptors as a function of receptor:G-protein stoichiometry. Neurophamacology. 1997. 36:451-459.

(56) References Cited

OTHER PUBLICATIONS

Nicolaou et al., Radiofrequency encoded combinatorial chemistry. Angew. Chem. Int. Ed. Engl. 1995. 34:2289-2291.

Nishibata et al., Automatic creation of drug candidate structures based on receptor structure. Starting point for artificial lead generation. Tetrahedron. 1991. 47:8985-8990.

Nunomura et al., Regulation of Protein 4.1R, p55, and Glycophorin C Ternary Complex in Human Erythrocyte Membrane. J. Biol. Chem. 2000. 275:24540-24546.

Ohlmeyer et al., Complex synthetic chemical libraries indexed with molecular tags. PNAS. 1993. 90:10922-10926.

Oldham et al., Mapping allosteric connections from the receptor to the nucleotide-binding pocket of heterotrimeric G proteins. PNAS. 2007. 104(19):7927-7932.

Omerovic et al., Induction of Cardiomyopathy in Immunodeficiency Mice by Transfer Patients with Idiopathic Dilated Cardiomyopathy. Autoimmunity. 2000. 32(4):271-280.

Osbourn et al., Directed selection of MIP-1 alpha neutralizing CCR5 antibodies from a phage display human antibody library. Nature Biotechnology. 1998. 16:778-781.

Ostermeier & Michel. Crystalization of Membrane Proteins. Curr. Opin. Struct. Biol. 1997. 7:697-701.

Ott et al., Engineering and functional immobilization of opioid receptors. Prot. Eng. Design & Selection. 2005. 18:153-160.

Overington et al., How many drug targets are there? Natur Rev. Drug Discovery. 2006. 5:993-996.

Palczewski et al., Crystal Structure of Rhodopsin: A G Protein-Coupled Receptor. Science. 2000. 289:739-745.

Palmer et al., Treatment of systemic lupus erythematosus by extracorporeal immunoadsorption. Lancet. 1988. 2(8605):272.

Pardo et al., The role of internal water molecules in the structure and function of the rhodopsin family of G protein-coupled receptors. Chembiochem. Jan. 2, 2007;8(1):19-24.

Park et al., Characterization of radioligand binding to a transmembrane receptor reconstituted into Lipobeads. FEBS Lett. 2004. 567:344-348.

Parker & Ross. Truncation of the Extended Carboxyl-terminal Domain Increases the Expression and Regulatory Activity of the Avian,& Adrenergic Receptor. J. Biol. Chem. 1991. 266:9987-9996.

Parker et al., Carboxyl terminal domains in the avian β1-adrenergic receptor that regulate agonist-promoted endocytosis. J. Biol. Chem. 1995. 270:6482-6487. Erratum in: J Biol Chem 1995. 270(17):10358.

Parker et al., Reconstitutively Active G Protein-coupled Receptors Purified from Baculovirus-infected Insect Cells. J. Biol. Chem. 1991. 266:519-527.

Parsons et al., Directing phage selections towards specific epitopes. Protein Engineering. 1996. 9:1043-1049.

Perez. From Plants to Man: The GPCR "Tree of Life". Mol. Pharmacol. 2005. 67:1383-1384.

Pin et al., Evolution, structure, and activation mechanism of family 3/C G-protein-coupled receptor, Pharm. & Ther. 2003 98 325-354.

Plant et al., Phospholipid/alkanethiol bilayers for cell-surface receptor studies by surface plasmon resonance. Analyt. Biochem. 1995. 226(2):342-348.

Ponsioen et al. Detecting cAMP-induced Epac activation by fluorescence resonance energy transfer: epac as a novel cAMP indicator, 2004 EMBO Rep.;5(12):1176-1180.

Qian et al., High-resolution structure prediction and the crystallographic phase problem. Nature. 2007. 450:259-264.

Quick & Javitch. Monitoring the function of membrane transport proteins in detergent-solubilized form. PNAS. 2007. 104(9):3603-3608.

Rarey et al., A fast flexible docking method using an incremental construction algorithm. J. Mol. Biol. 1996. 261:470-489.

Rasmussen et al., Crystal structure of the human β2 adrenergic g-protein-coupled receptor. Nature. 2007. 450:383-387.

Rasmussen et al., Mutation of a Highly Conserved Aspartic Acid in the β2 Adrenergic Receptor: Constitutive Activation, Structural Instability, and Conformational Rearrangement of Transmembrane Segment 6. Molecular Pharmacol. 1999. 56:175-84.

Riekel et al., Protein crystallography microdiffraction. Curr. Opin. Struct. Biol. 2005. 15(5):556-562.

Rigaut et al., A generic protein purification method for protein complex characterization and proteome exploration. Nature Biotechnol. 1999. 17(10):1030-1032.

Roberts & Strange. Mechanisms of inverse agonist action at D2 dopamine receptors. Br. J. Pharmacol. 2005. 145:34-42.

Robinson-Rechavi et al., Contribution of Electrostatic Interactions, Compactness and Quaternary Structure to Protein Thermostability: Lessons from Structural Genomics of Thermotoga maritima. J. Mol. Biol. 2006. 356:547-557.

Rodgers et al., Development of displacement binding and GTPγS scintillation proximity assays for the identification of antagonists of the μ-opiod receptor. Assay Drug Dev. Technol. 2003. 1(5):627-636.

Rosenbaum et al., GPCR Engineering Yields High-Resolution Structural Insights into b2-Adrenergic Receptor Function. Science. 2007. 318:1266-1273.

Rossmann & Argos. A Comparison of the Heme Binding Pocket in Globins and Cytochrome b. J. Biol. Chem. 1975. 250:7525-7532.

Roth et al., Stabilization of the β2-adrenergic Receptor 4-3-5 Helix Interface by Mutagenesis of Glu-1223.41, A Critical Residue in GPCR Structure. J. Mol. Biol. 2008. 376:1305-1319.

Rovati et al., The Highly Conserved DRY Motif of Class A G Protein-Coupled Receptors: Beyond the Ground State. Mol. Pharmacol. 2007. 71(4):959-964.

Rummel et al., Lipidic Cubic Phases: New Matrices for the Three-Dimensional Crystallization of Membrane Proteins. J. Struct. Biol. 1998. 121:82-91.

Sali & Blundell. Comparative protein modelling of satisfaction by spatial restraints. J. Mol. Biol. 1993. 234(3):779-815.

Samama et al., A mutation-induced activated state of the β2-adrenergic receptor. J Biol Chem. 1993 268(7):4625-4636.

Sarkar et al., Directed evolution of a G protein-coupled receptor for expression, stability, and binding selectivity. PNAS. 2008. 105(39):14808-14813.

Savinainen et al., Identification of WIN55212-3 as a competitive neutral antagonist of the human cannabinoid CB2 receptor. Br. J. Pharmacol. 2005. 145:636-645.

Sayle et al., RASMOL: biomolecular graphics for all. Trends in Biochemical Sciences. 1995. 20:374-376.

Scarselli et al., Multiple Residues in the Second Extracellular Loop Are Critical forM3 Muscarinic Acetylcholine Receptor Activation. J. Biol. Chem. 2007. 282:7385-7396.

Schaffner & Weissmann. A Rapid, Sensitive, and Specific Method for the Determination of Protein in Dilute Solution. Anal. Biochem. 1973. 56:502-514.

Schena et al., Quantitative monitoring of gene expression patterns with a complementary DNA microarray. Science. 1995. 270:467-470.

Schnare et al. Comprehensive comparison of structural characteristics in eukaryotic cytoplasmic large subunit (23S-like) ribosomal RNA. J. Mol. Biol. 1996. 256:701-719.

Schofield et al., Application of phage display to high throughput antibody generation and characterization. Genome Biology. 2007. 8(11):R254.

Schultz et al., Requirement of Specific Intrahelical Interactions for Stabilizing the Inactive Conformation of Glycoprotein Hormone Receptors. J. Biol. Chem. 2000. 275(48):37860-37869.

Screpanti et al., Crucial Steps in the Structure Determination of the Na+/H+ Antiporter NhaA in its Native Conformation. J. Mol. Biol. 2006. 362:192-202.

Sebestyen et al., Efficiency and limitations of the 'portioning-mixing' peptide synthesis. Pept. Proc. Eur. Pept. Symp. 22nd 1992. 1993. 63-64.

Sen et al., Functional studies with membrane-bound and detergent-solubilized alpha2-adrenergic receptors expressed in Sf9 cells. Biochim Biophys Acta. 2005 1712(1):62-70. Epub Apr. 26, 2005.

Serrano-Vega et al., Conformational thermostabilisation of the β1-adrenergic receptor in a detergent-resistant form. PNAS 2008 105(3):877-882.

(56) References Cited

OTHER PUBLICATIONS

Shi & Javitch. The second extracellular loop of the dopamine D2 receptor lines the binding-site crevice. PNAS 2004. 101:440-445.
Shi et al., Beta2 adrenergic receptor activation. Modulation of the proline kink in transmembrane 6 by a rotamer toggle switch. J Biol Chem. Oct. 25, 2002;277(43):40989-96. Epub Aug. 6, 2002.
Shibata et al. Thermostabilization of the Neurotensin Receptor NTS1, J. Mol. Biol. 2009 390(2):262-277.
Skerra. 'Anticalins': a new class of engineered ligand-binding proteins with antibody-like properties. J. Biotechnol. 2001. 74(4):257-275.
Sobek et al., Microarray technology as a universal tool for high-throughput analysis of biological systems. Combinat. Chem. & High Throughput Screening. 2006. 9:365-380.
Spalding et al., Structural Requirements of Transmembrane Domain 3 for Activation by the M1 Muscarinic Receptor Agonists AC-42, AC-260584, Clozapine, and N-Desmethylclozapine: Evidence for Three Distinct Modes of Receptor Activation. Mol. Pharmacol. 2006. 70:1974-1983.
Standfuss et al., Crystal Structure of a thermally stable rhodopsin mutant. J Mol Biol. 2007 372(5):1179-1188.
Steipe et al., Sequence statistics reliably predict stabilizing mutations in a protein domain. J. Mol. Biol. 1994. 240:188-192.
Stenlund et al., Capture and reconstitution of G protein-coupled receptors on a biosensor surface. Analytical Biochemistry. 2003. 316:243-250.
Stock et al., Robotic nanolitre protein crystallisation at the MRC Laboratory of Molecular Biology. Prog. Biophys. Mil. Biol. 2005. 88:311-327.
Sugimoto et al., Beta(1)-selective agonist (-)-1-(3,4-dimethoxyphenetylamino)-3-(3,4-dihydroxy)-2-propanol [(-)-R0363] differentially interacts with key amino acids responsible for beta(1)-selective binding in resting and active states. J Pharmacol Exp Ther. Apr. 2002;301(1):51-8.
Sung et al., Rhodopsin Mutations Responsible for Autosomal Dominant Retinitis Pigmentosa. J. Biol. Chem. 1993. 268(35):26645-26649.
Sutcliffe et al., Knowledge based modelling of homologous proteins, part I: three-dimensional frameworks derived from the simultaneous superposition of multiple structures. Protein Eng. 1987. 1:377-384.
Swaminath et al., Sequential Binding of Agonists to the 2 Adrenoceptor. J. Biol. Chem. 2004. 279(1):686-691.
Szldarz & Halpert. Use of homology modeling in conjunction with site-directed mutagenesis for analysis of structure-function relationships of mammalian cytochromes P450. Life Sci. 1997. 61:2507-2520.
Tan et al., FGF and stress regulate CREB and ATF-1 via a pathway involving p38 MAP kinase and MAPKAP kinase-2. EMBO J. 1996. 15(17):4629-4642.
Tao et al., Chimeras of the Rat and Human FSH Receptors (FSHRs) Identify Residues that Permit or Suppress Transmembrane 6 Mutation-Induced Constitutive Activation of the FSHR via Rearrangements of Hydrophobic Interactions Between Helices 6 and 7. Mol. Endocrinol. 2002. 16(8):1881-1892.
Tate. Overexpression of mammalian integral membrane proteins for structural studies. FEBS Lett. 2001. 504:94-98.
Tate. Baculovirus-Mediated Expression of Neurotransmitter Transporters. Methods Enzymol. 1998. 296:443-455.
Teng et al., Control of feeding behavior in C. elegans by human G protein-coupled receptors permits screenin for agonist-expressing bacteria. PNAS. 2008. 105(39):14826-14831.
Teng et al., Expression of mammalian GPCRs in C. elegans generates novel behavioural responses to human ligands. BMC Biology. 2006. 4:22.
Themmen & Huhtaniemi. Mutations of Gonadotropins and Gonadotropin Receptors: Elucidating the Physiology and Pathophysiology of Pituitary-Gonadal Function. Endocr. Rev. 2000. 21(5):551-583.

Thompson et al., CLUSTAL W: improving the sensitivity of progressive multiple sequence alignment through sequence weighting, position-specific gap penalties and weight matrix choice Nucl. Acids Res. 1994. 22:4673-4680.
Topiol & Sabio. Use of the X-ray structure of the β2-adrenergic receptor for drug discovery. Bioorganic & Medicinal Chemistry. 2008. 18(5):1598-1602.
Traunecker et al., Bispecific single chain molecules (Janusins) target cytotoxic lymphocytes on HIV infected cells. EMBO J. 1991. 10:3655-3659.
Tucker & Grisshammer. Purification of a rat neurotensin receptor expressed in *Escherichia coli*. Biochem. J. 1996. 317(Pt. 3):891-899.
Urizar et al. An activation switch in the rhodopsin family of G protein-coupled receptors: The Thyrotropin receptor J. Biol Chem 2005 280(17):17135-17141.
Vagin & Teplyakov. MOLREP: an automated program for molecular replacement. J. Appl. Cryst. 1997. 30:1022-1025.
Vakser. Evaluation of GRAMM low-resolution docking methodology on hemagglutinin-antibody complex. Proteins, Suppl. 1997. 1:226-230.
Venturi & Hunte. Monoclonal antibodies for the structural analysis of the Na+/H+ antiporter NhaA from Escherichia coli. Biochimica et aBiophysica Acta. 2003. 1610:46-50.
Walters et al., Virtual screening-an overview. Drug Discovery Today. 1998. 3(4):160-178.
Wang. Basic Amino Acids at the C-Terminus of the Third Intracellular Loop Are Required for the Activation of Phospholipase C by Cholecystokinin-B Receptors. J. Neurochem. 1997. 68(4):1728-1735.
Warne et al., Structure of a β1-adrenergic G protein-coupled receptor. Nature. 2008. 454:486-491.
Warne et al., Expression and purification of truncated, non-glycosylated turkey beta-adrenergic receptors for crystallization. Biochim. Biophys. Acta. 2003. 1610:133-140.
Warne et al., The purification of G-protein coupled receptors for crystallization, Structural Biology of Membrane Proteins, Royal Society of Chemistry. 2006. 51-71.
Weber et al., a 1,536-Well cAMP Assay for Gs- and Gi-Coupled Receptors Using Enzyme Fragmentation Complementation. Assay Drug Dev. Technol. 2004. 2(1):39-49.
Weiβ & Grisshammer. Purification and characterization of the human adenosine A2a receptor functionally expressed in *Escherichia coli*. Eur. J. Biochem. 2002. 269:82-92.
Wess. Molecular Basis of Receptor/G-Protein-Coupling Selectivity. Pharmacol. Ther. 1998. 80:231-264.
White. The progress of membrane protein structure determination. Protein Science. 2004. 13:1948-1949.
Williams & Addona. The integration of SPR biosensors with mass spectrometry: possible applications for proteome analysis. Trends Biotechnol. 2000. 18(2):45-48.
Williams. Biotechnology match making: screening orphan ligands and receptors. Curr. Opin. Biotechnol. 2000. 11(1):42-46.
Winter & Milstein. Man-made antibodies. Nature. 1991. 349:293-299.
Winter et al., Surface binding affinity measurements from order transitions of lipid-membranecoated colloidal particles. Anal. Chem. 2006. 78:174-180.
Wurch et al., Chimeric Receptor Analysis of the Ketanserin Binding Site in the Human 5-Hydroxytryptamine1D Receptor: Importance of the Second Extracellular Loop and Fifth Transmembrane Domain in Antagonist Binding. Mol. Pharmacol. 1998. 54(6):1088-1096.
Wyckoff. Diffractometry. Methods in Enzymology. 1985. 114:330-386.
Yano et al., Phe576 Plays an Important Role in the Secondary Structure and Intracellular Signaling of the Human Luteinizing Hormone/Chorionic Gonadotropin Receptor. J. Clin. Endocrinol. Metabl. 1997. 82(8):2586-2591.
Yao et al., Coupling ligand structure to specific conformational switches in the β2-adrenoceptor. Nat. Chem. Biol. 2006. 2(8):417-422.
Yarden et al., The avian beta-adrenergic receptor: Primary structure and membrane topology. Proc. Natl. Acad. Sci. USA. 1986. 83:6795-6799.

(56) References Cited

OTHER PUBLICATIONS

Yohannan et al., The evolution of transmembrane helix kinks and the structural diversity of G protein-coupled receptors. PNAS. 2004. 101(4):959-963.

Yokogawa et al., Bead-linked Proteoliposomes: A Reconstitution Method for NMR Analyses of Membrane Protein-Ligand Interactions. J. Am. Chem. So. 2005. 127:12021-12027.

Zeitoun, O. et al., 2006, Mutagenesis within Helix 6 of the Human β1-Adrenergic Receptor Identifies Lysine324 as a Residue Involved in Imparting the High-Affinity Binding State of Agonists, Molecular Pharmacology, 70(3):838-850.

Zhang et al., Structure modelling of all identified G-protein coupled receptors in the human genome. PloS Computational Biology. 2006. 2(2):88-99.

Zhao et al. A homogeneous enzyme fragement complementation-based {beta}-Arrestin translocation assay for high-throughput screening of G-Protein-Coupled receptors: J. Biomol Screen 2008;13(8):737-747; Epub 2008.

Zheng et al., An efficient one-step site-directed and site-saturation mutagenesis protocol. Nucl. Acids Res. 2004. 32:e115.

Zhou & Bowie. Building a Thermostable Membrane Protein. J. Biol. Chem. 2000. 275:6975-6979.

Zurawski et al., A novel biosensor assay for screening peptide antagonism of the interaction between HIV-1 envelope, CD4 and membrane-embedded CCR5. Biopolymers. 2003. 71:388-389. Abstract P395.

Robertson et al., "The properties of thermostabilized G protein-coupled receptors (StaRs) and their use in drug discovery," Neuropharmacology 60: 36-44, 2011.

Shoichet et al., "Structure-based drug screening for G-protein-coupled receptors," Trends in Pharma Science 33(5): 268-272, 2012.

Alberts et al., Solubilizing membrane proteins with a mild detergent. Molecular Biology of the Cell 2002;4th Edition. New York: Garland Science. Figure 10-24.

Hulme et al.,Phenotypic classification of mutants: a tool for understanding ligand binding and activation of muscarinic acetylcholine receptors. Biochem Soc Trans. 2007 Aug;35(Pt 4):742-5.

Lehmann et al., The consensus concept for thermostability engineering of proteins. Biochim Biophys Acta. Dec. 29, 2000;1543(2):408-415.

Lu et al., Transmembrane domains 4 and 7 of the M(1) muscarinic acetylcholine receptor are critical for ligand binding and the receptor activation switch. J Biol Chem. Sep. 7, 2001;276(36):34098-104. Epub Jul. 5, 2001.

Pogozheva et al., Interactions of human melanocortin 4 receptor with nonpeptide and peptide agonists. Biochemistry. Aug. 30, 2005;44(34):11329-41.

Schimerlik, Overview of membrane protein solubilization. Current Protocols in Neuroscience 2001;5.9.1-5.9.5. Abstract.

Scopes, 4.7 Precipitation by Selective Denaturation. General Principles. Purification: Principles and Practice. $3^{rd}$ Edition. 1994:95.

Voet et al., Protein Stability. Chapter 7: Three-Dimensional Structures of Proteins. Section 7-4. Protein Stability. Biochemistry $2^{nd}$ Edition. 1995. 179-180.

Zhang et al., Adopting selected hydrogen bonding and ionic interactions from *Aspergillus fumigatus phytase* structure improves the thermostability of *Aspergillus niger* PhyA phytase. Appl Environ Microbiol. May 2007 ;73(9):3069-76. Epub Mar. 9, 2007.

\* cited by examiner

Alignment of the turkey β-adrenergic receptor with human β1, β2 and β3

```
SEQ ID NO:1   adrb1_melga   1                 MGDGWLPPDCGPHNRSGGGGATAAPTGSR---------------  29
SEQ ID N0:2   adrb1_human   1   MGAGVLVLGASE------PGNLSSAAPLPDGAATAARLLVPASPPASLLP  44
SEQ ID N0:3   adrb2_human   1          MGQ---------PGNGSAFLLAPNRSHAPD---------------  21
SEQ ID N0:4   adrb3_human   1         MAPW------PHENSSLAPWPDLPTLAP----------------N  23
                                                  *  *
                                                                         a
SEQ ID NO:1   adrb1_melga   30  -QVSAEL-LSQQWEAGMSLLMALVVLIAVAGNVLVIAAIGTQRLQTLTN  77
SEQ ID N0:2   adrb1_human   45  PASESPEPLSQQWTAGMGLLMALIVLLIVAGNVLVIVAIAKTPRLQTLTN  94
SEQ ID N0:3   adrb2_human   22  -HDVTQQ-RDEVWVVGMGIVMSLIVLAIVFGNVLVITAIAKFERLQTVTN  69
SEQ ID N0:4   adrb3_human   24  TANTSGLPGVPWEAALAGALLALAVLATGGNLLVIVAIAWTPRLQTMTN  73
                                             bc
SEQ ID NO:1   adrb1_melga   78  LFITSLACADLVMGLLVVPFGATLVVRGTWLWGSFLCECWTSLDVLCVTA 127
SEQ ID N0:2   adrb1_human   95  LFIMSLASADLVMGLLVVPFGATIVVWGRWEYGSFFCELWTSVDVLCVTA 144
SEQ ID N0:3   adrb2_human   70  YFITSLACADLVMGLAVVPFGAAHILMKMWTFGNFWCEFWTSIDVLCVTA 119
SEQ ID N0:4   adrb3_human   74  VFVTSLAAADLVMGLLVVPPAATLALTGHWPLGATGCELWTSVDVLCVTA 123
                                       d                e
SEQ ID NO:1   adrb1_melga   128 SIETLCVIAIDRYLAITSPFRYQSLMTRARAKVIICTVWAISALVSFLPI 177
SEQ ID N0:2   adrb1_human   145 SIETLCVIALDRYLAITSPFRYQSLLTRARARGLVCTVWAISALVSFLPI 194
SEQ ID N0:3   adrb2_human   120 SIETLCVIAVDRYFAITSPFKYQSLLTKNKARVIILMVWIVSGLTSFLPI 169
SEQ ID N0:4   adrb3_human   124 SIETLCALAVDRYLAVTNPLRYGALVTKRCARTAVVLVWVVSAAVSFAPI 173
                                                       f
SEQ ID NO:1   adrb1_melga   178 MMHWWRDEDP-QALKCYQDPGCCDFVTNRAYAIASSIISFYIPLLIMIFV 226
SEQ ID N0:2   adrb1_human   195 LMHWWRAESD-EARRCYNDPKCCDFVTNRAYAIASSVVSFYVPLCIMAFV 243
SEQ ID N0:3   adrb2_human   170 QMHWYRATHQ-EAINCYANETCCDFFTNQAYAIASSIVSFYVPLVIMVFV 218
SEQ ID N0:4   adrb3_human   174 MSQWWRVGADAEAQRCHSNPRCCAFASNMPYVLLSSSVSFYLPLLVMLFV 223
                                      g
SEQ ID NO:1   adrb1_melga   227 YLRVYREAKEQIRKIDRCEGRFYGSQE-----QPQ--PPPLPQHQPILG- 268
SEQ ID N0:2   adrb1_human   244 YLRVFREAQKQVKKIDSCERRFLGGPARPPSPSPSPVPAPAPPPGPPRPA 293
SEQ ID N0:3   adrb2_human   219 YSRVFQEAKRQLQKIDKSEGRFHVQN--------------LSQVEQDGR- 253
SEQ ID N0:4   adrb3_human   224 YARVFVVATRQLRLLRGELGRFPPEES-PPAPSRSLAPAPVGTCAPPE-- 270
                                                                    h
SEQ ID NO:1   adrb1_melga   269 ---------NGRASKRKTSRVMSMREHKALKTLGIIMGVFTLCWLPFFLV 309
SEQ ID N0:2   adrb1_human   294 AAAATAPLANGRAGKRRPSRLVALREQKALKTLGIIMGVFTLCWLPFFLA 343
SEQ ID N0:3   adrb2_human   254 ---------TGHGLRR--SSKFCLKEHKALKTLGIIMGTFTLCWLPFFIV 292
SEQ ID N0:4   adrb3_human   271 ---------GVPACGRRPARLLPLREHRALCTLGLIMGTFTLCWLPFFLA 311
                                           i       j    k    l
SEQ ID NO:1   adrb1_melga   310 NIVNVFNR-DLVPDWLFVFFNWLGYANSALNPIIYCRSPDFRKAFKRLLC 358
SEQ ID N0:2   adrb1_human   344 NVVKAFHR-ELVPDRLFVFFNWLGYANSAFNPIIYCRSPDFRKAFQRLLC 392
SEQ ID N0:3   adrb2_human   293 NIVHVIQD-NLIRKEVYILLNWIGYVNSGFNPLIYCRSPDFRIAFQELLC 341
SEQ ID N0:4   adrb3_human   312 NVLRALGGPSLVPGPAFLALNWLGYANSAFNPIIYCRSPDFRSAFRRLLC 361
```

FIG. 9A

```
SEQ ID NO:1   adrb1_melga  359 FPRKADRRLHAGGQPAPLPGGFISTLGSPEHSPGGTWSDCNGGTRGGSES 408
SEQ ID NO:2   adrb1_human  393 CARRAARRRHATHGDRPR------------------ASGCLARPGPPPS 423
SEQ ID NO:3   adrb2_human  342 LRRSSLKAYGNG------------------YS-----SNGNTGEQSG--- 365
SEQ ID NO:4   adrb3_human  362 RCGRRLP-------PEP--------------------CAAARPALFPS 382

SEQ ID NO:1   adrb1_melga  409 SLEERHSKTSRSESKMEREKNILATTRFYCTFLGNGDKAVFCTVLRIVKL 458
SEQ ID NO:2   adrb1_human  424 PGAASDDDD--------DDVVGATPPARLLEPWAGCNGGAAADSDSSLDE 465
SEQ ID NO:3   adrb2_human  366 ----YHVEQ------EKENK-------LLCEDLPGTEDFVGHQGTVPSDN 398
SEQ ID NO:4   adrb3_human  383 GVPAARS---------------SPAQPRLCQRLDGASWGVS         408

SEQ ID NO:1   adrb1_melga  459 FEDATCTCPHTHKLKMKWRFKQHQA 483
SEQ ID NO:2   adrb1_human  466 PCRPGFASESKV              477
SEQ ID NO:3   adrb2_human  399 IDSQGRNCSTNDSLL           413
SEQ ID NO:4   adrb3_human  409                           408
```

SEE BELOW FOR KEY

■ Position of mutations in m23
▨ Position of other thermostabilising mutations
▧ Position of transmembrane domains
▩ Position of helix 8

Where other amino acid substitutions gave significant thermostability, the position is labelled with a lower case letter and the mutations are listed below in order of decreasing thermostability.

Alignment of human adenosine receptors

| | | | | |
|---|---|---|---|---|
| SEQ ID NO:5 | AA2AR_human | 1   | MPIMGSSVYITVELAIAVLAILGNVLVCWAVWLNSNLQNVTNYF | 44 |
| SEQ ID NO:6 | AA2BR_human | 1   | MLLETQDALYVALELVIAALSVAGNVLVCAAVGTANTLQTPTNYF | 45 |
| SEQ ID NO:7 | AA3R_human  | 1 MPNNSTALSLANVTYITMEIFIGLCAIVGNVLVICVVKLNPSLQTTTFYF | 50 |
| SEQ ID NO:8 | AA1R_human  | 1 MP---PSISAFQAAYIGIEVLIALVSVPGNVLVIWAVKVNQALRDATFCF | 47 |

| | | | | |
|---|---|---|---|---|
| SEQ ID NO:5 | AA2AR_human | 45  | VVSLAAADIVGLAIPFAITISTGFCAACGCLFIACFVLVLQSSIFS | 94 |
| SEQ ID NO:6 | AA2BR_human | 46  | LVSLAAADVAVGLFAIPFAITISLGFCTDFYGCLFLACFVLVLTQSSIFS | 95 |
| SEQ ID NO:7 | AA3R_human  | 51  | IVSLALADIAVGVLVMPLAIVVSLGITIHFYSCLFMTCLLLIFTHASIMS | 100 |
| SEQ ID NO:8 | AA1R_human  | 48  | IVSLAVADVAVGALVIPLAILINIGPQTYFHTCLMVACPVLILTQSSILA | 97 |

| | | | | |
|---|---|---|---|---|
| SEQ ID NO:5 | AA2AR_human | 95  | LLAIAIDRYIAIRIPLRYNGLVTGRAIIAICWVLSFAIGLTPMLGWN | 144 |
| SEQ ID NO:6 | AA2BR_human | 96  | LLAVAVDRYLAICVPLRYKSLVTGTRARGVIAVLWVLAFGIGLTPFLGWN | 145 |
| SEQ ID NO:7 | AA3R_human  | 101 | LLAIAVDRYLRVKLTVRYKRVTTHRRIWLALGLCWLVSFLVGLTPMFGWN | 150 |
| SEQ ID NO:8 | AA1R_human  | 98  | LLAIAVDRYLRVKIPLRYKMVVTPRRAAVAIAGCWILSFVVGLTPMFGWN | 147 |

| | | | | |
|---|---|---|---|---|
| SEQ ID NO:5 | AA2AR_human | 145 | --------NCGQPKKNHSQGCGEGQVACLFEDVVPMNYMVYFNFFACVL | 187 |
| SEQ ID NO:6 | AA2BR_human | 146 | SKDSATNNCTEPWDGTTNESCC---LVKCLFENVVPMSYMVYFNFFGCVL | 192 |
| SEQ ID NO:7 | AA3R_human  | 151 | --------MKLTSEYHRNVT------FLSCQFVSVMRMDYMVYFSFLTWIF | 187 |
| SEQ ID NO:8 | AA1R_human  | 148 | --------NLSAVERAWAANGSMGEPVIKCEFEKVISMEYMVYFNFFVWVL | 190 |

| | | | | |
|---|---|---|---|---|
| SEQ ID NO:5 | AA2AR_human | 188 | VPLLLMLGVYLRIFLAARRQLKQMESQPLPGERARSTLQKEVHAAKSAI | 237 |
| SEQ ID NO:6 | AA2BR_human | 193 | PPLLIMLVIYIKIFLVACRQLQRTELMDHS----RTTLQREIHAAKSLAM | 238 |
| SEQ ID NO:7 | AA3R_human  | 188 | IPLVVMCAIYLDIFYIIRNKLSLNLSNSK---ETGAFYGREFKTAKSLFL | 234 |
| SEQ ID NO:8 | AA1R_human  | 191 | PPLLLMVLIYLEVFYLIRKQLNKKVSASSG--DPQKYYGKELKIAKSLAL | 238 |

FIG. 10A

| | | | |
|---|---|---|---|
| SEQ ID NO:5 | AA2AR_human | 238 | I GLFALCWLPLHIINCFTFFCPDCS-HAPLWLMYLAIVLSHTNSVVNPF 286 |
| SEQ ID NO:6 | AA2BR_human | 239 | IVGIFALCWLPVHAVNCVTLFQPAQGKNKPKWAMNMAILLSHANSVVNPI 288 |
| SEQ ID NO:7 | AA3R_human | 235 | VLFLFALSWLPLSIINCIIYFNG----EVPQLVLYMGILLSHANSMMNPI 280 |
| SEQ ID NO:8 | AA1R_human | 239 | ILFLFALSWLPLHILNCITLFCPSC--HKPSILTYIAIFLTHGNSAMNPI 286 |

| | | | |
|---|---|---|---|
| SEQ ID NO:5 | AA2AR_human | 287 | IYAYRIREFRQTFRKIIRSHVLRQQEPFKAAGTSARVLAAHGSDGEQVSL 336 |
| SEQ ID NO:6 | AA2BR_human | 289 | VYAYRNRDFRYTFHKIISRYLLCQ---------ADVKSGNGQAGVQPAL 328 |
| SEQ ID NO:7 | AA3R_human | 281 | VYAYKIKKFKETYLLILKACVVCHP---------SDSLDTSIEKNSE 318 |
| SEQ ID NO:8 | AA1R_human | 287 | VYAFRIQKFRVTFLKIWNDHFRCQP---------APPIDEDLPEERPDD 326 |

| | | | |
|---|---|---|---|
| SEQ ID NO:5 | AA2AR_human | 337 | RLNGHPPGVWANGSAPHPERRPNGYALGLVSGGSAQESQGNTGLPDVELL 386 |
| SEQ ID NO:6 | AA2BR_human | 329 | GVGL 332 |
| SEQ ID NO:7 | AA3R_human | 319 | 318 |
| SEQ ID NO:8 | AA1R_human | 327 | 326 |

| | | | |
|---|---|---|---|
| SEQ ID NO:5 | AA2AR_human | 387 | SHELKGVCPEPPGLDDPLAQDGAGVS 412 |
| SEQ ID NO:6 | AA2BR_human | 333 | 332 |
| SEQ ID NO:7 | AA3R_human | 319 | 318 |
| SEQ ID NO:8 | AA1R_human | 327 | 326 |

A    Mutations determined by agonist binding
B    Mutations determined by antagonist binding
      Position of transmembrane domains
      Position of helix 8

FIG. 10B

Alignment of neurotensin receptors

```
SEQ ID NO:9  NTR1_rat     1 MHLNSSVPQGTPGEPDAQPFSGPQSEMEATFLALSLSNGSGNTSESDTAG  50
SEQ ID NO:10 NTR1_human   1 MRLNSSAP-GTPGTPAADPFQRAQAGLEEALLAPGFGNASGNASERVLAA  49
SEQ ID NO:11 NTR2_human   1   METSSP--RPPRPSSNPG-----------------------------LS  18
                             . .* *    *  *..*

SEQ ID NO:9  NTR1_rat    51 PNSDLDVNTDIYSKVLVTAIYLSLFVVGTVGNSVTAFTLARKKSLQSLQS 100
SEQ ID NO:10 NTR1_human  50 PSSELDVNTDIYSKVLVTAVYLALFVVGTVGNTVTAFTLARKKSLQSLQS  99
SEQ ID NO:11 NTR2_human  19 LDARLGVDTRLWAKVLFTALYALIWALGAAGNALSVHVVLKAR--AGRAG  66
                             . * * *  *   **/**/**/**/*/**/.

SEQ ID NO:9  NTR1_rat   101 TVHYHLGSLALSDLLILLLAMPVELYNFIWVHHPWAFGDAGCRGYYFLRD 150
SEQ ID NO:10 NTR1_human 100 TVHYHLGSLALSDLLTLLLAMPVELYNFIWVHHPWAFGDAGCRGYYFLRD 149
SEQ ID NO:11 NTR2_human  67 RLRHHVLSLALAGLLLLLVGVPVELYSFVWFHYPWVFGDLGCRGYYFVHE 116
                             /*/*/*/**/**/**/.* * ** /*/*****/

SEQ ID NO:9  NTR1_rat   151 ACTYATALNVASLSVERYLAICHPFKAKTLMSRSRTKKFISAIWLASALL 200
SEQ ID NO:10 NTR1_human 150 ACTYATALNVASLSVERYLAICHPFKAKTLMSRSRTKKFISAIWLASALL 199
SEQ ID NO:11 NTR2_human 117 LCAYATVLSVAGLSAERCLAVCQPLRARSLLTPRRTRWLVALSWAASLGL 166
                             /*/**/*/**/**/**/.* .*..* ../*/*****/

SEQ ID NO:9  NTR1_rat   201 AIPMLFTMGLQNR--SGDG-THPGGLVCTPIVDTATVKVVIQVNTFMSFL 247
SEQ ID NO:10 NTR1_human 200 AVPMLFTMGEQNR--SADG-QHAGGLVCTPTIHTATVKVVIQVNTFMSFI 246
SEQ ID NO:11 NTR2_human 167 ALPMAVIMGQKHELETADGEPEPASRVCTVLVSRTALQVFIQVNVLVSFV 216
                             /*** **  ..  .**      ***   . . /*/**/**/

SEQ ID NO:9  NTR1_rat   248 FPMLVISILNTVAANKLTVMVHQAAEQ---G-----RVCAVGTHNGLEHS 289
SEQ ID NO:10 NTR1_human 247 FPMVVISVLNTIIANKLTVMVRQAAEQ---G-----QVCTVGG-----EHS 284
SEQ ID NO:11 NTR2_human 217 LPLALTAFLNGVTVSHLLALCSQVPSTSTPGSSTPSRLELLSEEGLLSFI 266
                             /*/***/*/    . *     *      .. .
```

FIG. 11A

```
SEQ ID NO:9  NTR1_rat    290 TFNM IE------------PGRVQALRH V VLRAVVIAFVVCWLPYHVR 327
SEQ ID NO:10 NTR1_human  285 TFSMAIE------------PGRVQALRHGVRVLRAVVIAFVVCWLPYHVR 322
SEQ ID NO:11 NTR2_human  267 VWKKTFIQGGQVSLVRHKDVRRIRSLQRSVQVLRAIVVMYVICWLPYHAR 316

SEQ ID NO:9  NTR1_rat    328 RLMFCYISDEQWTT LFDFYHYFYMLTNAL YVS AINPILY LVSANFR 377
SEQ ID NO:10 NTR1_human  323 RLMFCYISDEQWTPFLYDFYHYFYMVTNALFYVSSTINPILYNLVSANFR 372
SEQ ID NO:11 NTR2_human  317 RLMYCYVPDDAWTDPLYNFYHYFYMVTNTLFYVSSAVTPLLYNAVSSSFR 366

SEQ ID NO:9  NTR1_rat    378 QVFLSTL CLC WRHR KKRPTFSRKPNSMSSNHAFSTSATRETLY 424
SEQ ID NO:10 NTR1_human  373 HIFLATLACLCPVWRRRRK-RPAFSRKADSVSSNHTLSSNATRETLY 418
SEQ ID NO:11 NTR2_human  367 KLFLEAVSSLC-GEHHPMKRLPPKPQSPTLMDTASGFGD--PPETR  409
```

A   Mutations determined by heating in the absence of neurotensin
B   Mutations determined by heating in the presence of neurotensin
€   Mutations that significantly improve expression levels in E. coli
▨   Position of transmembrane domains
▧   Position of helix 8

(a) H103: Thermostability obtained with A, N, S, V, L, M
     Only H103N and H103S gave wt levels of expression

| SEQ ID NO:3 | adrB2_human | 237 | ---GRFH--------------------------VQNLSQVEQ | 25 |
| SEQ ID NO:9 | NTR1_rat | 274 | GRVCTVNGTHNGLEHSTFNMTIEPG | 29 |
| SEQ ID NO:12 | muscM1_human | 234 | GGSSSSERSQPGAEGSPETPPGRCCRCCRAPRL | 26 |
| SEQ ID NO:1 | adrB1_melga | 245 | ---GRFYGSQEQP-------------QPPIPQHQP | 26 |
| SEQ ID NO:5 | ADORA2A | 215 | ------------------------- | 21 |

| SEQ ID NO:3 | adrB2_human | 250 | LQAYS---------------------------- | 25 |
| SEQ ID NO:9 | NTR1_rat | 293 | --------------------------------- | 29 |
| SEQ ID NO:12 | muscM1_human | 269 | KEEEEED--EGSMESLTSSEGEE--PG---NEVV | 30 |
| SEQ ID NO:1 | adrB1_melga | 265 | --------------------------------- | 26 |
| SEQ ID NO:5 | ADORA2A | 215 | --------------------------------- | 21 |

| SEQ ID NO:3 | adrB2_human | 250 | --------------------------------- | 25 |
| SEQ ID NO:9 | NTR1_rat | 298 | --------------------------------- | 29 |
| SEQ ID NO:12 | muscM1_human | 302 | TKMP--MVDPEAQAPTKQPP-------------FSSPNTVKRPTKK | 33 |
| SEQ ID NO:1 | adrB1_melga | 265 | --------------------------------- | 26 |
| SEQ ID NO:5 | ADORA2A | 215 | --------------------------------- | 21 |

| SEQ ID NO:3 | adrB2_human | 250 | ------DGRTGHGLRRSSKFCLKEHKALKTLGIIM | 27 |
| SEQ ID NO:9 | NTR1_rat | 298 | ------RVQALRHGVLVLRAVV | 31 |
| SEQ ID NO:12 | muscM1_human | 332 | GRDRAGKGQKPRGKEQLAKRKTFSLVKEKKAARTLSAIL | 37 |
| SEQ ID NO:1 | adrB1_melga | 265 | ILGNSRASK---RKTSRVMAMREHKALKTLGIIM | 29 |
| SEQ ID NO:5 | ADORA2A | 215 | LPGERARSTLQKEVHAAKSLAIIV | 23 |

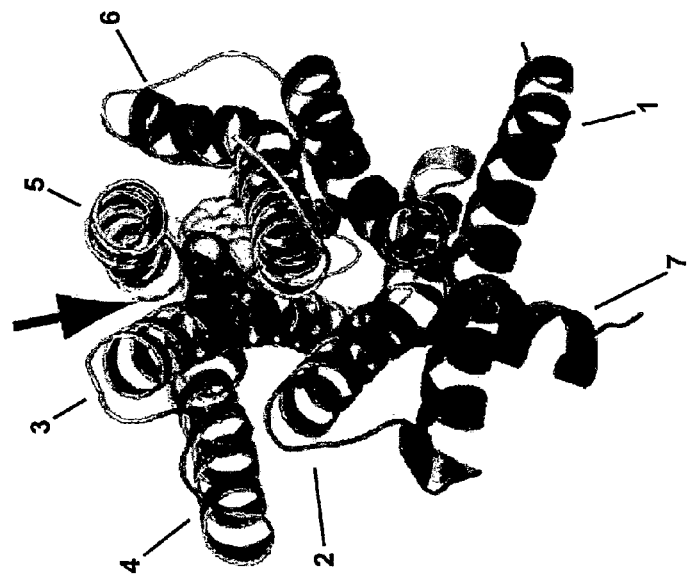
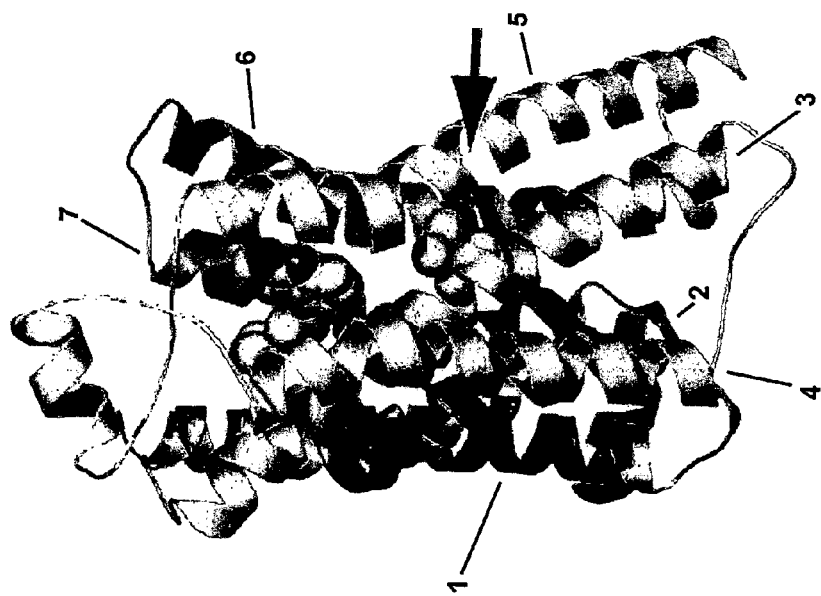
FIG. 21

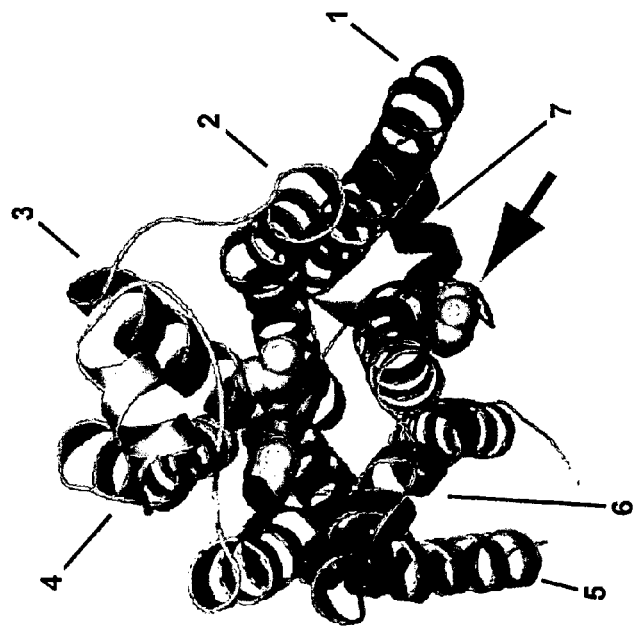
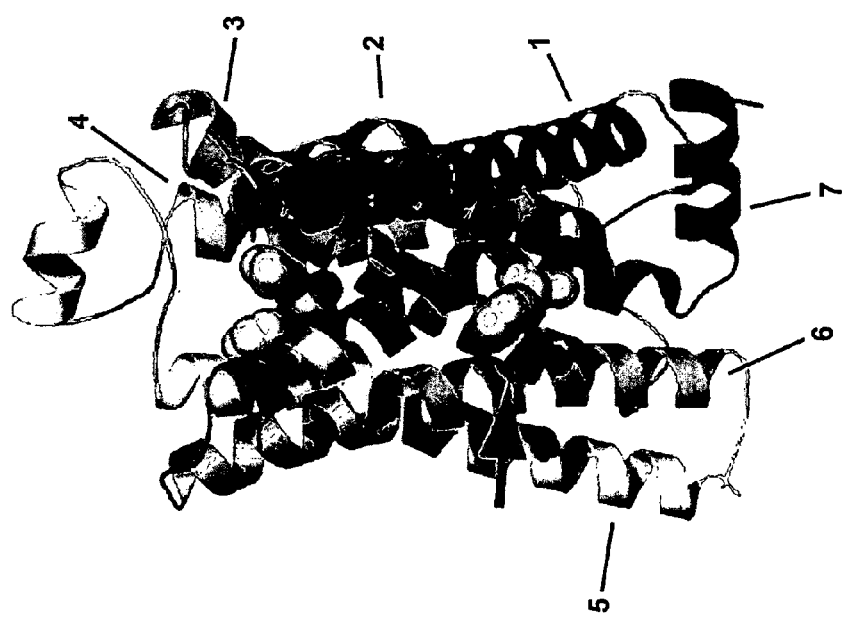
FIG. 22

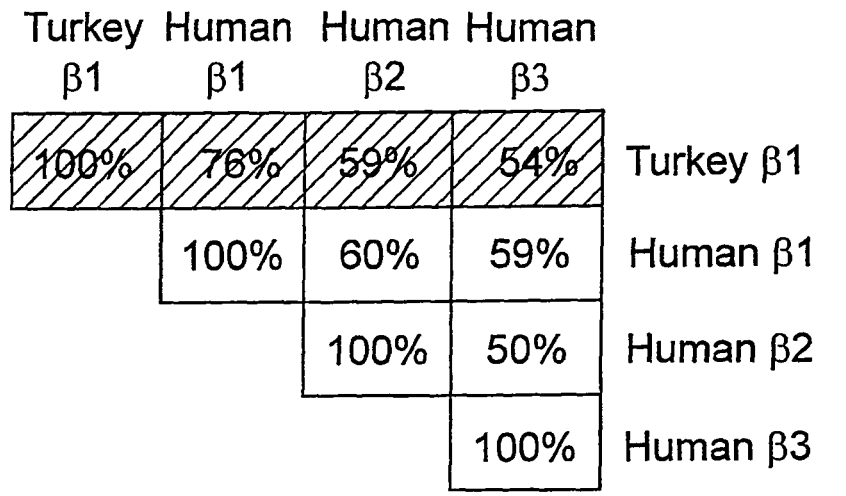
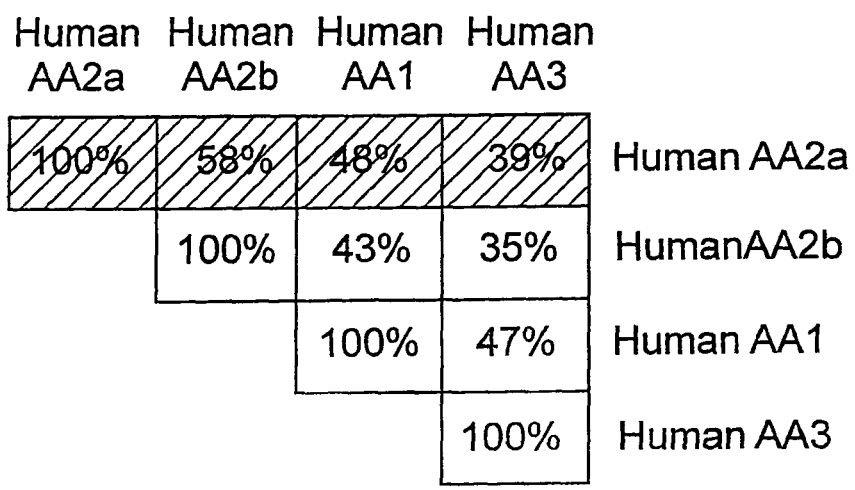
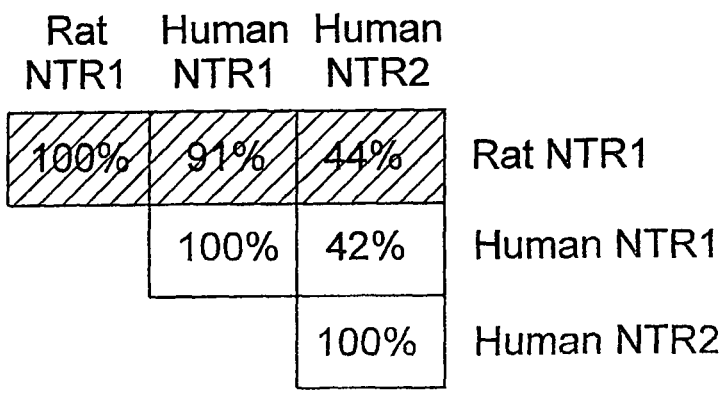
FIG. 27

Alignment of neurotensin receptors

| | | | |
|---|---|---|---|
| SEQ ID NO:9 | NTR1_rat | 1 MHLNSSVPQGTPGEPDAQPFSGPQSEMEATFLALSLSNGSGNTSESDTAG | 50 |
| SEQ ID NO:10 | NTR1_human | 1 MRLNSSAP-GTPGTPAADPFQRAQAGLEEALLAPGFGNASGNASERVLAA | 49 |
| SEQ ID NO:11 | NTR2_human | 1 METSSP--RPPRPSSNPG-------------------------------LS | 18 |

| | | | |
|---|---|---|---|
| SEQ ID NO:9 | NTR1_rat | 51 PNSDLDVNTDIYSKVLVTAIYLALFVVGTVGNSVTAFTLARKKSLQSLQS | 100 |
| SEQ ID NO:10 | NTR1_human | 50 PSSELDVNTDIYSKVLVTAVYLALFVVGTVGNTVTAFTLARKKSLQSLQS | 99 |
| SEQ ID NO:11 | NTR2_human | 19 LDARLGVDTRLWAKVLFTALYALIWALGAAGNALSVHVVLKAR--AGRAG | 66 |

| | | | |
|---|---|---|---|
| SEQ ID NO:9 | NTR1_rat | 101 TVYYHLGSLAESDLLLLLLAMPVELYNFIWVHHPWAFGDAGCRGYYFLRD | 150 |
| SEQ ID NO:10 | NTR1_human | 100 TVHYHLGSIALSDLLTLLLAMPVELYNFIWVHHPWAFGDAGCRGYYFLRD | 149 |
| SEQ ID NO:11 | NTR2_human | 67 RLRHHVLSLALAGLLLLLLGVPVELYSFVWFHYPWVFGDLGCRGYYFVHE | 116 |

| | | | |
|---|---|---|---|
| SEQ ID NO:9 | NTR1_rat | 151 ACTYATALNVASLSVERYLAICHPFKAKTLMSRSRTKKFISAIWLASALL | 200 |
| SEQ ID NO:10 | NTR1_human | 150 ACTYATALNVASLSVERYLAICHPFKAKTLMSRSRTKKFISAIWLASALL | 199 |
| SEQ ID NO:11 | NTR2_human | 117 LCAYATVLSVAGLSAERCLAVCQPIRARSLLTPRRTRWLVALSWAASLGL | 166 |

| | | | |
|---|---|---|---|
| SEQ ID NO:9 | NTR1_rat | 201 AIPMFFMGLQNR--SGDG-THPGGLVCTPIVDTATVKVVIQVNTFMSFL | 247 |
| SEQ ID NO:10 | NTR1_human | 200 AVPMLFTMGEQNR--SADG-QHAGGIVCTPTIHTATVKVVIQVNTFMSFI | 246 |
| SEQ ID NO:11 | NTR2_human | 167 ALPMAVIMGQKHELETADGEPEPASRVCTVLVSRTALQVFIQVNVLVSFV | 216 |

FIG. 28A

```
SEQ ID NO:9   NTR1_RAT      MHLNSSVPQGTPGEPDAQPFSGPQSEMEATFLALSLSNGSGNTSESD-TAGPNSDLDVNT
SEQ ID NO:1   ADRB1_MELGA   ----------MGDGWLPPDCGPHNR----------SGGGGATAAPTGSRQVSAELLSQQ
SEQ ID NO:5   AA2AR_HUMAN   --------------------------------------------------MPIMGSS

SEQ ID NO:9   NTR1_RAT      DIYSKVLVTAIYLALFVVGTV-GNSVTAFTLARKKSLQSLQSTVHYHLGSLALSDLLILL
SEQ ID NO:1   ADRB1_MELGA   ---WE-AGMSLLMALVVLLIVAGNVLVIAAIGRTQRLQTL---TNLFITSLACADLVMGL
SEQ ID NO:5   AA2AR_HUMAN   ------VYITVELAIAVLAIL-GNVLVCWAVWLNSNLQNV---TNYFVVSLAAADIAVGV

SEQ ID NO:9   NTR1_RAT      LAMPVELYNFIWVHHPWAFGDAGCRGYYFLRDACTYATALNVASLSVERYLAICHPFKAK
SEQ ID NO:1   ADRB1_MELGA   LVVPFGATLV--VRGTWLWGSFLCECWTSLDVLCVTASIETLCVIAIDRYLAITSPFRYQ
SEQ ID NO:5   AA2AR_HUMAN   LAIPFAIT----ISTGFCAACHGCLFIACFVLVLTQSSIFSLLAIAIDRYIAIRIPLRYN

SEQ ID NO:9   NTR1_RAT      TLMSRSRTKKFISAIWLASALLA-IP-MLFTMGLQNRS-----GDGTHPGGLVCTPIVDT
SEQ ID NO:1   ADRB1_MELGA   SLMTRARAKVIICTVWAISALVSFLPIMMHWWRDEDPQ-----ALKCYQDPGCC----DF
SEQ ID NO:5   AA2AR_HUMAN   GLVTGTRAKGIIAICWVLSFAIG-LTPMLGWNNCGQPKEGKNHSQGCGEGQVACLF-EDV

SEQ ID NO:9   NTR1_RAT      ATVKVVIQVNTFMSFLFPMLVISILNTVIANKLTVMVHQAAE-QGRVC-TVG--------
SEQ ID NO:1   ADRB1_MELGA   VTNRAYAIASSIISFYIPILIMIFVYLRVYREAKEQIRKIDRCEGRFYGSQEQPQPPPLP
SEQ ID NO:5   AA2AR_HUMAN   VPMNYMVYFNFFACVLVPLLLMLGVYLRIFLAARRQLKQM--------------------

SEQ ID NO:9   NTR1_RAT      THNGLEHST---FNMTIEPGRVQALRHGVLVLRAVVIAFVVCWLPYHVRRLMFCYISDEQ
SEQ ID NO:1   ADRB1_MELGA   QHQPILGNGRASKRKTSRV-MAMREHKALKTLGIIMGVFTLCWLPFFLVNIVNVFNRDL-
SEQ ID NO:5   AA2AR_HUMAN   ESQPLPGER---ARSTLQ-----KEVHAAKSLAIIVGLFALCWLPLHIINCFTFFCPDCS

SEQ ID NO:9   NTR1_RAT      WTTTFLFDFYHYFYMLTNALEYVSSAINPILYNLVSANFRQVELSTLAC-LCPGWRHRRKK
SEQ ID NO:1   ADRB1_MELGA   -------VPDWLFVFFNWLGYANSAFNPIIYC-RSPDFRKAFKRLLCFPRKADRRLHAGG
SEQ ID NO:5   AA2AR_HUMAN   ------HAPLWLMYLAIVLSHTNSVVNPFIYAYRIREFRQTFRKII---RSHVLRQQEPF

SEQ ID NO:9   NTR1_RAT      RPTFSRKPNSMSSNHAFSTSATRETLY---------------------------------
SEQ ID NO:1   ADRB1_MELGA   QP--APLPGGFISTLGSPEHSPGGTWSDCNGGTRGGSESSLEERHSKTSRSESKMEREKN
SEQ ID NO:5   AA2AR_HUMAN   KA--AGTSARVLAAHGSDGEQVSLRLNGHPPGV--WANGSAP--HPERRPNGYALGLVSG

SEQ ID NO:9   NTR1_RAT      ------------------------------------------------------------
SEQ ID NO:1   ADRB1_MELGA   ILATTRFYCTFLGNGDKAVFCTVLRIVKLFE-DATCTCPHTHKLKMKW-RFKQHQA
SEQ ID NO:5   AA2AR_HUMAN   GSAQESQ-----GN-------TGLPDVELLSHELKGVCPEPPGLDDPLAQDGAGVS
```

Key :  A  — mutant co-occurrence between aligned sequences
       A  — mutant co-occurrence with i->i+4 window
       A  — mutant without co-occurrence

FIG. 33

| | | |
|---|---|---|
| SEQ ID NO:9 | 1 | MHLNSSVPQGTPGEPDAQPFSGPQSEMEATFLALSLSNGSGNTSESDTAG··PNSDL·D |
| SEQ ID NO:1 | 2 | ················MGDGWLPPDCGPHNR·········SGG·GGATAAPTGS··RQVSA·E |
| SEQ ID NO:5 | 3 | |
| SEQ ID NO:12 | 4 | ························································MNTSAPPAVS··PNITVLA |
| SEQ ID NO:3 | 5 | ········MGQP····················GNG·SAFLLAPNRSHAPDHDVTQ |
| SEQ ID NO:17 | 6 | ········MNGTEGPNFYVPF···········SNA··TGVVRSPFEY··PQYYL· |

| | | |
|---|---|---|
| SEQ ID NO:9 | 1 | VNTDIYSKVLVTAIYLALFVVGTVGNSVTAFTLARKKSLQSLQSTVHYHLGSLALSDLL |
| SEQ ID NO:1 | 2 | LLSQQWEAGM·SLLMALVVLLIVAGNVLVIAAIGRTQRLQTL···TNLFITSLACADLV |
| SEQ ID NO:5 | 3 | ·MPIMGSSVYITVELAIAVLAILGNVLVCWAVWLNSNLQNV···TNYFVVSLAAADIA |
| SEQ ID NO:12 | 4 | PGKGPWQVAFIGITTGLLSLATVTGNLLVLISFKVNTELKTV···NNYFLLSLACADLI |
| SEQ ID NO:3 | 5 | QRDEVWVVGM··GIVMSLIVLAIVFGNVLVITAIAKFERLQTV···TNYFITSLACADLV |
| SEQ ID NO:17 | 6 | ·AEPWQFSMLAAYMFLLIVLGFPINFLTLYVTVQHKKLRTP···LNYILLNLAVADLF |

| | | |
|---|---|---|
| SEQ ID NO:9 | 1 | ILLLAMPVELYNFIWVHHPWAFGDAGCRGYYFLRDACTYATALNVASLSVERYLAICHP |
| SEQ ID NO:1 | 2 | MGLLVVPFGATLVVRG···TWLWGSFLCECWTSLDVLCVTASIETLCVIAIDRYLATSP |
| SEQ ID NO:5 | 3 | VGVLAIPFAIT··ISTG··FCA·ACHGCLFIACFVLVLTQSSIFSLLAIAIDRYIAIRIP |
| SEQ ID NO:12 | 4 | IGTFSMNLYTTYLLMG···HWALGTLACDLWLALDYVASNASVMNLLLISFDRYFSVTRP |
| SEQ ID NO:3 | 5 | MGLAVVPFGAAHILMK···MWTFGNFWCEFWTSIDVLCVTASIETLCVIAVDRYFAITSP |
| SEQ ID NO:17 | 6 | MVLGGFTSTLYTSLHG···YFVFGPTGCNLEGFFATLGGEIALWSLVVLAIERYVVVCKP |

| | | |
|---|---|---|
| SEQ ID NO:9 | 1 | FKAKTLMSRSRTKKFISAIWLASALL··AIPML··FTMGLQNRSGD·······GTHPGGLVCT |
| SEQ ID NO:1 | 2 | FRYQSLMTRARAKVIICTVWAISALVSFLPIMMHWWRDEDPQALK·······CYQDPGCCD |
| SEQ ID NO:5 | 3 | LRYNGLVTGTRAKGIIAICWVLSFAI··GLTPMLGWNNCGQPKEGKNHSQGCGEGQVACL |
| SEQ ID NO:12 | 4 | LSYRAKRTPRRAALMICLAWLVSFVL··WAPAILFWQLVGERTVL········AGQ···CY |
| SEQ ID NO:3 | 5 | FKYQSLLTKNKARVIILMVWIVSGLTSFLPIQMHWYRATHQEAIN········CYANETCCD |
| SEQ ID NO:17 | 6 | MS·NFRFGENHAIMGVAFTWVMALAC··AAPPLAGWSRYI·PEGLQ·······CS····CG |

| | | |
|---|---|---|
| SEQ ID NO:9 | 1 | PIV····DTATVKVVIQVNTFMSFLFPMLVISILNTVIANKLTVMVHQAAE·QGRVC·· |
| SEQ ID NO:1 | 2 | F·······VTNRAYAIASSIISFYIPLLIMIFVYLRVYREAKEQIRKIDRCEGRFY |
| SEQ ID NO:5 | 3 | FE·····DVVPMNYMVYFNFFACVLVPLLLMLGVYLRIFLAARRQLKQM····· |
| SEQ ID NO:12 | 4 | IQF·····LSQPIITFGTAMAAFYLPVTVMCTLYWRIYRETENRARELAALQGSETPG |
| SEQ ID NO:3 | 5 | F······FTNQAYAIASSIVSFYVPLVIMVFVYSRVFQEAKRQLQKIDKSEGRFH·· |
| SEQ ID NO:17 | 6 | IDYYTLKPEVNNESFVIYMFVVHFTIPMIIIFFCYGQLVFTVKEAAAQ·· |

| | | |
|---|---|---|
| SEQ ID NO:9 | 1 | ······················TVG·················THNGLEHST······· |
| SEQ ID NO:1 | 2 | ················GSQEQPQPPP·······LP·········QHQPILGNG |
| SEQ ID NO:5 | 3 | ················································ESQPLPGER |
| SEQ ID NO:12 | 4 | KGGGSSSSERSQPGAEGSPETPPGRCCRCCRAPRLLQAYSWKEEEEEDEGSMESLTSS |
| SEQ ID NO:3 | 5 | ················VQNLSQV··············EQDGRTGHG |
| SEQ ID NO:17 | 6 | ············································QQESAT······· |

| | | |
|---|---|---|
| SEQ ID NO:9 | 1 | ························FNMTIEP····G······· |
| SEQ ID NO:1 | 2 | ·····················RAS····KRKTSRV··· |
| SEQ ID NO:5 | 3 | ·····················ARSTLQ |
| SEQ ID NO:12 | 4 | EGEEPGSEVVIKMPMVDPEAQAPTKQPPRSSPNTVKRPTKKGRDRAGKGQKPRGKEQLA |
| SEQ ID NO:3 | 5 | ····················LRRSSK········ |
| SEQ ID NO:17 | 6 | ····················TQK·········· |

FIG. 34A

| | | |
|---|---|---|
| SEQ ID NO:9 | 1 | ····RVQALRHGVLVLRAVVIAFVVCWLPYHVRRLMFCYISDEQWTTFLFDFYHYFYM |
| SEQ ID NO:1 | 2 | ····MAMREHKALKTLGIIMGVFTLCWLPFFLVNIVNVFNRDL········VPDWLFV |
| SEQ ID NO:5 | 3 | ······KEVHAAKSLAIIVGLFALCWLPLHIINCFTFFCPDCS·······HAPLWLMY |
| SEQ ID NO:12 | 4 | KRKTFSLVKEKKAARTLSAILLAFILTWTPYNIMVLVSTFCKDC·······VPETLWE |
| SEQ ID NO:3 | 5 | ······FCLKEHKALKTLGIIMGTFTLCWLPFFIVNIVHVIQDNL······IRKEVYI |
| SEQ ID NO:17 | 6 | ····AEKEVTRMVIIMVIAFLICWVPYASV·AFYIFTHQGS········NFGPIFMT |

| | | |
|---|---|---|
| SEQ ID NO:9 | 1 | LTNALFYVSSAINPILYNLVSANFRQVFLSTLACLCPGWRHRRKKRPTFSRKPNS·MSS |
| SEQ ID NO:1 | 2 | FFNWLGYANSAFNPIIYC·RSPDFRKAFKRLLCF···PRKADRRLHAGGQPAPLPGGFIS |
| SEQ ID NO:5 | 3 | LAIVLSHTNSVVNPFIYAYRIREFRQTFRKII·····RSHVLRQQEPFKAAGTSARVLA |
| SEQ ID NO:12 | 4 | LGYWLCYVNSTINPMCYALCNKAFRDTFRLLLC····RWDKRRWRKIPKRPGSVHRTPS |
| SEQ ID NO:3 | 5 | LLNWIGYVNSGFNPLIYC·RSPDFRIAFQELLCL···RRSSLKAYGNGYSSNGNTGEQS |
| SEQ ID NO:17 | 6 | IPAFFAKSAAIYNPVIYIMMNKQFRNCMLTTICC···GKNPL···GDDEASATVSKTET |

| | | |
|---|---|---|
| SEQ ID NO:9 | 1 | NHAFSTSATRETLY |
| SEQ ID NO:1 | 2 | TLGSPEHSPGGTWSDCNGGTRGGSESSLEERHSKTSRSESKMEREKNILATTRFYCTFL |
| SEQ ID NO:5 | 3 | AHGSDGEQVSLRLNGHPPGV·WANGSAP··HPERRPNGYALGLVSGGSAQESQ···· |
| SEQ ID NO:12 | 4 | RQC |
| SEQ ID NO:3 | 5 | GYHVEQEKENKLLCEDLPGT····EDFVG··HQGTVPSDNIDSQGRNCSTNDSLL |
| SEQ ID NO:17 | 6 | SQVAPA |

| | | |
|---|---|---|
| SEQ ID NO:9 | 1 | |
| SEQ ID NO:1 | 2 | GNGDKAVFCTVLRIVKLFE·DATCTCPHTHKLKMKW·RFKQHQA |
| SEQ ID NO:5 | 3 | GN·····TGLPDVELLSHELKGVCPEPPGLDDPLAQDGAGVS |
| SEQ ID NO:12 | 4 | |
| SEQ ID NO:3 | 5 | |
| SEQ ID NO:17 | 6 | |

Key:
1: NTR Rat
2: B1 Melga
3: A2AA Human
4: M1 Human
5: B2 Human
6: Rhodopsin

FIG. 34B

MUTANT PROTEINS AND METHODS FOR PRODUCING THEM

RELATED APPLICATIONS

This application is a national stage filing under 35 U.S.C. §371 of international application PCT/GB2008/004032, filed Dec. 8, 2008, which was published under PCT Article 21(2) in English, the disclosure of which is incorporated in its entirety herein by reference. This application claims the benefit under §119(a)-(d) of United Kingdom Application No. 0724051.8, filed Dec. 8, 2007, the entire disclosure of which is incorporated herein by reference.

BACKGROUND OF THE INVENTION

The present invention relates to mutant G protein coupled receptors (GPCRs) and methods for selecting those with increased stability. In particular, it relates to the selection and preparation of mutant GPCRs which have increased stability under a particular condition compared to their respective parent proteins. Such proteins are more likely to be crystallisable, and hence amenable to structure determination, than the parent proteins. They are also useful for drug discovery and development studies.

BRIEF SUMMARY OF THE INVENTION

Over the past 20 years the rate of determination of membrane protein structures has gradually increased, but most success has been in crystallising membrane proteins from bacteria rather than from eukaryotes [1]. Bacterial membrane proteins have been easier to overexpress using standard techniques in *Escherichia coli* than eukaryotic membrane proteins [2,3] and the bacterial proteins are sometimes far more stable in detergent, detergent-stability being an essential prerequisite to purification and crystallisation. Genome sequencing projects have also allowed the cloning and expression of many homologues of a specific transporter or ion channel, which also greatly improves the chances of success during crystallisation. However, out of the 120 different membrane protein structures that have been solved to date, there are only seven structures of mammalian integral membrane proteins (blanco.biomol.uci.edu/); five of these membrane proteins were purified from natural sources and are stable in detergent solutions. Apart from the difficulties in overexpressing eukaryotic membrane proteins, they often have poor stability in detergent solutions, which severely restricts the range of crystallisation conditions that can be explored without their immediate denaturation or precipitation. Ideally, membrane proteins should be stable for many days in any given detergent solution, but the detergents that are best suited to growing diffraction-quality crystals tend to be the most destabilising detergents ie those with short aliphatic chains and small or charged head groups. It is also the structures of human membrane proteins that we would like to solve, because these are required to help the development of therapeutic agents by the pharmaceutical industry; often there are substantial differences in the pharmacology of receptors, channels and transporters from different mammals, whilst yeast and bacterial genomes may not include any homologous proteins. There is thus an overwhelming need to develop a generic strategy that will allow the production of detergent-stable eukaryotic integral membrane proteins for crystallisation and structure determination and potentially for other purposes such as drug screening, bioassay and biosensor applications.

Membrane proteins have evolved to be sufficiently stable in the membrane to ensure cell viability, but they have not evolved to be stable in detergent solution, suggesting that membrane proteins could be artificially evolved and detergent-stable mutants isolated [4]. This was subsequently demonstrated for two bacterial proteins, diacylglycerol kinase (DGK) [5,6] and bacteriorhodopsin [7]. Random mutagenesis of DGK identified specific point mutations that increased thermostability and, when combined, the effect was additive so that the optimally stable mutant had a half-life of 35 minutes at 80° C. compared with a half-life of 6 minutes at 55° C. for the native protein [6]. It was shown that the trimer of the detergent-resistant DGK mutant had become stable in SDS and it is thus likely that stabilisation of the oligomeric state played a significant role in thermostabilisation. Although the aim of the mutagenesis was to produce a membrane protein suitable for crystallisation, the structure of DGK has yet to be determined and there have been no reports of successful crystallization. A further study on bacteriorhodopsin by cysteine-scanning mutagenesis along helix B demonstrated that it was not possible to predict which amino acid residues would lead to thermostability upon mutation nor, when studied in the context of the structure, was it clear why thermostabilisation had occurred [7].

GPCRs constitute a very large family of proteins that control many physiological processes and are the targets of many effective drugs. Thus, they are of considerable pharmacological importance. A list of GPCRs is given in Foord et al (2005) *Pharmacol Rev.* 57, 279-288, which is incorporated herein by reference. GPCRs are generally unstable when isolated, and despite considerable efforts, it has not been possible to crystallise any except bovine rhodopsin, which naturally is exceptionally stable. GPCRs are druggable targets, and reference is made particularly to Overington et al (2006) *Nature Rev. Drug Discovery* 5, 993-996 which indicates that over a quarter of present drugs have a GPCR as a target.

GPCRs are thought to exist in multiple distinct conformations which are associated with different pharmacological classes of ligand such as agonists and antagonists, and to cycle between these conformations in order to function (Kenakin T. (1997) *Ann N Y Acad Sci* 812, 116-125).

It will be appreciated that the methods of the invention do not include a method as described in D'Antona et al., including binding of [$^3$H]CP55940 to a constitutively inactive mutant human cannabinoid receptor 1 (T210A) in which the Thr residue at position 210 is replaced with an Ala residue.

The listing or discussion of an apparently prior-published document in this specification should not necessarily be taken as an acknowledgement that the document is part of the state of the art or is common general knowledge.

Aspects of the invention relate to methods of producing a mutant GPCR with increased stability relative to its parent GPCR. In some embodiments, the methods comprise (a) identifying in the amino acid sequence of one or more mutants of a first parent GPCR with increased stability relative to the first parent GPCR, the position or positions at which the one or more mutants have at least one different amino acid residue compared to the first parent GPCR, and (b) making one or more mutations in the amino acid sequence that defines a second GPCR at the corresponding position or positions, to provide one or more mutants of a second parent GPCR with increased stability relative to the second parent GPCR.

Further aspects of the invention relate to methods for producing a mutant GPCR with increased stability relative to its parent GPCR that comprise (a) identifying in the amino acid sequence of one or more mutants of a first parent GPCR with increased stability relative to the first parent GPCR, the position or positions at which the one of more mutants have at least one different amino acid residue compared to the first parent GPCR, and (b) making one or more mutations in the amino acid sequence that defines a second GPCR within a window or windows of plus or minus 5 residues where i is the corresponding position or positions, to provide one or more mutants of a second parent GPCR with increased stability relative to the second parent GPCR.

Further aspects of the invention relate to methods for producing a mutant GPCR with increased stability relative to a parent GPCR that comprise (a) identifying in the amino acid sequence of one or more mutants of a first parent GPCR with increased stability relative to the first parent GPCR, the position or positions at which the one or more mutants have at least one different amino acid residue compared to the first parent GPCR, and (b) making one or more mutations in the amino acid sequence that defines a second GPCR within a distance of 12 Å from the C atom of, or within a distance of 8 Å from any atom of, the amino acid residue i, where i is the corresponding position or positions, to provide one or more mutants of a second parent GPCR with increased stability relative to the second parent GPCR.

Further aspects of the invention relate to methods for producing a mutant GPCR with increased stability relative to a parent GPCR that comprise (a) providing one or more mutants of a first parent GPCR with increased stability relative to the first parent GPCR, (b) identifying in a structural membrane protein model the structural motif or motifs in which the one or more mutants have at least one different amino acid residue compared to the first parent GPCR, and (c) making one or more mutations in the amino acid sequence that defines a corresponding structural motif or motifs in a second parent GPCR, to provide one or more mutants of a second parent GPCR with increased stability relative to the second parent GPCR.

In some embodiments of the methods, the one or more mutants of the first parent GPCR in step (a) are obtainable by a method comprising: (i) providing one or more mutants of a first parent GPCR, (ii) selecting a ligand, the ligand being one which binds to the parent GPCR when the GPCR is residing in a particular conformation, (iii) determining whether the or each mutant GPCR when residing in a particular conformation has increased stability with respect to binding the selected ligand compared to the stability of the first parent GPCR when residing in the same particular conformation with respect to binding that ligand, and (iv) selecting those mutants that have an increased stability compared to the first parent GPCR with respect to binding the selected ligand. In certain embodiments, the particular conformation in which the GPCR resides in step (iii) corresponds to the class of ligand selected in step (ii). In certain embodiments, the selected ligand is from the agonist class of ligands and the particular conformation is an agonist conformation, or the selected ligand is from the antagonist class of ligands and the particular conformation is an antagonist conformation. In certain embodiments, the selected ligand is from the agonist class of ligands and the particular conformation in which the GPCR resides in step (iii) is the agonist conformation. In certain embodiments, the binding affinity of the one or more mutants of the first GPCR is substantially the same or greater than the binding affinity of the parent for the selected ligand. In certain embodiments, steps (i)-(iv) are repeated for one or more rounds, with the selected mutants of the first GPCR having increased stability in step (iv) representing the parent GPCR in a subsequent round of the method. In certain embodiments, the ligand is any one of a full agonist, a partial agonist, an inverse agonist, an antagonist. In certain embodiments, the ligand is a polypeptide which binds to the GPCR. In certain embodiments, the polypeptide is any of an antibody, an ankyrin, a G protein, an RGS protein, an arrestin, a GPCR kinase, a receptor tyrosine kinase, a RAMP, a NSF, a GPCR, an NMDA receptor subunit NR1 or NR2a, or calcyon, or a fragment or derivative thereof that binds to the GPCR. In certain embodiments, in step (ii) two or more ligands are selected, the presence of each causes the GPCR to reside in the same particular conformation. In certain embodiments, a mutant GPCR in step (iv) is selected which has reduced ability to bind a ligand of a different class to the ligand selected in step (ii) compared to its parent. In certain embodiments, it is determined whether the mutant GPCR selected in step (iv) is able to couple to a G protein. In certain embodiments, it is determined whether the mutant GPCR selected in step (iv) is able to bind a plurality of ligands of the same class as the selecting ligand with a comparable spread and/or rank order of affinity as the parent GPCR.

In some embodiments of the methods, the one or more mutants of the first parent GPCR in step (a) are obtainable by a method comprising: (I) selecting one or mutants that have increased stability relative to a parent GPCR (e.g., according to steps (i) to (iv) referred to above), (II) identifying the position or positions of the mutated amino acid residues or residues in the mutant GPCR or GPCRs which have been selected for increased stability, and (III) synthesizing one or more mutant GPCRs which contain a replacement amino acid at one or more of the positions identified.

In some embodiments of the methods, the one or more mutants of the first parent GPCR in step (a) contain a plurality of mutations compared to the first parent GPCR. In some embodiments of the methods, the one or more mutants of the first parent GPCR in step (a) have increased stability to any one or more of heat, a detergent, a chaotropic agent and an extreme of pH. In certain embodiments, the one or more mutants have increased thermostability.

In some embodiments of the methods, the first parent GPCR is any one of a β-adrenergic receptor, an adenosine receptor and a neurotensin receptor. In some embodiments of the methods, the mutant GPCR of the first parent GPCR is a mutant β-adrenergic receptor which, when compared to its corresponding parent receptor, has a different amino acid at a position which corresponds to any one or more of the following positions according to the numbering of the turkey β-adrenergic receptor as set out in FIGS. 9A and 9B: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338. In certain embodiments, the mutant β-adrenergic receptor has an amino acid sequence which is at least 20% identical to that of the turkey β-adrenergic receptor (SEQ ID NO: 1) whose sequence is set out in FIGS. 9A and 9B.

In some embodiments of the methods, the mutant GPCR of the first parent GPCR is a mutant adenosine receptor which, when compared to its corresponding parent receptor, has a different amino acid at a position which corresponds to any one or more of the following positions according to the numbering of the human adenosine A2a receptor as set out in FIGS. 10A and 10B (SEQ ID NOS: 5-8): Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315. In certain embodiments, the mutant adenosine receptor has an amino acid sequence which is at least 20% identical to that of the human adenosine $A_{2a}$ receptor whose sequence is set out in FIGS. 10A and 10B (SEQ ID NOS: 5-8).

In some embodiments of the methods, the mutant GPCR of the first parent GPCR is a mutant neurotensin receptor which, when compared to its corresponding parent receptor, has a different amino acid at a position which corresponds to any one or more of the following positions according to the numbering of the rat neurotensin receptor as set out in FIGS. 11A and 11B (SEQ ID NO: 9): Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399. In certain embodiments, the mutant neurotensin receptor has an amino acid sequence which is at least 20% identical to that of the rat neurotensin receptor whose sequence is set out in FIGS. 11A and 11B (SEQ ID NO: 9).

In some embodiments of the methods, the mutant GPCR of the first parent GPCR is a mutant muscarinic receptor which, when compared to the corresponding wild-type muscarinic receptor, has a different amino acid at a position which corresponds to any one or more of the following positions according to the numbering of the human muscarinic receptor as set out in FIGS. 17A-17C (SEQ ID NO: 12): Leu 65, Met 145, Leu 399, Ile 383 and Met 384. In certain embodiments, the mutant muscarinic receptor has an amino acid sequence which is at least 20% identical to that of the rat neurotensin receptor whose sequence is set out in FIGS. 17A-17C (SEQ ID NO: 9). In one embodiment, the structural membrane protein model is of an integral membrane protein. In one embodiment, the integral membrane protein has at least 20% sequence identity with the mutant of the first parent GPCR in step (a) across the protein domain in which the mutant has at least one different amino acid relative to the first parent GPCR. In some embodiments, the integral membrane protein is a GPCR. In certain embodiments, the GPCR is of the same GPCR class or family as the first parent GPCR. In some embodiments, the structural membrane protein model is a model of human β2 adrenergic receptor or bovine rhodopsin.

In some embodiments of the methods, the structural motif is any of a helical interface, a helix kink, a helix opposite a helix kink, a helix surface pointing into the lipid bilayer, a helix surface pointing into the lipid bilayer at the hydrophobic-hydrophilic boundary layer, a loop region or a protein binding pocket.

In some embodiments of the methods, the second parent GPCR is the first parent GPCR. In some embodiments, the second parent GPCR is not the first parent GPCR. In some embodiments, the second parent GPCR is a GPCR which has at least 20% sequence identity with the first parent GPCR. In some embodiments, the second parent GPCR is of the same GPCR class or family as the first parent GPCR.

Further aspects of the invention relate to methods for producing a mutant GPCR with increased stability relative to its parent GPCR that comprise (a) providing one or aligning more than one three-dimensional model of one or more mutants of a GPCR with increased stability relative to a parent GPCR; (b) identifying in the amino acid sequence of the one of more mutants, the position or positions at which the one or more mutants have at least one different amino acid residue compared to the parent GPCR; (c) determining within a set distance d Å from the Cα atom or any atom of an amino acid residue at the position or positions at which the one or more mutants have a different amino acid residue compared to the parent GPCR, the number of other positions from the model or the more than one aligned model at which the one or more mutants have at least one different amino acid residue compared to the parent GPCR; (d) determining whether the number of other positions represents a statistically significant cluster, and if so, making one or more mutations in the amino acid sequence that defines a second GPCR within a distance of d Å from the Cα atom or any atom of the amino acid residue at the corresponding position or positions at which the one or more mutants have at least one different amino acid residue compared to the parent GPCR, to provide one or more mutants of a second parent GPCR with increased stability relative to the second parent GPCR.

Further aspects of the invention relate to methods for producing a mutant GPCR with increased stability relative to its parent GPCR that comprise (a) providing one or aligning more than one three-dimensional model of one or more mutants of a GPCR with increased stability relative to a parent GPCR; (b) identifying in the amino acid sequence of the one of more mutants, the position or positions at which the one or more mutants have at least one different amino acid residue compared to the parent GPCR; (c) determining within a set distance d Å from the Cα atom or any atom of an amino acid residue at the position or positions at which the one or more mutants have a different amino acid residue compared to the parent GPCR, the number of other positions from the model or the more than one aligned model at which the one or more mutants have at least one different amino acid residue compared to the parent GPCR; (d) determining whether the number of other positions represents a statistically significant cluster; (e) determining the centre of two or more statistically significant clusters identified in (d); and (f) making one or more mutations in the amino acid sequence that defines a second GPCR within a distance of x Å from the position that corresponds to the centre of the two or more statistically significant clusters, to provide one or more mutants of a second parent GPCR with increased stability relative to the second parent GPCR.

In some embodiments, the one or more three-dimensional model is a model of any one or more of a mutant GPCR. In some embodiments, at least 2, 3, 4, 5 or 10 models are aligned. In some embodiments, the set distance d Å from the Cα atom is 12 Å or less. In some embodiments, the set distance d Å from any atom is 12 Å or less. In some embodiments, the statistically significant cluster is one that is one that is significant at the 95% level (p<0.05).

In some embodiments, the methods for producing a mutant GPCR with increased stability relative to its parent GPCR further comprise (I) selecting a ligand, the ligand being one which binds to the second parent GPCR when the GPCR is residing in a particular conformation, (II) determining whether the or each mutant of the second parent GPCR when residing in a particular conformation has increased stability with respect to binding the selected ligand compared to the stability of the second parent GPCR when residing in the same particular conformation with respect to binding that ligand, and (III) selecting those mutants that have an increased stability compared to the second parent GPCR with respect to binding the selected ligand. In some embodiments, the particular conformation in which the GPCR resides in step (II) corresponds to the class of ligand selected in step (I). In some embodiments, the selected ligand is from the agonist class of ligands and the particular conformation is an agonist conformation, or the selected ligand is from the antagonist class of ligands and the particular conformation is an antagonist conformation. In some embodiments, the binding affinity of the one or more mutants of the second GPCR is substantially the same or greater than the binding affinity of the second parent GPCR for the selected ligand.

According to further aspects of the invention, a mutant GPCR with increased stability relative to its parent GPCR is provided. In some embodiments, the mutant GPCR is produced by any of the methods disclosed herein. In some embodiments, the mutant GPCR is in a solubilized form. In some embodiments, the mutant GPCR is substantially free of other proteins. In some embodiments, the mutant GPCR is immobilized to a solid support. Accordingly, in some aspects of the invention a solid support is provided, to which is immobilized one or more mutant GPCRs. The mutant GPCRs provided herein are useful, in some embodiments, for crystallization, in drug discovery, in a ligand binding screen or in assay development, or as a biosensor.

In some embodiments, the mutant GPCR has increased stability to any one of heat, a detergent, a chaotropic agent and an extreme of pH. In some embodiments, the mutant GPCR has increased thermostability. In some embodiments, the mutant GPCR has increased thermostability compared to its parent when in the presence of a ligand. In some embodiments, the mutant GPCR is at least 1° C. more stable than its parent. In some embodiments, the mutant GPCR has, compared to its parent receptor, at least one different amino acid at a position which corresponds to any one or more of the following positions: (i) according to the numbering of the turkey β-adrenergic receptor (SEQ ID NO: 1) as set out in FIGS. 9A and 9B: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338, (ii) according to the numbering of the human adenosine A2a receptor as set out in FIGS. 10A and 10B (SEQ ID NOS: 5-8): Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, (iii) according to the numbering of the rat neurotensin receptor as set out in FIGS. 11A and 11B: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399, and (iv) according to the numbering of the muscarinic receptor as set out in FIGS. 17A-17C (SEQ ID NO: 12): Leu 65, Met 145, Leu 399, Ile 383 and Met 384.

In some embodiments, the mutant GPCR is a mutant β-adrenergic receptor. In some embodiments, the mutant β-adrenergic receptor, when compared to the corresponding wild-type adrenergic receptor, has a different amino acid at a position which corresponds to any one or more of the following positions according to the numbering of the turkey β-adrenergic receptor as set out in FIGS. 9A and 9B (SEQ ID NO:1): Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338. In some embodiments, the mutant β-adrenergic receptor has at least one different amino acid residue in a structural motif in which the mutant receptor compared to its parent receptor has a different amino acid at a position which corresponds to any of the following positions according to the numbering of the turkey β-adrenergic receptor as set out in FIGS. 9A and 9B (SEQ ID NO: 1): Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338. In some embodiments, the mutant GPCR is a mutant adenosine receptor.

In some embodiments, the mutant adenosine receptor, when compared to the corresponding wild-type adenosine receptor, has a different amino acid at a position which corresponds to any one or more of the following positions according to the numbering of the human adenosine A2a receptor as set out in FIGS. 10A and 10B (SEQ ID NO: 5-8): Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315. In some embodiments, the mutant adenosine receptor has at least one different amino acid residue in a structural motif in which the mutant receptor compared to its parent receptor has a different amino acid at a position which corresponds to any of the following positions according to the numbering of the human adenosine A2a receptor as set out in FIGS. 10A and 10B (SEQ ID NO: 5-8): Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315.

In some embodiments, the mutant GPCR is a mutant neurotensin receptor. In some embodiments, the neurotensin receptor, when compared to the corresponding wild-type neurotensin receptor, has a different amino acid at a position which corresponds to any one or more of the following positions according to the numbering of the rat neurotensin receptor as set out in FIGS. 11A and 11B (SEQ ID NO: 9): Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399. In some embodiments, the mutant neurotensin receptor has at least one different amino acid residue in a structural motif in which the mutant receptor compared to its parent receptor has a different amino acid at a position which corresponds to any of the following positions according to the numbering of the rat neurotensin receptor as set out in FIGS. 11A and 11B (SEQ ID NO: 9): Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Val 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

In some embodiments, the mutant GPCR is a mutant muscarinic receptor. In some embodiments, the muscarinic receptor, when compared to the corresponding wild-type muscarinic receptor, has a different amino acid at a position which corresponds to any one or more of the following positions according to the numbering of the human muscarinic receptor as set out in FIGS. 17A-17C (SEQ ID NO:12): Leu 65, Met 145, Leu 399, Ile 383 and Met 384. In some embodiments, the mutant muscarinic receptor has at least one different amino acid residue in a structural motif in which the mutant receptor compared to its parent receptor has a different amino acid at a position which corresponds to any of the following positions according to the numbering of the human muscarinic receptor as set out in FIGS. 17A-17C (SEQ ID NO: 12): Leu 65, Met 145, Leu 399, Ile 383 and Met 384.

According to some aspects of the invention polynucleotides encoding the mutant GPCRs are provided. According to some aspects of the invention, host cells comprising the polynucleotides are provided.

BRIEF DESCRIPTION OF THE DRAWINGS

The invention will now be described in more detail with respect to the following FIGs. and Examples wherein:

FIGS. 9A and 9B Alignment of the turkey β-adrenergic receptor with human β1, β2 and β3 receptors (SEQ ID NOS: 1-4).

FIGS. 10A and 10B Alignment of human adenosine receptors (SEQ ID NOS: 5-8).

FIGS. 11A and 11B Alignment of neurotensin receptors (SEQ ID NOS: 9-11).

Exchange of buffer containing the appropriate concentration of DDM and/or lipids was performed during washes and elution from the Ni-NTA beads.

Figure 15:
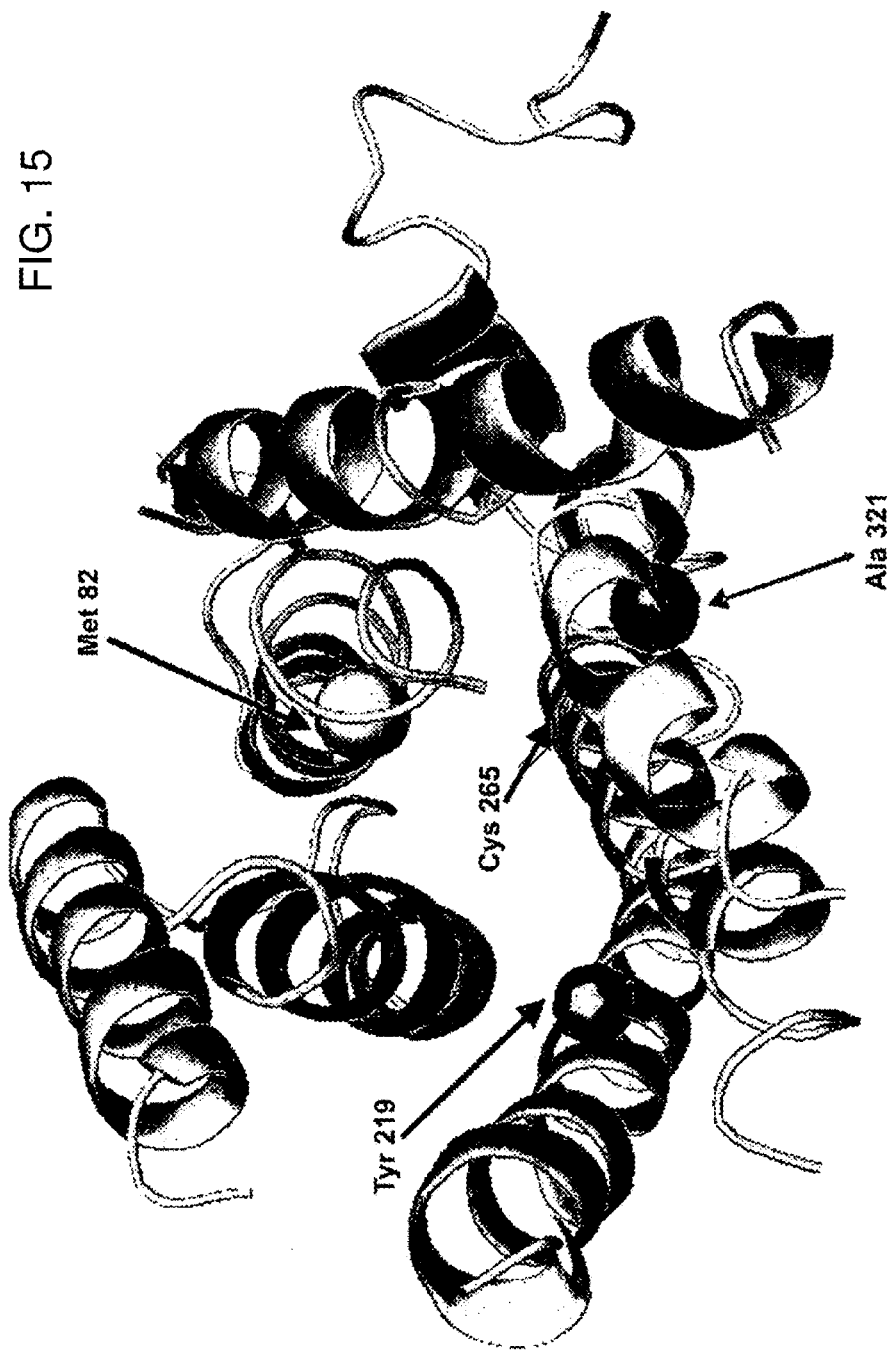

FIG. 15 Mapping of the M90V, Y227A, A282L and F338M m23 mutations in turkey beta1 adrenergic receptor onto homologous residues (M82, Y219, C265 and A321 respectively) in the human beta2 adrenergic receptor structure (Rasmussen et al (2007) Nature 15; 383-387; pdb accession codes 2R4R and 2R4S) reveals their position at a helical interface and helical kink respectively. Amino acid residues in equivalent positions to the thermostabilising mutations in the turkey β1 adrenergic receptor are shown as labelled space filling models.

Figure 16:
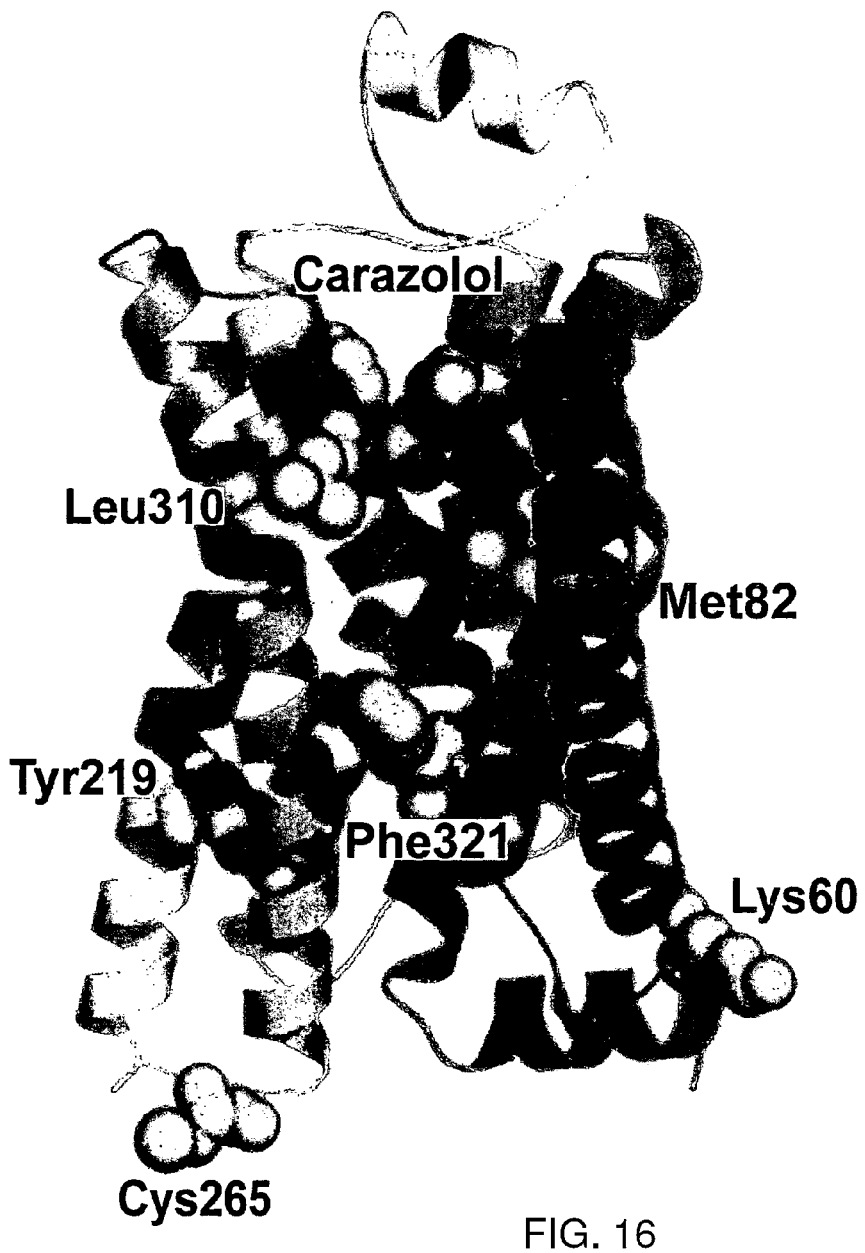

FIG. 16 Mapping of m23 mutations in turkey beta1 adrenergic receptor onto homologous residues in the human beta2 adrenergic receptor structure (Cherezov et al (2007) Science, 318:1258-65; pdb accession code 2RH1). The Cα trace of the β2AR is shown with the fusion moiety (T4 lysozyme) removed. The six mutations in βAR-m23 (R68S, M90V, Y227A, A282L, F327A, F338M) are equivalent to amino acid residues K60, M82, Y219, C265, L310, F321 in the human β2AR. Lys60 is on the intracellular end of Helix 1 and points into the lipid-water interface. Met82 is near the middle of Helix 2 and points into the ligand binding pocket; the nearest distance between the substrate carazolol and the Met side chain is 5.7 Å. Tyr219 is towards the intracellular end of helix 5 and is at the helix5-helix 6 interface. Cys265 is at the end of the loop region between helices 5 and 6 and points away from the transmembrane regions. Leu310 and Phe321 are both in helix 7 and both point out into the lipid bilayer.

Figure 17A:
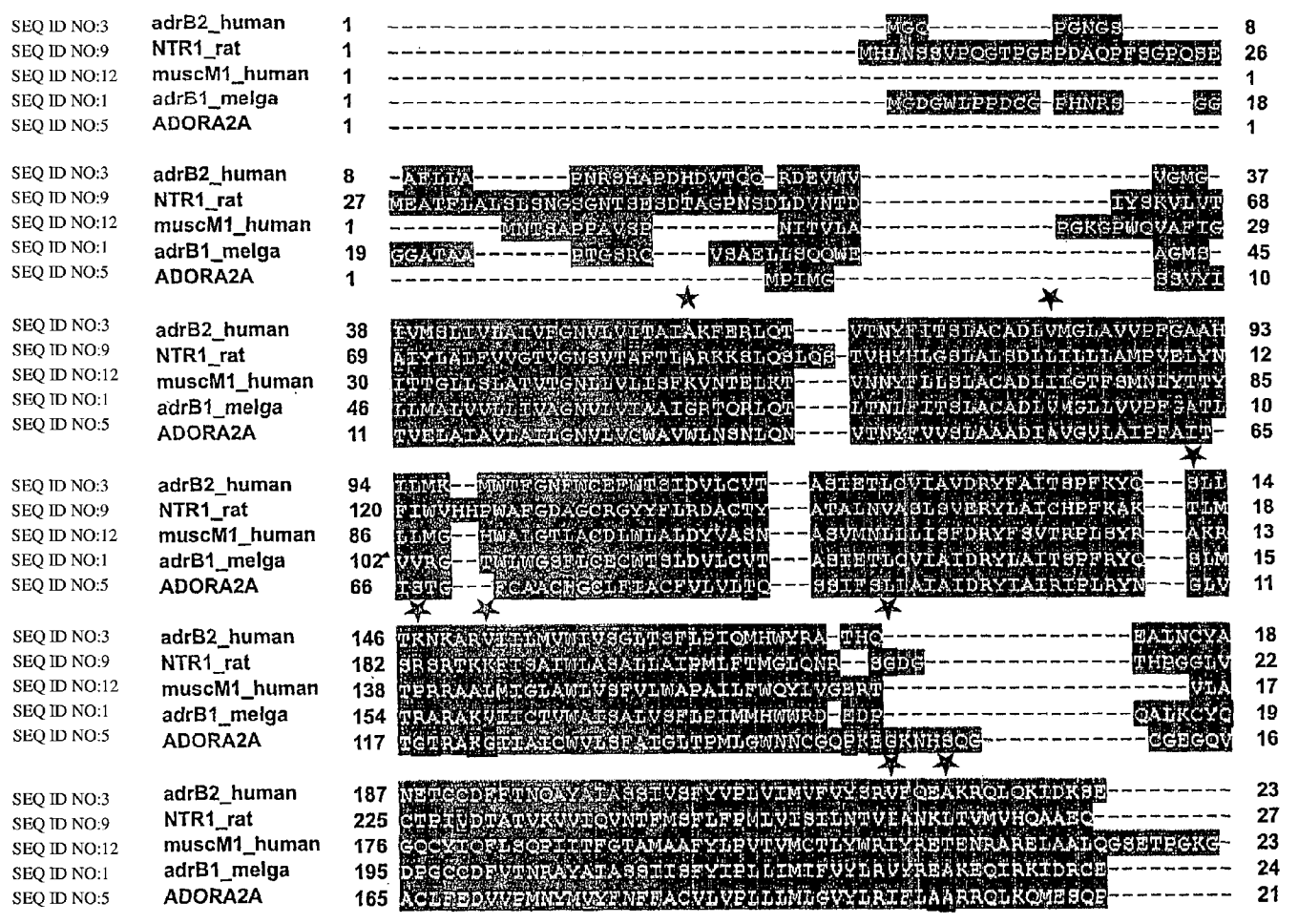
Figure 17C:
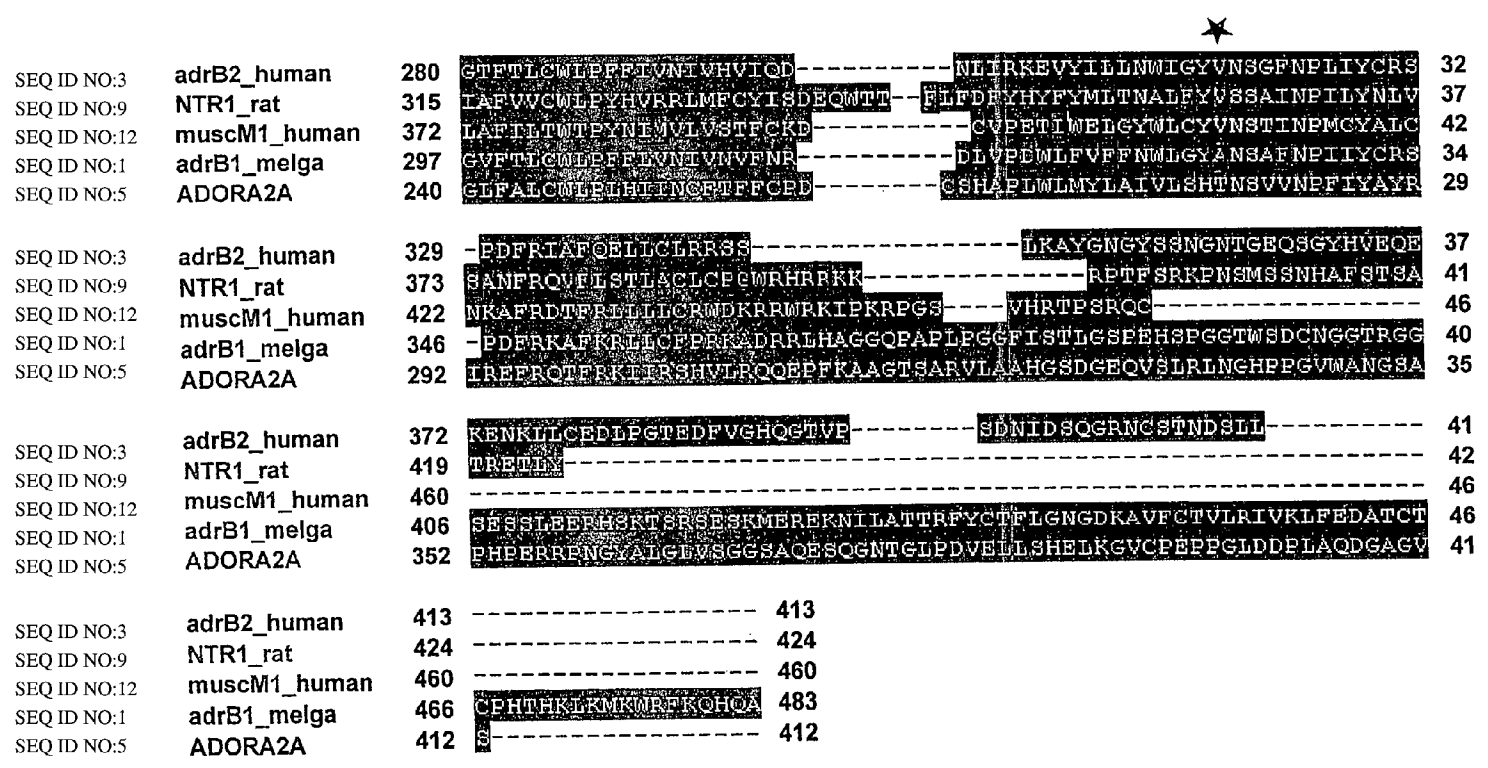

FIGS. 17A-17C Multiple sequence alignment of human beta-2AR (SEQ ID NO:3), rat NTR1 (SEQ ID NO: 9), turkey beta-1 AR (SEQ ID NO: 1), human Adenosine A2aR (SEQ ID NO: 5) and human muscarinic M1 receptors (SEQ ID NO: 12). In each sequence, thermostabilising mutations are marked with a box. Mutations occurring in two or more sequences are denoted with a star.

Figure 18:

FIG. 18 Mapping of turkey beta1AR mutation I55A (human beta2AR I47) onto human beta2AR structure (pdb accession code 2RH1). Mutation is at the interface between 3 helices (H1, H2 kink, H7 kink). Left: side view; right: top view.

Figure 19:
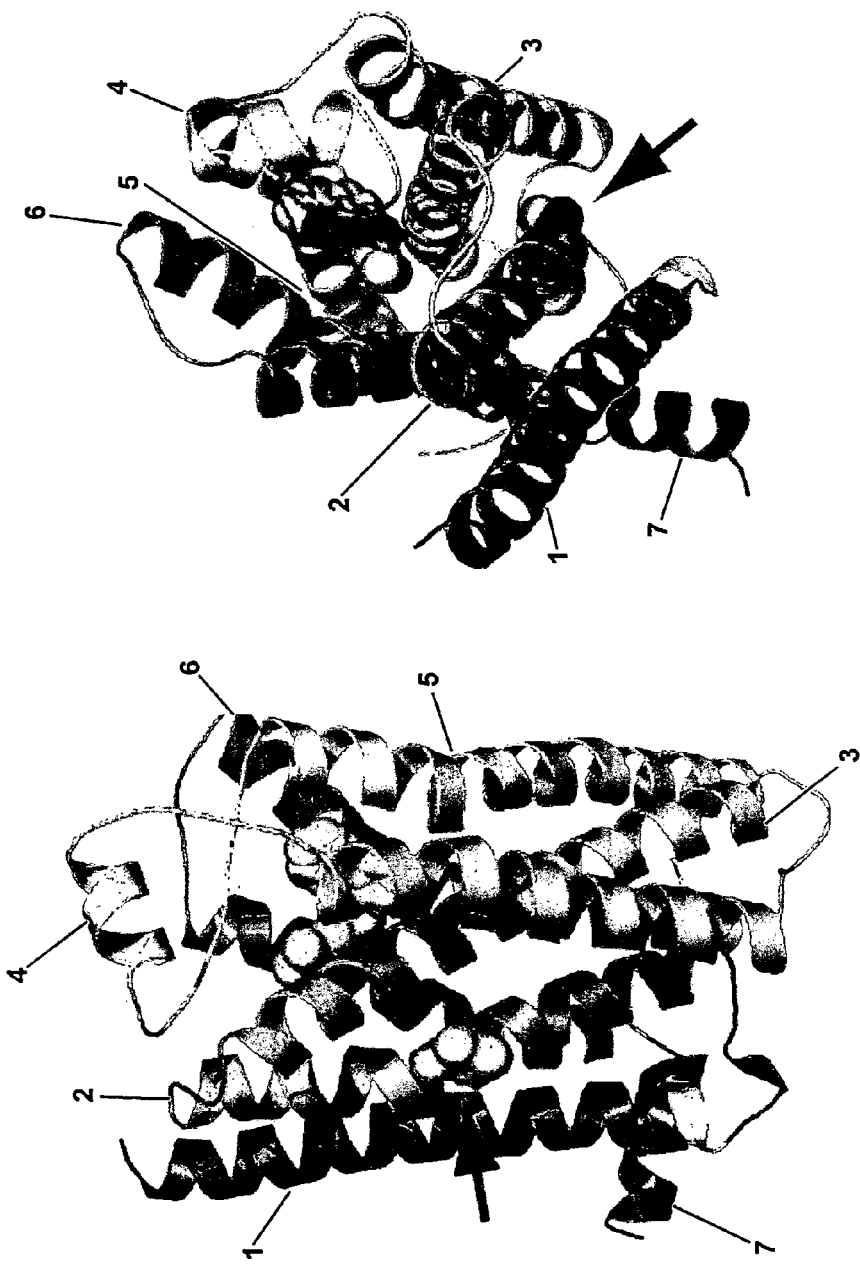

FIG. 19 Mapping of turkey beta1AR V89L mutation (human beta2AR V81) onto human beta2AR structure (pdb accession code 2RH1). Mutation is in the kink in helix 2. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.

Figure 20:
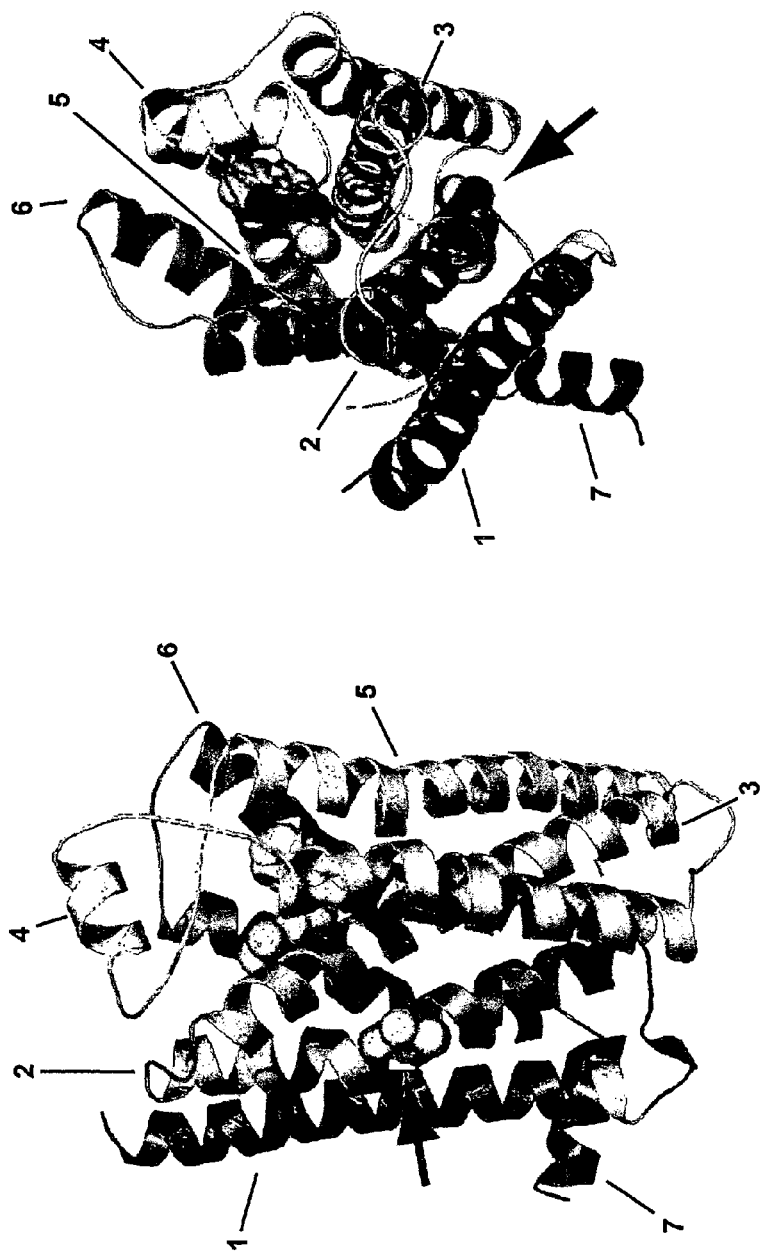

FIG. 20 Mapping of turkey beta1AR M90V mutation (human beta2AR M82) onto human beta2AR structure (pdb accession code 2RH1). Mutation is in kink in helix 2 oriented towards the binding pocket. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.

FIG. 21 Mapping of turkey beta1AR I129V mutation (human beta2AR I121) onto human beta2AR structure (pdb accession code 2RH1). Mutation is opposite a kink in helix 5. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: bottom view.

FIG. 22 Mapping of turkey beta1AR F338M mutation (human beta2AR F321) onto human beta2AR structure (pdb accession code 2RH1). Mutation is in kink in helix 7. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.

Figure 23:
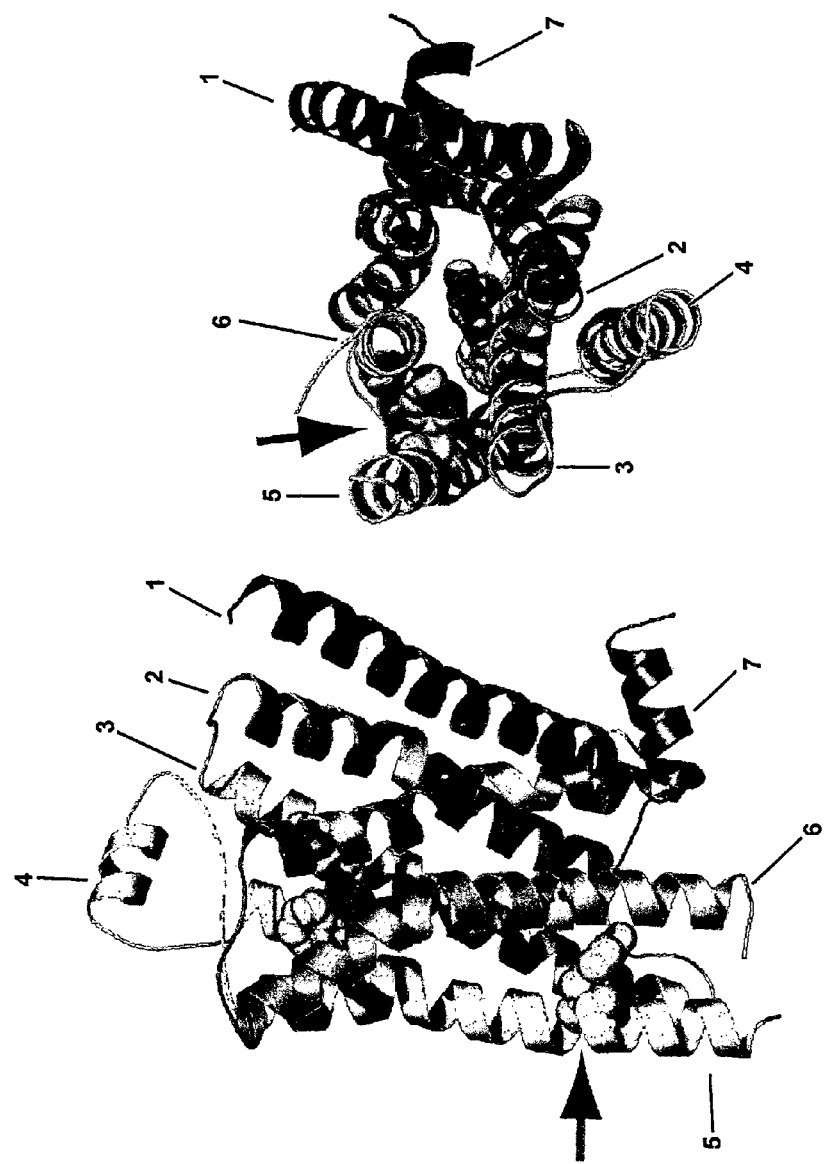

FIG. 23 Mapping of turkey beta1AR Y227A mutation (human beta2AR Y219) onto human beta2AR structure (pdb accession code 2RH1). Mutation is at helix-helix interface. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: bottom view.

Figure 24:
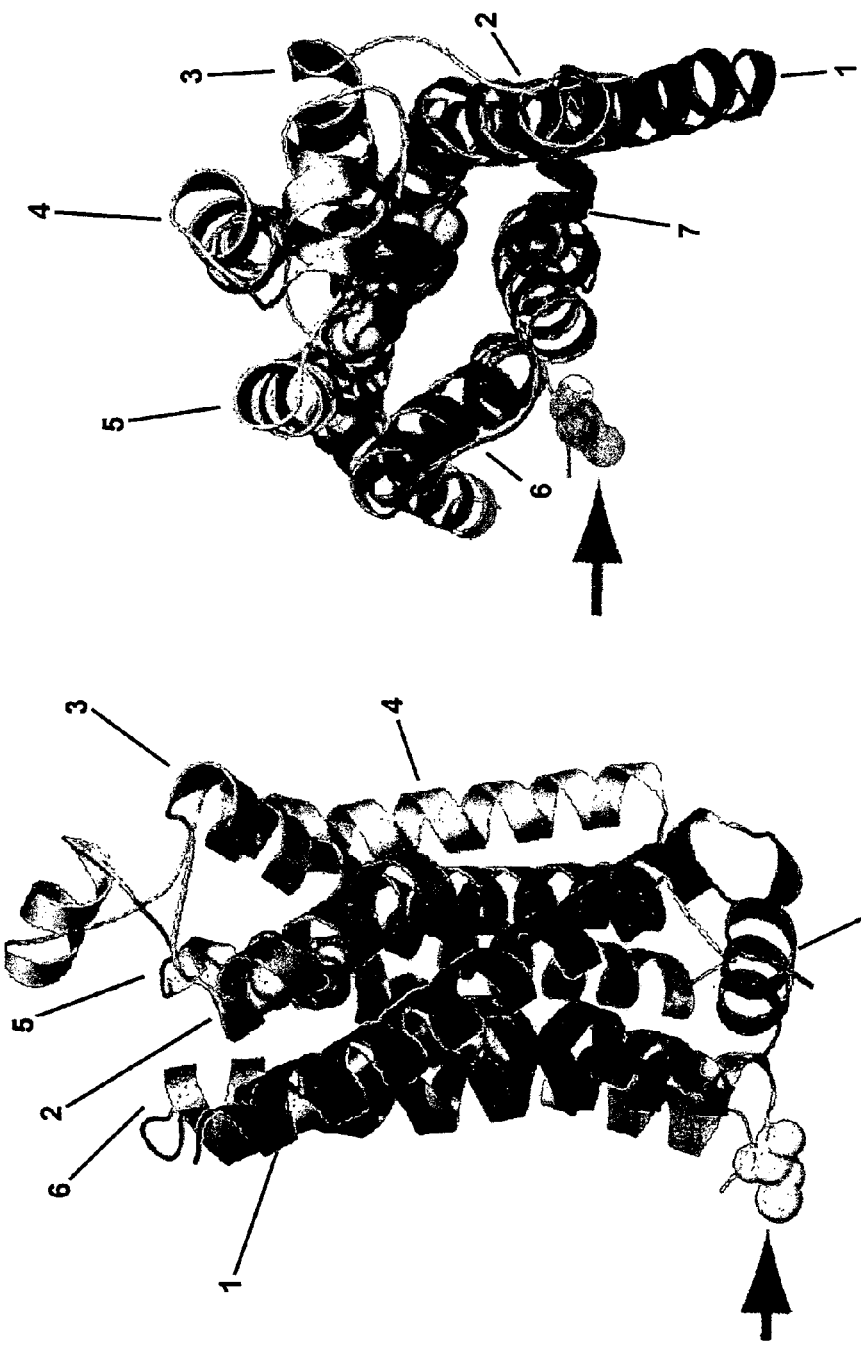

FIG. 24 Mapping of turkey beta1AR A282L mutation (human beta2AR C265) onto human beta2AR structure (pdb accession code 2RH1). Mutation is in loop region. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.

Figure 25:
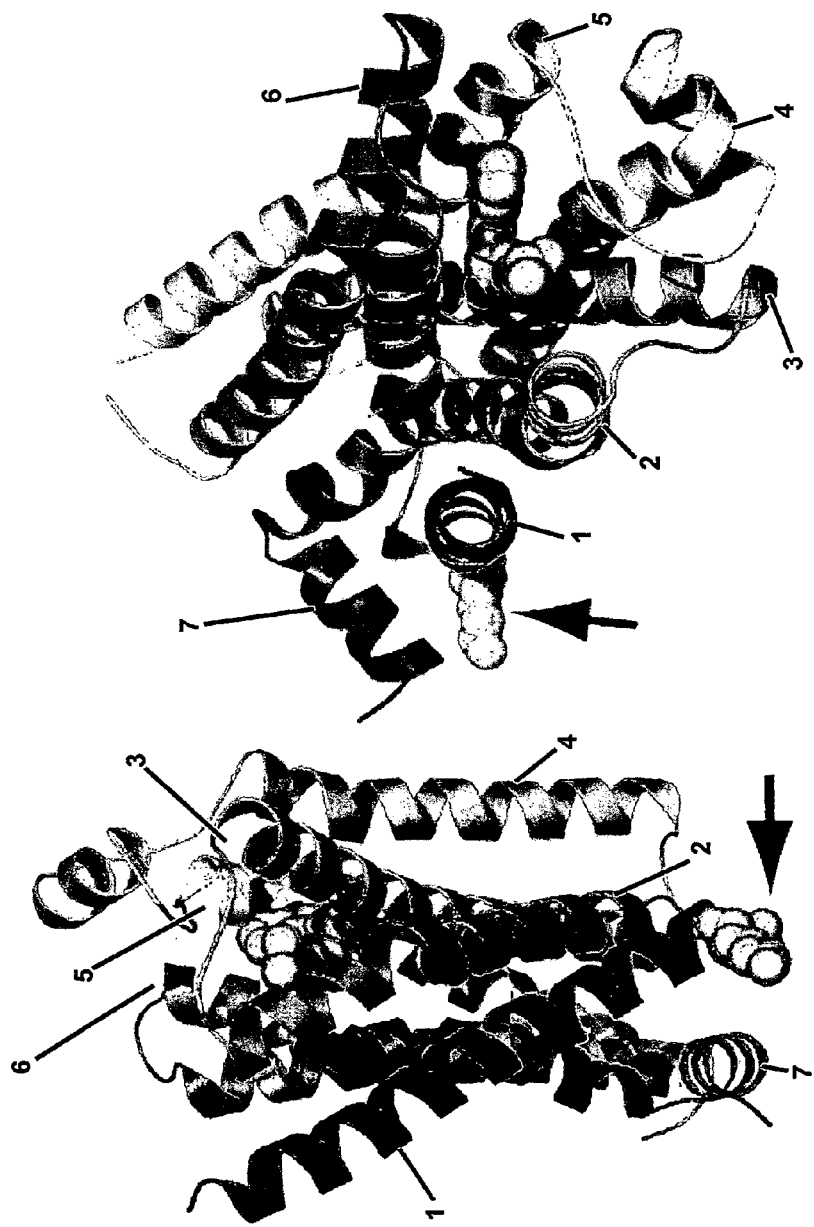

FIG. 25 Mapping of turkey beta1AR R68S mutation (human beta2AR K60) onto human beta2AR structure (pdb accession code 2RH1). Mutation is at the lipid-water boundary, pointing into the solvent. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: angled top view.

Figure 26:
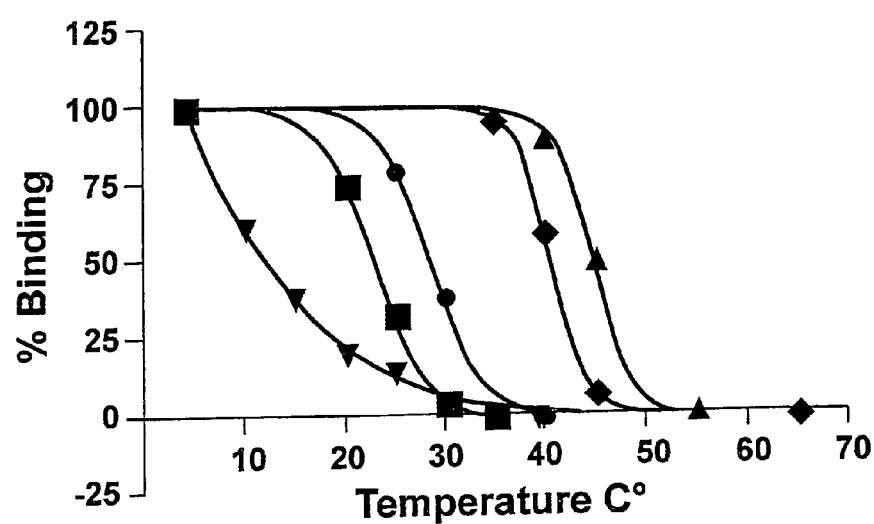

FIG. 26 Comparison of the thermostabilities of three β adrenergic receptors (turkey β1 (■), human β1 (▼) and human β2 (●)) and two thermostabilised receptors (turkey β1-m23 (▲) and human β2-m23 (♦)). The six thermostabilising mutations in β1-m23 (R68S, M90V, Y227A, A282L, F327A, F338M) were all transferred directly to the human β2 receptor (K60S, M82V, Y219A, C265L, L310A, F321M) making β2-m23, based upon the alignment in FIGS. 9A and 9B. The resulting mutants were transiently expressed in mammalian cells, solubilised in 0.1% dodecylmaltoside and assayed for thermostability in the minus-ligand format (heating the apo-state, quenching on ice, adding 3H-DHA). The apparent Tms for turkey β1 and β2-m23 were 23° C. and 45° C. respectively, giving a ΔTm of 22° C. as seen previously in *E. coli* expressed receptor. The Tms for human β2 and β2-m23 were 29° C. and 41° C. respectively, showing that the apo receptor was stabilised by 12° C. This exemplifies the principle of the transferability of thermostabilising mutations from one receptor to another receptor, which in this case are 59% identical. The human β1 receptor (Tm~12° C.) is much less stable than the turkey β1 receptor.

FIG. 27 Percentage identity of the turkey β1 adrenergic receptor, human adenosine receptor and rat neurotensin receptor to human β adrenergic receptors, human adenosine receptors and human neurotensin receptors, respectively.

Figure 28B:
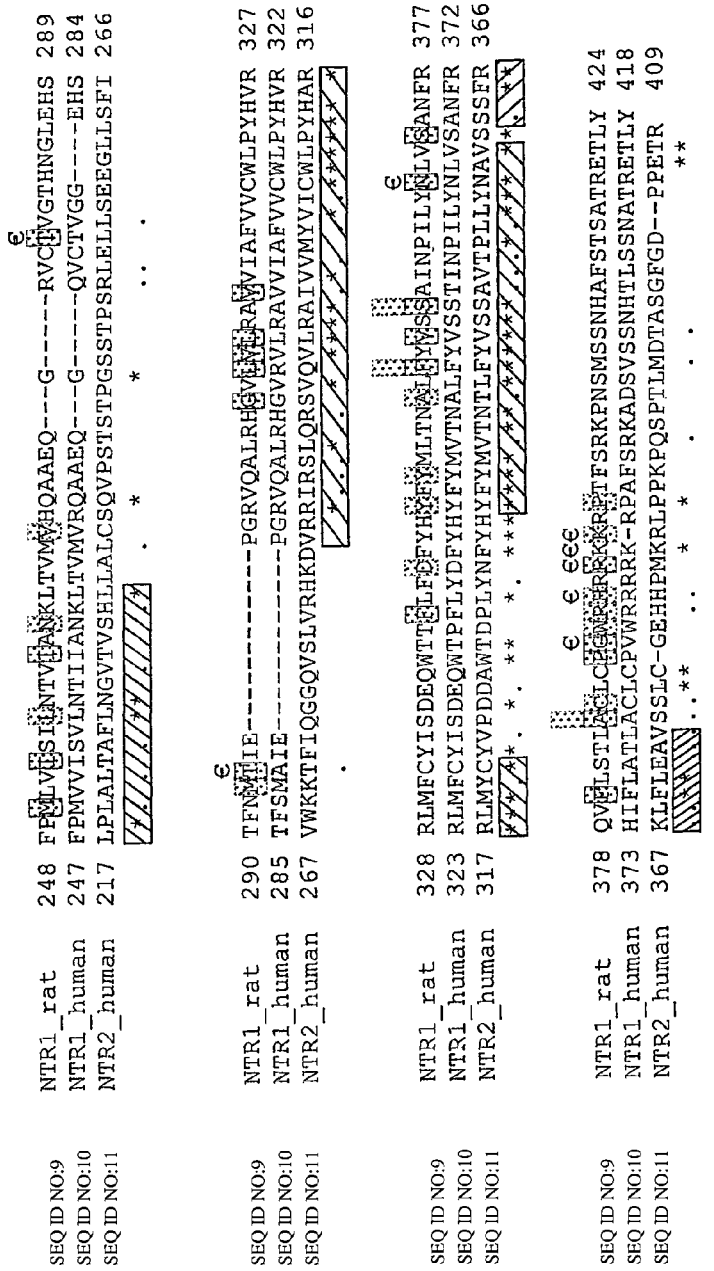

FIGS. 28A and 28B Alignment of neurotensin receptors (SEQ ID NOs: 9-11).

Figure 29:
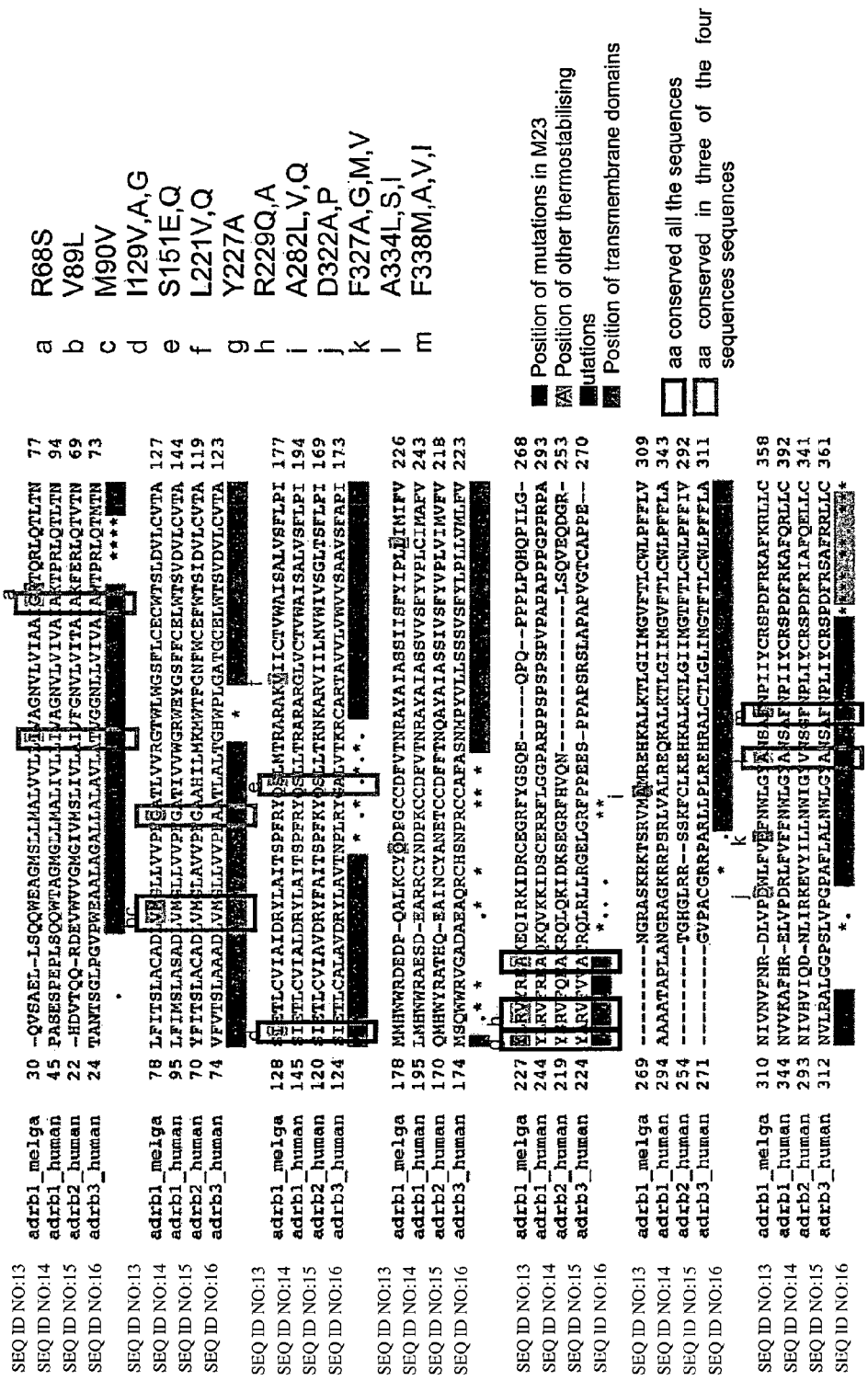

FIG. 29 Sequence alignment between turkey β1AR (SEQ ID NO: 13) and human β3ARs (SEQ ID NO:14-16). The N- and C-termini of the sequences were removed in the alignments. Mutations in the turkey sequence that correspond to those present in m23 (R68S, M90V, Y227A, A282L, F327A and F338M) are highlighted, as are those that correspond with other thermostabilising mutations (see key). Rectangles below the alignment indicate the position of transmembrane domains and the position of helix 8. Opened rectangles indicate residues conserved in all the sequences and residues conserved in three of the four sequences (see key).

Figure 30A:
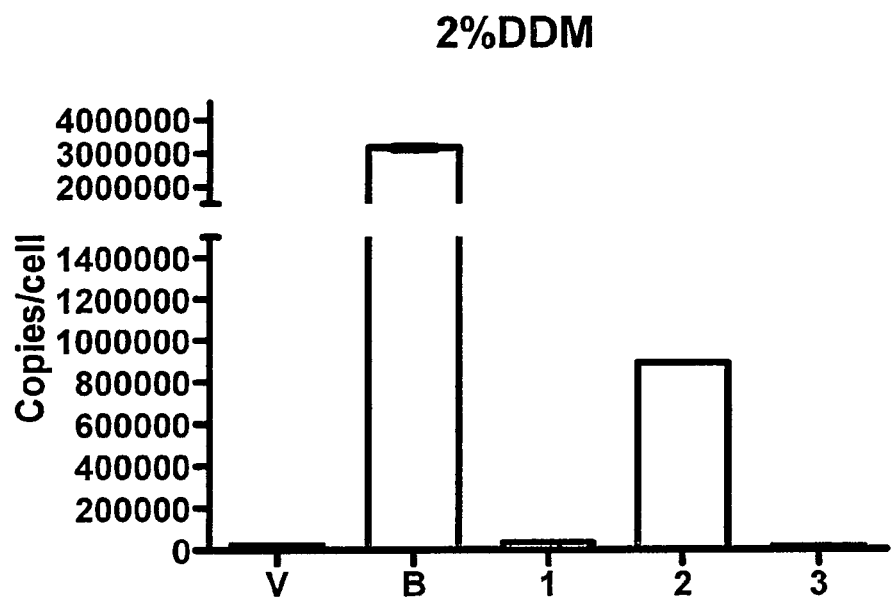
Figure 30B:
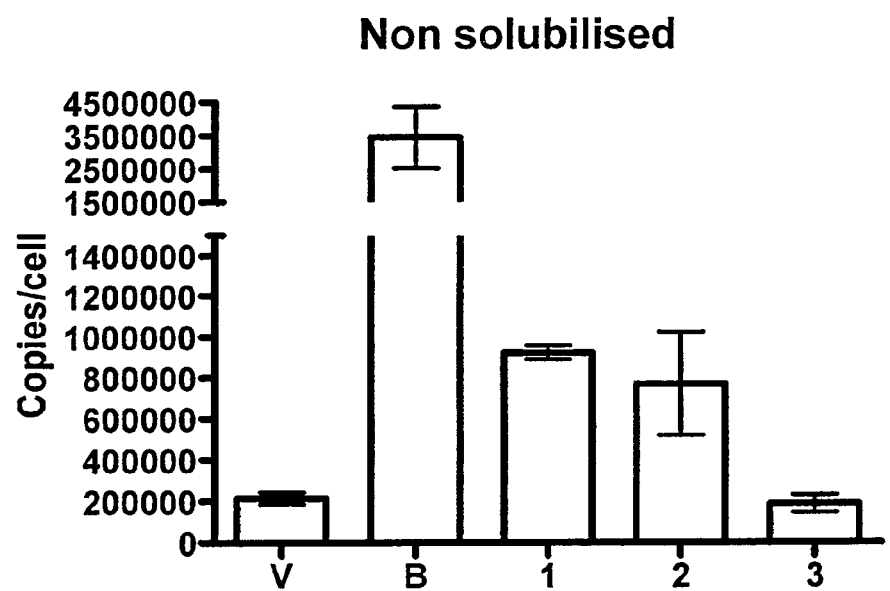
Figure 30C:
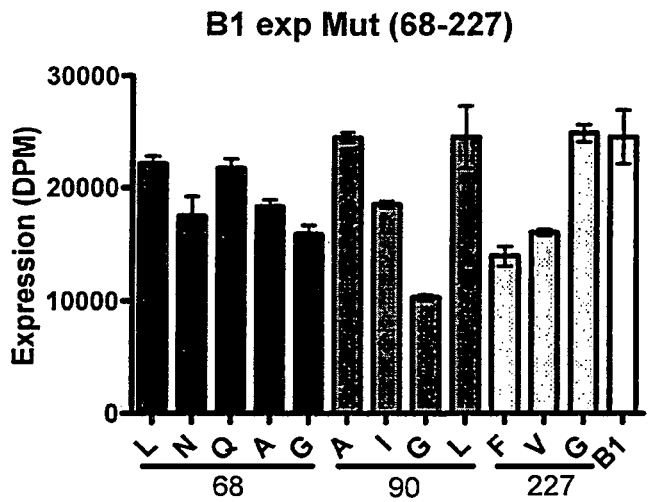
Figure 30D:
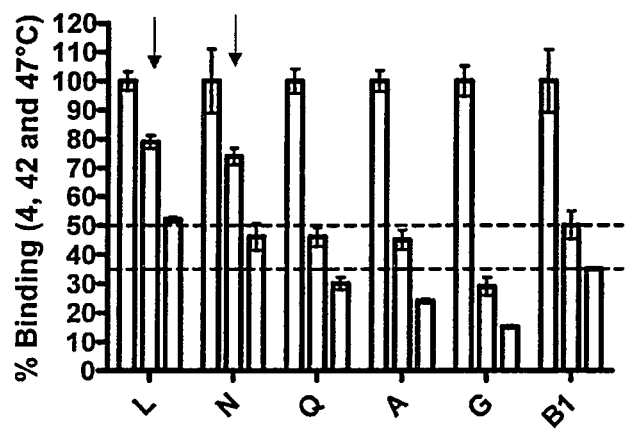
Figure 30E:
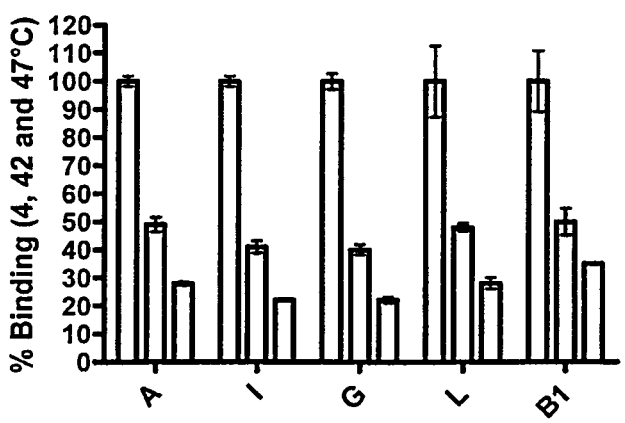
Figure 30F:
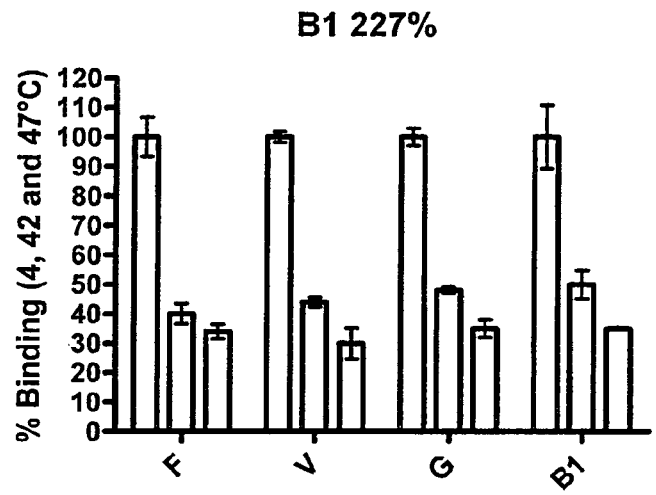
Figure 30G:
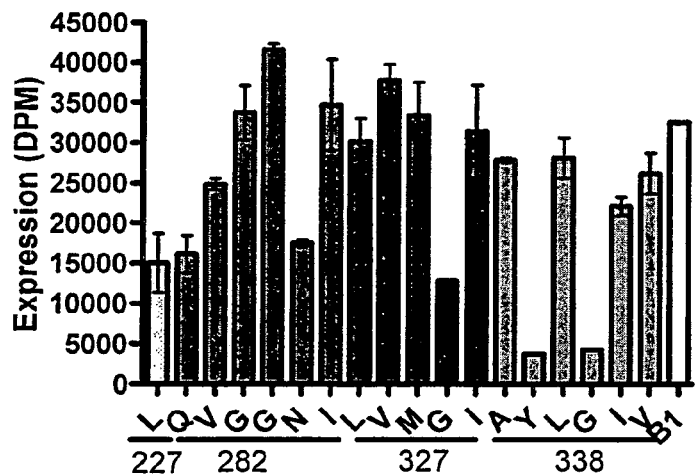
Figure 30H:
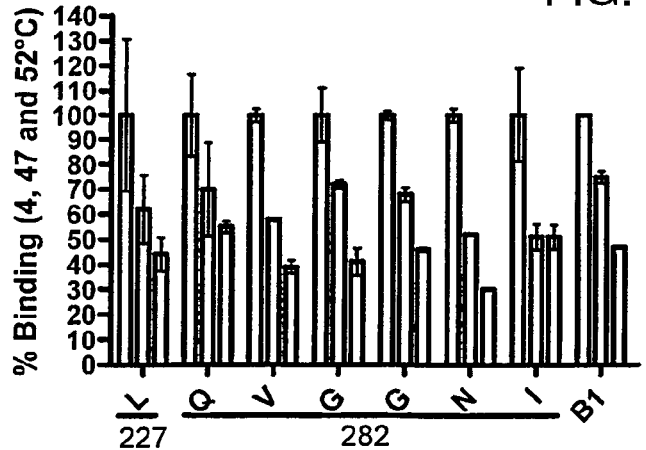
Figure 30I:
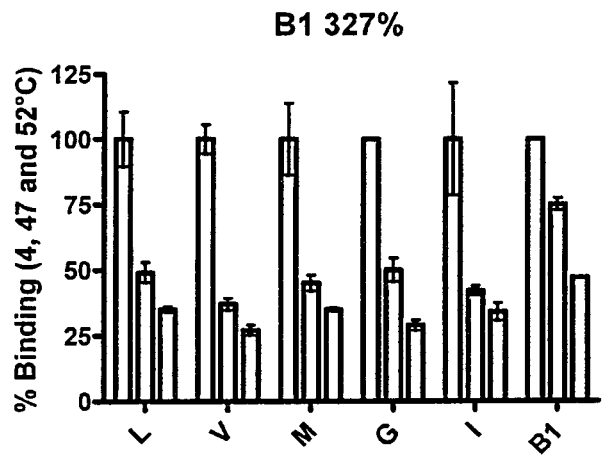
Figure 30J:
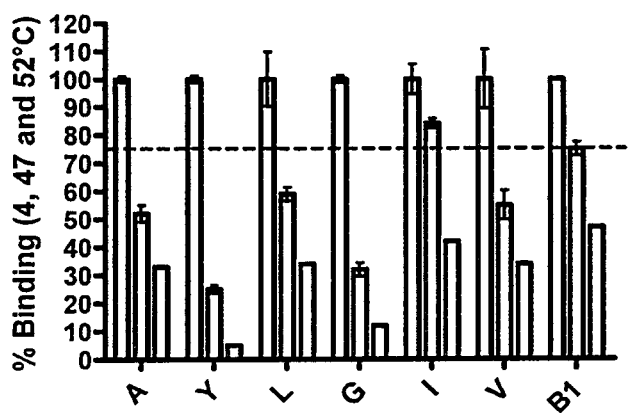
Figure 30K:
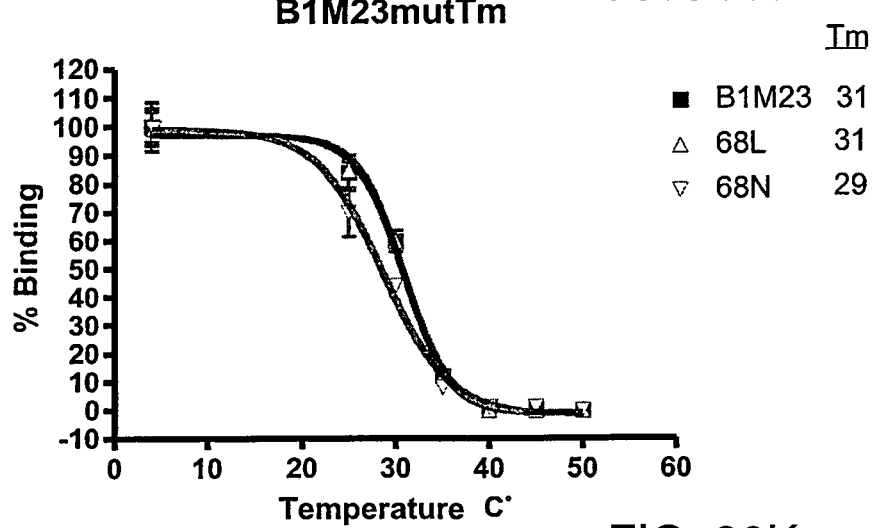
Figure 30L:
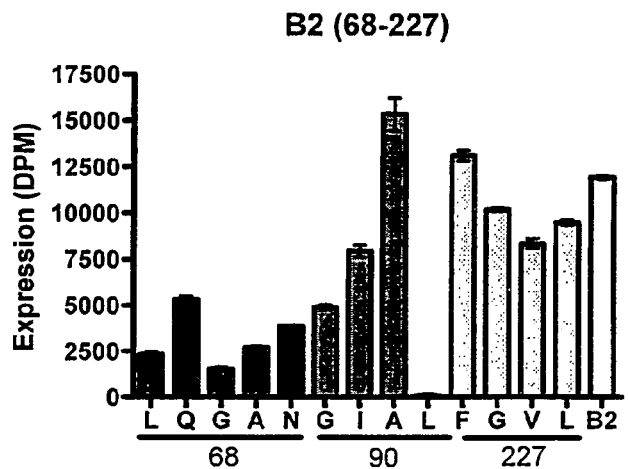
Figure 30M:
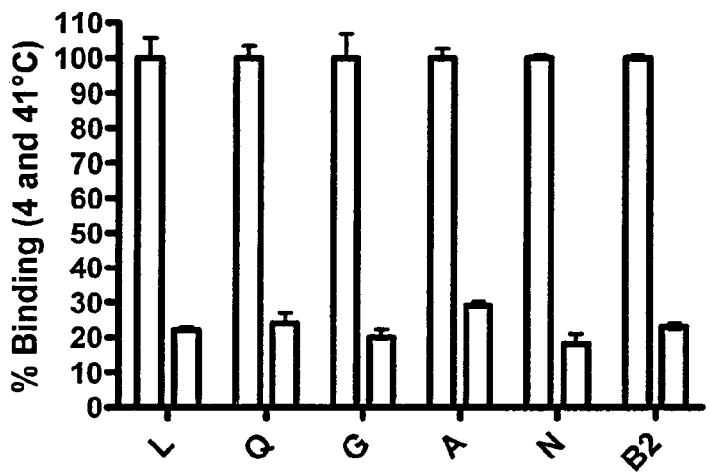
Figure 30N:
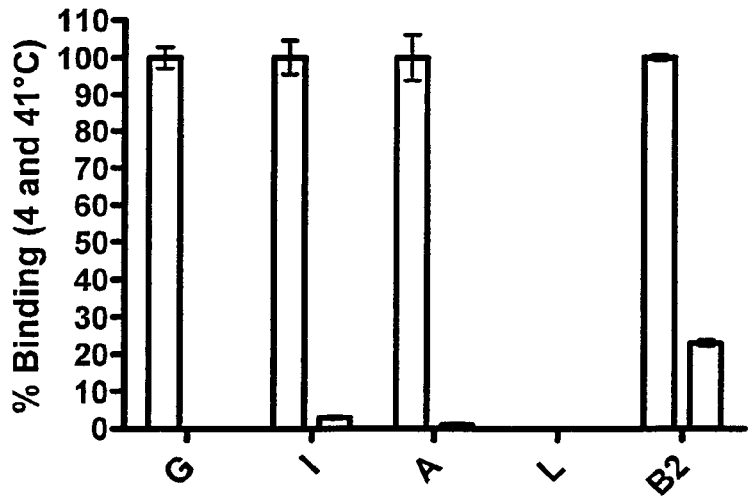
Figure 30O:
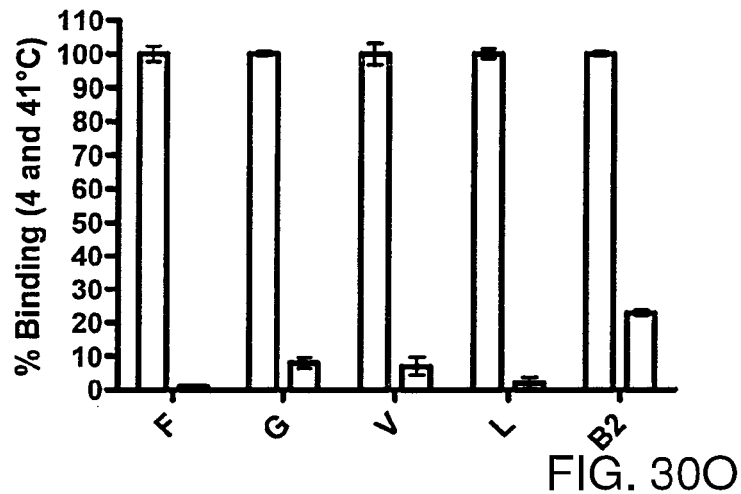
Figure 30P:
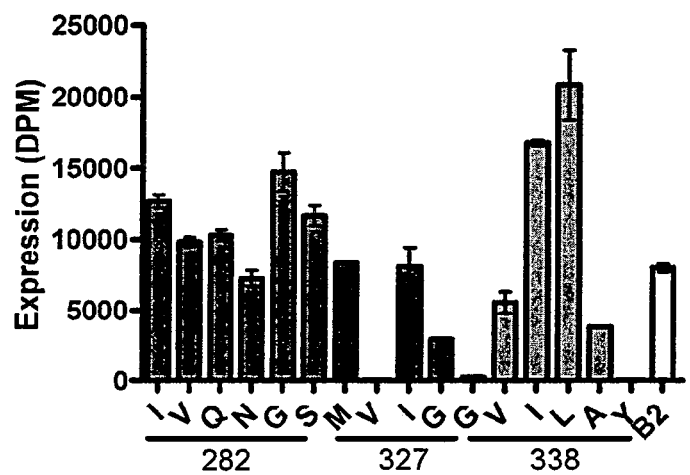
Figure 30Q:
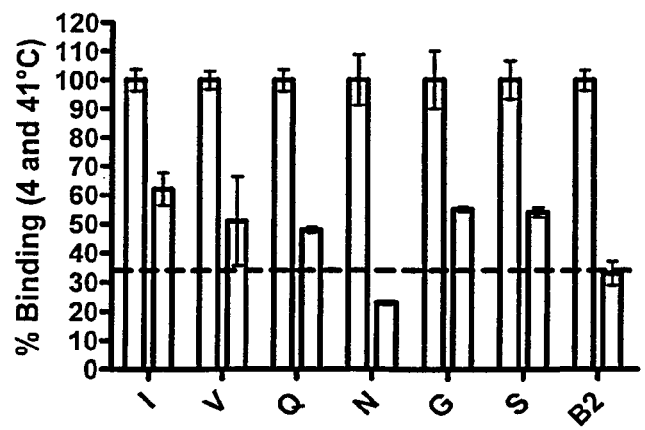
Figure 30R:
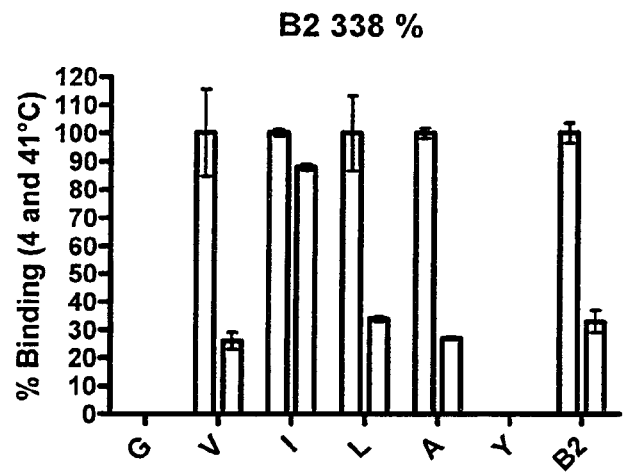
Figure 30S:
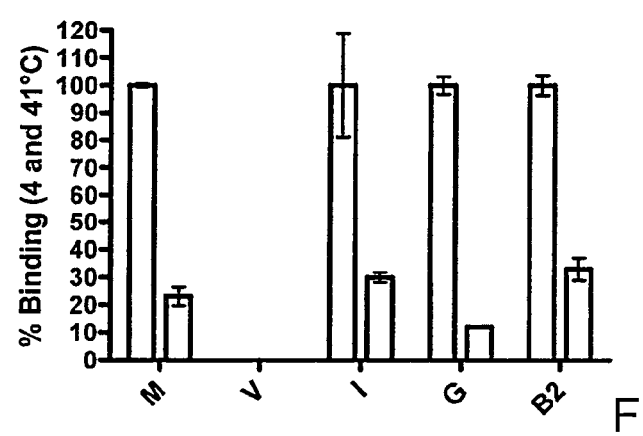
Figure 30T:
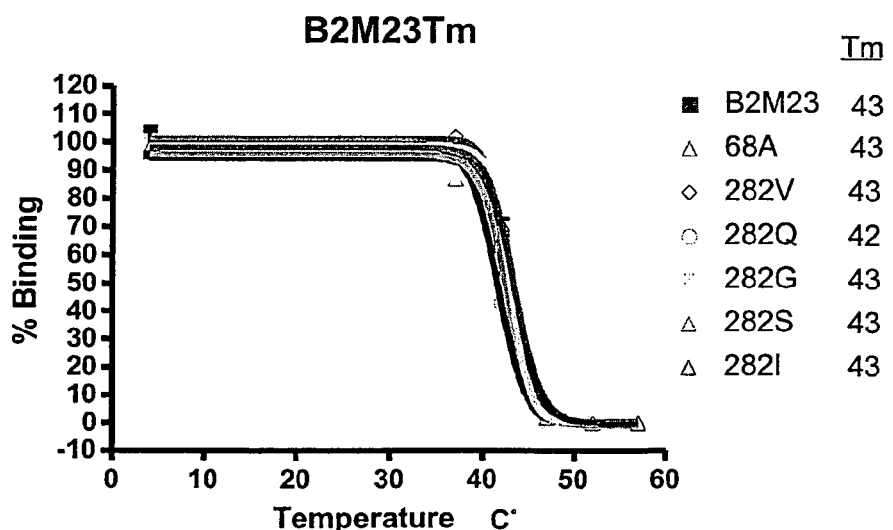

FIGS. 30A-30T Expression and binding assays of turkey β1AR and human βARs in HEK cells. Ligand binding was calculated with the radioligand [³H]DHA in a concentration of 80 nM. (a) Ligand binding from solubilized cells with 2% DDM, (b) Ligand binding from membranes; (c) Expression of human beta1AR-m23 mutant receptors in transiently transfected HEK293 cells measured by radioligand binding of tritiated dihydroalprenolol. All receptors in this figure initially contain the six mutants equivalent to R68S, M90V, Y227A, A282L, F327A, and F338M in turkey beta1AR. The expression levels are shown for individual receptors with the additional amino acid replacement; (d) The stabilities of human beta1AR-m23 mutants in which the amino acid at position 68 is altered are indicated on the graph. Each mutant was heated at three different temperatures for 30 minutes and the bar graphs show the percentage of binding remaining at 4° C., 42° C. and 47° C.; (e) The stabilities of human beta1AR-m23 mutants in which the amino acid at position 90 is altered are indicated on the graph. Each mutant was heated at three different temperatures for 30 minutes and the bar graphs show the percentage of binding remaining at 4° C., 42° C. and 47° C.; (f) The stabilities of human beta1AR-m23 mutants in which the amino acid at position 227 is altered are indicated on the graph. Each mutant was heated at three different temperatures for 30 minutes and the bar graphs show the percentage of binding remaining at 4° C., 42° C. and 47° C.; (g) Expression of human beta1AR-m23 mutant receptors in transiently transfected HEK293 cells measured by radioligand binding of tritiated dihydroalprenolol. All receptors in this figure initially contain the six mutants equivalent to R68S, M90V, Y227A, A282L, F327A, and F338M in turkey beta1AR. The expression levels are shown for individual receptors with the additional amino acid replacement; (h) The stabilities of human beta1AR-m23 mutants in which the amino acid at position 227 or 282 is altered are indicated on the graph. Each mutant was heated at three different temperatures for 30 minutes and the bar graphs show the percentage of binding remaining at 4° C., 47° C. and 52° C.; (i) The stabilities of human beta1AR-m23 mutants in which the amino acid at position 327 is altered are indicated on the graph. Each mutant was heated at three different temperatures for 30 minutes and the bar graphs show the percentage of binding remaining at 4° C., 47° C. and 52° C.; (j) The stabilities of human beta1AR-m23 mutants in which the amino acid at position 338 is altered are indicated on the graph. Each mutant was heated at three different temperatures for 30 minutes and the bar graphs show the percentage of binding remaining at at 4° C., 47° C. and 52° C.; (k) Thermostability curves for human beta1AR-m23 and m23 with different residues at position 68; (l) Expression of human beta2AR-m23 mutant receptors in transiently transfected HEK293 cells measured by radioligand binding of tritiated dihydroalprenolol. All receptors in this figure initially contain the six mutants equivalent to R68S, M90V, Y227A, A282L, F327A, and F338M in turkey beta1AR. The expression levels are shown for individual receptors with the additional amino acid replacement; (m) The stabilities of human beta2AR-m23 mutants in which the amino acid at position 68 is altered are indicated on the graph. Each mutant was heated at three different temperatures for 30 minutes and the bar graphs show the percentage of binding remaining at 4° C. and 41° C.; (n) The stabilities of human beta2AR-m23 mutants in which the amino acid at position 90 is altered are indicated on the graph. Each mutant was heated at three different temperatures for 30 minutes and the bar graphs show the percentage of binding remaining at 4° C. and 41° C.; (o) The stabilities of human beta2AR-m23 mutants in which the amino acid at position 227 is altered are indicated on the graph. Each mutant was heated at three different temperatures for 30 minutes and the bar graphs show the percentage of binding remaining at 4° C. and 41° C.; (p) Expression of human beta2AR-m23 mutant receptors in transiently transfected HEK293 cells measured by radioligand binding of tritiated dihydroalprenolol. All receptors in this figure initially contain the six mutants equivalent to R68S, M90V, Y227A, A282L, F327A, and F338M in turkey beta1 AR. The expression levels are shown for individual receptors with the additional amino acid replacement; (q) The stabilities of human beta2AR-m23 mutants in which the amino acid at position 282 is altered are indicated on the graph. Each mutant was heated at three different temperatures for 30 minutes and the bar graphs show the percentage of binding remaining at 4° C. and 41° C.; (r) The stabilities of human beta2AR-m23 mutants in which the amino acid at position 327 is altered are indicated on the graph. Each mutant was heated at three different temperatures for 30 minutes and the bar graphs show the percentage of binding remaining at 4° C. and 41° C.; (s) The stabilities of human beta2AR-m23 mutants in which the amino acid at position 327 is altered are indicated on the graph. Each mutant was heated at three different temperatures for 30 minutes and the bar graphs show the percentage of binding remaining at at 4° C. and 41° C.; (t) Thermostability curves for human beta2AR-m23 with different residues at positions 68 or 282. V, vector control; B, turkey β1AR; 1, human β1AR-Cdel; 2, human β2AR. Experiments were performed as explained in the methods of Example 5. Copies of receptor/cells were calculated from the radioactivity bound to the receptor. The measurements were taken in duplicates.

Figure 31A:
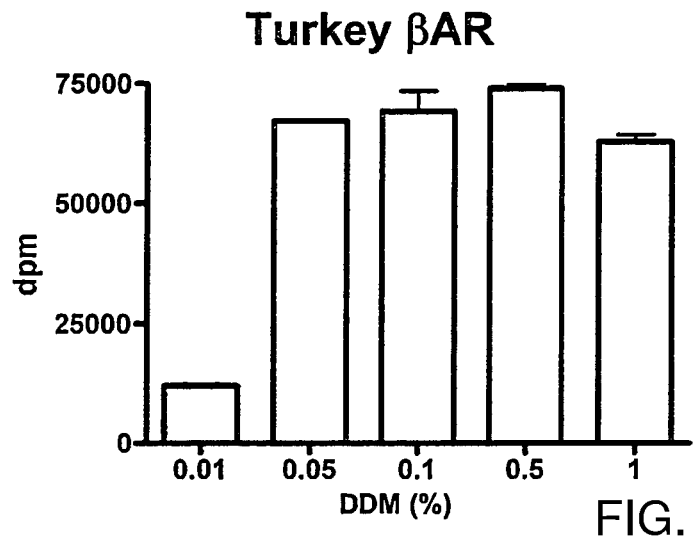
Figure 31B:
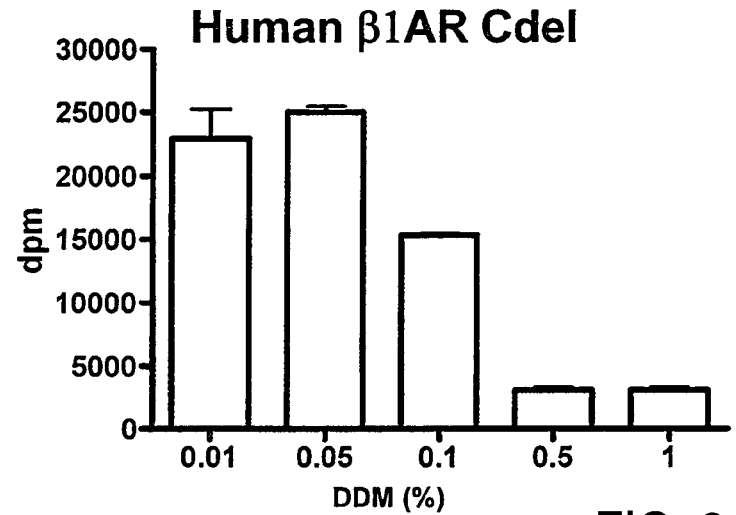
Figure 31C:
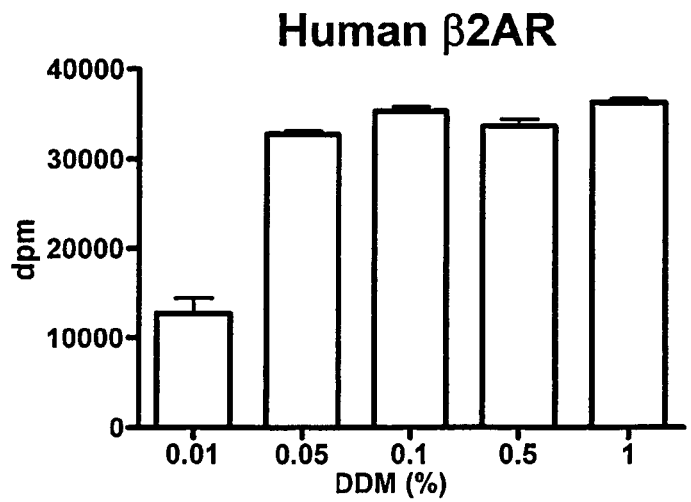

FIGS. 31A-31C Effect of increasing amount of detergent in the activity of βARs. (a) Turkey β1AR, (b) human β1AR-Cdel and (c) human β2AR. Ligand binding was calculated with 80 nM [³H]DHA. Bars represent the activity, in dpm, of the receptor solubilized with 0.01%, 0.05%, 0.1%, 0.5% and 1% of DDM. Experiments were performed as explained in methods. The measurements were taken in duplicates.

FIGS. 32A-32F Stability of turkey β1AR and human β1AR-Cdel and β2AR with and without stabilizing mutations. Tm was determined incubating the sample 30 min at different temperatures before assay with 80 nM [³H]DHA. The experiments were performed with samples solubilized in 0.1% (X lines) and 0.01% DDM (X lines). (A) Turkey β1AR, (B) human β1AR-Cdel, (C) human β2AR, (D) turkey β1AR-m23, (E) human β1AR-Cdel-m23 and (F) human β2AR-m23. Data points are from duplicate measurements.

FIG. 33 Alignment of A2A (SEQ ID NO: 5), B1 (SEQ ID NO: 1) and NTR (SEQ ID NO: 9) with experimentally determined stabilising mutations highlighted and shaded depending on co-occurrence between sequences.

FIGS. 34A and 34B Alignment of human A2AA, turkey B1 AR, rat NTR and human M1 receptors, with some variation in loop regions. From top to bottom (SEQ ID NOs: 9, 1, 5, 12, 3 and 17)

Figure 35A:
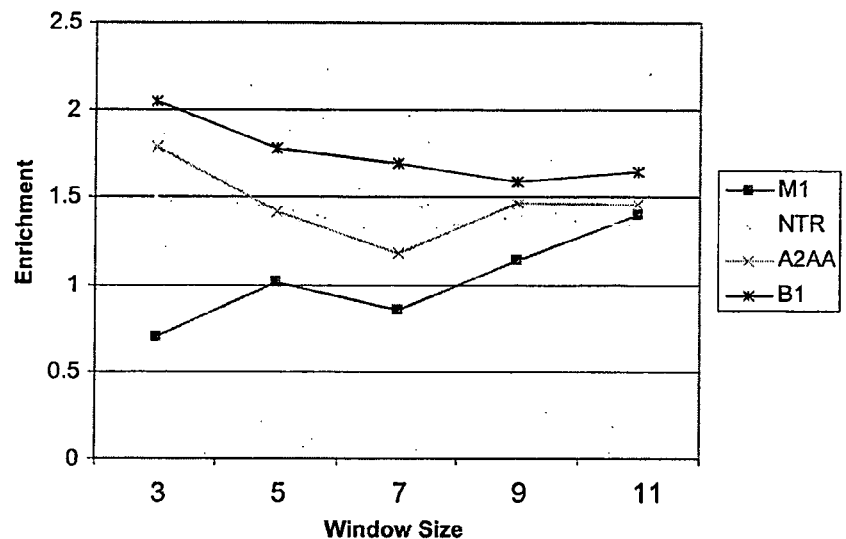
Figure 35B:
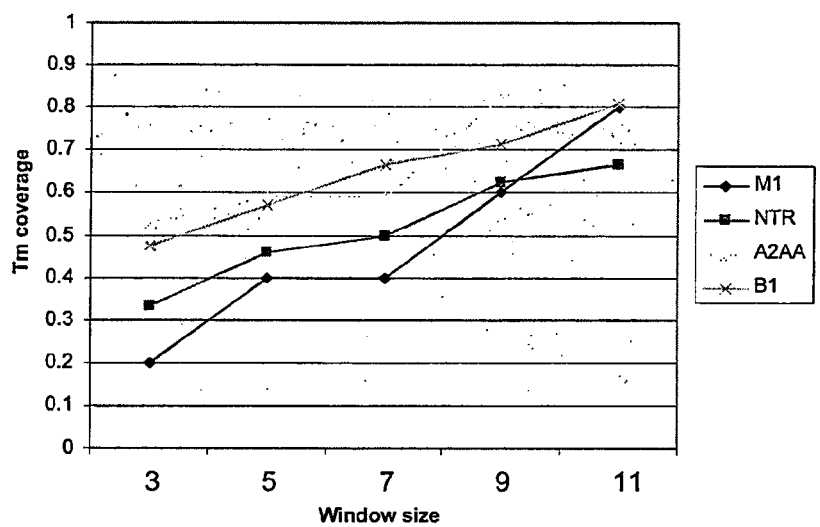

FIG. 35 Effect of window size on enrichment (A) and coverage (B).

Figure 36:
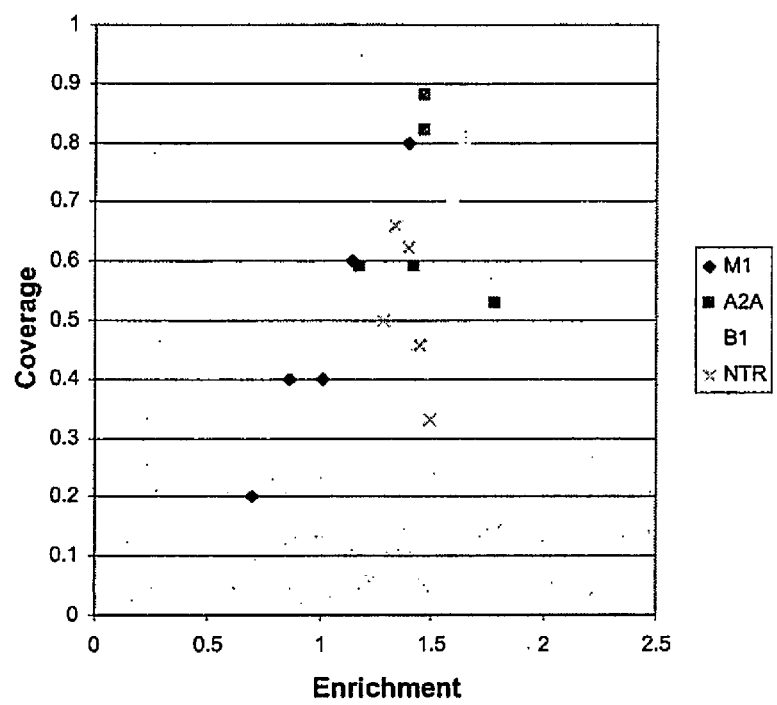

FIG. 36 Coverage vs enrichment for all receptors for different window sizes.

Figure 37:
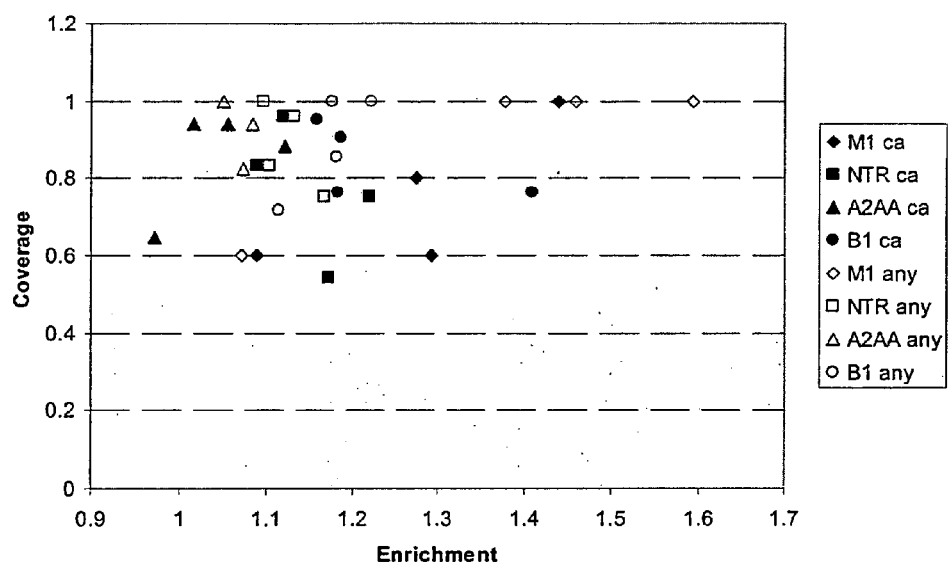

FIG. 37 Top: enrichment vs coverage for Tm identification based upon the CI and any-atom method. bottom: enrichment vs coverage for Tm identification based upon the sequence based method.

Figure 38:
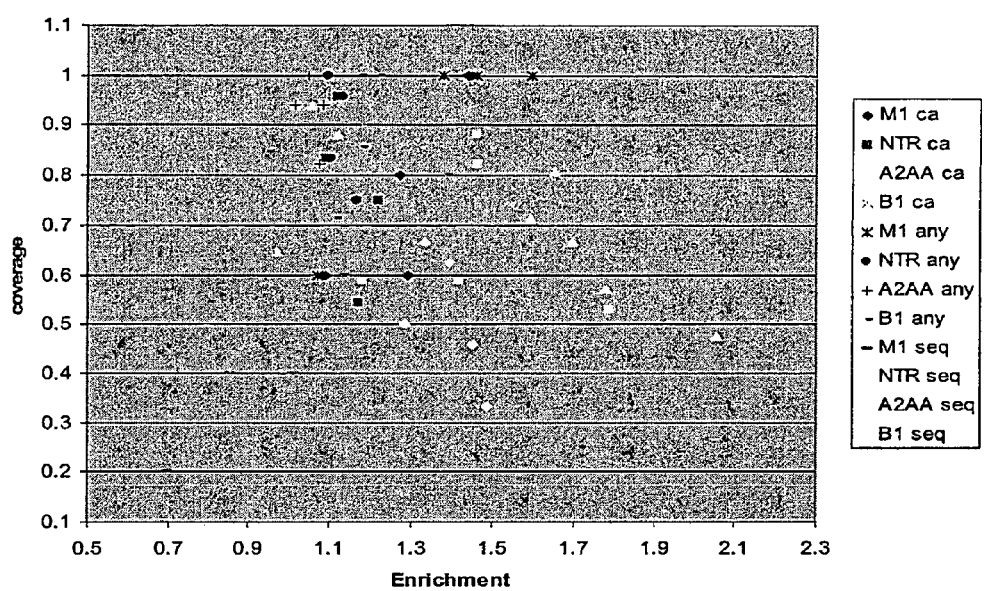
Figure 39A:
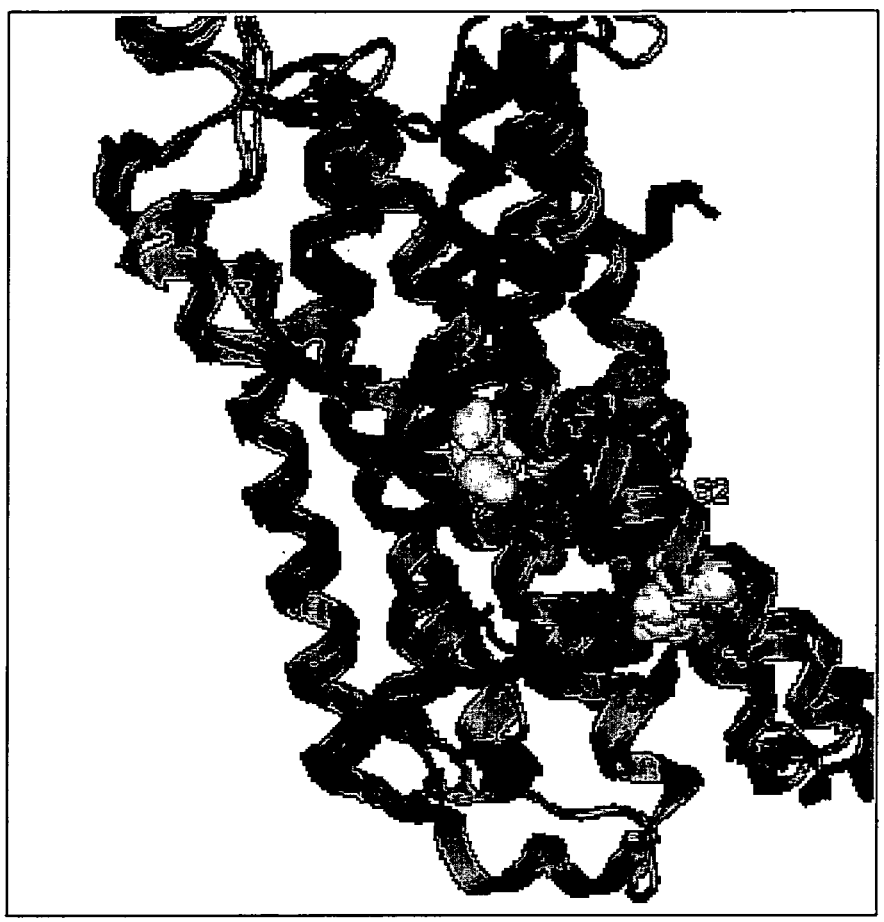
Figure 39B:
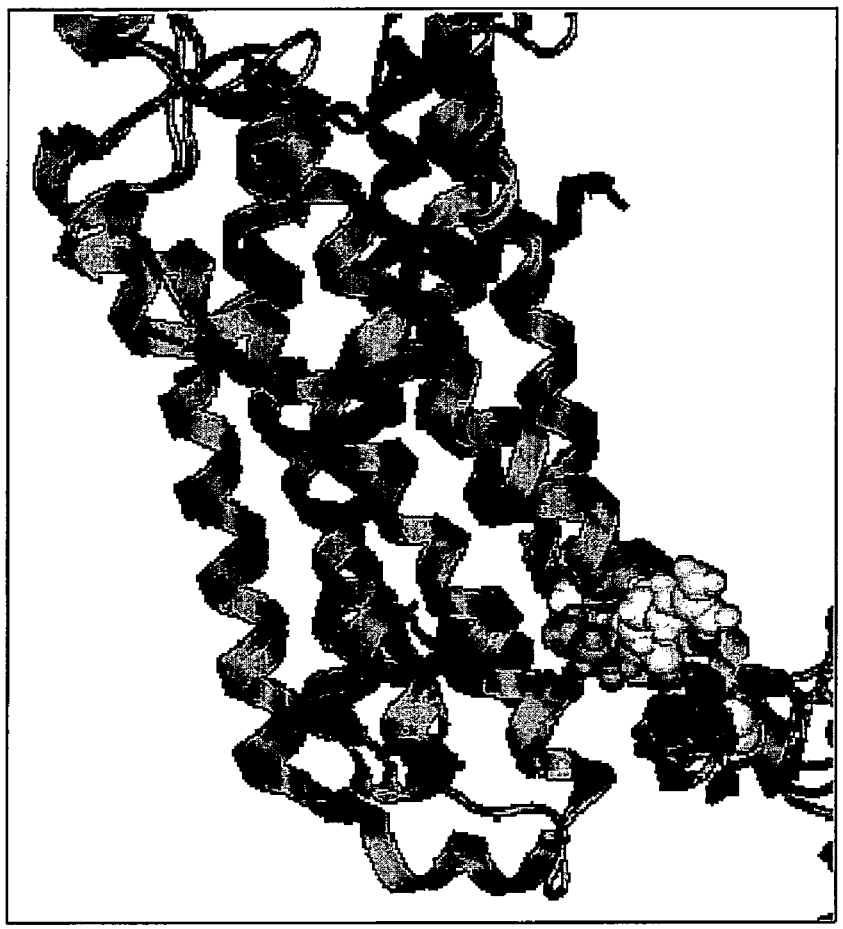
Figure 39C:
Figure 39D:
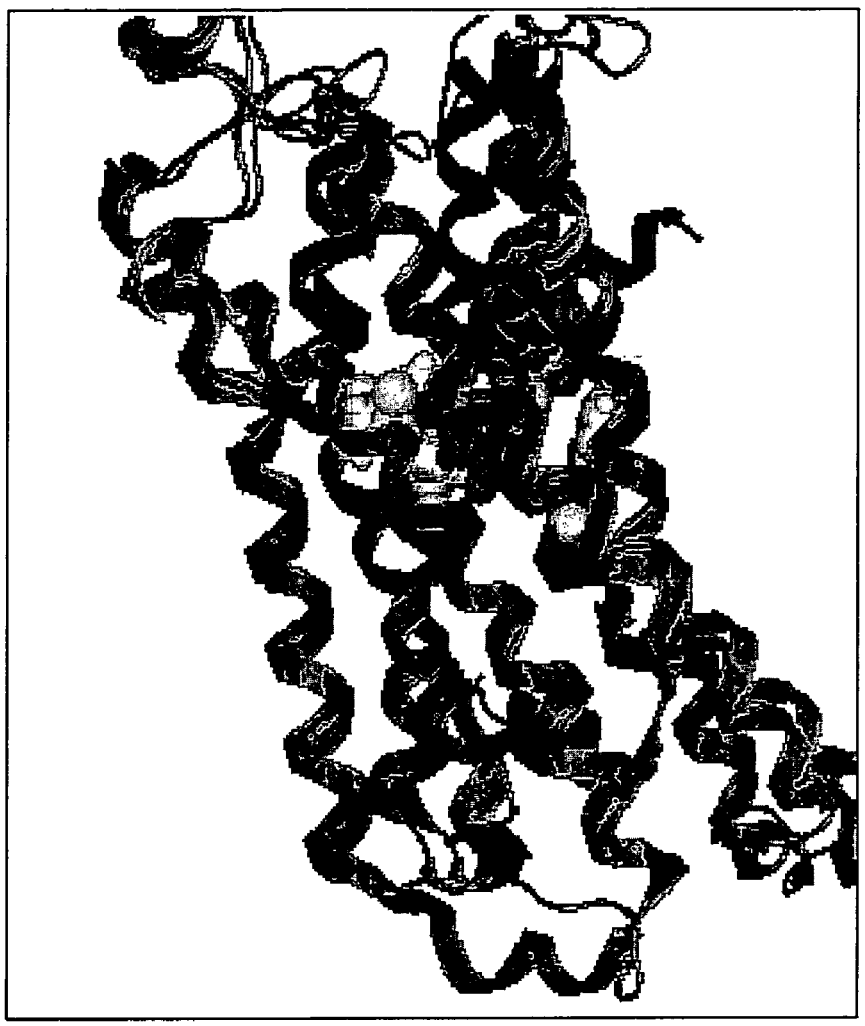
Figure 39E:
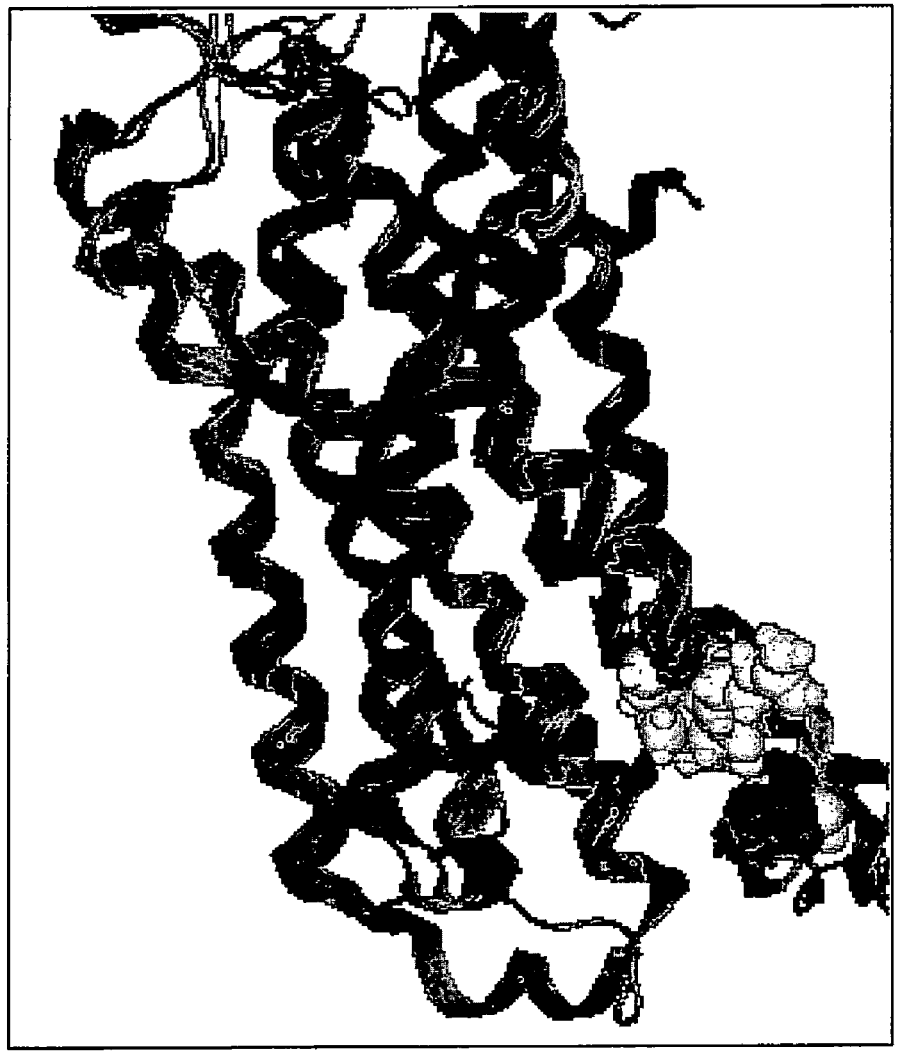
Figure 39F:
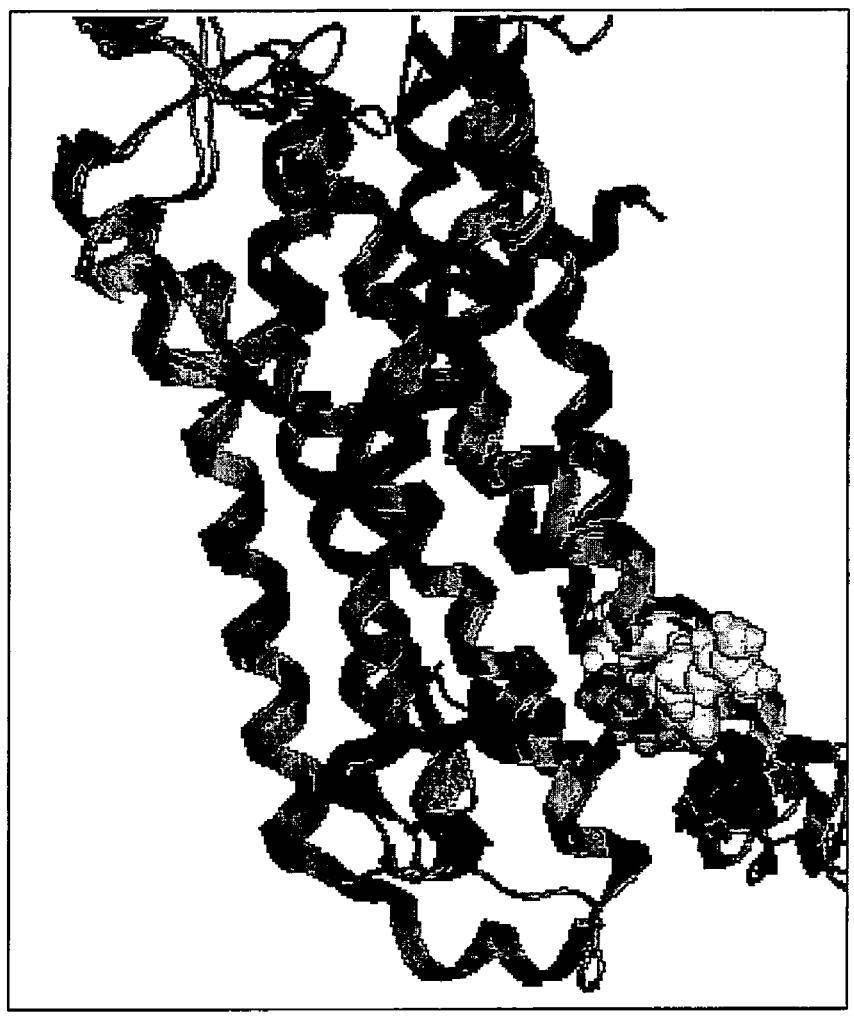
Figure 39G:
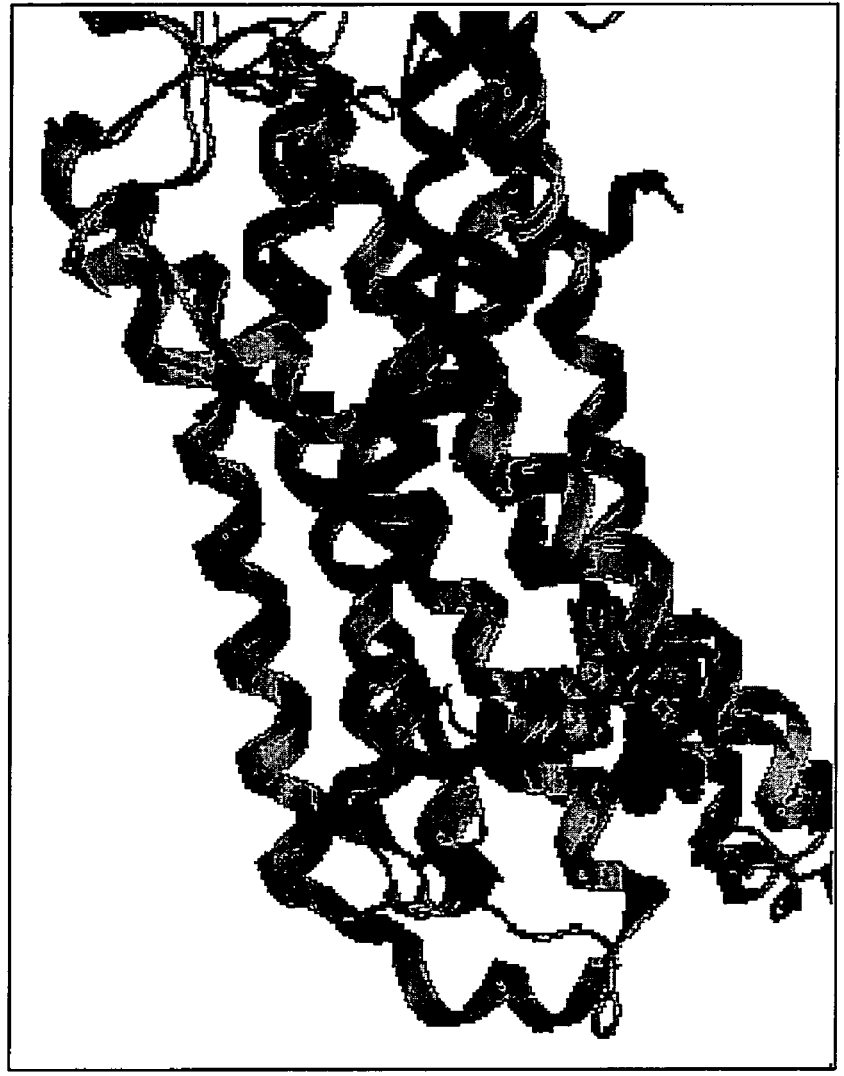
Figure 39H:
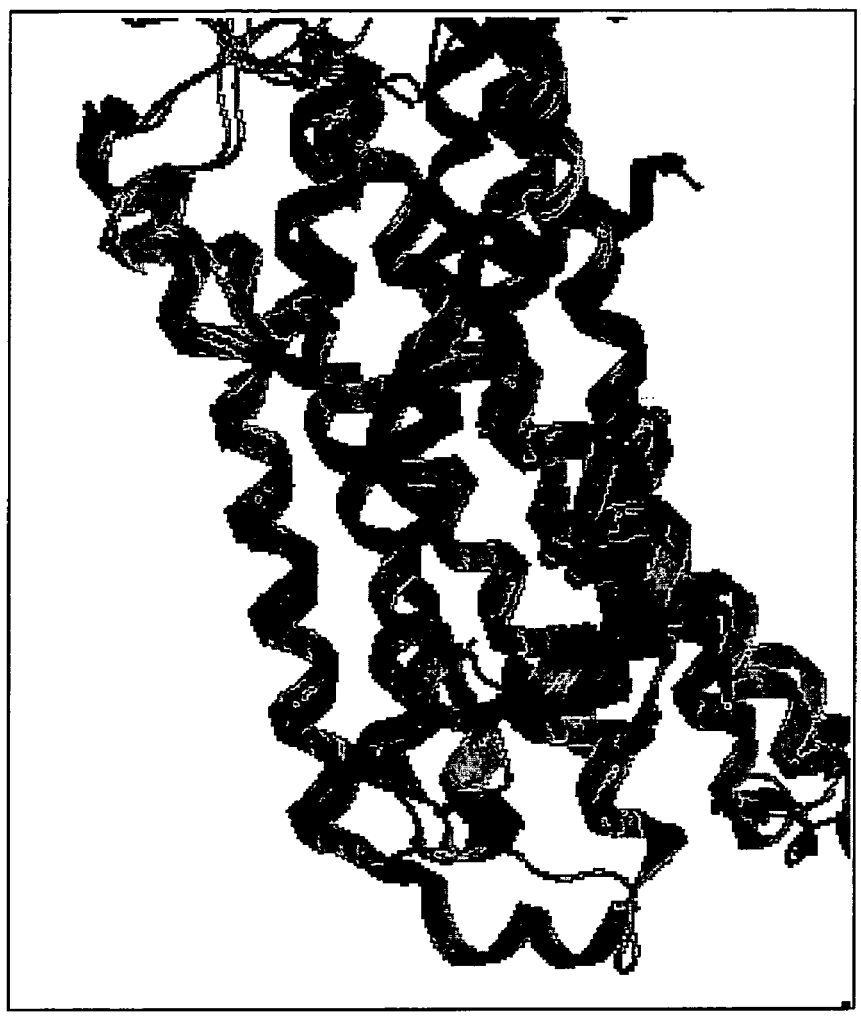
Figure 39I:
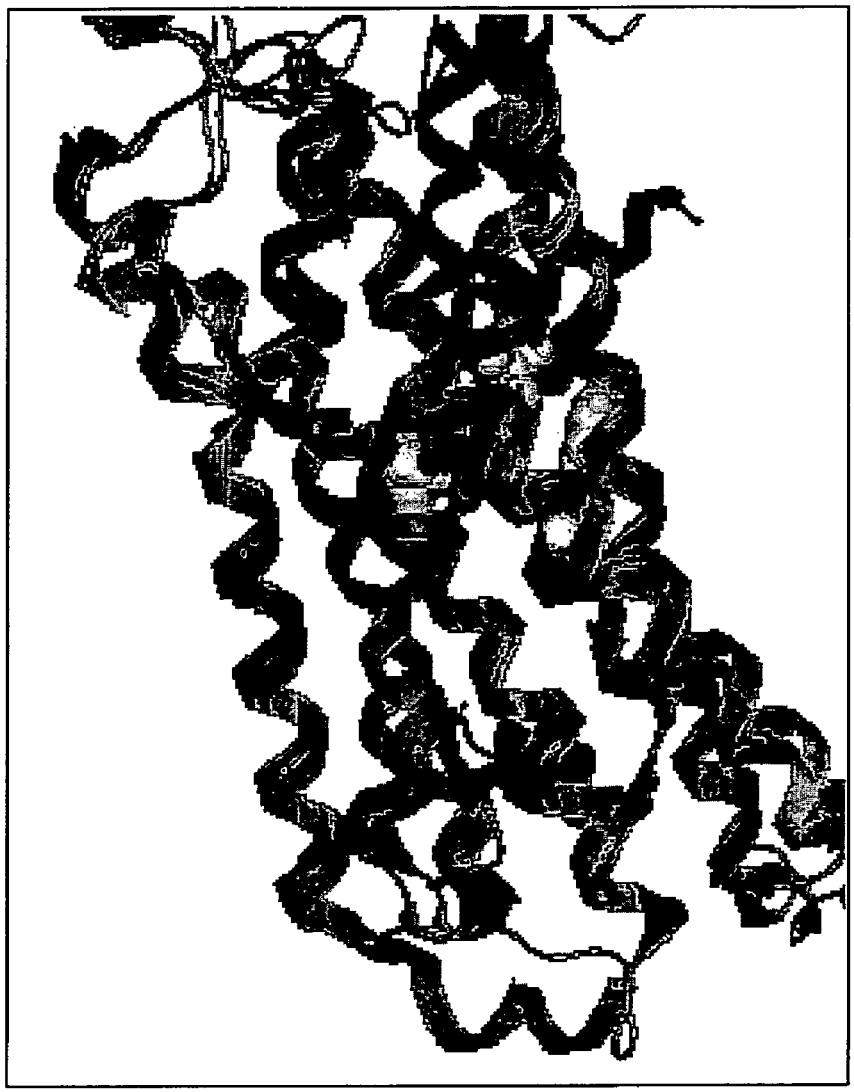
Figure 39J:
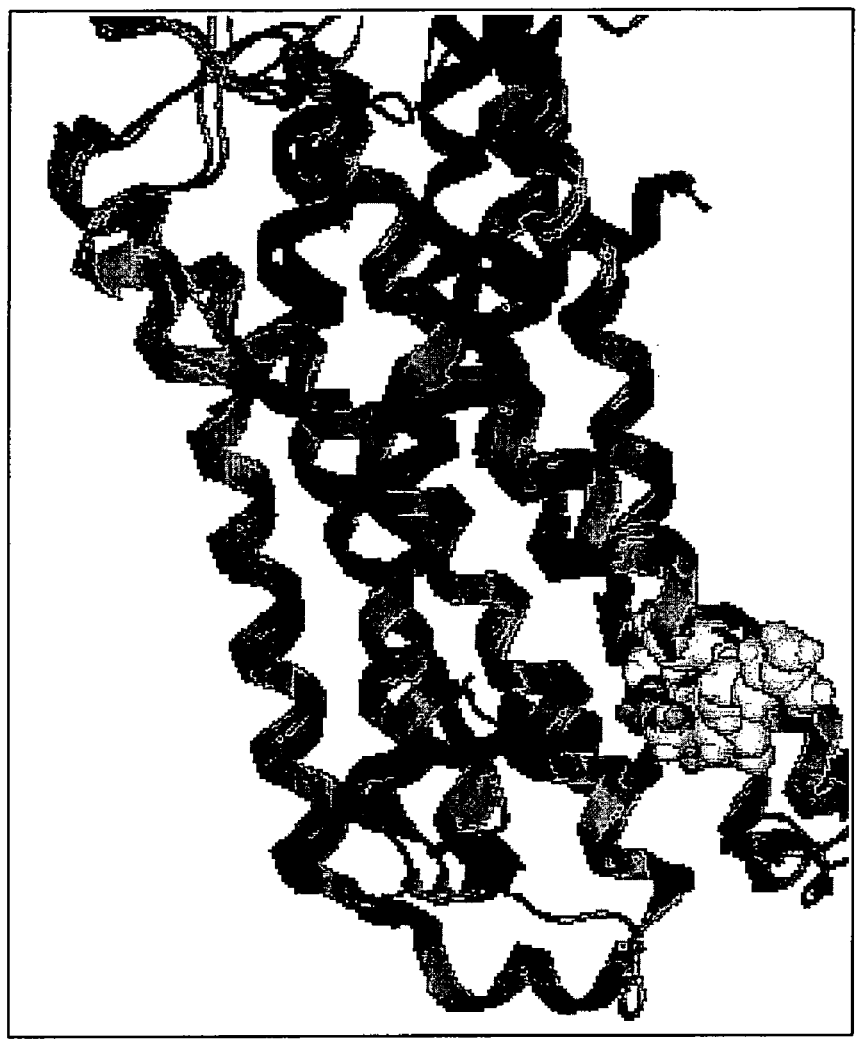
Figure 39K:
Figure 39L:
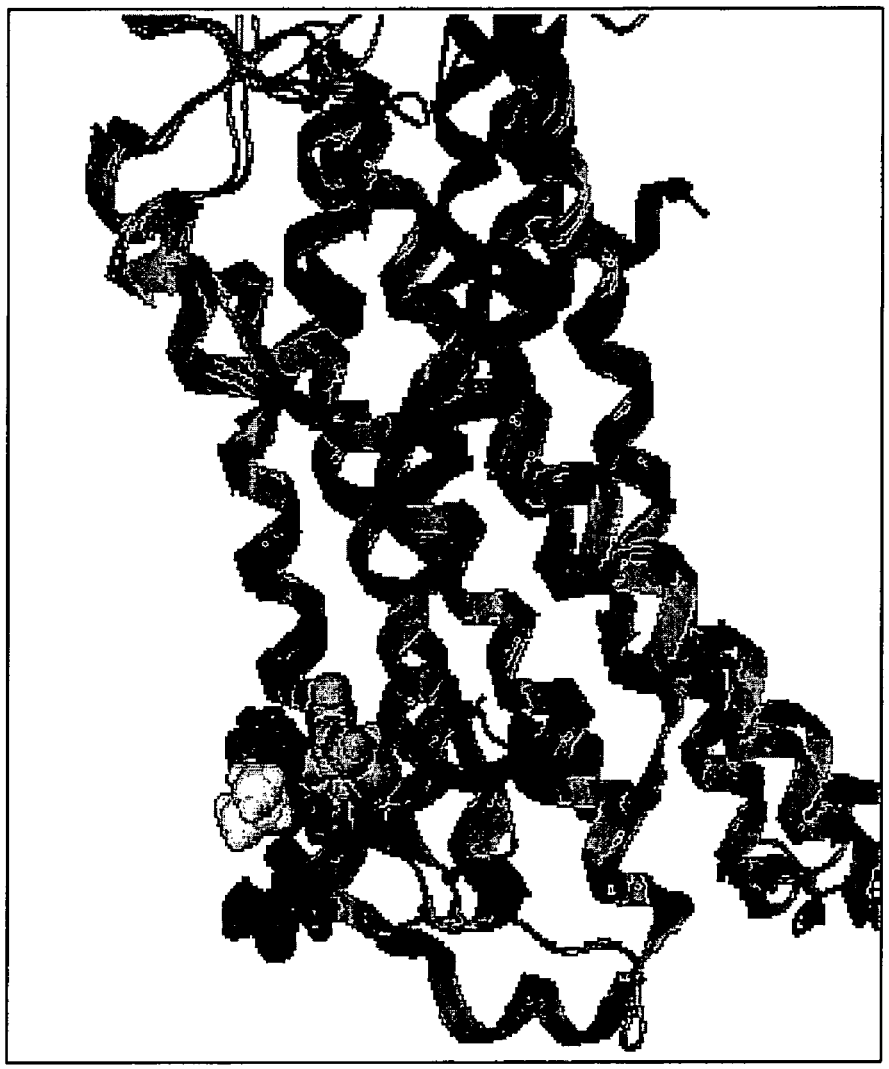
Figure 39M:
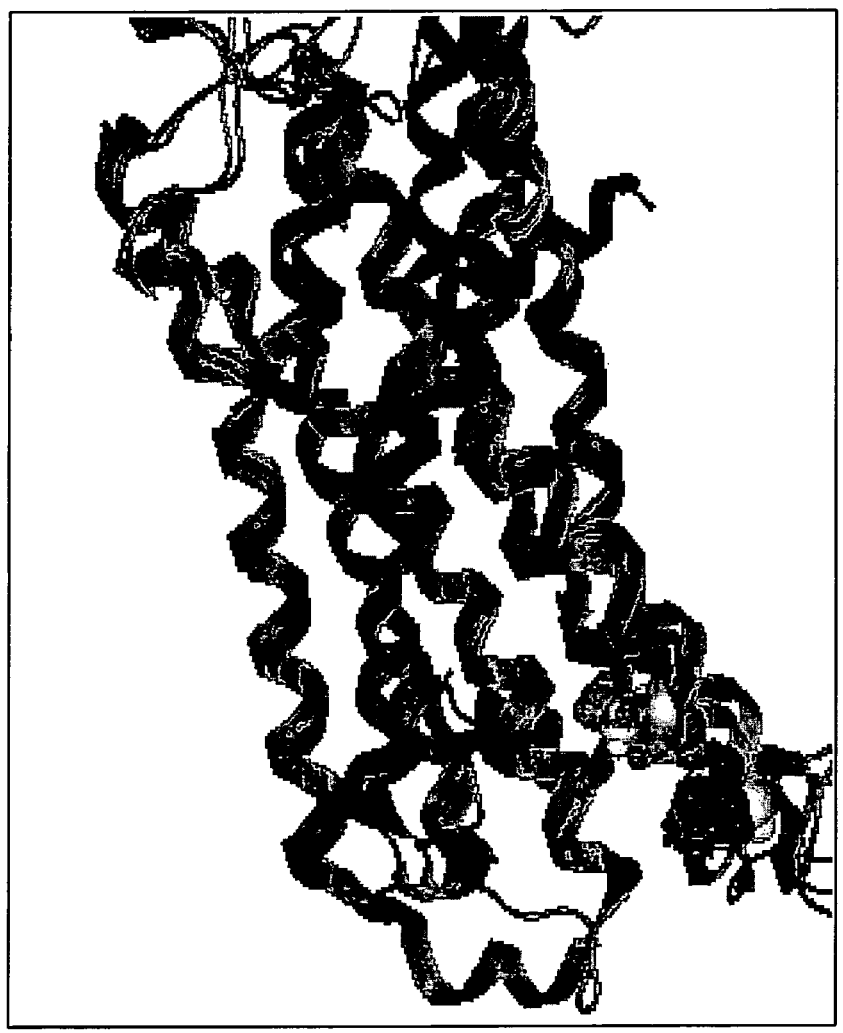

FIG. 38 Sequence and structure based enrichment and coverage statistics. Structure derived datapoints are enclosed within the dark line, whilst sequence derived statistics are enclosed within the light line.

FIGS. 39A-39M (A) Cluster 1. Cluster maps to TM3/5/6 of NTR (red), TM3/5 of B1 (green) and TM6 of A2AA (blue). (B) Cluster 2. Cluster maps to bottom of TM5 NTR (red), B1 (green) and A2AA (blue). (C) Cluster 3. Cluster maps to bottom of TM6 A2AA (blue) and NTR (red). (D) Cluster 4. Cluster maps to TM1/2 and 7 of B1 (green) and TM7 of NTR (red). (E) Cluster 5. Cluster maps to TM5 of B1 (green), NTR (red) and A2AA (blue). (F) Cluster 6. Cluster 6 maps to TM5 of B1 (green), NTR (red) and A2AA (blue). (G) Cluster 7. Cluster maps to TM6 of NTR (red) and A2AA (blue). (H) Cluster 8. Cluster 8 maps to TM6 of NTR (red) and A2AA (blue). (I) Cluster 9. Cluster 9 maps to TM1 and 7 of B1 (green) and TM7 of NTR (red). (J) Cluster 10. Cluster 10 maps to TM5 of NTR (red) and B1 (green). (K) Cluster 11. Cluster 11 maps to TM5 of NTR (red), B1 (green) and A2AA (blue). (L) Cluster 12. Cluster 12 maps to TM4 of B1 (green), A2AA (blue) and M1 (magenta). (M) Cluster 13. Cluster 13 maps to TM5 of B1 (green), A2AA (blue) and NTR (red).

Figure 40:
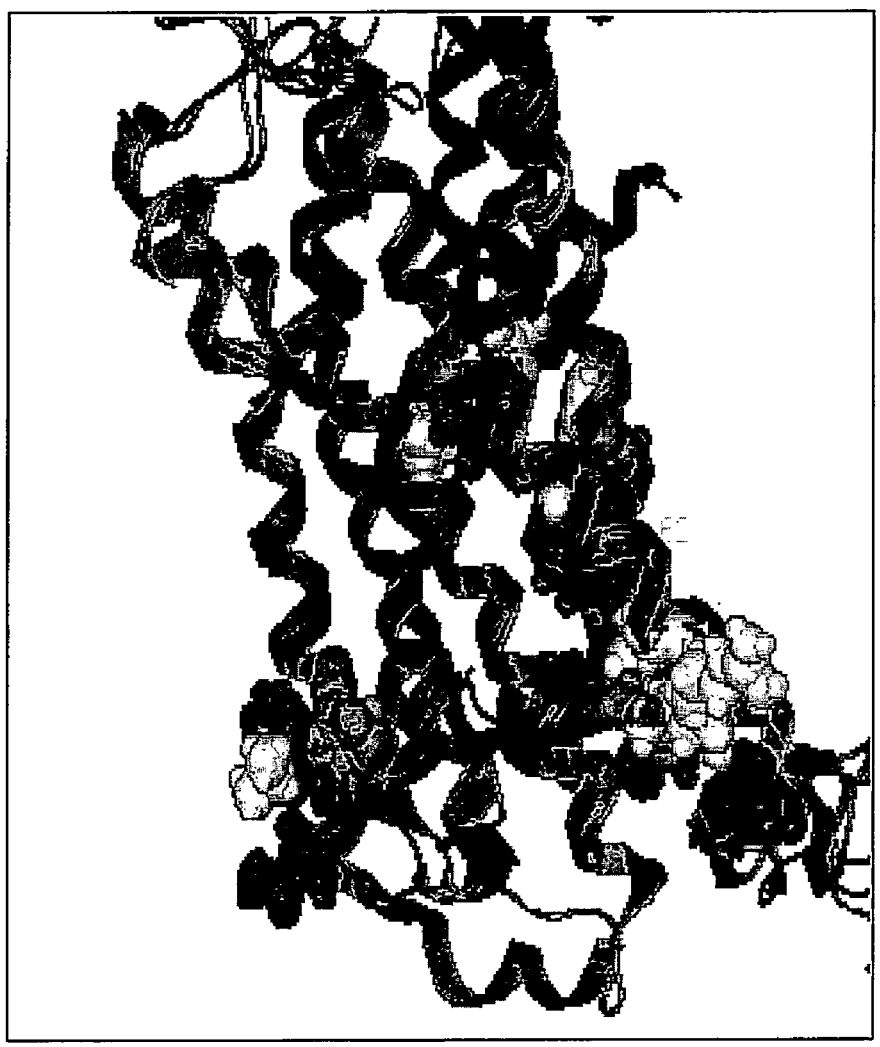

FIG. 40 Shows a superimposition of all the clusters at a 6 A radius.

Figure 41:
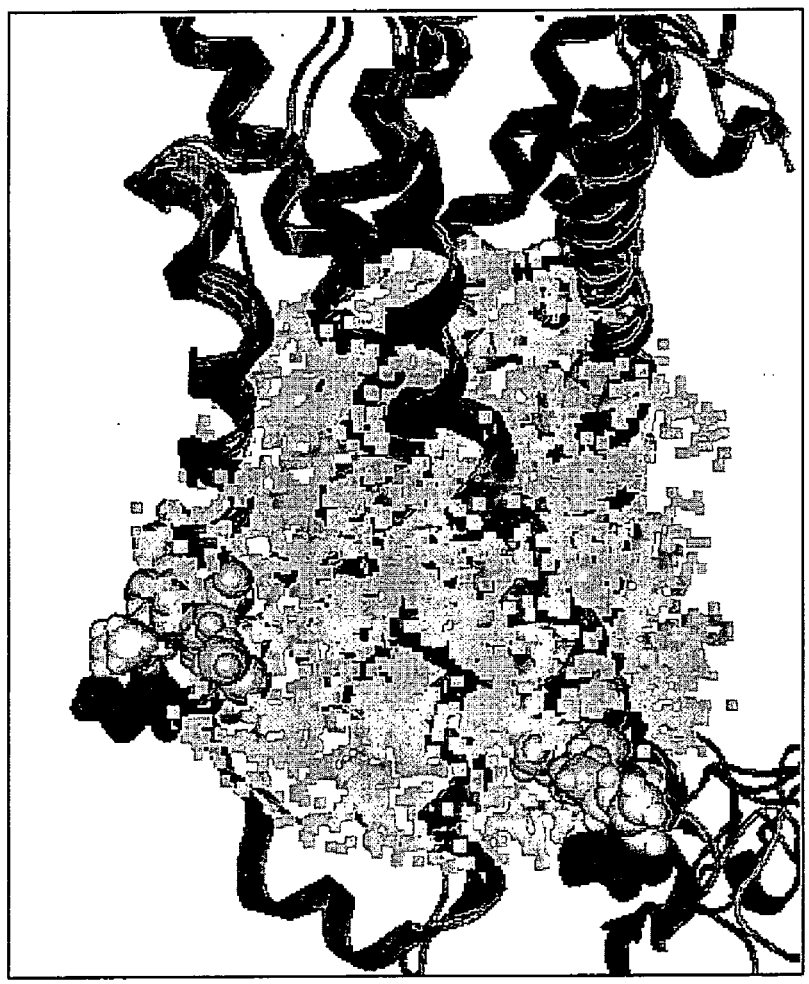

FIG. 41 A proposed cluster of clusters of 15 Å radius covering all statistically significant clusters identified.

DETAILED DESCRIPTION OF THE INVENTION

We have realised that there are two serious problems associated with trying to crystallise GPCRs, namely their lack of stability in detergent and the fact that they exist in multiple conformations. In order to function, GPCRs have evolved to cycle through at least two distinct conformations, the agonist-bound form and the antagonist-bound form, and changes between these two conformations can occur spontaneously in the absence of ligand. It is thus likely that any purified receptors populate a mixture of conformations. Just adding ligands to GPCRs during crystallisation trials has not resulted in their structure determination. To improve the likelihood of crystallisation, we therefore selected mutations that improved the stability of the GPCR and, in addition, preferentially locked the receptor in a specific biologically relevant conformation.

We decided to see whether stabilisation of a GPCR in a particular, biologically relevant conformation was possible and whether the effect was sufficiently great that it would significantly improve the chances of obtaining diffraction-quality crystals. In Example 1, the β1-adrenergic receptor (βAR) from turkey erythrocytes [8] was chosen as a test subject for this study for a number of reasons. The βAR is a G protein-coupled receptor (GPCR) that has well-developed pharmacology with many ligands commercially available and in a radiolabelled form. In addition, overexpression of βAR has been particularly successful using the baculovirus expression system and it can be purified in milligram quantities in a functional form [9]. In Example 2, a human adenosine receptor was used, and in Example 3, a rat neurotensin receptor was used.

Thermostabilising mutations were found to be scattered widely throughout the sequences of the turkey beta1 adrenergic receptor, human adenosine receptor, rat neurotensin receptor and human muscarinic receptor. FIGS. 17A-17C (SEQ ID NOs: 3, 9, 1, 5 and 12) show an alignment of such sequences with the sequence of the human beta-2AR such that when the thermostabilising mutations are positioned onto the sequences then, in 11 instances out of a total of 70, two sequences contain mutations at the same position (denoted in FIGS. 17A-17C (SEQ ID NOs: 3, 9, 1, 5 and 12) with a star). This has been determined to be statistically highly significant (ρ<0.00002). Thus, it will be appreciated that once one or more stabilising mutations have been identified in one GPCR, a further GPCR with increased stability can be generated by aligning the amino acid sequences of the GPCRs and making the same one or more mutations at the corresponding position or positions. This concept is clearly exemplified in FIG. 26 wherein the six thermostabilising mutations in turkey β1-m23 were transferred directly to the human β2 receptor. The resultant mutant, β2-m23, had a Tm 12° C. higher than that of the human β2 receptor.

In addition, we have found that not only are corresponding positions of an aligned sequence of a further GPCR predictive in identifying thermostabilising mutations, but also that windows of amino acids around an identified thermostabilising mutations from aligned sequences are also statistically more likely to contain further thermostabilising mutations when compared to random. This is clearly exemplified in FIG. 33 in which aligned sequences of B1 (SEQ ID NO:1), NTR (SEQ ID NO:9), A2A (SEQ ID NO:5) are shown with thermostabilising mutations marked. Out of 62 mutations, of which 18 are aligned exactly in corresponding positions, a further 31 are aligned within a window of i plus or minus 4 residues where another thermostabilising mutation is in the ith position. This is statistically highly significant (ρ<0.00001).

Thus, it is appreciated that once one or more stabilising mutations have been identified in one GPCR, a further GPCR with increased stability can be generated by aligning the amino acid sequences of the GPCRs and making one or more mutations within the window of amino acids either side of the position that corresponds to the thermostabilising mutation.

Accordingly, a first aspect of the invention provides a method for producing a mutant GPCR with increased stability relative to its parent GPCR, the method comprising:
  (a) identifying in the amino acid sequence of one or more mutants of a first parent GPCR with increased stability relative to the first parent GPCR, the position or positions at which the one or more mutants have at least one different amino acid residue compared to the first parent GPCR, and
  (b) making one or more mutations in the amino acid sequence that defines a second GPCR at the corresponding position or positions, to provide one or more mutants of a second parent GPCR with increased stability relative to the second parent GPCR.

Method for providing one or more mutants of a first parent GPCR with increased stability relative to the first parent GPCR Any method can be used to provide the one or more mutants of a first parent GPCR with increased stability relative to the first parent GPCR, such that its amino acid sequence can be analysed. For example, a stabilised mutant can be selected for and prepared as described below and in the examples.

In particular, a preferred method for selecting a mutant G-protein coupled receptor (GPCR) with increased stability comprises:
  (i) providing one or more mutants of a parent GPCR,
  (ii) selecting a ligand, the ligand being one which binds to the parent GPCR when the GPCR is residing in a particular conformation,
  (iii) determining whether the or each mutant GPCR when residing in the particular conformation has increased stability with respect to binding the selected ligand compared to the stability of the parent GPCR when residing in the same particular conformation with respect to binding that ligand, and (iv) selecting those mutants that have an increased stability compared to the parent GPCR with respect to binding of the selected ligand.

The inventors have appreciated that, in order to improve the likelihood of crystallisation of a GPCR in a biologically relevant form (which is therefore pharmacologically useful), it is desirable not only to increase the stability of the protein, but also for the protein to have this increased stability when in a particular conformation. The conformation is determined by a selected ligand, and is a biologically relevant conformation in particular a pharmacologically relevant conformation. Thus, the mutants of a first parent GPCR which have increased stability are preferably mutants that have increased stability of a particular conformation, for example they may have increased conformational thermostability. The method of the first aspect of the invention may thus be used to create stable, conformationally locked GPCRs by mutagenesis. For example, following the selection of mutant GPCRs which have increased stability in a particular conformation, the position of the stabilising mutations in the amino acid sequence can be identified. Making one or more mutations in the amino acid sequence in another GPCR at the corresponding position or positions can then be used to produce a mutant GPCR with increased stability in a particular conformation relative to its parent GPCR. The mutant GPCRs are effectively purer forms of the parent molecules in that a much higher proportion of them occupies a particular conformational state. The deliberate selection of a chosen receptor conformation resolved from other conformations by use of a ligand (or ligands) that bind preferentially to this conformation is an important feature of the selection method described above. The method of the first aspect of the invention may thus be considered to be a method for producing mutant GPCRs which are more tractable to crystallisation.

In a review of the druggable genome by Hopkins & Groom (2002) *Nature Rev. Drug Discovery* 1, 727-730, Table 1 contains a list of protein families many of which are GPCRs. Overington et al (2006) *Nature Rev. Drug Discovery* 5, 993-996 provides more details of drug targets, and FIG. 1 indicates that more than a quarter of current drugs target GPCRs. There are 52 GPCR targets for orally available drugs out of a total of 186 total targets in this category.

Suitable GPCRs for use in the practice of the invention include, but are not limited to β-adrenergic receptor, adenosine receptor, in particular adenosine $A_{2a}$ receptor, and neurotensin receptor (NTR). Other suitable GPCRs are well known in the art and include those listed in Hopkins & Groom supra. In addition, the International Union of Pharmacology produce a list of GPCRs (Foord et al (2005) *Pharmacol. Rev.* 57, 279-288, incorporated herein by reference and this list is periodically updated at www.iuphar-db.org/GPCR/ReceptorFamiliesForward). It will be noted that GPCRs are divided into different classes, principally based on their amino acid sequence similarities. They are also divided into families by reference to the natural ligands to which they bind. All GPCRs are included in the scope of the invention.

The amino acid sequences (and the nucleotide sequences of the cDNAs which encode them) of many GPCRs are readily available, for example by reference to GenBank. In particular, Foord et al supra gives the human gene symbols and human, mouse and rat gene IDs from Entrez Gene. It should be noted, also, that because the sequence of the human genome is substantially complete, the amino acid sequences of human GPCRs can be deduced therefrom.

Although the GPCR may be derived from any source, it is particularly preferred if it is from a eukaryotic source. It is particularly preferred if it is derived from a vertebrate source such as a mammal or a bird. It is particularly preferred if the GPCR is derived from rat, mouse, rabbit or dog or non-human primate or man, or from chicken or turkey. For the avoidance of doubt, we include within the meaning of "derived from" that a cDNA or gene was originally obtained using genetic material from the source, but that the protein may be expressed in any host cell subsequently. Thus, it will be plain that a eukaryotic GPCR (such as an avian or mammalian GPCR) may be expressed in a prokaryotic host cell, such as *E. coli*, but be considered to be avian- or mammalian-derived, as the case may be.

In some instances, the GPCR may be composed of more than one different subunit. For example, the calcitonin generelated peptide receptor requires the binding of a single transmembrane helix protein (RAMP1) to acquire its physiological ligand binding characteristics. Effector, accessory, auxiliary or GPCR-interacting proteins which combine with the GPCR to form or modulate a functional complex are well known in the art and include, for example, receptor kinases, G-proteins and arrestins (Bockaert et al (2004) *Curr Opinion Drug Discov and Dev* 7, 649-657).

When selecting for a mutant GPCR with increased stability in the selection method described above, the mutants of the parent GPCR may be produced in any suitable way and provided in any suitable form. Thus, for example, a series of specific mutants of the parent protein may be made in which each amino acid residue in all or a part of the parent protein is independently changed to another amino acid residue. For example, it may be convenient to make mutations in those parts of the protein which are predicted to be membrane spanning. The three-dimensional structure of rhodopsin is known (Li et al (2004) *J Mol Biol* 343, 1409-1438; Palczewski et al (2000) *Science* 289, 739-745) as is the structure of human β2-adrenergic receptor (Rasmussen et al (2007) *Nature* 450, 383-387; Cherezov et al (2007) *Science* 318: 1258-65; Rosenbaum et al (2007) *Science* 318:1266-1273), and it is possible to model certain GPCRs using these structures. Thus, conveniently, parts of the GPCR to mutate may be based on modelling. Similarly, computer programs are available which model transmembrane regions of GPCRs based on hydrophobicity (Kyle & Dolittle (1982) *J. Mol. Biol.* 157, 105-132), and use can be made of such models when selecting parts of the protein to mutate. Conventional site-directed mutagenesis may be employed, or polymerase chain reactionbased procedures well known in the art may be used. It is possible, but less desirable, to use ribosome display methods in the selection of the mutant protein.

Typically, each selected amino acid is replaced by Ala (ie Ala-scanning mutagenesis), although it may be replaced by any other amino acid. If the selected amino acid is Ala, it may conveniently be replaced by Leu. Alternatively, the amino acid may be replaced by Gly (ie Gly-scanning mutagenesis), which may allow a closer packing of neighbouring helices that may lock the protein in a particular conformation. If the selected amino acid is Gly, it may conveniently be replaced by Ala.

Although the amino acid used to replace the given amino acid at a particular position is typically a naturally occurring amino acid, typically an "encodeable" amino acid, it may be a non-natural amino acid (in which case the protein is typically made by chemical synthesis or by use of non-natural amino-acyl tRNAs). An "encodeable" amino acid is one which is incorporated into a polypeptide by translation of mRNA. It is also possible to create non-natural amino acids or introduce non-peptide linkages at a given position by covalent chemical modification, for example by post-translational treatment of the protein or semisynthesis. These post-translational modifications may be natural, such as phosphorylation, glycosylation or palmitoylation, or synthetic or biosynthetic.

Alternatively, the mutants may be produced by a random mutagenesis procedure, which may be of the whole protein or of a selected portion thereof. Random mutagenesis procedures are well known in the art.

Conveniently, when selecting for a mutant GPCR with increased stability, the mutant GPCR has one replaced amino acid compared to the parent protein (ie it is mutated at one amino acid position). In this way, the contribution to stability of a single amino acid replacement may be assessed. However, the mutant GPCR assayed for stability may have more than one replaced amino acid compared to the parent protein, such as 2 or 3 or 4 or 5 or 6 replacements.

As is discussed in more detail below, combinations of mutations may be made based on the results of the selection method. It has been found that in some specific cases combining mutations in a single mutant protein leads to a further increase in stability. Thus, it will be appreciated that the selection method can be used in an iterative way by, for example, carrying it out to identify single mutations which increase stability, combining those mutations in a single mutant GPCRs which is the GPCR then provided in part (i) of the method. Thus, multiply-mutated mutant proteins can be selected using the selection method.

When selecting for a mutant GPCR with increased stability, the parent GPCR need not be the naturally occurring protein. Conveniently, it may be an engineered version which is capable of expression in a suitable host organism, such as *Escherichia coli*. For example, as described in Example 1, a convenient engineered version of the turkey β-adrenergic receptor is one which is truncated and lacks residues 1-33 of the amino acid sequence (ie $\beta AR_{34-424}$). The parent GPCR may be a truncated form of the naturally occurring protein (truncated at either or both ends), or it may be a fusion, either to the naturally occurring protein or to a fragment thereof. Alternatively or additionally, the parent GPCR, compared to a naturally-occurring GPCR, may be modified in order to improve, for example, solubility, proteolytic stability (eg by truncation, deletion of loops, mutation of glycosylation sites or mutation of reactive amino acid side chains such as cysteine). In any event, the parent GPCR is a protein that is able to bind to the selected ligand which ligand is one which is known to bind the naturally occurring GPCR. Conveniently, the parent GPCR is one which, on addition of an appropriate ligand, can affect any one or more of the downstream activities which are commonly known to be affected by G-protein activation.

However, it will be appreciated that, when selecting for a mutant GPCR with increased stability, the stability of the mutant is to be compared to a parent in order to be able to assess an increase in stability.

In the selection method, a ligand is selected, the ligand being one which binds to the parent GPCR when residing in a particular conformation. Typically, the ligand will bind to one conformation of the parent GPCR (and may cause the GPCR to adopt this conformation), but does not bind as strongly to another conformation that the GPCR may be able to adopt. Thus, the presence of the ligand may be considered to encourage the GPCR to adopt the particular conformation. Thus, the selection method may be considered to be a way of selecting mutant GPCRs which are trapped in a conformation of biological relevance (eg ligand bound state), and which are more stable with respect to that conformation.

Preferably the particular conformation in which the GPCR resides in step (iii) corresponds to the class of ligand selected in step (ii).

Preferably the selected ligand is from the agonist class of ligands and the particular conformation is an agonist conformation, or the selected ligand is from the antagonist class of ligands and the particular conformation is an antagonist conformation.

Preferably the selected ligand is from the agonist class of ligands and the particular conformation in which the GPCR resides in step (iii) is the agonist conformation.

Preferably, the selected ligand binding affinity for the mutant receptor should be equal to or greater than that for the wild type receptor; mutants that exhibit significantly reduced binding to the selected ligand are typically rejected.

By "ligand" we include any molecule which binds to the GPCR and which causes the GPCR to reside in a particular conformation. The ligand preferably is one which causes more than half of the GPCR molecules overall to be in a particular conformation.

Many suitable ligands are known.

Typically, the ligand is a full agonist and is able to bind to the GPCR and is capable of eliciting a full (100%) biological response, measured for example by G-protein coupling, downstream signalling events or a physiological output such as vasodilation. Thus, typically, the biological response is GDP/GTP exchange in a G-protein, followed by stimulation of the linked effector pathway. The measurement, typically, is GDP/GTP exchange or a change in the level of the end product of the pathway (eg cAMP, cGMP or inositol phosphates). The ligand may also be a partial agonist and is able to bind to the GPCR and is capable of eliciting a partial (<100%) biological response.

The ligand may also be an inverse agonist, which is a molecule which binds to a receptor and reduces its basal (ie unstimulated by agonist) activity sometimes even to zero.

The ligand may also be an antagonist, which is a molecule which binds to a receptor and blocks binding of an agonist, so preventing a biological response. Inverse agonists and partial agonists may under certain assay conditions be antagonists.

The above ligands may be orthosteric, by which we include the meaning that they combine with the same site as the endogenous agonist; or they may be allosteric or allotopic, by which we include the meaning that they combine with a site distinct from the orthosteric site. The above ligands may be syntopic, by which we include the meaning that they interact with other ligand(s) at the same or an overlapping site. They may be reversible or irreversible.

In relation to antagonists, they may be surmountable, by which we include the meaning that the maximum effect of agonist is not reduced by either pre-treatment or simultaneous treatment with antagonist; or they may be insurmountable, by which we include the meaning that the maximum effect of agonist is reduced by either pre-treatment or simultaneous treatment with antagonist; or they may be neutral, by which we include the meaning the antagonist is one without inverse agonist or partial agonist activity. Antagonists typically are also inverse agonists.

Ligands for use in the selection method may also be allosteric modulators such as positive allosteric modulators, potentiators, negative allosteric modulators and inhibitors. They may have activity as agonists or inverse agonists in their own right or they may only have activity in the presence of an agonist or inverse agonist in which case they are used in combination with such molecules in order to bind to the GPCR.

Neubig et al (2003) *Pharmacol. Rev.* 55, 597-606, incorporated herein by reference, describes various classes of ligands.

Preferably, the above-mentioned ligands are small organic or inorganic moieties, but they may be peptides or polypeptides. Typically, when the ligand is a small organic or organic moiety, it has a $M_r$ of from 50 to 2000, such as from 100 to 1000, for example from 100 to 500.

Typically, the ligand binds to the GPCR with a $K_d$ of from mM to pM, such as in the range of from μM (micromolar) to nM. Generally, the ligands with the lowest Kd are preferred.

Small organic molecule ligands are well known in the art, for example see the Examples below. Other small molecule ligands include 5HT which is a full agonist at the 5HT1A receptor; eltoprazine which is a partial agonist at the 5HT1A receptor (see Newman-Tancredi et al (1997) *Neurophamacology* 36, 451-459); (+)-butaclamol and spiperone are dopamine D2 receptor inverse agonists (see Roberts & Strange (2005) *Br. J. Pharmacol.* 145, 34-42); and WIN55212-3 is a neutral antagonist of CB2 (Savinainen et al (2005) *Br. J. Pharmacol.* 145, 636-645).

The ligand may be a peptidomimetic, a nucleic acid, a peptide nucleic acid (PNA) or an aptamer. It may be an ion such as $Na^+$ or $Zn^{2+}$, a lipid such as oleamide, or a carbohydrate such as heparin.

The ligand may be a polypeptide which binds to the GPCR. Such polypeptides (by which we include oligopeptides) are typically from $M_r$ 500 to $M_r$ 50,000, but may be larger. The polypeptide may be a naturally occurring GPCR-interacting protein or other protein which interacts with the GPCR, or a derivative or fragment thereof, provided that it binds selectively to the GPCR in a particular conformation. GPCR-interacting proteins include those associated with signalling and those associated with trafficking, which often act via PDZ domains in the C terminal portion of the GPCR.

Polypeptides which are known to bind certain GPCRs include any of a G protein, an arrestin, a RGS protein, G protein receptor kinase, a RAMP, a 14-3-3 protein, a NSF, a periplakin, a spinophilin, a GPCR kinase, a receptor tyrosine kinase, an ion channel or subunit thereof, an ankyrin and a Shanks or Horner protein. Other polypeptides include NMDA receptor subunits NR1 or NR2a calcyon, or a fibronectin domain framework. The polypeptide may be one which binds to an extracellular domain of a GPCR, such as fibulin-1. The polypeptide may be another GPCR, which binds to the selected GPCR in a hetero-oligomer. A review of protein-protein interactions at GPCRs is found in Milligan & White (2001) *Trends Pharmacol. Sci.* 22, 513-518, or in Bockaert et al (2004) *Curr. Opinion Drug Discov. Dev.* 7, 649-657 incorporated herein by reference.

The polypeptide ligand may conveniently be an antibody which binds to the GPCR. By the term "antibody" we include naturally-occurring antibodies, monoclonal antibodies and fragments thereof. We also include engineered antibodies and molecules which are antibody-like in their binding characteristics, including single chain Fv (scFv) molecules and domain antibodies (dAbs). Mention is also made of camelid antibodies and engineered camelid antibodies. Such molecules which bind GPCRs are known in the art and in any event can be made using well known technology. Suitable antibodies include ones presently used in radioimmunoassay (RIAs) for GPCRs since they tend to recognise conformational epitopes.

The polypeptide may also be a binding protein based on a modular framework, such as ankyrin repeat proteins, armadillo repeat proteins, leucine rich proteins, tetratriopeptide repeat proteins or Designed Ankyrin Repeat Proteins (DARPins) or proteins based on lipocalin or fibronectin domains or Affilin scaffolds based on either human gamma crystalline or human ubiquitin.

In one embodiment of the invention, the ligand is covalently joined to the GPCR, such as a G-protein or arrestin fusion protein. Some GPCRs (for example thrombin receptor) are cleaved N-terminally by a protease and the new N-terminus binds to the agonist site. Thus, such GPCRs are natural GPCR-ligand fusions.

It will be appreciated that the use of antibodies, or other "universal" binding polypeptides (such as G-proteins which are known to couple with many different GPCRs) may be particularly advantageous in the use of the method on "orphan" GPCRs for which the natural ligand, and small molecule ligands, are not known.

Once the ligand has been selected in the selection method, it is then determined whether the or each mutant GPCR has increased stability with respect to binding the selected ligand compared to the parent GPCR with respect to binding that ligand. It will be appreciated that this step (iii) is one in which it is determined whether the or each mutant GPCR has an increased stability (compared to its parent) for the particular conformation which is determined by the selected ligand. Thus, the mutant GPCR has increased stability with respect to binding the selected ligand as measured by ligand binding or whilst binding the selected ligand. As is discussed below, it is particularly preferred if the increased stability is assessed whilst binding the selected ligand.

The increased stability is conveniently measured by an extended lifetime of the mutant under the imposed conditions which may lead to instability (such as heat, harsh detergent conditions, chaotropic agents and so on). Destabilisation under the imposed condition is typically determined by measuring denaturation or loss of structure. As is discussed below, this may manifest itself by loss of ligand binding ability or loss of secondary or tertiary structure indicators.

Figure 12:
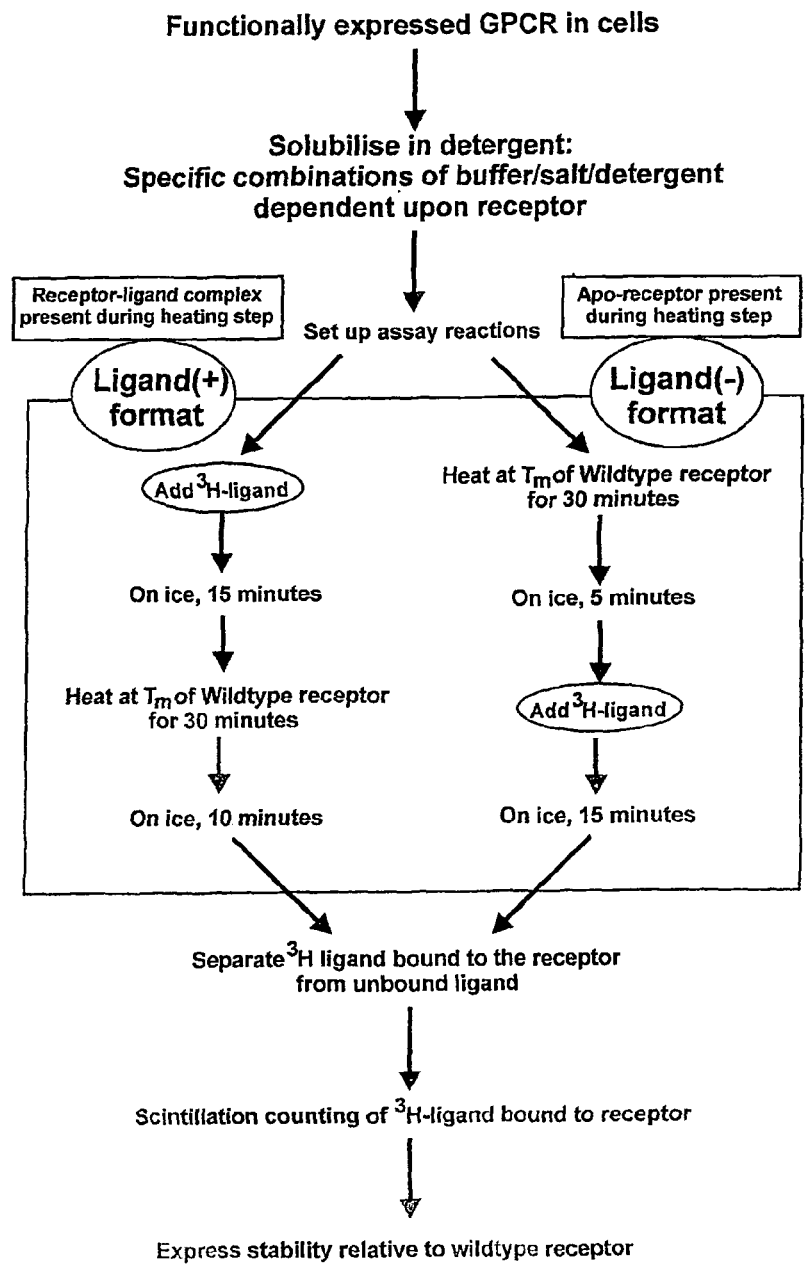
FIG. 12 Flow chart showing the two different assay formats of ligand (+) and ligand (−) used to determine receptor thermostablity.
Figure 13A:
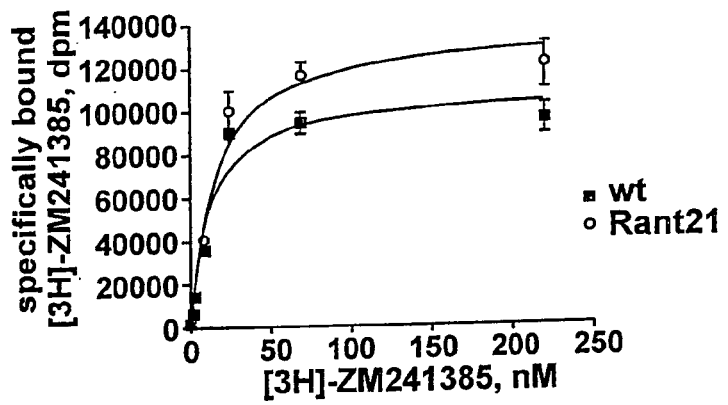
FIGS. 13A-13F Pharmacological profile of thermostable mutant adenosine A2a receptor, Rant21. Saturation binding of (A) antagonist and (B) agonist to solubilised receptors. (C-F) Inhibition of [$^3$H]ZM241385 binding by increasing concentrations of antagonists (C) XAC and (D) Theophylline, and agonists (E) NECA and (F) R-PIA; binding of [$^3$H] ZM241385 (10 nM) in the absence of unlabelled ligand was set to 100%. Each solubilised receptor was incubated with ligands for one hour on ice in binding buffer (50 mM Tris pH7.5 and 0.025% DDM) containing 400 mM NaCl (A, C-F). Data shown are from two independent experiments with each data point measured in triplicate. $K_D$ and $K_i$ values are given in Table (iii).
Figure 13B:
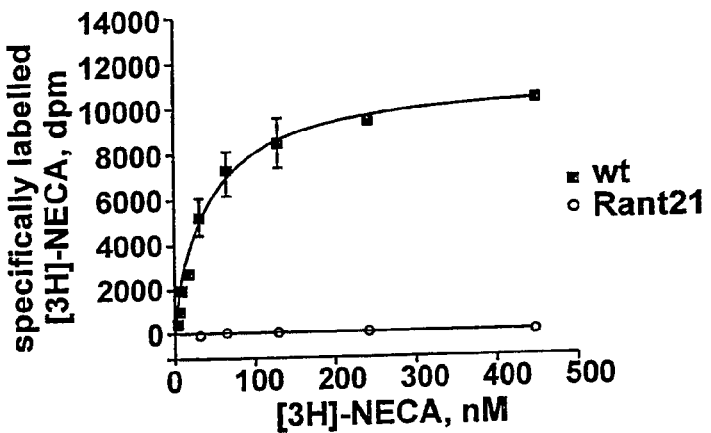
Figure 13C:
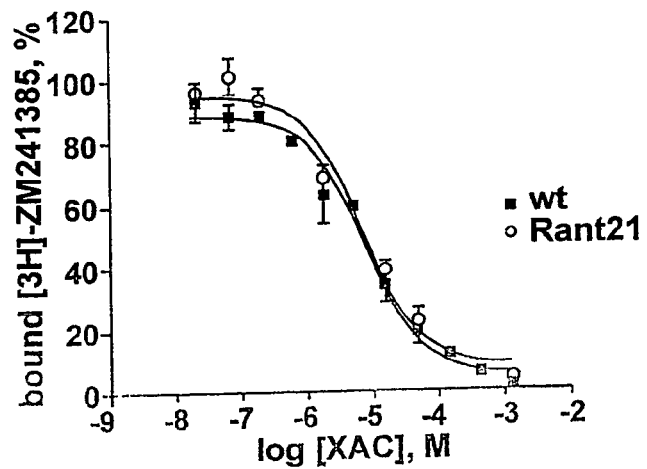
Figure 13D:
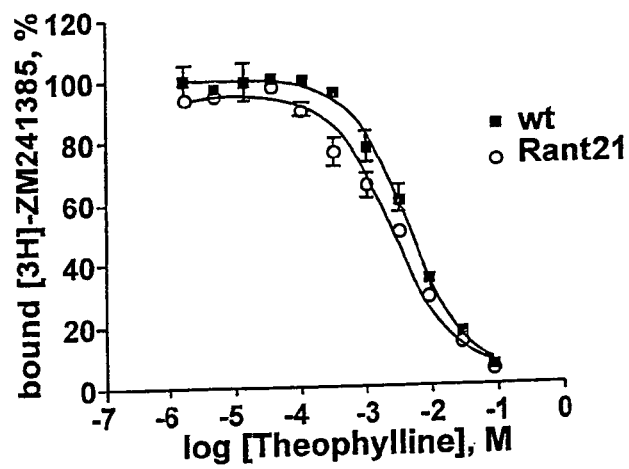
Figure 13E:
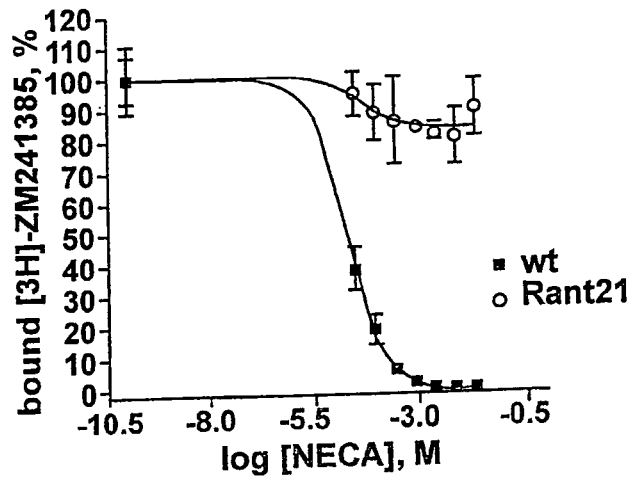
Figure 13F:
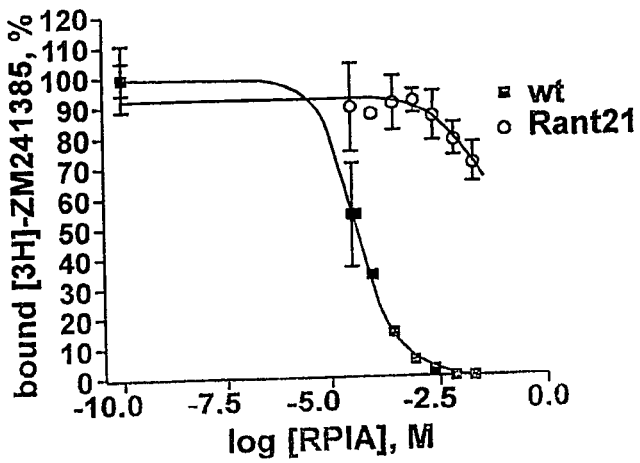
Figure 14A:
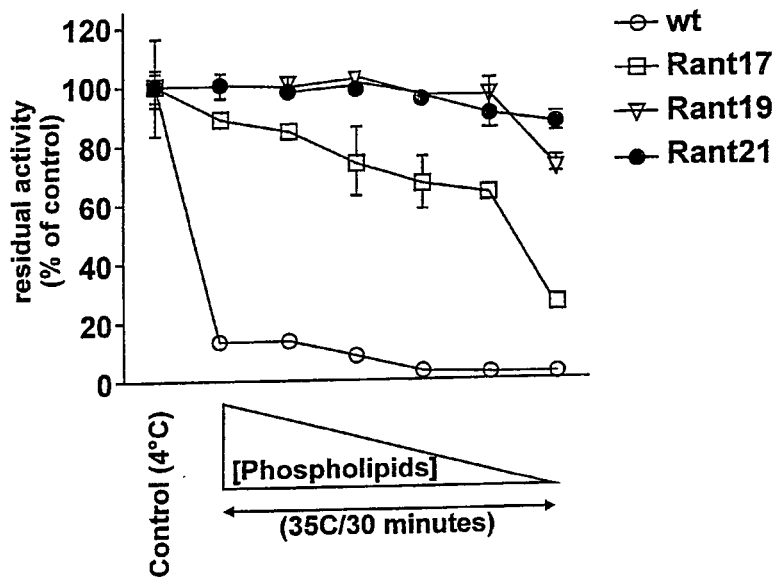
FIGS. 14A and 14B Thermostable mutants show a decreased dependence on lipids (A) and an increased survival at higher concentration of DDM (B) upon heating compared to the wild-type receptor. Receptors were solubilised in 1% DDM (diluted in 50 mM Tris pH7.5 and 400 mM NaCl) and immobilised on Ni-NTA agarose for the IMAC step.
Figure 14B:
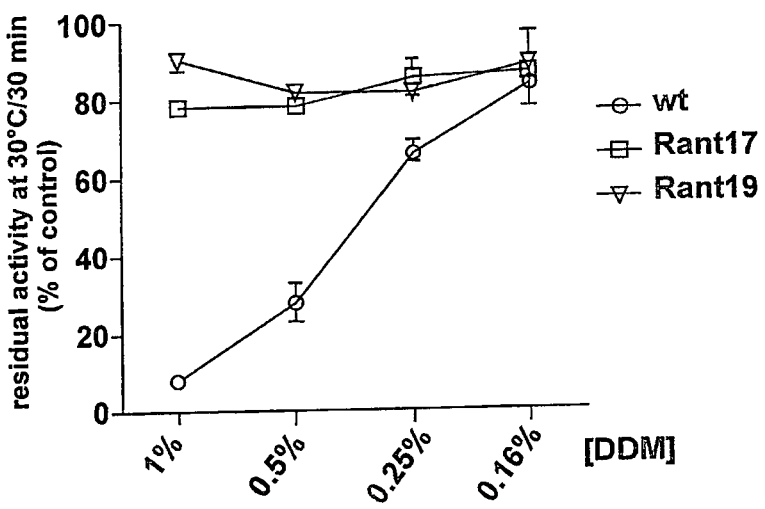

As is described with respect to FIG. 12 below (which depicts a particular, preferred embodiment), there are different assay formats which may be used to determine stability of the mutant GPCR.

In one embodiment the mutant GPCR may be brought into contact with a ligand before being subjected to a procedure in which the stability of the mutant is determined (the mutant GPCR and ligand remaining in contact during the test period). Thus, for example, when the method is being used to select for mutant GPCRs which in one conformation bind to a ligand and which have improved thermostablity, the receptor is contacted with the ligand before being heated, and then the amount of ligand bound to the receptor following heating may be used to express thermostability compared to the parent receptor. This provides a measure of the amount of the GPCR which retains ligand binding capacity following exposure to the denaturing conditions (eg heat), which in turn is an indicator of stability.

In an alternative (but less preferred) embodiment, the mutant GPCR is subjected to a procedure in which the stability of the mutant is determined before being contacted with the ligand. Thus, for example, when the method is being used to select for mutant membrane receptors which in one conformation bind to a ligand and which have improved thermo-stability, the receptor is heated first, before being contacted with the ligand, and then the amount of ligand bound to the receptor may be used to express thermostability. Again, this provides a measure of the amount of the GPCR which retains ligand binding capacity following exposure to the denaturing conditions.

In both embodiments, it will be appreciated that the comparison of stability of the mutant is made by reference to the parent molecule under the same conditions.

It will be appreciated that in both of these embodiments, the mutants that are selected are ones which have increased stability when residing in the particular conformation compared to the parent protein residing in the same particular conformation.

The preferred route may be dependent upon the specific GPCR, and will be dependent upon the number of conformations accessible to the protein in the absence of ligand. In the embodiment described in FIG. 12, it is preferred if the ligand is present during the heating step because this increases the probability that the desired conformation is selected.

From the above, it will be appreciated that the selection method includes a method for selecting a mutant GPCR with increased thermostability, the method comprising (i) providing one or more mutants of a parent GPCR, (ii) selecting an antagonist or an agonist which binds the parent GPCR, (iii) determining whether the or each mutant has increased thermostability when in the presence of the said antagonist or agonist by measuring the ability of the mutant GPCR to bind the selected said antagonist or agonist at a particular temperature and after a particular time compared to the parent GPCR and (iv) selecting those mutant GPCRs that bind more of the selected said antagonist or agonist at the particular temperature and after the particular time than the parent GPCR under the same conditions. In step (iii), a fixed period of time at the particular temperature is typically used in measuring the ability of the mutant GPCR to bind the selected said antagonist or agonist. In step (iii), typically a temperature and a time is chosen at which binding of the selected said antagonist or agonist by the parent GPCR is reduced by 50% during the fixed period of time at that temperature (which is indicative that 50% of the receptor is inactivated; "quasi" Tm).

Conveniently, when the ligand is used to assay the GPCR (ie used to determine if it is in a non-denatured state), the ligand is detectably labelled, eg radiolabelled or fluorescently labelled. In another embodiment, ligand binding can be assessed by measuring the amount of unbound ligand using a secondary detection system, for example an antibody or other high affinity binding partner covalently linked to a detectable moiety, for example an enzyme which may be used in a colorimetric assay (such as alkaline phosphatase or horseradish peroxidase). FRET methodology may also be used. It will be appreciated that the ligand used to assay the mutant GPCR in determining its stability need not be the same ligand as selected in step (ii) of the method, but must be a member of the same ligand class eg agonist or antagonist, such that the same receptor conformational class is being measured.

Although it is convenient to measure the stability of the parent and mutant GPCR by using the ability to bind a ligand as an indicator of the presence of a non-denatured protein, other methods are known in the art. For example, changes in fluorescence spectra, can be a sensitive indicator of unfolding, either by use of intrinsic tryptophan fluorescence or the use of extrinsic fluorescent probes such as 1-anilino-8-napthaleneulfonate (ANS), for example as implemented in the Thermofluor™ method (Mezzasalma et al, J Biomol Screening, 2007, April; 12(3):418-428). Proteolytic stability, deuterium/hydrogen exchange measured by mass spectrometry, blue native gels, capillary zone electrophoresis, circular dichroism (CD) spectra and light scattering may also be used to measure unfolding by loss of signals associated with secondary or tertiary structure. However, all these methods require the protein to be purified in reasonable quantities before they can be used (eg high pmol/nmol quantities), whereas the method described in the Examples makes use of pmol amounts of essentially unpurified GPCR.

In a preferred embodiment, in step (ii) two or more ligands of the same class are selected, the presence of each causing the GPCR to reside in the same particular conformation. Thus, in this embodiment, one or more ligands (whether natural or non-natural) of the same class (eg full agonist or partial agonist or antagonist or inverse agonist) may be used. Including multiple ligands of the same class in this process, whether in series or in parallel, minimises the theoretical risk of inadvertently engineering and selecting multiply mutated receptor conformations substantially different to the parent, for example in their binding site, but still able, due to compensatory changes, to bind ligand. The following steps may be used to mitigate this risk:

1. Select a chemically distinct set (eg n=2-5) of ligands, in a common pharmacological class as evidenced by for example a binding or functional or spectroscopic assay. These ligands should be thought to bind to a common spatial region of the receptor, as evidenced for example by competitive binding studies using wild type and/or mutated receptors, and/or by molecular modelling, although they will not necessarily express a common pharmacophore.

2. Make single or multiple receptor mutants intended to increase stability, and assay for tight binding using the full set of ligands. The assays can be parallelised, multiplexed or run in series.

3. Confirm authenticity of stabilised receptor mutant by measurement for example of the binding isotherm for each ligand, and by measurement of the stability shift with ligand (the window should typically be narrowed compared to wild type).

In order to guard against changes in apparent affinity caused by perturbations to the binding site upon mutation, preferably ligands of the same pharmacological class, but different chemical class, should be used to profile the receptor. These should typically show similar shifts in affinity (mutant versus parent, e.g. wild type) in spite of having different molecular recognition properties. Binding experiments should preferably be done using labelled ligand within the same pharmacological class.

Nonetheless it should be recognised that conformational substrates may exist that are specific to chemical classes of ligand within the same pharmacological class, and these may be specifically stabilised in the procedure depending on the chemical class of the selected ligand.

Typically the selected ligand binds to the mutant GPCR with a similar potency to its binding to the parent GPCR. Typically, the $K_d$ values for the particular ligand binding the mutant GPCR and the parent GPCR are within 5-10 fold of each other, such as within 2-3 fold. Typically, the binding of the ligand to the mutant GPCR compared to the parent GPCR would be not more than 5 times weaker and not more than 10 times stronger.

Typically, mutant receptors which have been stabilised in the selected conformation should bind the selected ligand with approximately equal affinity (that is to say typically within 2-3 fold) or greater affinity than does the parent receptor. For agonist-conformation mutants, the mutants typically bind the agonists with the same or higher affinity than the parent GPCR and typically bind antagonists with the same or lower affinity than the parent GPCR. Similarly for antagonist-conformation mutants, the mutants typically bind the antagonists with the same or higher affinity than the parent GPCR and typically bind agonists with the same or lower affinity than the parent GPCR. Mutants that exhibit a significant reduction (typically greater than 2-3 fold) in affinity for the selecting ligand are typically rejected.

Typically, the rank order of binding of a set of ligands of the same class are comparable, although there may be one or two reversals in the order, or there may be an out-lier from the set.

In a further embodiment, two or more ligands that bind simultaneously to the receptor in the same conformation may be used, for example an allosteric modulator and orthosteric agonist.

For the avoidance of doubt, and as is evident from the Examples, it is not necessary to use multiple ligands for the method to be effective.

In a further embodiment of the selection method, it may be advantageous to select those mutant GPCRs which, while still being able to bind the selected ligand, are not able to bind, or bind less strongly than the parent GPCR, a second selected ligand which is in a different class to the first ligand. Thus, for example, the mutant GPCR may be one that is selected on the basis that it has increased stability with respect to binding a selected antagonist, but the mutant GPCR so selected is further tested to determine whether it binds to a full agonist (or binds less strongly to a full agonist than its parent GPCR). Mutants are selected which do not bind (or have reduced binding of) the full agonist. In this way, further selection is made of a GPCR which is locked into one particular conformation.

It will be appreciated that the selected ligand (with respect to part (ii) of the method) and the further (second) ligand as discussed above, may be any pair of ligand classes, for example: antagonist and full agonist; full agonist and antagonist; antagonist and inverse agonist; inverse agonist and antagonist; inverse agonist and full agonist; full agonist and inverse agonist; and so on.

It is preferred that the mutant receptor binds the further (second) ligand with an affinity which is less than 50% of the affinity the parent receptor has for the same further (second) ligand, more preferably less than 10% and still more preferably less than 1% or 0.1% or 0.01% of affinity for the parent receptor. Thus, the $K_d$ for the interaction of the second ligand with mutant receptor is higher than for the parent receptor. As is shown in Example 1, the mutant β-adrenergic receptor βAR-m23 (which was selected by the method of the invention using an antagonist) binds an agonist 3 orders of magnitude more weakly than its parent (ie $K_d$ is 1000× higher). Similarly, in Example 2, the mutant adenosine A2a receptor Rant21 binds agonist 2-4 orders of magnitude more weakly than its parent.

This type of counter selection is useful because it can be used to direct the mutagenesis procedure more specifically (and therefore more rapidly and more efficiently) along a pathway towards a pure conformation as defined by the ligand.

Preferably, the mutant GPCR in the selection method is provided in a suitable solubilised form in which it maintains structural integrity and is in a functional form (e.g is able to bind ligand). An appropriate solubilising system, such as a suitable detergent (or other amphipathic agent) and buffer system is used, which may be chosen by the person skilled in the art to be effective for the particular protein. Typical detergents which may be used include, for example, dodecylmaltoside (DDM) or CHAPS or octylglucoside (OG) or many others. It may be convenient to include other compounds such as cholesterol hemisuccinate or cholesterol itself or heptane-1,2,3-triol. The presence of glycerol or proline or betaine may be useful. It is important that the GPCR, once solubilised from the membrane in which it resides, must be sufficiently stable to be assayed. For some GPCRs, DDM will be sufficient, but glycerol or other polyols may be added to increase stability for assay purposes, if desired. Further stability for assay purposes may be achieved, for example, by solubilising in a mixture of DDM, CHAPS and cholesterol hemisuccinate, optionally in the presence of glycerol. For particularly unstable GPCRs, it may be desirable to solubilise them using digitonin or amphipols or other polymers which can solubilise GPCRs directly from the membrane, in the absence of traditional detergents and maintain stability typically by allowing a significant number of lipids to remain associated with the GPCR. Nanodiscs may also be used for solubilising extremely unstable membrane proteins in a functional form.

Typically, the mutant GPCR in the selection method is provided in a crude extract (eg of the membrane fraction from the host cell in which it has been expressed, such as *E. coli*). It may be provided in a form in which the mutant protein typically comprises at least 75%, more typically at least 80% or 85% or 90% or 95% or 98% or 99% of the protein present in the sample. Of course, it is typically solubilised as discussed above, and so the mutant GPCR is usually associated with detergent molecules and/or lipid molecules.

The mutant GPCR of the first parent GPCR may be one which has increased stability to any denaturant or denaturing condition such as to any one or more of heat, a detergent, a chaotropic agent or an extreme of pH.

In relation to an increased stability to heat (ie thermostability), this can readily be determined by measuring ligand binding or by using spectroscopic methods such as fluorescence, CD or light scattering at a particular temperature. Typically, when the GPCR binds to a ligand, the ability of the GPCR to bind that ligand at a particular temperature may be used to determine thermostability of the mutant. It may be convenient to determine a "quasi $T_m$" ie the temperature at which 50% of the receptor is inactivated under stated conditions after incubation for a given period of time (eg 30 minutes). Mutant GPCRs of higher thermostability have an increased quasi Tm compared to their parents.

In relation to an increased stability to a detergent or to a chaotrope, typically the GPCR is incubated for a defined time in the presence of a test detergent or a test chaotropic agent and the stability is determined using, for example, ligand binding or a spectroscopic method as discussed above.

In relation to an extreme of pH, a typical test pH would be chosen (eg in the range 4.5 to 5.5 (low pH) or in the range 8.5 to 9.5 (high pH)).

Because relatively harsh detergents are used during crystallisation procedures, it is preferred that the mutant GPCR is stable in the presence of such detergents. The order of "harshness" of certain detergents is DDM, $C_{11} \rightarrow C_{10} \rightarrow C_9 \rightarrow C_8$ maltoside or glucoside, lauryldimethylamine oxide (LDAO) and SDS. It is particularly preferred if the mutant GPCR is more stable to any of $C_9$ maltoside or glucoside, $C_8$ maltoside or glucoside, LDAO and SDS, and so it is preferred that these detergents are used for stability testing.

Because of its ease of determination, it is preferred that thermostability is determined, and the mutants of the first parent GPCR are those mutants which have an increased thermostability compared to the parent protein. It will be appreciated that heat is acting as the denaturant, and this can readily be removed by cooling the sample, for example by placing on ice. It is believed that thermostability may also be a guide to the stability to other denaturants or denaturing conditions. Thus, increased thermostability is likely to translate into stability in denaturing detergents, especially those that are more denaturing than DDM, eg those detergents with a smaller head group and a shorter alkyl chain and/or with a charged head group. We have found that a thermostable GPCR is also more stable towards harsh detergents.

When an extreme of pH is used as the denaturing condition, it will be appreciated that this can be removed quickly by adding a neutralising agent. Similarly, when a chaotrope is used as a denaturant, the denaturing effect can be removed by diluting the sample below the concentration in which the chaotrope exerts its chaotropic effect.

In a further embodiment of the selection method it is determined whether the selected mutant GPCR is able to couple to a G protein. It is also preferred if it is determined whether the selected mutant GPCR is able to bind a plurality of ligands of the same class as the selecting ligand with a comparable spread and/or rank order of affinity as the parent GPCR.

In a particular embodiment of the selection method, the GPCR is β-adrenergic receptor (for example from turkey) and the ligand is dihydroalprenolol (DHA), an antagonist.

In a further preferred embodiment of the selection method, the GPCR is the adenosine $A_{2a}$ receptor ($A_{2a}R$) (for example, from man) and the ligand is ZM 241385 (4-[2-[[7-amino-2-(2-furyl) [1,2,4]-triazolo[2,3-α][1,3,5]triazin-5-yl]amino] ethyl]phenol), an antagonist or NECA (5'-N-ethylcarboxamido adenosine), an agonist.

In a still further preferred embodiment of the selection method, the GPCR is the neurotensin receptor (NTR) (for example, from rat) and the ligand is neurotensin, an agonist.

A method for preparing a mutant GPCR with increased stability comprises:
(i) carrying out the selection method described above
(ii) identifying the position or positions of the mutated amino acid residue or residues in the mutant GPCR or GPCRs which has been selected for increased stability, and
(iii) synthesising a mutant GPCR which contains a mutation at one or more of the positions identified.

As can be seen in the Examples, surprisingly, changes to a single amino acid within the GPCR may increase the stability of the protein compared to the parent protein with respect to a particular condition in which the protein resides in a particular conformation. Thus, in one embodiment of the method of preparing a mutant GPCR with increased stability, a single amino acid residue of the parent protein is changed in the mutant protein. Typically, the amino acid residue is changed to the amino acid residue found in the mutant tested in the selection. However, it may be replaced by any other amino acid residue, such as any naturally-occurring amino acid residue (in particular, a "codeable" amino acid residue) or a non-natural amino acid. Generally, for convenience, the amino acid residue is replaced with one of the 19 other codeable amino acids. Preferably, it is the replaced amino acid residue which is present in the mutant selected in the selection method.

Also as can be seen in the Examples, a further increase in stability may be obtained by replacing more than one of the amino acids of the parent protein. Typically, each of the amino acids replaced is one which has been identified using the selection method. Typically, each amino acid identified is replaced by the amino acid present in the mutant protein although, as noted above, it may be replaced with any other amino acid.

Typically when preparing a mutant GPCR with increased stability, the mutant GPCR contains, compared to the parent protein, from 1 to 10 replaced amino acids, preferably from 1 to 8, typically from 2 to 6 such as 2, 3, 4, 5 or 6 replaced amino acids.

It will be appreciated that the multiple mutants may be subject to the selection method. In other words, multiple mutants may be provided in step (i) of the selection method. It will be appreciated that by the selection and preparation methods described above, multiple mutagenised GPCRs may be made, whose conformation has been selected to create a very stable multiple point mutant protein.

Thus, the one or more mutants of the first parent GPCR in step (a) may contain a plurality of mutations compared to the first parent GPCR.

The one or more mutants of a first parent GPCR in step (a) may be prepared by any suitable method. Conveniently, the mutant protein is encoded by a suitable nucleic acid molecule and expressed in a suitable host cell. Suitable nucleic acid molecules encoding the mutant GPCR may be made using standard cloning techniques, site-directed mutagenesis and PCR as is well known in the art. Suitable expression systems include constitutive or inducible expression systems in bacteria or yeasts, virus expression systems such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris, Spodoptera frugiperda* and *Trichoplusiani* cells. Suitable animal host cells include HEK 293, COS, S2, CHO, NSO, DT40 and so on. It is known that some GPCRs require specific lipids (eg cholesterol) to function. In that case, it is desirable to select a host cell which contains the lipid. Additionally or alternatively the lipid may be added during isolation and purification of the mutant protein. It will be appreciated that these expression systems and host cells may also be used in the provision of the mutant GPCR in part (a) of the method of the first aspect of the invention.

Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y., incorporated herein by reference.

Mutant β-Adrenergic Receptor

β-adrenergic receptors are well known in the art. They share sequence homology to each other and bind to adrenalin.

In one embodiment, the mutant GPCR of a first parent GPCR is a mutant β-adrenergic receptor which, when compared to the corresponding wild-type β-adrenergic receptor, has a different amino acid at a position which corresponds to any one or more of the following positions according to the numbering of the turkey β-adrenergic receptor as set out in FIGS. 9A and 9B (SEQ ID NO:1): Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

The mutant β-adrenergic receptor may be a mutant of any β-adrenergic receptor provided that it is mutated at one or more of the amino acid positions as stated by reference to the given turkey β-adrenergic receptor amino acid sequence.

It is particularly preferred if the mutant GPCR of a first parent GPCR is one which has at least 20% amino acid sequence identity when compared to the given turkey β-adrenergic receptor sequence, as determined using MacVector and CLUSTALW (Thompson et al (1994) *Nucl. Acids Res.* 22, 4673-4680). More preferably, the mutant receptor of a first parent GPCR has at least 30% or at least 40% or at least 50% amino acid sequence identity. There is generally a higher degree of amino acid sequence identity which is conserved around the orthosteric ("active") site to which the natural ligand binds.

Figure 1:
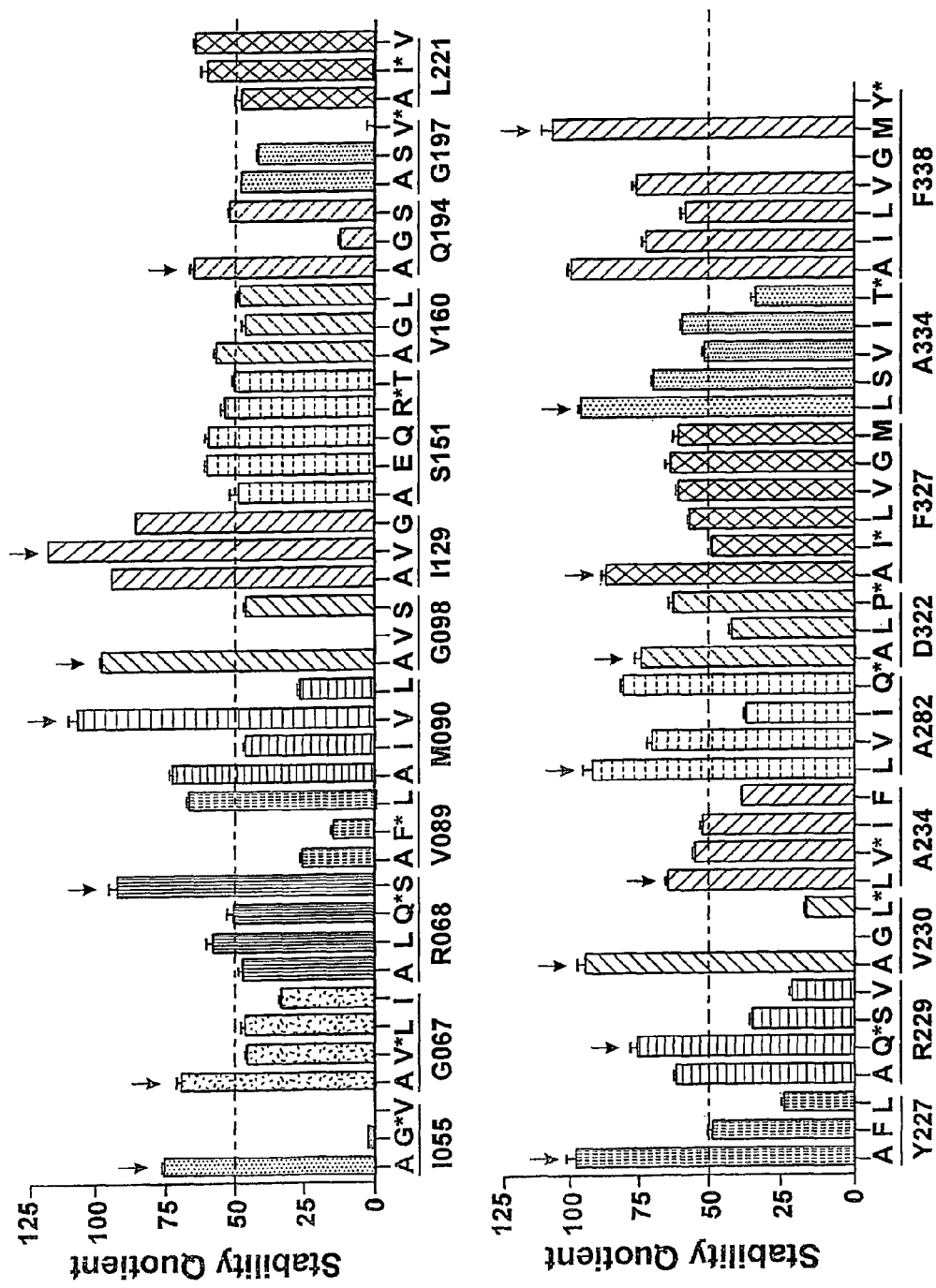
FIG. 1 Amino acid changes in βAR that lead to thermostability. Stability quotient indicates the % remaining binding activity of the mutants after heating the sample for 30 min at 32° C. All values are normalized to $\beta AR_{34-424}$ (50%, showed as a discontinuous line) to remove any experimental variability between assays. Bars show the stability for each mutant. The letters on the x-axis indicate the amino acid present in the mutant. The original amino acid and its position in $\beta AR_{34-424}$ is indicated below. Bars corresponding to the same amino acid in $\beta AR_{34-424}$ are in the same colour with arrows indicating the best mutations. Errors were calculated from duplicate measurements; the best mutants were subsequently re-assayed to determine the Tm for each individual mutation and to give an accurate rank order of stability for each mutant (see Example 1).

As is described in Example 1 and FIG. 1 below, individual replacement of the following amino acid residues in the parent turkey β-adrenergic sequence (SEQ ID NO: 1) (as shown in FIGS. 9A and 9B) lead to an increase in thermostability: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

Thus, the mutant GPCR of a first parent GPCR may be a mutant turkey β-adrenergic receptor in which, compared to its parent, one or more of these amino acid residues have been replaced by another amino acid residue. The mutant GPCRs of a first parent GPCR may also be mutant β-adrenergic receptors from other sources in which one or more corresponding amino acids in the parent receptor are replaced by another amino acid residue. For the avoidance of doubt, the parent may be a β-adrenergic receptor which has a naturally-occurring sequence, or it may be a truncated form or it may be a fusion, either to the naturally occurring protein or to a fragment thereof, or it may contain mutations compared to the naturally-occurring sequenced provided that it retains ligand-binding ability.

By "corresponding amino acid residue" we include the meaning of the amino acid residue in another β-adrenergic receptor which aligns to the given amino acid residue in turkey β-adrenergic receptor when the turkey β-adrenergic receptor and the other β-adrenergic receptor are compared using MacVector and CLUSTALW.

FIGS. 9A and 9B show an alignment between turkey β-adrenergic receptor and human β1, β2 and β3 β-adrenergic receptors (SEQ ID NOS: 1-4).

It can be seen that Ile 72 of human β1 corresponds to Ile 55 of turkey β-adrenergic receptor; Ile 47 of human β2 corresponds to Ile 55 of turkey β-adrenergic receptor; and Thr 51 of human β3 corresponds to Ile 55 of turkey β-adrenergic receptor. Other corresponding amino acid residues in human β1, β2 and β3 can readily be identified by reference to FIGS. 9A and 9B (SEQ ID NOS: 1-4).

It is preferred that the particular amino acid is replaced with an Ala. However, when the particular amino acid residue is an Ala, it is preferred that it is replaced with a Leu (for example, see turkey β-adrenergic Ala 234, Ala 282 and Ala 334 in FIG. 1).

It is preferred if the mutant GPCR of a first parent GPCR is a mutant β-adrenergic receptor which has a different amino acid compared to its parent at more than one amino acid position since this is likely to give greater stability. Particularly preferred human β1 receptor mutants are those in which one or more of the following amino acid residues are replaced with another amino acid residue: K85, M107, Y244, A316, F361 and F372. Typically, the given amino acid residue is replaced with Ala or Val or Met or Leu or Ile (unless they are already that residue).

Mutant human β1 receptors which have combinations of 3 or 4 or 5 or 6 mutations as described above may be used.

Particularly preferred human β2 receptor mutants are those in which one or more of the following amino acids are replaced with another amino acid residue: K60, M82, Y219, C265, L310 and F321. Typically, the given amino acid residue is replaced with Ala or Val or Met or Leu or Ile (unless they are already that residue).

Mutant human β2 receptors which have combinations of 3 or 4 or 5 or 6 mutations as described above may be used.

FIG. 26 shows the effect on thermostability when six thermostabilising mutations in β1-m23 (R68S, M90V, Y227A, A282L, F327A, F338M) were transferred directly to the human β2 receptor (equivalent mutations K60S, M82V, Y219A, C265L, L310A, F321M), making human β2-m23. The Tms for human β2 and β2-m23 were 29° C. and 41° C. respectively, thus exemplifying the transferability of thermostabilising mutations from one receptor to another receptor. Thus, a particularly preferred human β2 receptor mutant is one which comprises the mutations K60S, M82V, Y219A, C265L, L310A, F321M.

Particularly preferred human β3 receptor mutants are those in which one or more of the following amino acids are replaced with another amino acid residue: W64, M86, Y224, P284, A330 and F341. Typically, the given amino acid residue is replaced with Ala or Val or Met or Leu or Ile (unless they are already that residue).

Mutant human β3 receptors which have combinations of 3 or 4 or 5 or 6 mutations as described above may be used.

Particularly preferred combinations of mutations are described in detail in Tables 1 and 2 in Example 1, and the one or more mutant GPCRs of a first parent GPCR include the mutant turkey β-adrenergic receptors, and also include mutant β-adrenergic receptors where amino acids in corresponding position have been replaced by another amino acid, typically the same amino acid as indicated in Tables 1 and 2 in Example 1.

Particularly preferred mutants are those which contain mutations in the amino acids which correspond to the given amino acid residue by reference to turkey β-adrenergic receptor: (R68S, Y227A, A282L, A334L) (see m6-10 in Table 2 below); (M90V, Y227A, F338M) (see m7-7 in Table 2 below); (R68S, M90V, V230A, F327A, A334L) (see m10-8 in Table 2 below); and (R68S, M90V, Y227A, A282L, F327A, F338M) (see m23 in Table 2 below).

Mutant Adenosine Receptor

Adenosine receptors are well known in the art. They share sequence homology to each other and bind to adenosine.

In one embodiment, the mutant GPCR of a first parent GPCR is a mutant adenosine receptor which, when compared to the corresponding wild-type adenosine, has a different amino acid at a position which corresponds to any one or more of the following positions according to the numbering of the human adenosine $A_{2a}$ receptor as set out in FIGS. 10A and 10B (SEQ ID NOS: 5-8): Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, Ala 54, Val 57, His 75, Thr 88, Gly 114, Gly 118, Thr 119, Lys 122, Gly 123, Pro 149, Glu 151, Gly 152, Ala 203, Ala 204, Ala 231, Leu 235, Val 239.

The mutant adenosine receptor may be a mutant of any adenosine receptor provided that it is mutated at one or more of the amino acid positions as stated by reference to the given human adenosine $A_{2a}$ receptor amino acid sequence.

It is particularly preferred if the mutant GPCR of a first parent GPCR is one which has at least 20% amino acid sequence identity when compared to the given human adenosine $A_{2a}$ receptor sequence, as determined using MacVector and CLUSTALW. Preferably, the mutant GPCR of a first parent GPCR has at least 30% or at least 40% or at least 50% or at least 60% sequence identity. Typically, there is a higher degree of sequence conservation at the adenosine binding site.

As is described in Example 2 below, individual replacement of the following amino acid residues in the human adenosine $A_{2a}$ receptor sequence (as shown in FIGS. 10A and 10B) (SEQ ID NOS: 5-8) lead to an increase in thermostability when measured with the agonist 5'-N-ethylcarboxamidoadenosine (NECA):

```
Gly 114, Gly 118, Leu 167, Ala 184, Arg 199,

Ala 203, Leu 208, Gln 210, Ser 213, Glu 219,

Arg 220, Ser 223, Thr 224, Gln 226, Lys 227,

His 230, Leu 241, Pro 260, Ser 263, Leu 267,

Leu 272, Thr 279, Asn 284, Gln 311, Pro 313,

Lys 315.
```

Replacement of the following amino acid residues in the human $A_{2a}$ receptor sequence (as shown in FIGS. 10A and 10B) (SEQ ID NOS: 5-8) lead to an increase in thermostability when measured with the antagonist ZM 241385 (4-[2-[[7-amino-2-(2-furyl) [1,2,4]-triazolo[2,3-a][1,3,5]triazin-5-yl] amino]ethyl]phenol):

```
Ala 54, Val 57, His 75, Thr 88, Gly 114,

Gly 118, Thr 119, Lys 122, Gly 123, Pro 149,

Glu 151, Gly 152, Ala 203, Ala 204, Ala 231,

Leu 235, Val 239.
```

Thus, the mutant GPCR of a first parent GPCR may be a mutant human adenosine $A_{2a}$ receptors in which, compared to its parent, one or more of these amino acid residues have been replaced by another amino acid residue. The mutant GPCRs of a first parent GPCR may also be mutant adenosine receptors from other sources in which one or more corresponding amino acids in the parent receptor are replaced by another amino acid residue. For the avoidance of doubt, the parent may be an adenosine receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another adenosine receptor which aligns to the given amino acid residue in human adenosine $A_{2a}$ receptor when the human adenosine $A_{2a}$ receptor and the other adenosine receptor are compared using MacVector and CLUSTALW.

FIGS. 10A and 10B (SEQ ID NOS: 5-8) show an alignment between human adenosine $A_{2a}$ receptor and three other human adenosine receptors (A2b, A3 and A1).

It can be seen that, for example, Ser 115 in the $A_{2b}$ receptor (indicated as AA2BR) corresponds to Gly 114 in the $A_{2a}$ receptor. Similarly, it can be seen that Ala 60 in the $A_3$ receptor (indicated as AA3R) corresponds to Ala 54 in the $A_{2a}$ receptor, and so on. Other corresponding amino acid residues in human adenosine receptors $A_{2b}$, $A_3$ and $A_1$ can readily be identified by reference to FIGS. 10A and 10B (SEQ ID NOS: 5-8).

It is preferred that the particular amino acid in the parent is replaced with an Ala. However, when the particular amino acid residue in the parent is an Ala, it is preferred that it is replaced with a Leu.

It is preferred if the mutant GPCR of a first parent GPCR is a mutant adenosine receptor which has a different amino acid compared to its parent at more than one amino acid position.

Particularly preferred human adenosine A2b receptors are those in which one or more of the following amino acid residues are replaced with another amino acid residue: A55, T89, R123, L236 and V240. Typically, the given amino acid residue is replaced with Ala or Val or Met or Leu or Ile (unless they are already that residue).

Mutant human adenosine A2b receptors which have combinations of 3 or 4 or 5 mutations as described above may be used.

Particularly preferred human adenosine A3 receptors are those in which one or more of the following amino acid residues are replaced with another amino acid residue: A60, T94, W128, L232 and L236. Typically, the given amino acid residue is replaced with Ala or Val or Met or Leu or Ile (unless they are already that residue).

Mutant human adenosine A3 receptors which have combinations of 3 or 4 or 5 mutations as described above may be used.

Particular preferred human adenosine A1 receptors are those in which one or more of the following residues are replaced: A57, T91, A125, L236, and L240. Typically, the given amino acid residue is replaced with Ala or Val or Met or Leu or Ile (unless they are already that residue).

Particularly preferred combinations of mutations are described in detail in Example 2. The one or more mutant GPCRs of a first parent GPCR include these mutant human adenosine $A_{2a}$ receptors, and also include other mutant adenosine receptors where amino acids in corresponding positions have been replaced by another amino acid, typically the same amino acid as indicated in Example 2.

Particularly preferred adenosine receptor mutants are those which contain mutations in the amino acids which correspond to the given amino residue by reference to human adenosine A2a receptor: (A54L, K122A, L235A) (Rant 17); (A54L, T88A, V239A, A204L) (Rant 19); and (A54L, T88A, V239A, K122A) (Rant 21).

Mutant Neurotensin Receptor

Neurotensin receptors are known in the art. They share sequence homology and bind neurotensin.

In one embodiment, the mutant GPCR of a first parent GPCR is a mutant neurotensin receptor which, when compared to the corresponding wild-type neurotensin receptor, has a different amino acid at a position which corresponds to any one or more of the following positions according to the numbering of the rat neurotensin receptor as set out in FIGS. 11A and 11B (SEQ ID NO:9): Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

It is particularly preferred if the mutant GPCR of a first parent GPCR is one which has at least 20% amino acid sequence identity when compared to the given rat neurotensin receptor sequence, as determined using MacVector and CLUSTALW. Preferably, the mutant GPCR has at least 30% or at least 40% or at least 50% amino acid sequence identity.

The mutant neurotensin receptor may be a mutant of any neurotensin receptor provided that it is mutated at one or more of the amino acid positions as stated by reference to the given rat neurotensin receptor amino acid sequence.

As is described in Example 3 below, individual replacement of the following amino acid residues in the rat neurotensin receptor sequence (as shown in FIGS. 11A, 11B (SEQ ID NO: 9 and 28) lead to an increase in thermostability when considered with respect to the absence of neurotensin. Leu 72, Ala 86, Ala 90, Ser 100, His 103, Ser 108, Leu 109, Leu 111, Asp 113, Ile 116, Ala 120, Asp 139, Phe 147, Ala 155, Lys 176, Thr 179, Met 181, Ser 182, Phe 189, Leu 205, Thr 207, Gly 209, Gly 215, Leu 256, Asn 262, Val 268, Met 293, Asp 345, Tyr 349, Tyr 351, Ala 356, Phe 358, Ser 362, Ala 385, Cys 386, Trp 391, Arg 392, His 393, Lys 397, Pro 399.

As is described in Example 3 below, individual replacement of the following amino acid residues in the rat neurotensin receptor sequence (as shown in FIGS. 11A, 11B and 28 (SEQ ID NO: 91) lead to an increase in thermostability when considered with respect to the presence of neurotensin. Ala 69, Ala 73, Ala 86, Ala 90, His 103, Val 165, Glu 166, Ala 177, Arg 183, Gly 215, Val 229, Met 250, Ile 253, Ile 260, Thr 279, Thr 294, Gly 306, Leu 308, Val 309, Leu 310, Val 313, Phe 342, Phe 358, Val 360, Ser 362, Asn 370, Ser 373, Phe 380, Ala 385, Pro 389, Gly 390, Arg 395.

Thus, the mutant GPCR of a first parent GPCR may be a mutant rat neurotensin receptor in which, compared to its parent, one or more of these amino acid residues have been replaced by another amino acid residue. The mutant GPCRs of a first parent GPCR may also be mutant neurotensin receptors from other sources in which one or more corresponding amino acids in the parent receptor are replaced by another amino acid residue. For the avoidance of doubt the parent may be a neurotensin receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

By "corresponding amino acid residue" we include the meaning of the amino acid residue in another neurotensin receptor which aligns to the given amino acid residue in rat neurotensin receptor when the rat neurotensin receptor and the other neurotensin receptor are compared using MacVector and CLUSTALW.

FIGS. 11A and 11B (SEQ ID NOS: 9-11) show an alignment between rat neurotensin receptor and two human neurotensin receptors 1 and 2. It can be seen, for example, that Ala 85 of the human neurotensin receptor 1 corresponds to Ala 86 of the rat neurotensin receptor, that Phe 353 of the human neurotensin receptor 1 corresponds to Phe 358 of the rat neurotensin receptor, and so on. Other corresponding amino acid residue in the human neurotensin receptors 1 and 2 can readily be identified by reference to FIGS. 11A and 11B (SEQ ID NOS: 10-11).

It is preferred that the particular amino acid in the parent is replaced with an Ala. However, when the particular amino acid residue in the parent is an Ala, it is preferred that it is replaced with a Leu.

It is preferred if the mutant GPCR of a first parent GPCR is a mutant neurotensin receptor which has a different amino acid compared to its parent at more than one amino acid position. Particularly preferred human neurotensin receptors (NTR1) are those in which one or more of the following amino acid residues are replaced with another amino acid residue: Ala 85, His 102, Ile 259, Phe 337 and Phe 353. Typically, the given amino acid residues is replaced with Ala or Val or Met or Leu or Ile (unless they are already that residue).

Mutant human neurotensin receptors (NTR1) which have combinations of 3 or 4 or 5 mutations as described above may be used.

Particularly preferred human neurotensin receptors (NTR2) are those in which one or more of the following amino acid residues are replaced with another amino acid residue: V54, R69, T229, P331 and F347. Typically, the given amino acid residue is replaced with Ala or Val or Met or Leu or Ile (unless they are already that residue). Mutant human neurotensin receptors (NTR2) which have combinations of 3 or 4 or 5 mutations as described above are preferred.

Particularly preferred combinations of mutations are described in detail in Example 3. The one or more mutant GPCRs of a first parent GPCR include these mutant rat neurotensin receptors, and also include other mutant neurotensin receptors where amino acids in corresponding positions have been replaced by another amino acid, typically the same amino acid as indicated in Example 3.

Particularly preferred neurotensin receptor mutants are those which contain mutations in the amino acid residues which correspond to the given amino acid residue by reference to the rat neurotensin receptor: (F358A, A86L, I260A, F342A) (Nag7m); (F358A, H103A, I260A, F342A) (Nag7n).

Mutant Muscarinic Receptor

Muscarinic receptors are known in the art. They share sequence homology and bind muscarine.

In one embodiment, the mutant GPCR of a first parent GPCR is a mutant muscarinic receptor which, when compared to the corresponding wild-type muscarinic receptor, has a different amino acid at a position which corresponds to any one or more of the following positions according to the numbering of the human muscarinic receptor M1 as set out in FIGS. 17A-17C (SEQ ID NO: 12): Leu 65, Met 145, Leu 399, Ile 383 and Met 384.

It is particularly preferred if the mutant GPCR is one which has at least 20% amino acid sequence identity when compared to the given human muscarinic receptor sequence, as determined using MacVector and CLUSTALW. Preferably, the mutant GPCR has at least 30% or at least 40% or at least 50% amino acid sequence identity.

The mutant muscarinic receptor may be a mutant of any muscarinic receptor provided that it is mutated at one or more of the amino acid positions as stated by reference to the given muscarinic receptor amino acid sequence.

Thus, mutant GPCR of a first parent GPCR may be a mutant human muscarinic receptor which, when compared to its parent, one or more of these amino acid residues have been replaced by another amino acid residue. The mutant GPCR of a first parent GPCR may also be a mutant muscarinic receptor from other sources in which one or more corresponding amino acids in the parent receptor are replaced by another amino acid residue. For the avoidance of doubt the parent may be a muscarinic receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

By "corresponding amino acid residue" we include the meaning of the amino acid residue in another muscarinic receptor which aligns to the given amino acid residue in human muscarinic receptor when the human muscarinic receptor and the other muscarinic receptor are compared using MacVector and CLUSTALW.

It is preferred that the particular amino acid is replaced with an Ala. However, when the particular amino acid residue is an Ala, it is preferred that it is replaced with a Leu.

It is preferred that the mutant GPCRs of a first parent GPCR, including the mutant β-adrenergic, adenosine and neurotensin receptors, have an increased thermostability compared to its parent when in the presence or absence of a ligand thereto. Typically, the ligand is an antagonist, a full agonist, a partial agonist or an inverse agonist, whether orthosteric or allosteric. As discussed above, the ligand may be a polypeptide, such as an antibody.

It is preferred that the mutant GPCR of a first parent GPCR, for example a mutant β-adrenergic receptor or a mutant adenosine receptor or a mutant neurotensin receptor is at least 2° C. more stable than its parent preferably at least 5° C. more stable, more preferably at least 8° C. more stable and even more preferably at least 10° C. or 15° C. or 20° C. more stable than its parent. Typically, thermostability of the parent and mutant receptors are measured under the same conditions. Typically, thermostability is assayed under a condition in which the GPCR resides in a particular conformation. Typically, this selected condition is the presence of a ligand which binds the GPCR.

It is preferred that the mutant GPCR of a first parent GPCR, when solubilised and purified in a suitable detergent has a similar thermostability to bovine rhodopsin purified in dodecyl maltoside. It is particularly preferred that the mutant GPCR of a first parent GPCR retains at least 50% of its ligand binding activity after heating at 40° C. for 30 minutes. It is further preferred that the mutant GPCR of a first parent GPCR retains at least 50% of its ligand binding activity after heating at 55° C. for 30 minutes.

Once a mutant GPCR with increased stability relative to a first parent GPCR has been identified, the inventors have reasoned that further GPCRs can be generated by making the same one or more stabilising mutations at corresponding positions in a further GPCR.

For the avoidance of doubt the parent of the first parent GPCR may be a GPCR which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

Typically, identifying the position or positions at which the one or more mutants have at least one different amino acid residue compared to the first parent GPCR involves aligning their amino acid sequences with that of the parent GPCR, for example using the Clustal W program (Thompson et al., 1994).

By "corresponding position or positions", we include the meaning of the position in the amino acid sequence of a second GPCR which aligns to the position in the amino acid sequence of the first GPCR, when the first and second GPCRs are compared by alignment, for example by using MacVector and Clustal W. For example, as shown in the alignment in FIGS. 17A-17C (SEQ ID NOs: 3, 9, 12, 1, 5), the six stabilising mutations in turkey β1-m23 (R68S, M90V, Y227A, A282L, F327A, F338M) are at positions which correspond to residues K60, M82, Y219, C265, L310, F321 in the human β2 receptor.

Having identified the corresponding position or positions in the amino acid sequence of a second GPCR, the amino acids at those positions are replaced with another amino acid. Typically, the amino acids are replaced with the same amino acids which replaced the amino acids at the corresponding positions in the mutant of the first parent GPCR (unless they are already that residue). For example, at position 68 in turkey β1-m23 (R68S), an arginine residue was replaced with a serine residue. Therefore, at the corresponding position in the human β2 receptor, position 60 (K60), the lysine residue is preferably replaced with a serine residue.

Mutations can be made in an amino acid sequence, for example, as described above and using techniques well-established in the art.

It will be appreciated that the second GPCR may be any other GPCR. For example, stabilising mutations in a GPCR from one species may be transferred to a second GPCR from another species. Similarly, stabilising mutations in one particular GPCR isoform may be transferred to a second GPCR which is a different isoform. Preferably, the second parent GPCR is of the same GPCR class or family as the first parent GPCR. Phylogenetic analyses have divided GPCRs into three main classes based on protein sequence similarity, i.e., classes 1, 2, and 3 whose prototypes are rhodopsin, the secretin receptor, and the metabotropic glutamate receptors, respectively (Foord et al (2005) *Pharmacol. Rev.* 57, 279-288). Thus, the second GPCR may be a GPCR which is of the same GPCR class as the first parent GPCR. Similarly, GPCRs have been divided into families by reference to natural ligands such as glutamate and GABA. Thus, the second GPCR may be of the same GPCR family as the first parent GPCR. A list of GPCR classes and families has been produced by the International Union of Pharmacology (Foord et al (2005) *Pharmacol. Rev.* 57, 279-288) and this list is periodically updated at www.iuphar-db.org/GPCR/ReceptorFamiliesForward.

It will be appreciated that the second parent GPCR must be able to be aligned with the first parent GPCR such that the corresponding positions of the mutations in the first GPCR can be determined in the second GPCR. Thus typically, the second parent GPCR has at least 20% sequence identity to the first parent GPCR and more preferably at least 30%, 40%, 50%, 60%, 70%, 80% or 90% sequence identity to the first parent GPCR. However, some GPCRs have low sequence identity (e.g. family B and C GPCRs) and at the same time are very similar in structure. Thus the 20% sequence identity threshold is not absolute.

As described in Example 6, a statistical analysis conducted on alignments of mutant GPCRs indicates that not only are corresponding positions of an aligned sequence of a further GPCR predictive in identifying stabilising mutations but also that windows of amino acids around an identified stabilising mutation from aligned sequences are statistically more likely to contain further stabilising mutations when compared to a random distribution.

This is clearly exemplified in FIG. 33 in which aligned sequences of the beta 1 adrenergic receptor (SEQ ID NO: 1), neurotensin receptor (SEQ ID NO: 9) and adenosine A2A receptor (SEQ ID NO 5) are shown with thermostabilising mutations marked. Out of 62 mutations, of which 18 are aligned exactly in corresponding positions, a further 31 are aligned within a window of i plus or minus 4 residues where another thermostabilising mutation is in the ith position. This is statistically highly significant ($\rho<0.0004$). Moreover, statistical significance is observed for identifying thermostabilising mutations within a residue window of size i plus or minus 3 ($\rho=0.0015$), i plus or minus 2 ($\rho=0.0053$) and i plus or minus 1 ($\rho=0.008$) from any other given thermostabilisation position within the alignment of GPCR sequences.

Accordingly, the inventors have reasoned that once a mutant GPCR with increased stability relative to a first parent GPCR has been identified, further GPCRs can be generated by making one or more stabilising mutations in the amino acid sequence of the further GPCR within a window of i plus or minus 5 residues, where i is the position corresponding to the stabilising mutation in the parent GPCR.

Thus, a second aspect of the invention provides a method for producing a mutant GPCR with increased stability relative to a parent GPCR, the method comprising:

(a) identifying in the amino acid sequence of one or more mutants of a first parent GPCR with increased stability relative to the first parent GPCR, the position or positions at which the one of more mutants have at least one different amino acid residue compared to the first parent GPCR, and (b) making one or more mutations in the amino acid sequence that defines a second GPCR within a window or windows of i plus or minus 5 residues where i is the corresponding position or positions, to provide one or more mutants of a second parent GPCR with increased stability relative to the second parent GPCR.

As described above, typically, identifying the position or positions at which the one or more mutants have at least one different amino acid residue compared to the first parent GPCR involves aligning their amino acid sequence with that of the parent GPCR, for example using the Clustal W program (Thompson et al., 1994).

By "window or windows of i plus or minus 5 residues" we include the amino acid residue or residues at the corresponding position or positions of the one or more stabilising mutations in the mutant of the first parent GPCR, and the five amino acid residues before and the five amino acid residues after, each such residue or residues. Thus, where the mutant of the first parent GPCR has two stabilising mutations, there would be two windows of i plus or minus 5 residues, the first corresponding to i plus or minus 5 residues where i is the position corresponding to the first stabilising mutation and the second corresponding to i plus or minus 5 residues where i is the position corresponding to the second stabilising mutation, and so on. The same applies for each of the i plus or minus 4, i plus or minus 3, i plus or minus 2 and i plus or minus 1 windows mentioned below.

It is appreciated that where there is more than one window, one or more mutations may be made in one or more of the windows. For example, within each i plus or minus 5 window, one or more of the i−5, i−4, i−3, i−2, i−−1, i, i+1, i+2, i+3, i+4 and i+5 amino acid residues may be mutated. Alternatively, only one or more of the amino acid residues in one window may be mutated.

In a particularly preferred embodiment, in step (b), one or more mutations in the amino acid sequence that defines a second GPCR are made within a window or windows of i plus or minus 4 residues, where i is the corresponding position or positions, to provide one or more mutants of a second parent GPCR with increased stability relative to the second parent GPCR. By "window or windows of i plus or minus 4 residues" we include the amino acid residue or residues at the corresponding position or positions of the one or more stabilising mutations in the mutant of the first parent GPCR, and the three amino acid residues before and the three amino acid residues after, each such residue or residues. Thus, within each i plus or minus 4 window, one or more of the i−4, i−3, i−2, i−1, i, i+1, i+2, i+3 and i+4 amino acid residues may be mutated.

In another embodiment, in step (b), one or more mutations in the amino acid sequence that defines a second GPCR are made within a window or windows of i plus or minus 3 residues, where i is the corresponding position or positions, to provide one or more mutants of a second parent GPCR with increased stability relative to the second parent GPCR. By "window or windows of i plus or minus 3 residues" we include the amino acid residue or residues at the corresponding position or positions of the one or more stabilising mutations in the mutant of the first parent GPCR, and the three amino acid residues before and the three amino acid residues after, each such residue or residues. Thus, within each i plus or minus 3 window, one or more of the i−3, i−2, i−1, i, i+1, i+2 and i+3 amino acid residues may be mutated.

In another embodiment, in step (b), one or more mutations in the amino acid sequence that defines a second GPCR are made within a window or windows of i plus or minus 2 residue, where i is the corresponding position or positions, to provide one or more mutants of a second parent GPCR with increased stability relative to the second parent GPCR. By "window or windows of i plus or minus 2 residue" we include the amino acid residue or residues at the corresponding position or positions of the one or more stabilising mutations in the mutant of the first parent GPCR, and the two amino acid residues before and the two amino acid residues after, each such residue or residues. Thus, within each i plus or minus 2 window, one or more of the i−2, i−1, i, i+1 and i+2 amino acid residues may be mutated.

In another embodiment, in step (b), one or more mutations in the amino acid sequence that defines a second GPCR are made within a window or windows of i plus or minus 1 residues, where i is the corresponding position or positions, to provide one or more mutants of a second parent GPCR with increased stability relative to the second parent GPCR. By "window or windows of i plus or minus 1 residues" we include the amino acid residue or residues at the corresponding position or positions of the one or more stabilising mutations in the mutant of the first parent GPCR, and the amino acid residue before and the amino acid residue after, each such residue or residues. Thus, within each i plus or minus 1 window, one or more of the i−1, i and i+1 amino acid residue may be mutated.

Mutations can be made in an amino acid sequence, for example, as described above and using techniques well-established in the art.

Preferences for the first and second GPCR are defined above with respect to the first aspect of the invention.

As described in Example 7, a statistical analysis conducted on mutant GPCRs revealed that not only are stabilising mutations close together in primary sequence, but they are also spatially close together in three dimensional space.

Accordingly, the inventors have reasoned that once a mutant GPCR with increased stability relative to a first parent GPCR has been identified, further GPCRs can be generated by making one or more stabilising mutations in the amino acid sequence of the further GPCR which is spatially close in three dimensions to the position corresponding to the stabilising mutation in the parent GPCR.

Thus, a third aspect of the invention provides a method for producing a mutant GPCR with increased stability relative to a parent GPCR, the method comprising:

(a) identifying in the amino acid sequence of one or more mutants of a first parent GPCR with increased stability relative to the first parent GPCR, the position or positions at which the one or more mutants have at least one different amino acid residue compared to the first parent GPCR, and (b) making one or more mutations in the amino acid sequence that defines a second GPCR within a distance of 12 Å from the Cα atom of, or within a distance of 8 Å from any atom of, the amino acid residue i, where i is the corresponding position or positions, to provide one or more mutants of a second parent GPCR with increased stability relative to the second parent GPCR.

By the "amino acid sequence that defines a second GPCR within a distance of", we mean all of the amino acid residues which are within that distance of the Cα atom or any atom of, the amino acid residue i, where i is the amino acid residue at the corresponding position or positions at which the one or more mutants have at least one different amino acid residue compared to the first parent GPCR. For example, the amino acid sequence that defines a second GPCR within a distance of 12 Å from the Cα atom of residue i, includes all those amino acid residues that are within 12 Å from the Cα atom of residue i, eg within 11 Å, 10 Å, 9 Å, 8 Å, 7 Å, 6 Å, 5 Å, 4 Å or 3 Å from the Cα atom of residue i. The amino acid sequence that defines a second GPCR within a distance of 8 Å of any atom of residue i, includes all those amino acid residues that are within 8 Å of any atom of residue i, eg within 7 Å, 6 Å, 5 Å, 4 Å or 3 Å from any atom of residue i.

An amino acid residue is said to be within a particular distance of the Cα atom of residue i, if the Cα atom of that amino acid residue is within the particular distance from the Cα atom of residue i. For example, an amino acid residue will be deemed to be within a distance of 12 Å from the Cα of residue i if the Cα atom of that amino acid residue is within a distance of 12 Å from the Cα of residue i, and so on. Similarly, an amino acid residue is said to be within a particular distance of any atom of residue i, if any atom of that amino acid residue is within the particular distance from any atom of residue i. For example, an amino acid residue will be deemed to be within a distance of 8 Å from any atom of residue i, if any atom of that amino acid residue is within a distance of 8 Å from any atom of residue i. Thus, it will be appreciated that there are two distance criteria, the first between Cα atoms of both residues and the second between any atoms of both residues, and either method may be used.

The distances are those measured based on coordinates in three-dimensions. For example, distances are typically measured by standard geometry from the X, Y and Z coordinates of the two atoms (e.g. SQUAREROOT $(;((x1-x2)^2+(y1-y2)^2+(z1-z2)^2))$.

By 'any atom' we include any atom of the amino acid residue i. For example, it may be a hydrogen atom or a non-hydrogen atom. The atom may be an atom of the amino acid side chain or it may be an atom of the main chain.

It is appreciated that where the structure of the second GPCR is known, the distances are measured when the protein is folded in its native state. Otherwise, the distances may be measured within a structural model of the second GPCR. Structural models can be generated using any suitable method known in the art, including those described below with respect to the fourth aspect of the invention. For example, the structural model may be a computer generated model based upon homology or using de novo structure prediction methods (Qian et al Nature (2007) 450: 259-64).

It is appreciated that any amino acid residue in the amino acid sequence that defines a second GPCR within said distance can be mutated. Mutations can be made in an amino acid sequence, for example, as described above and using techniques well-established in the art.

Preferences for the first and second GPCR are defined above with respect to the first aspect of the invention.

The inventors have also reasoned that the identification of structural motifs in which the one or more mutations in a mutant GPCR with increased stability reside, will be useful in producing further mutant GPCRs with increased stability.

Accordingly, a fourth aspect of the invention provides a method for producing a mutant G-protein coupled receptor (GPCR) with increased stability relative to its parent GPCR, the method comprising:
a) providing one or more mutants of a first parent GPCR with increased stability relative to the first parent GPCR b) identifying in a structural membrane protein model the structural motif or motifs in which the one or more mutants have at least one different amino acid residue compared to the first parent GPCR, and
c) making one or more mutations in the amino acid sequence that defines a corresponding structural motif or motifs in a second parent GPCR, to provide one or more mutants of a second parent GPCR with increased stability relative to the second parent GPCR.

Mapping stabilising mutations onto one or more known structural models can be used to identify particular structural motifs in which such stabilising mutations reside. We have mapped stabilising mutations of the β1-adrenergic receptor onto structural models of the β2-adrenergic receptor (Rasmussen et al (2007) Nature 450, 383-387; Cherezov et al (2007) Science 318:1258-65; Rosenbaum et al (2007) Science 318:1266-1273) in order to identify such motifs. For example, Table (vi) lists the turkey β1-adrenergic receptor mutations which we have mapped onto the human β2-adrenergic receptor and describes the corresponding structural motifs in which they reside. As discussed in Example 4, mapping of the Y227A mutation (equivalent to Y219 in the human β2 receptor) onto the human $\beta_2$-adrenergic receptor reveals its position at the interface between helices such that the mutation may improve packing at the helical interface (see FIGS. 15, 16 and 23). Similarly, mapping of the M90V mutation (equivalent to M82 in the human $\beta_2$ receptor) onto the human $\beta_2$-adrenergic receptor reveals it to be in helix 2 at a point where the helix is kinked (see FIGS. 15, 16 and 20). Other mutations were found to reside in further structural motifs including transmembrane helix surfaces pointing into the lipid bilayer, hydrophobic-hydrophilic boundary regions, protein binding pockets and loop regions (see Table (vi) and FIGS. 18-19, 21-22 and 24-25).

Such structural motifs, by virtue of them containing stabilising mutations, are important in determining protein stability. Therefore, targeting mutations to these motifs will facilitate the generation of stabilised mutant GPCRs. Indeed, there were several instances where more than one mutation mapped to the same structural motif. For example, the Y227A, V230A and A234L mutations in the turkey β1 adrenergic receptor mapped to the same helical interface, the V89L and M90V mutations mapped to the same helical kink and the F327A and A334L mutations mapped to the same helical surface pointing towards the lipid bilayer (Table (vi)). Thus, when one stabilising mutation has been identified, the determination of the structural motif in which that mutation is located will enable the identification of further stabilising mutations.

It will be appreciated that the one or more mutants of a first parent GPCR in the second aspect of the invention, may be selected or prepared as described above. Accordingly, the one or more mutants of a first parent GPCR may be any of the specific mutants described above, for example mutant β-adrenergic receptors, adenosine receptors, neurotensin receptors or muscarinic receptors. Hence, the method of the second aspect of the invention may also be used to create stable, conformationally locked GPCRs by mutagenesis. For example, following the selection of mutant GPCRs which have increased stability in a particular conformation, the structural motifs in which such stabilising mutations reside can be identified. Making one or more mutations in the amino acid sequence that defines the corresponding structural motif in another GPCR can then be used to produce a mutant GPCR with increased stability in a particular conformation relative to its parent GPCR.

We have performed a multiple sequence alignment of the human beta-2AR, rat NTR1, turkey beta-1 AR, human Adenosine A2aR and human muscarinic M1 receptor amino acid sequences (FIGS. 17A-17C) (SEQ ID NO: 3, 9, 1, 5 and 121 which shows that, when the thermostabilising mutations identified (see Examples 1-3) are positioned on the sequences then, in 11 instances out of a total of 70, two sequences contain mutations at the same position (denoted in FIGS. 17A-17C (SEQ ID NO: 3, 9, 1, 5 and 12) with a star). Without wishing to be bound by any theory, the inventors believe that thermostabilising mutations at these positions should be of enhanced transferability for mapping onto a structural membrane protein model. Thus in one embodiment, the mutant of the first parent GPCR is a mutant human beta-2AR, rat NTR1, turkey beta-1 AR, human Adenosine A2aR or human muscarinic M1 receptor which, when compared to its corresponding parent receptor, has a different amino acid at a position which corresponds to any one or more of the following positions according to the numbering of the human beta2 AR as set out in FIGS. 17A-17C (SEQ ID NO: 3, 9, 1, 5 and 12): Ala 59, Val 81, Ser 143, Lys 147, Val 152, Glu 180, Val 222, Ala 226, Ala 271, Leu 275 and Val 317.

In order to identify the structural motif or motifs, the stabilising mutations are mapped onto a known structure of a membrane protein.

By "membrane protein" we mean a protein that is attached to or associated with a membrane of a cell or organelle. Preferably, the membrane protein is an integral membrane protein that is permanently integrated into the membrane and can only be removed using detergents, non-polar solvents or denaturing agents that physically disrupt the lipid bilayer.

The structural model of a membrane protein may be any suitable structural model. For example, the model may be a known crystal structure. Examples of GPCR crystal structures include bovine rhodopsin (Palczewski, K. et al., Science 289, 739-745. (2000)) and human $\beta_2$ adrenergic receptor (Rasmussen et al, Nature 450, 383-7 (2007); Cherezov et al (2007) Science 318:1258-65; Rosenbaum et al (2007) Science 318:1266-1273). The coordinates for the human $\beta_2$ adrenergic receptor structure can be found in the RCSB Protein Data Bank under accession codes: 2rh1, 2r4r and 2r4s. Other examples of a GPCR crystal structure include the turkey $\beta$ adrenergic receptor (Warne et al (2008) Nature 454: 486-91), the co-ordinates for which can be found in the RCSB Protein Data Bank (PDB) under accession code: 2vt4 and the human A2A adenosine receptor (Jaakola et al (2008) Science 322: 1211-1217), the coordinates for which can be found in the RCSB PDB under accession code: 3eml. Alternatively, the structural model may be a computer generated model based upon homology or using de novo structure prediction methods (Qian et al Nature (2007) 450: 259-64).

It will be appreciated that stabilising mutations of a given mutant GPCR can be mapped onto a structural model of any membrane protein which has sufficient structural similarity to the GPCR. In particular, the domain of the membrane protein must have sufficient structural similarity to the GPCR domain in which the stabilising mutation resides, for a given mutation to be transferable.

A protein domain is typically defined as a discretely folded assembly of secondary structure elements which may stand alone as a single protein or be part of a larger protein in combination with other domains. It is commonly a functional evolutionary unit. GPCRs are essentially single domain proteins excluding those with large N-terminal domains. Therefore, typically, the structural model is of a membrane protein which comprises at least one domain that has sufficient structural similarity to the GPCR.

Structural similarity can be determined indirectly by the analysis of sequence identity, or directly by comparison of structures.

With regard to sequence identity, the amino acid sequence encoding the GPCR domain in which the mutant has at least one different amino acid residue compared to the first parent GPCR, is aligned with an amino acid sequence encoding a domain of a membrane protein for which a structural model is available. It will be appreciated that one or more of these sequences may contain an inserted sequence or N-terminal or C-terminal extensions which are additional to the core conserved domain. For optimal alignment, such sequences are removed so as not to skew the analysis. Membrane proteins with sufficient sequence identity across the domain in question may then be used as the structural model for mapping mutations. It has been shown for soluble protein domains that their 3D structure is broadly conserved above 20% sequence identity and well conserved above 30% identity, with the level of structural conservation increasing as sequence identity increases up to 100% (Ginalski, K. Curr Op Struc Biol (2006) 16, 172-177). Thus, it is preferred if the structural membrane protein model is a model of a membrane protein which contains a domain that shares at least 20% sequence identity with the mutant GPCR domain containing the at least one different amino acid residue compared to the first parent GPCR, and more preferably at least 30%, 40%, 50%, 60%, 70%, 80% or 90% sequence identity, and yet more preferably at least 95% or 99% sequence identity.

Sequence identity may be measured by the use of algorithms such as BLAST or PSI-BLAST (Altschul et al, NAR (1997), 25, 3389-3402) or methods based on Hidden Markov Models (Eddy S et al, J Comput Biol (1995) Spring 2 (1) 9-23). Typically, the percent sequence identity between two polypeptides may be determined using any suitable computer program, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., 1994). The parameters used may be as follows: Fast pairwise alignment parameters: K-tuple (word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

In addition to sequence identity, structural similarity can be determined directly by comparison of structural models. Structural models may be used to detect regions of structural similarity not evident from sequence analysis alone, and which may or may not be contiguous in the sequence. For example, family B and C GPCRs are thought to share similar structures; however, their sequence identity is very low. Similarly, the water transporting aquaporins spinach SoPip2, E. coli AqpZ, Methanococcus AqpM, rat Aqp4, human Aqp1 and sheep Aqp0 share low sequence identity but all have similar structures.

Structural models of high fidelity may be constructed for proteins of unknown structure using standard software packages such as MODELLER (Sall A and Blundell T, J Mol Biol (1993) 234(3) 779-815), wherein the structure is modelled on a known structure of a homologous protein. Such modelling improves with increasing sequence identity. Typically, the sequence identity between the sequence of unknown structure and a sequence of known 3D structure is more than 30% (Ginalski, K. Curr Op Struc Biol (2006) 16, 172-177). In addition, de novo structure prediction methods based on sequence alone may be used to model proteins of unknown structure (Qian et al, (2007) Nature 450:259-64). Once structures have been experimentally determined or derived by modelling, regions of structural similarity may be detected by direct comparison of two or more 3D structures. They may, for example, comprise secondary structure elements of a particular architecture and topology which can be detected by the use of software such as DALI (Holm, L and Sander, C (1996) Science 273, 595-603). They may comprise local arrangements of amino acid side chains and the polypeptide backbone, or specific sets of atoms or groups of atoms in a particular spatial arrangement, which may for example also be detected by the use of graph theoretical representations (Artymiuk, P et al, (2005) J Amer Soc Info Sci Tech 56 (5) 518-528). In this approach, the atoms or groups of atoms within the proteins or regions of proteins to be compared are typically represented as the nodes of a graph, with the edges of the graph describing the angles and distances between the nodes. Common patterns in these graphs indicate common structural motifs. This approach may be extended to include any descriptor of atoms or groups of atoms, such as hydrogen bond donor or acceptor, hydrophobicity, shape, charge or aromaticity; for example proteins may be spatially mapped according to such descriptors using GRID and this representation used as a basis for similarity searching (Baroni et al (2007) J Chem Inf Mod 47, 279-294). Descriptions of the methods, availability of software, and guidelines for user-defined selection of parameters, thresholds and tolerances are described in the references given above.

In a preferred embodiment, the structural membrane protein model is a structural GPCR model. It will be appreciated that the structural model of a GPCR may be a model of the first parent GPCR. For example, stabilising mutations within a mutant GPCR having increased stability can be directly mapped onto the first parent GPCR structure and the structural motifs in which such mutations are located, identified. Where the structure of the first parent GPCR is unknown, structural models of other GPCRs may be used. For example, stabilising mutations in a GPCR from one species may be mapped onto a known structural model of the same GPCR from another species. Similarly, stabilising mutations in one particular GPCR isoform may be mapped onto a known structural model of another GPCR isoform. Moreover, stabilising mutations from one GPCR may be mapped onto a GPCR of the same class or family. A list of GPCR classes and families has been produced by the International Union of Pharmacology (Foord et al (2005) *Pharmacol. Rev.* 57, 279-288) and this list is periodically updated at. www.iuphar-db.org/GPCR/ReceptorFamiliesForward.

As described above, it will be appreciated that the structural model may be of any GPCR provided it has sufficient structural similarity across the domain in which the mutant GPCR has at least one different amino acid compared to the first parent GPCR. Thus, it is preferred if the GPCR shares at least 20% sequence identity with the mutant of the first parent GPCR across the protein domain containing the at least one different amino acid residue compared to the first parent GPCR, and more preferably at least 30%, 40%, 50%, 60%, 70%, 80% or 90% sequence identity, and yet more preferably at least 95% or 99% sequence identity. However, the inventors recognise that the 20% sequence identity threshold is not absolute. GPCRs with less than 20% sequence identity to the first parent GPCR may also serve as a structural model to which stabilising mutations are transferred, wherein the low sequence identity is counterbalanced by other similarities, including, for example, the presence of the same sequence motifs, binding to the same G-protein or having the same function, or having substantially the same hydropathy plots compared to the first parent GPCR.

Mapping of stabilising mutations onto the structural model can be done using any suitable method known in the art. For example, typically, the amino acid sequence of the GPCR for which the structural model is available is aligned with the amino acid sequence of the mutant of the first parent GPCR. The position or positions of the at least one different amino acid residue in the mutant GPCR relative to the first parent GPCR can then be located in the amino acid sequence of the GPCR for which a structural model is available.

By 'structural motif' we include the meaning of a three dimensional description of the location in a GPCR structural model of a thermostabilising mutation. For example, the structural motif may be any secondary or tertiary structural motif within the GPCR. By 'tertiary structural motif' we include any descriptor of atoms or groups of atoms, such as hydrogen bond donor or acceptor, hydrophobicity, shape, charge or aromaticity. For example, proteins may be spatially mapped according to such descriptors using GRID and this representation used as a basis for defining a structural motif (Baroni et al (2007) J Chem Inf Mod 47, 279-294).

Table (vi) lists the structural motifs in which the turkey β1 adrenergic receptor stabilising mutations were found to reside. As seen from the table, the mutations are positioned in a number of distinct localities. Three mutations are in loop regions that are predicted to be accessible to aqueous solvent. Eight mutations are in the transmembrane α-helices and point into the lipid bilayer; three of these mutations are near the end of the helices and may be considered to be at the hydrophobic-hydrophilic boundary layer. Eight mutations are found at the interfaces between transmembrane α-helices, three of which are either within a kinked or distorted region of the helix and another two mutations occur in one helix but are adjacent to one or more other helices which contain a kink adjacent in space to the mutated residue. These latter mutations could affect the packing of the amino acids within the kinked region, which could result in thermostabilisation. Another mutation is in a substrate binding pocket.

Accordingly, in one embodiment, the structural motif is any of a helical interface, a helix kink, a helix opposite a helix kink, a helix surface pointing into the lipid bilayer, a helix surface pointing into the lipid bilayer at the hydrophobic-hydrophilic boundary layer, a loop region or a protein binding pocket.

Identifying a structural motif in which a stabilising mutation resides suggests the importance of that motif in protein stability. Therefore, making one or more mutations in the amino acid sequence that defines a corresponding structural motif or motifs in a second parent GPCR, should provide one or more mutants of a second parent GPCR with increased stability relative to the second parent GPCR.

The amino acid sequence which defines a structural motif is the primary amino acid sequence of the amino acid residues which combine in the secondary or tertiary structure of the protein to form the structural motif. It will be appreciated that such a primary amino acid sequence may comprise contiguous or non-contiguous amino acid residues. Thus, identifying the amino acid sequence which defines the structural motif will involve determining the residues involved and subsequently defining the sequence. Mutations can be made in an amino acid sequence, for example as described above and using techniques well-established in the art.

By "corresponding structural motif or motifs", we mean the analogous structural motif or motifs identified in the structural model which are present in the second parent GPCR. For example, if a helical interface was identified, the corresponding helical interface in the second parent GPCR would be the interface between the helices which are analogous to the helices present in the structural model. If a helical kink was identified, the corresponding helical kink would be the kink in the helix which is analogous to the kinked helix present in the structural model. An analogous structural motif or motifs in the second parent GPCR can be identified by searching for similar amino acid sequences in the sequence of the second parent GPCR which define the motif or motifs in the structural model, for example, by sequence alignment. Moreover, computer based algorithms are widely available in the art that can be used to predict the presence of protein motifs based on an amino acid sequence. Thus, based upon the relative position of a particular motif within the amino acid sequence and its position relative to other motifs, an analogous structural motif can readily be identified. It will be appreciated that if a structural model of the second parent GPCR is available, the analogous structural motif or motifs can be directly mapped onto the structure of the protein. Typically, the amino acid sequence defining the analogous structural motif has at least 20% sequence identity with the sequence defining the motif in the structural model, more preferably at least 30%, 40%, 50%, 60%, 70%, 80% and 90% sequence identity and yet more preferably 95% and 99% sequence identity.

In one embodiment, the second parent GPCR is the first parent GPCR. For the avoidance of doubt, the second parent GPCR may have the naturally-occurring sequence of the first parent GPCR, or it may be a truncated form or it may be a fusion, either to the naturally occurring protein or to a fragment thereof, or it may contain mutations compared to the naturally-occurring sequence, providing that it retains ligand-binding.

In an alternative embodiment, the second parent GPCR is not the first parent GPCR. For example, a mutant of a first parent GPCR may have been identified that has increased stability but it is desired to generate a mutant of a different GPCR with increased stability. Preferably, the second parent GPCR is of the same GPCR class or family as the first parent GPCR as described above. However, it will be appreciated that the second parent GPCR may be any known GPCR provided that it shares sufficient structural similarity with the first parent GPCR, such that it contains a corresponding structural motif in which the stabilising mutation of the mutant of the first parent GPCR resides. Thus typically, the second parent GPCR has at least 20% sequence identity to the first parent GPCR and more preferably at least 30%, 40%, 50%, 60%, 70%, 80% or 90% sequence identity. However, as mentioned above, some GPCRs have low sequence identity (e.g. family B and C GPCRs) but are similar in structure. Thus the 20% sequence identity threshold is not absolute.

As discussed in Example 8, the inventors have discovered by superimposing homology models of the adenosine A2A, muscarinic 1 and neurotensin receptors, with the structure of the turkey beta 1 adrenergic receptor, that not only can spatial relationships between mutants be determined, but 'hotspots' of mutants can be assessed for statistical significance. By 'hotspots' we mean a cluster of amino acid residues which, when mutated, give rise to an increased stability relative to a parent GPCR. Such hotspots which are highly statistically significant are likely to be present in other GPCR structures and so their determination may be used to identify mutant GPCRs with increased stability relative to a parent GPCR. It is appreciated that hotspots may or may not correspond with the structural motifs outlined in the third aspect of the invention. For example, the residues which define a hotspot do not necessarily belong to the same structural motif such as a helix or beta strand.

Thus, a fourth aspect of the invention provides a method for producing a mutant GPCR with increased stability relative to its parent GPCR, the method comprising:
(a) providing one or aligning more than one three-dimensional model of one or more mutants of a GPCR with increased stability relative to a parent GPCR;
(b) identifying in the amino acid sequence of the one of more mutants, the position or positions at which the one or more mutants have at least one different amino acid residue compared to the parent GPCR;
(c) determining within a set distance d Å from the Cα atom or any atom of an amino acid residue at the position or positions at which the one or more mutants have a different amino acid residue compared to the parent GPCR, the number of other positions from any aligned model at which the one or more mutants have at least one different amino acid residue compared to the parent GPCR;
(d) determining whether the number of other positions represents a statistically significant cluster, and if so, making one or more mutations in the amino acid sequence that defines a second GPCR within a distance of d Å from the Cα atom or any atom of the amino acid residue at the corresponding position or positions at which the one or more mutants have at least one different amino acid residue compared to the parent GPCR, to provide one or more mutants of a second parent GPCR with increased stability relative to the second parent GPCR.

By 'three-dimensional' model, we include both known structures and predictive models of a three-dimensional structure of a mutant GPCR that has increased stability relative to a parent GPCR, for example models generated based upon homology or using de novo structure prediction methods known in the art (Quian et al, *Nature* (2007) 450:259-64), as described above. It is appreciated that where there is more than one model, the models may be of mutant GPCRs of different parent GPCRs. Conveniently, where there is more than one model, the models are of mutant GPCRs that belong to the same family or class. A list of GPCR classes and families has been produced by the International Union of pharmacology (Foord et al (2005) *Pharmacol. Rev.* 57, 279-288) and this list is periodically updated at www.iuphar-db.org/GPCR/ReceptorFamiliesForward. It is further appreciated that three-dimensional models of any mutant GPCR may be aligned provided that they share sufficient structural similarity. Thus, where there is more than one model of a mutant GPCR, it is preferred if the mutant GPCRs share at least 20% sequence identity with each other and more preferably at least 30%, 40%, 50%, 60%, 80% or 90% sequence identity, and yet more preferably at least 95% or 99% sequence identity. However, GPCRs with less than 20% sequence identity to one another may still be aligned where the low sequence identity is counterbalanced by other similarities, including for example, the presence of the same sequence motifs, binding to the same G-protein or have the same function, or having substantially the same hydropathy plots.

In a particularly preferred embodiment, the three-dimensional model may be any one or more of the turkey β1-AR crystal structure (Warne et al (2008) *Nature* 454: 486-91; PDB accession code 2vt4), the human A2A adenosine receptor crystal structure (Jaakola et al (2008) *Science* 322: 1211-1217; PDB accession code 3eml), or generated models of a mutant GPCR with increased stability relative to a parent GPCR, such as the adenosine A2A receptor, muscarinic 1 receptor or neurotensin receptor, based on their homology with for example the turkey β1-AR. It is appreciated that any one or more models of a mutant GPCR disclosed herein such as the β-adrenergic receptor, adenosine receptor, neurotensin receptor and muscarinic receptor described above, may be used.

Typically, the model is computer generated. Computer models can be generated or displayed by commercially available software programs. Examples of software programs include but are not limited to QUANTA (Accelrys .COPYRIGHT.2001, 2002), O (Jones et al., Acta Crystallogr. A47, pp. 110-119 (1991)) and RIBBONS (Carson, J. Appl. Crystallogr., 24, pp. 9589-961 (1991)).

Preferably, more than one three-dimensional model is provided, ie at least 2, 3, 4, 5, 6, 7, 8, 9 or 10 models. It is appreciated that the more models that are provided, the greater the chances of defining a statistically significant cluster that can be mapped onto other GPCRs to produce GPCRs with increased stability. Nevertheless, significant clusters may still be defined using only one model, in which case the model is not aligned with any other model.

By 'aligning' we mean that the three-dimensional models of one or more mutants of a GPCR with increased stability relative to a parent GPCR are superimposed so as to minimise the average (or root mean square) distance between equivalent atoms from each model. For example, the models may be rotated and translated to minimise the average (or root mean square) distance. Three-dimensional models can be aligned using any suitable method known in the art, for example algorithms such as in LSQMAN (Kleywegt & Jones (1994) A super position, CCP4/ESF-EAC BM, Newsletter on Protein Crystallography, 31: 9-14) or the Superpose algorithm in MOE (Chemical Computing Group Inc) or the Superpose Folding Motif program in QUANTA (Accelrys Inc) may be used.

Once the models have been aligned, it is determined within a set distance d Å from the Cα atom or any atom of an amino acid residue at the position or positions at which the one or more mutants have a different amino acid residue compared to the parent GPCR, the number of other positions from any aligned model at which the one or more mutants have at least one different amino acid residue compared to the parent GPCR. For example, for a given position in a three-dimensional model of a mutant GPCR, at which that mutant has one different amino acid residue compared to its parent GPCR, the number of other positions from any aligned model (at which the one or more mutants have at least one different amino acid residue compared to the parent GPCR) within a set distance of d Å from the Cα atom or any atom of the amino acid residue at that position is determined.

A position at which the one or more mutants have at least one different amino acid residue compared to the parent GPCR, is said to be within a set distance of d Å from the Cα atom or any atom of a particular amino acid residue, if the Cα atom or any atom of the amino acid at that position (depending on whether the 'Cα atom' or 'any atom' method is being used) is within d Å from the Cα atom or any atom of the particular amino acid residue. For example, when using the 'Cα atom' method, a position at which the one or more mutants have at least one different amino acid residue compared to the parent GPCR, is said to be within a set distance of d Å from the Cα atom of a particular amino acid residue, if the Cα atom of the amino acid at that position is within d Å from the Cα atom of the particular amino acid residue. Similarly, when using the 'any atom' method, a position at which the one or more mutants have at least one different amino acid residue compared to the parent GPCR, is said to be within a set distance of d Å from the any atom of a particular amino acid residue, if any atom of the amino acid at that position is within d Å from any atom of the particular amino acid residue. It is appreciated that in the case of only one model, only the number of positions within that mutant, at which the mutant has at least one different amino acid residue compared to its parent GPCR, is determined within a set distance of d Å from the Cα atom or any atom of a particular amino acid residue. Where there is more than one model, the number of positions within any aligned model of the one or more mutant GPCRs, at which the one or more mutants have at least one different amino acid residue compared to the parent GPCR, is determined within a set distance of d Å from the Cα atom or any atom of a particular amino acid residue.

The set distance d Å is that measured based upon coordinates in three dimensions as described above, from the Cα atom or any atom of a particular amino acid residue, and covers one model (in the case of only one model being used) or covers all aligned models (in the case of more than one model being used).

Preferably, the set distance d Å from the Cα atom of an amino acid residue at the position or positions at which the one or more mutants have a different amino acid residue compared to the parent GPCR, is at least 2 Å, 3 Å, 4 Å, 5 Å, 6 Å, 7 Å, 8 Å, 9 Å, 10 Å, 11 Å or 12 Å. Preferably the set distance d Å is at least 4 Å. In a particularly preferred embodiment, the set distance d Å from the Cα atom is any of 6 Å or 8 Å or 10 Å or 12 Å and most preferably 10 Å or 12 Å. Typically, the set distance d Å is 12 Å or less.

Preferably, the set distance d Å from any atom of an amino acid residue at the position or positions at which the one or more mutants have a different amino acid residue compared to the parent GPCR, is at least 2 Å, 3 Å, 4 Å, 5 Å, 6 Å, 7 Å, 8 Å, 9 Å, 10 Å, 11 Å or 12 Å. In a particularly preferred embodiment, the set distance d Å from any atom is any of 4 Å, 6 Å, 8 Å or 10 Å and most preferably 8 Å or 10 Å. Typically, the set distance d Å is 12 Å or less.

It is appreciated that the preferred distances are ones that give rise to a statistically significant cluster as described below.

By 'any atom', we include any atom of the amino acid residue at the position or positions at which the one or more mutants have a different amino acid residue compared to the parent GPCR. For example, it may be a hydrogen atom or a non-hydrogen atom. The atom may be an atom of the amino acid side chain or it may be an atom of the main chain.

Once the number of other positions from any aligned model at which the one or more mutants have at least one different amino acid residue compared to the parent GPCR has been determined, it is necessary to assess whether this represents a statistically significant cluster.

By a "statistically significant cluster" we mean that the number of other positions identified within a set distance d from the Cα atom or any atom of an amino acid residue at the position or positions at which the one or more mutants have a different amino acid residue compared to the parent GPCR, is greater than the number that would be expected by chance. Typically, a cluster is said to be statistically significant if the number of other positions identified is significant at the 95% level (ie $\rho<0.05$). It is particularly preferred if clusters are statistically significant such that $\rho<0.001$.

The significance of a cluster can be determined using any suitable method in the art. For example, as described in Example 8, a random distribution was generated to represent the baseline number of positions at which the one or more mutants have at least one different amino acid residue compared to the parent GPCR, within a set distance from the Cα atom or any atom of an amino acid residue at the position or positions at which the one or more mutants have a different amino acid residue compared to the parent GPCR. Such a random distribution was generated by randomly assigning N positions to the whole of a mutant GPCR, where N is the number of true stabilising mutations (i.e. the number of positions at which the mutant has at least one different amino acid residue compared to the parent GPCR). This is repeated for any aligned models where more than one model is being used. Once these randomly assigned mappings are complete, the distribution (average and standard deviation) of cluster sizes at different distances can be determined. Typically, such a random distribution will be produced from at least 5000, 10000 or 20000 such random assignments and is assumed to be normally distributed around a mean. It is appreciated that such random distributions would need to be computed for a given set distance, eg a random distribution for 6 Å and a random distribution for 8 Å. Having determined the average size and standard deviation of cluster sizes from a random distribution at a given distance, the significance of the existence of a cluster of a given size can be computed using standard statistical principles. For example, using the normal distribution, the significance of a cluster of size n can be computed according to formula: $Z=(x-\mu/\sigma)$, where x is the size of the cluster, $\mu$ is the average cluster size, $\sigma$ is the standard deviation of the distribution of clusters and Z is the significance value. It will be appreciated that the number of positions identified may be close in terms of standard deviations to the number expected by chance and still be significant at the 95% level.

If the number of positions identified within a set distance from the Cα atom or any atom of an amino acid residue, at the position or positions at which the one or more mutants have a different amino acid residue compared to the parent GPCR, is found to be significant, then a statistically significant cluster has been identified comprising amino acids that are more likely to be important in determining protein stability, ie a hotspot or hotspots have been defined. The centre of the cluster, ie the amino acid residue at the position or positions at which the mutant has a different amino acid residue compared to its parent GPCR, can then be mapped onto a second GPCR to provide one or more mutants of a second parent GPCR with increased stability relative to the second parent GPCR. For example, one or more mutations can be made in the amino acid sequence that defines a second GPCR within the same set distance from the Cα or any atom of the amino acid residue at the corresponding position or positions at which the one or more mutants have at least one different amino acid residue compared to the parent GPCR. For example, if a cluster was identified within 10 Å from Cα of residue X in a particular mutant GPCR, then one or more mutations may be made in the amino acid sequence that defines a second GPCR within 10 Å from Cα of the amino acid residue that corresponds to residue X in the second GPCR. Thus, once statistically significant clusters have been identified on one mutant GPCR, they may be used to identify stabilising mutations in other GPCRs.

As described in Example 8, where more than one cluster has been identified, it may be useful to define the centre of a number of clusters and using this as the radius centre for a super cluster which can be used to identify mutation positions in other sequences.

Thus, the invention includes a method for producing a mutant GPCR with increased stability relative to its parent GPCR, the method comprising:

(a) providing one or aligning more than one three-dimensional model of one or more mutants of a GPCR with increased stability relative to a parent GPCR;

(b) identifying in the amino acid sequence of the one or more mutants, the position or positions at which the one or more mutants have at least one different amino acid residue compared to the parent GPCR;

(c) determining within a set distance d Å from the Cα atom or any atom of an amino acid residue at the position or positions at which the one or more mutants have a different amino acid residue compared to the parent GPCR, the number of other positions from the model or the more than one aligned model at which the one or more mutants have at least one different amino acid residue compared to the parent GPCR;

(d) determining whether the number of other positions represents a statistically significant cluster;

(e) determining the centre of two or more statistically significant clusters identified in (d); and (f) making one or more mutations in the amino acid sequence that defines a second GPCR within a distance of x Å from the position that corresponds to the centre of the two or more statistically significant clusters, to provide one or more mutants of a second parent GPCR with increased stability relative to the second parent GPCR.

By the 'centre of two or more statistically significant clusters' we mean the point in three-dimensional space that corresponds to the centre of the two or more clusters. This may be the geometric centre determined by the coverage of all (x, y and z) co-ordinates of the centre points of each cluster, or the centre of gravity of the two or more clusters. Typically, the centre in each case is determined using computer software packages as is well known in the art. Alternatively, by the 'centre of two or more statistically significant clusters' we mean the amino acid residue that is closest to the centre of the two or more clusters as defined above (geometric centre or centre of gravity). By 'amino acid residue that is closest to' we mean that any atom of that amino acid is the atom that is closest to the centre, from all atoms in the protein.

It is appreciated that the centre may correspond to the centre of at least 2, 3, 4, 5. 6, 7, 8, 9, 10, 15 or 20 clusters.

The centre of statistically significant clusters can then be mapped onto a second GPCR and used to provide one or more mutants of a second parent GPCR with increased stability relative to the second parent GPCR. For example, one or more mutations can be made in the amino acid sequence that defines a second GPCR within a distance of x Å from the position that corresponds to the centre of the statistically significant clusters, to provide one or more mutants of a second parent GPCR with increased stability relative to the second parent GPCR.

When the centre is defined as a point in three dimensional space in a particular mutant GPCR, the position that corresponds to the centre is the point in the second GPCR that aligns to the centre point when a three-dimensional model of the second GPCR is compared with the model of the mutant GPCR. When the centre is defined as the amino acid residue closest to said point in a particular mutant GPCR, the position that corresponds to the centre is the CI atom of the amino acid residue in the second GPCR which aligns to the said amino acid residue in the mutant GPCR when the two GPCRs are compared using MacVector and CLUSTALW.

The distance x Å is the distance from the position that corresponds to the centre of the statistically significant clusters, that provides a sufficient radius to capture all of the individual clusters that together make up the super cluster. As discussed above, it will be appreciated that the distance x Å may be from a CI atom or from a point in three-dimensional space.

It is appreciated that any amino acid residue in the amino acid sequence that defines a second GPCR within the said distance can be mutated. Mutations can be made in an amino acid sequence, for example, as described above and using techniques well-established in the art.

Preferences for the second GPCR are defined above with respect to the first aspect of the invention, wherein reference to the first GPCR corresponds to the mutant GPCR in which a statistically significant cluster has been identified in step (d).

Since there are potentially thousands of mutations that can be screened in a GPCR for increased stability, it is advantageous to target particular mutations which are known to be important in conferring stability. Therefore, it will be appreciated that the methods of the first, second, third and fourth aspects of the invention may be used in a method of selecting mutant GPCRs with increased stability. In particular, carrying out the methods of the first, second, third and fourth aspects of the invention can be used to target mutations to particular amino acid residues (i.e. those at particular positions, those close to a particular position in terms of primary sequence proximity, and those close to a particular position in terms of three-dimensional proximity) or to amino acid sequences which define structural motifs important in determining stability, or to amino acid residues that are part of a cluster for which it has been determined is significantly more likely to comprise amino acids important in determining stability.

Accordingly, in one embodiment, the method of the first, second, third or fourth aspect of the invention further comprises:

(I) selecting a ligand, the ligand being one which binds to the second parent GPCR when the GPCR is residing in a particular conformation (II) determining whether the or each mutant of the second parent GPCR when residing in a particular conformation has increased stability with respect to binding the selected ligand compared to the stability of the second parent GPCR when residing in the same particular conformation with respect to binding that ligand, and (III) selecting those mutants that have an increased stability compared to the second parent GPCR with respect to binding the selected ligand.

It will be noted that steps (I), (II) and (III) correspond to steps (ii), (iii) and (iv) of the selection method described above. Accordingly, preferences for the ligand and methods of assessing stability are as defined above with respect to the selection method.

Conveniently, the methods of the first, second, third and fourth aspects of the invention are performed and the stability of the resulting mutants assessed as above. The methods of the first, second and third aspects of the invention may then be repeated, with the resulting one or more mutants generated in the first round becoming the first parent GPCR in the first step of each method in a subsequent round. Thus, it will be appreciated that the methods can be used in an iterative way by, for example, carrying out a method to identify single mutations with increased stability, combining those mutations in a single mutant GPCR, which is then the parent GPCR provided in the first step of each method. The methods may be repeated until sufficient stabilising mutations have been identified.

For example, in a particularly preferred embodiment of the second aspect of the invention, the one or more mutations in the amino acid sequence that defines a second GPCR are made within progressively increasing window sizes. Typically, a small window size is used first, and the stabilising mutations from that sequence subset identified, followed by scanning further residues at increasing window sizes until the desired number of mutations have been found. Thus in a first round, one or more mutations may be made in the amino acid sequence that defines a second GPCR within a window or windows of i plus or minus one residue, where i is the corresponding position or positions at which the one of more mutants have at least one different amino acid residue compared to the first parent GPCR. The stability of the resulting mutants may be assessed and those mutants that have an increased stability compared to the second parent GPCR selected. The method may then be repeated by making one or more mutations in the in the amino acid sequence that defines a second GPCR within a window or windows of i plus or minus two residues, and so on. Alternatively, the first window size analysed may be i plus or minus two, three or four residues. It is appreciated that once sufficient mutations have been identified there is no need to expand the window further.

Similarly, in a particularly, preferred embodiment of the third aspect of the invention, the one or more mutations in the amino acid sequence that defines a second GPCR are made within progressively increasing distances from the Cα atom or any atom of the amino acid residue i. Typically, a small distance is used first, and the stabilising mutations from that sequence subset identified, followed by scanning further residues at increasing distances until the desired number of mutations have been found. Thus in a first round, one or more mutations may be made in the amino acid sequence that defines a second GPCR within a distance of 6 Å from the Cα atom of, or within a distance of 4 Å from any atom of, the amino acid residue i, where i is the corresponding position or positions at which the one of more mutants have at least one different amino acid residue compared to the first parent GPCR. The stability of the resulting mutants may be assessed and those mutants that have an increased stability compared to the second parent GPCR selected. The method may then be repeated by making one or more mutations in the in the amino acid sequence that defines a second GPCR within a distance of 8 Å from the Cα atom of, or within a distance of 6 Å from any atom of amino acid residue i, and so on. It is appreciated that once sufficient mutations have been identified there is no need to increase the distance further.

A fifth aspect of the invention provides a mutant GPCR with increased stability relative to its parent GPCR produced by the methods of the first, second, third or fourth aspects of the invention.

It is preferred that the mutant GPCRs of the fifth aspect of the invention, have increased stability to any one of heat, a detergent, a chaotrpic agent and an extreme of pH.

It is preferred if the mutant GPCRs of the fifth aspect of the invention, have increased thermostability.

It is preferred if the mutant GPCRs of the fifth aspect of the invention have an increased thermostability compared to its parent when in the presence or absence of a ligand thereto. Typically, the ligand is an antagonist, a full agonist, a partial agonist or an inverse agonist, whether orthosteric or allosteric. As discussed above, the ligand may be a polypeptide, such as an antibody.

It is preferred that the mutant GPCR of the fifth aspect of the invention is at least 2° C. more stable than its parent preferably at least 5° C. more stable, more preferably at least 8° C. more stable and even more preferably at least 10° C. or 15° C. or 20° C. more stable than its parent. Typically, thermostability of the parent and mutant receptors are measured under the same conditions. Typically, thermostability is assayed under a condition in which the GPCR resides in a particular conformation. Typically, this selected condition is the presence of a ligand which binds the GPCR.

It is preferred that the mutant GPCR of the fifth aspect of the invention, when solubilised and purified in a suitable detergent has a similar thermostability to bovine rhodopsin purified in dodecyl maltoside. It is particularly preferred that the mutant GPCR retains at least 50% of its ligand binding activity after heating at 40° C. for 30 minutes. It is further preferred that the mutant GPCR retains at least 50% of its ligand binding activity after heating at 55° C. for 30 minutes.

In one embodiment the mutant GPCR of the fifth aspect of the invention is a mutant GPCR which compared to its parent receptor has at least one different amino acid at a position which corresponds to any one or more of the following positions: (i) according to the numbering of the turkey β-adrenergic receptor as set out in FIGS. 9A and 9B (SEQ ID NO: 1): Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338, (ii) according to the numbering of the human adenosine $A_{2a}$ receptor as set out in FIGS. 10A and 10B (SEQ ID NOS: 5-8): Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, (iii) according to the numbering of the rat neurotensin receptor as set out in FIGS. 11A and 11B (SEQ ID NO: 9): Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399, and (iv) according to the numbering of the muscarinic receptor as set out in FIG. 17A-17C (SEQ ID NO: 12): Leu 65, Met 145, Leu 399, Ile 383 and Met 384.

Alignment of the turkey β1 AR, human adenosine receptor, rat neurotensin receptor and human muscarinic receptor amino acid sequences in FIGS. 17A-17C (SEQ ID NOs: 3, 9, 12, 1, 5), shows that in 11 instances out of 70, two sequences contain mutations art the same position, namely at the following positions according to the numbering of the human beta2 AR as set out in FIGS. 17A-17C (SEQ ID NO: 3): Ala 59, Val 81, Ser 143, Lys 147, Val 152, Glu 180, Val 222, Ala 226, Ala 271, Leu 275 and Val 317. Therefore, in a preferred embodiment, the mutant GPCR of the fifth aspect of the invention is one which has, compared to its parent receptor, a different amino acid at any one or more of these positions.

In one embodiment the mutant GPCR of the fifth aspect of the invention is a mutant β-adrenergic receptor. For example, the mutant β-adrenergic receptor may have at least one different amino acid residue in a structural motif in which the mutant receptor compared to its parent receptor has a different amino acid at a position which corresponds to any of the following positions according to the numbering of the turkey β-adrenergic receptor as set out in FIGS. 9A and 9B (SEQ ID NO: 1): Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

In one embodiment the mutant GPCR of the fifth aspect of the invention is a mutant adenosine receptor. For example, the mutant adenosine receptor may have at least one different amino acid residue in a structural motif in which the mutant receptor compared to its parent receptor has a different amino acid at a position which corresponds to any of the following positions according to the numbering of the human adenosine $A_{2a}$ receptor as set out in FIGS. 10A and 10B (SEQ ID NOS: 5-8): Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315.

In one embodiment the mutant GPCR of the fifth aspect of the invention is a mutant neurotensin receptor. For example, the mutant neurotensin receptor may have at least one different amino acid residue in a structural motif in which the mutant receptor compared to its parent receptor has a different amino acid at a position which corresponds to any of the following positions according to the numbering of the rat neurotensin receptor as set out in FIGS. 11A and 11B (SEQ ID NO: 9): Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

The mutant GPCRs disclosed herein are useful for crystallisation studies and are useful in drug discovery programmes. They may be used in biophysical measurements of receptor/ligand kinetic and thermodynamic parameters eg by surface plasmon resonance or fluorescence based techniques. They may be used in ligand binding screens, and may be coupled to solid surfaces for use in high throughput screens or as biosensor chips. Biosensor chips containing the mutant GPCRs may be used to detect molecules, especially biomolecules.

The invention also includes a polynucleotide which encodes a mutant GPCR of the first or second aspects of the invention. In particular, polynucleotides are included which encode the mutant β-adrenergic receptor or the mutant adenosine receptors or the mutant neurotensin receptors of the invention. The polynucleotide may be DNA or it may be RNA. Typically, it is comprised in a vector, such as a vector which can be used to express the said mutant GPCR. Suitable vectors are ones which propagate in and/or allow the expression in bacterial or mammalian or insect cells.

The invention also includes host cells, such as bacterial or eukaryotic cells, which contain a polynucleotide which encodes the mutant GPCR. Suitable cells include E. coli cells, yeast cells, mammalian cells and insect cells.

Example 1

Conformational Stabilisation of the β-Adrenergic Receptor in Detergent-Resistant Form Summary There are over 500 non-odorant G protein-coupled receptors (GPCRs) encoded by the human genome, many of which are predicted to be potential therapeutic targets, but there is only one structure available, that of bovine rhodopsin, to represent the whole of the family. There are many reasons for the lack of progress in GPCR structure determination, but we hypothesise that improving the detergent-stability of these receptors and simultaneously locking them into one preferred conformation will greatly improve the chances of crystallisation. A generic strategy for the isolation of detergent-solubilised thermostable mutants of a GPCR, the β-adrenergic receptor, was developed based upon alanine scanning mutagenesis followed by an assay for receptor stability. Out of 318 mutants tested, 15 showed a measurable increase in stability. After optimisation of the amino acid residue at the site of each initial mutation, an optimally stable receptor was constructed by combining specific mutations. The most stable mutant receptor, βAR-m23, contained 6 point mutations that led to a Tm 21° C. higher than the native protein and, in the presence of bound antagonist, βARm23 was as stable as bovine rhodopsin. In addition, βAR-m23 was significantly more stable in a wide range of detergents ideal for crystallisation and was preferentially in an antagonist conformation in the absence of ligand.

Results

Selection of Single Mutations that Increase the Thermostability of the β1 Adrenergic Receptor βAR from turkey erythrocytes is an ideal target for structural studies because it is well characterised and is expressed at high-levels in insect cells using the baculovirus expression system[10,11]. The best overexpression of βAR is obtained using a truncated version of the receptor containing residues 34-424 ($\beta AR_{34-424}$) [9] and this was used as the starting point for this work. Alanine scanning mutagenesis was used to define amino residues in $\beta AR_{34-424}$ that, when mutated, altered the thermostability of the receptor; if an alanine was present in the sequence it was mutated to a leucine residue. A total of 318 mutations were made to amino acid residues 37-369, a region that encompasses all seven transmembrane domains and 23 amino acid residues at the C terminus; mutations at 15 amino residues were not obtained due to strong secondary structure in the DNA template. After sequencing each mutant to ensure the presence of only the desired mutation, the receptors were functionally expressed in E. coli and assayed for stability.

Figure 7:
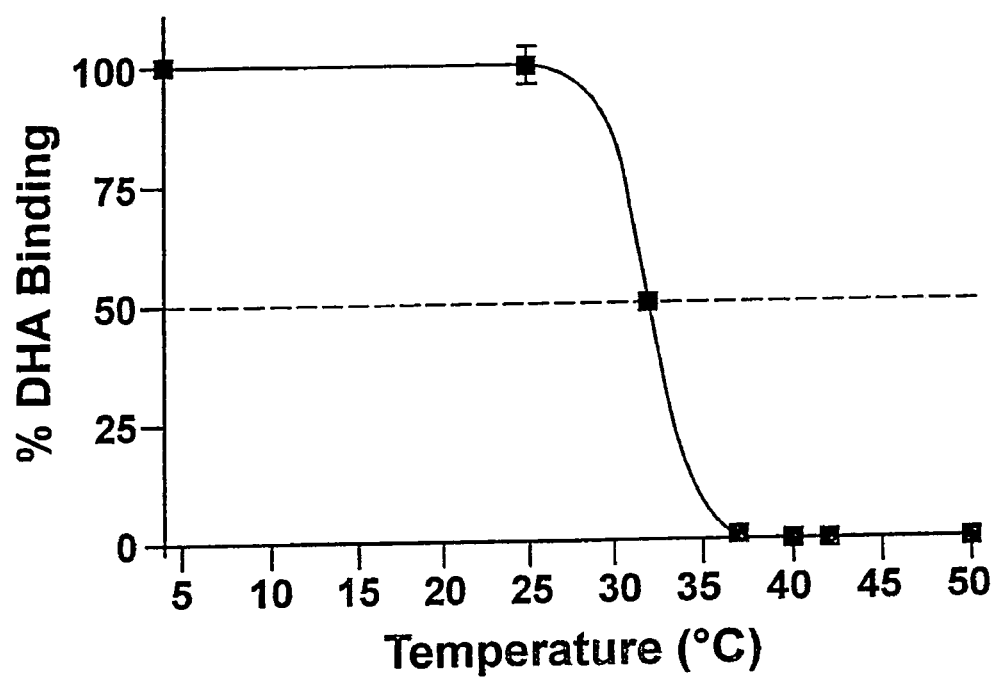
FIG. 7 Curve of thermostability of $\beta AR_{34-424}$ (Tm). Binding assays were performed using [$^3$H]-dihydroalprenolol (DHA) as radioligand as described under "Methods". Samples were heated for 30 minutes at different temperatures before the assay. Tm represents the temperature at which the binding decreased to the 50%, value showed as a discontinuous line. Data points are from duplicates of one single experiment. This experiment has been repeated several times with similar results.

The assay for thermostability was performed on unpurified detergent-solubilised receptors by heating the receptors at 32° C. for 30 minutes, quenching the reaction on ice and then performing a radioligand binding assay, using the antagonist [$^3$H]-dihydroalprenolol, to determine the number of remaining functional $\beta AR_{34-424}$ molecules compared to the unheated control. Heating the unmutated $\beta AR_{34-424}$ at 32° C. for 30 min before the assay reduced binding to approximately 50% of the unheated control (FIG. 7); all the data for the mutants were normalised by including the unmutated $\beta AR_{34-424}$ as a control in every assay performed. In the first round of screening, eighteen mutants showed an apparent increase in stability, maintaining more than 75% of antagonist binding after heating and being expressed in E. coli to at least 50% of the native $\beta AR_{34-424}$ levels. In view of the possibility of increasing further the stability of these mutants, each of the 18 residues was mutated to 2-5 alternative amino acid residues of varying size or charge (FIG. 1). Out of these 18 mutants, 12 were not improved by further changes, 5 had better thermostability if another amino acid was present and one mutation from the first screen turned out to be a false positive. In addition, three residues that were not stabilised upon mutation to alanine (V89, S151, L221) were mutated to a range of other amino acid residues; the two positions that when mutated to alanine did not affect thermostability, were also unaffected by other changes. In contrast, V89 showed less thermostability when mutated to alanine, but thermostability increased when it was mutated to Leu. Thus the initial alanine scanning successfully gave two-thirds of the best amino acid residues of those tested for any given position.

Figure 2:
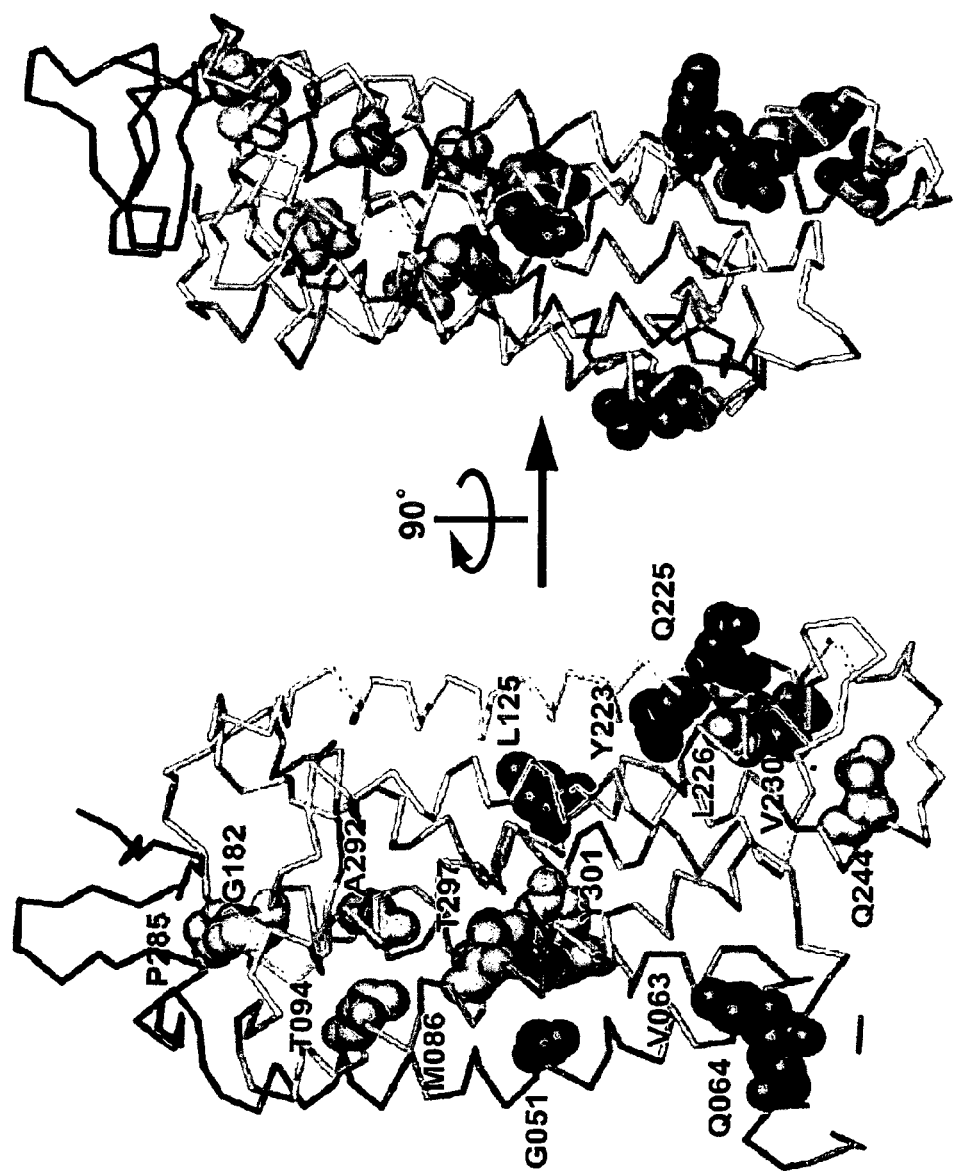
FIG. 2 Side chains in rhodopsin that are at equivalent positions to the thermostable mutations in $\beta AR_{34-424}$. The equivalent amino acid residues in rhodopsin to the amino acid residues mutated in $\beta AR_{34-424}$ were located in the rhodopsin structure, based upon an alignment among rhodopsin, β1 adrenergic receptor, neurotensin receptor, and adenosine $A_{2a}$ receptor (data not shown). Side chains in the same transmembrane helix are shown as space filling models in the same colour. The name and position of the amino acid residues are those in rhodopsin.

The position and environment predicted for each of the 16 amino residues that gave the best increases in thermostability when mutated were determined by aligning the βAR sequence with that of rhodopsin whose structure is known (FIG. 2). Fourteen of these residues were predicted to be present in transmembrane α-helices, with five of the residues predicted to be lipid-facing, 4 being deeply buried and the remainder were predicted to be at the interfaces between the helices. Some of these residues would be expected to interact with each other in the βAR structure, such as the consecutive amino acids G67 and R68 (V63 and Q64 in rhodopsin), or the amino acids within the cluster Y227, R229, V230 and A234 in helix 5 (Y223, Q225, L226 and V230 in rhodopsin). Other amino acid residues that could interact in βAR were Q194A in external loop 2 and D322A in external loop 3 (G182 and P285 in rhodopsin, respectively).

The increase in stability that each individual mutation gave to $\beta AR_{34-424}$ was determined by measuring the Tm for each mutant (results not shown); Tm in this context is the temperature that gave a 50% decrease in functional binding after heating the receptor for 30 minutes. Each mutation increased the Tm of $\beta AR_{34-424}$ by 1-3° C., with the exception of M90A and Y227A that increased the Tm by 8° C.

Combining Mutations to Make an Optimally Stable Receptor

Initially, mutations that improved thermostability that were adjacent to one another in the primary amino sequence of βAR were combined. Constructions containing the mutations G67A and R68S, or different combinations of the mutations at the end of helix 5 (Y227A, R229Q, V230A and A234L) were expressed and assayed; the Tm values (results not shown) were only 1-3° C. higher than the Tm for $\beta AR_{34-424}$ and one mutant was actually slightly less stable, suggesting that combining mutations that are adjacent to one another in the primary amino acid sequence does not greatly improve thermostability. Subsequently, mutations predicted to be distant from one another in the structure were combined. PCR reactions were performed using various mixes of primers to combine up to 5 different mutations in a random manner and then tested for thermostability (Table 1). The best of these combinations increased the Tm more than 10° C. compared to the Tm of $\beta AR_{34-424}$. In some cases, there was a clear additive effect upon the Tm with the sequential incorporation of individual mutations. This is seen in a series of 3 mutants, m4-1, m4-7 and m4-2, with the addition of V230A to m4-1 increasing the Tm by 2° C. and the additional mutation D332A in m4-7 increasing the Tm a further 3° C. Mutants that contained Y227A and M90A all showed an increase in Tm of 10° C. or more. Just these two mutations together increased the Tm of $\beta AR_{34-424}$ by 13° C. (m7-5), however, the total antagonist binding was less than 50% of $\beta AR_{34-424}$ suggesting impaired expression of this mutant. The addition of F338M to m7-5 did not increase the thermostability, but it increased levels of functional expression in E. coli.

Table 1

Combinations of mutations by PCR. 10 PCR reactions were performed combining different pairs of primers that contained the selected mutations. Successful PCR reactions are shown in the table. The stability of these new mutants was assayed as described in FIG. 7 and the Tm calculated. The results are shown as the mean±S.E. from duplicates.

TABLE 1

| Combinations of mutations by PCR. | | | |
|---|---|---|---|
| PCR | Receptor | Mutations | $T_m$ (° C.) |
| 4 | $\beta AR_{34-424}$ | | 31.7 ± 0.1 |
|  | m4-1 | G67A, G98A | 35.5 ± 0.9 |
|  | m4-2 | G67A, G98A, V230A, D322A | 40.9 ± 0.9 |
|  | m4-6 | G98A, D322A | 35.0 ± 0.2 |
|  | m4-7 | G67A, G98A, V230A | 38.0 ± 1.2 |

TABLE 1-continued

Combinations of mutations by PCR.

| PCR | Receptor | Mutations | $T_m$ (° C.) |
|---|---|---|---|
| 6 | m6-1 | Y227A, A234L, A282L, A334L | 41.6 ± 0.9 |
|   | m6-4 | R68S, Y227A, A234L, A282L | 41.6 ± 0.1 |
|   | m6-5 | R68S, A234L, A282L, A334L | 41.9 ± 0.5 |
|   | m6-9 | R68S, Y227A, A234L, A282L, A334L | 43.7 ± 0.4 |
|   | m6-10 | R68S, Y227A, A282L, A334L | 47.4 ± 1.1 |
|   | m6-11 | R68S, A282L, A334L | 39.1 ± 0.5 |
| 7 | m7-1 | M90V, A282L, F338M | 43.0 ± 0.8 |
|   | m7-2 | M90V, A282L | 38.9 ± 0.6 |
|   | m7-5 | M90V, Y227A | 45.2 ± 1.0 |
|   | m7-6 | M90V, I129V | 40.0 ± 0.6 |
|   | m7-7 | M90V, Y227A, F338M | 45.2 ± 2.0 |
| 10 | m10-4 | R68S, M90V, V230A, A334L | 46.9 ± 1.0 |
|   | m10-8 | R68S, M90V, V230A, F327A, A334L | 47.3 ± 1.4 |

10 PCR reactions were performed combining different pairs of primers that contained the selected mutations. Successful PCR reactions are shown in the table. The stability of these new mutants was assayed as described in FIG. 7 and the Tm calculated. The results are shown as the mean ± S.E. from duplicates.

Figure 3:
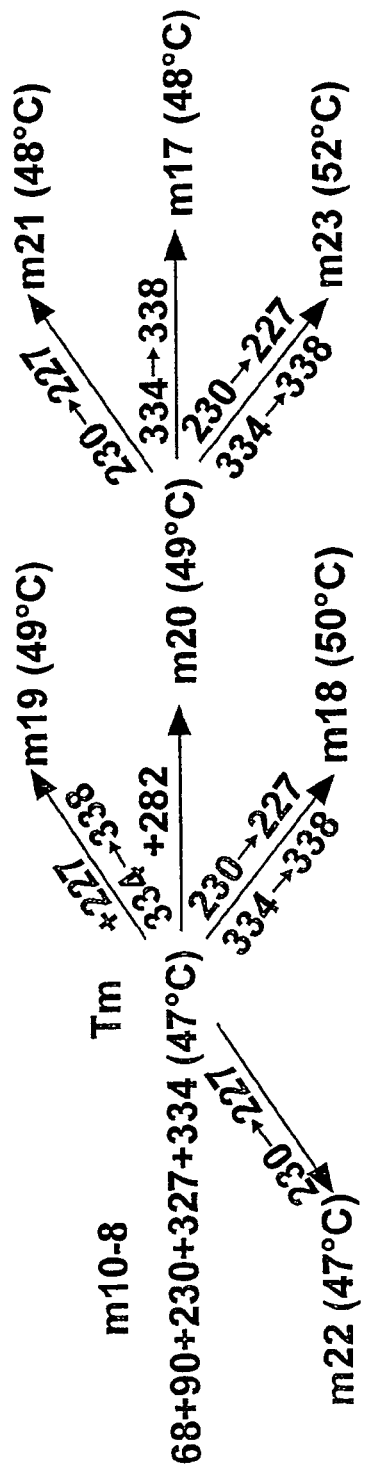
FIG. 3 Evolution of thermostability in βAR. Starting from βAR-m10-8, combinations of mutations were rearranged systematically to find the optimum combination of mutations (see also Table 2).

The most thermostable mutants obtained, which were still expressed at high levels in *E. coli*, were m6-10, m7-7 and m10-8. These mutants contained collectively a total of 10 different mutations, with 8 mutations occurring in at least two of the mutants. A second round of mutagenesis was performed using m10-8 as the template and adding or replacing mutations present in m6-10 and m7-7 (FIG. 3); some of these mutations were very close in the primary amino acid sequence of βAR and therefore were not additive as noted above, but many mutations improved the Tm further (Table 2). For example, exchanging two mutations in m10-8, to create m18, raised the Tm to 49.6° C. and adding A282L to make m23 increased the Tm a further 3° C. to 52.8° C. This produced the most thermostable βAR$_{34-424}$ mutant so far and will be referred to as βAR-m23.

TABLE 2

Improvement of best combination of mutations. These new mutants were obtained mixing the changes present in mutants m6-10, m7-7 and m10-8 by PCR. The stability of these new mutants was assayed as described in FIG. 7 and the Tm calculated. The results are shown as the mean ± S.E. from duplicates.

| | Mutations | | | | | | | $T_m$ (° C.) |
|---|---|---|---|---|---|---|---|---|
| m17 | R68S | M90V | Y227A | V230A | — | F327A | A334L | — | 48.2 ± 1.4 |
| m18 | R68S | M90V | Y227A | V230A | A282L | F327A | — | F338M | 49.6 ± 0/9 |
| m19 | R68S | M90V | Y227A | — | A282L | F327A | — | F338M | 49.0 ± 0.8 |
| m20 | R68S | M90V | — | — | — | F327A | A334L | — | 48.4 ± 0.7 |
| m21 | R68S | M90V | Y227A | — | — | F327A | A334L | — | 47.0 ± 1.3 |
| m22 | R68S | M90V | Y227A | | | F327A | A334L | — | 47.4 ± 0.5 |
| m23 | R68S | M90V | Y227A | — | A282L | F327A | — | F338M | 52.8 ± 1.4 |

Figure 4:
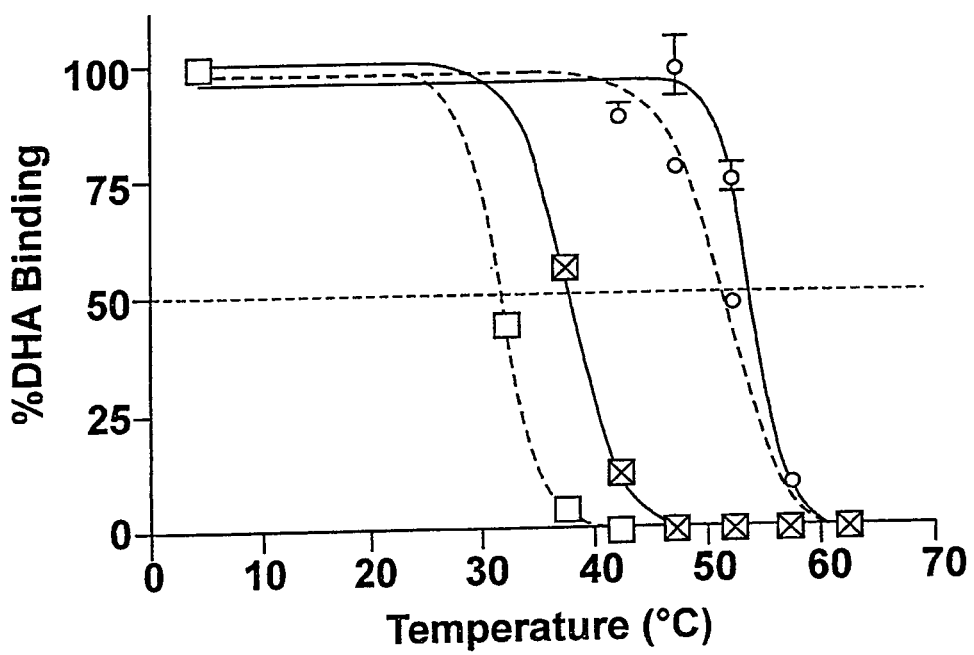
FIG. 4 Stability of βAR-m23 and $\beta AR_{34-424}$ in the apo-state or containing the bound antagonist [$^3$H]-DHA. To determine Tm in the absence of ligand (apo-state, discontinuous lines), detergent-solubilised receptors were incubated for 30 minutes at the temperatures indicated before carrying out the binding assay. For the Tm determination of the antagonist-bound form (continuous lines), detergent-solubilised receptors were pre-incubated with [$^3$H]-DHA, followed by incubation at the temperatures indicated. βAR-m23 (circles), and $\beta AR_{34-424}$ (squares). Data points are from duplicates measurements in a representative experiment.

The thermostability assays used to develop βAR$_{34-424}$ mutants were performed by heating the receptor in the absence of the antagonist, but it is well known that bound ligand stabilises receptors. Therefore, stability assays for βAR$_{34-424}$ and βAR-m23 were repeated with antagonist bound to the receptors during the heating step (FIG. 4). As expected, the Tm of the receptor that contained bound antagonist during the incubation was higher than that for the receptor without antagonist. For βAR$_{34-424}$ the Tm was 6° C. higher with bound antagonist and for βAR-m23 the Tm increased 2° C. to 55° C.; the smaller increase in thermostability observed for βAR-m23 when antagonist binds suggests that the receptor is already in a more stable conformation similar to the antagonist bound state than βAR$_{34-424}$ (see also below). The Tm of βAR-m23 with antagonist bound is very similar to the Tm of dark-state rhodopsin in dodecylmaltoside (DDM)[12], whose structure has been solved by two independent laboratories[13,14]. This suggested that βAR-m23 is sufficiently stable for crystallisation.

Characterization of βAR-m23

Figure 5A:
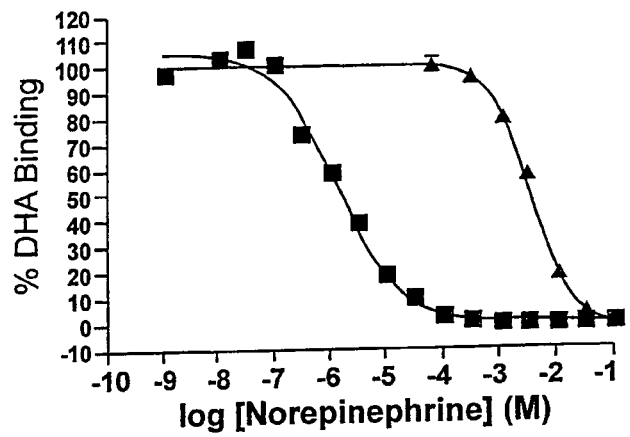
FIGS. 5A-5C Competition binding of agonists to βAR-m23 and $\beta AR_{34-424}$. Binding assays were performed on receptors partially purified in DDM; βAR-m23 (triangles) and $\beta AR_{34-424}$ (squares). [$^3$H]-DHA was used at a concentration three times greater than the $K_D$ of partially purified receptor (see Methods). [$^3$H]-DHA binding was competed with increasing concentrations of the agonists, norepinephrine (a) and isoprenaline (b), or with an antagonist, alprenolol (c). Log $EC_{50}$ and corresponding $EC_{50}$ values for the different ligands were calculated by nonlinear regression using Graph-Pad Prism software and the error for $logEC_{50}$s were lower than 10%. The $EC_{50}$s for ligand binding to $\beta AR_{34-424}$ and βAR-m23 are: norepinephrine, $\beta AR_{34-424}$ 1.5 μM, βAR-m23 3.7 mM; isoprenaline, $\beta AR_{34-424}$ 330 nM, βAR-m23 20 μM; alprenolol, βAR 78 nM, βAR-m23 112 nM.
Figure 5B:
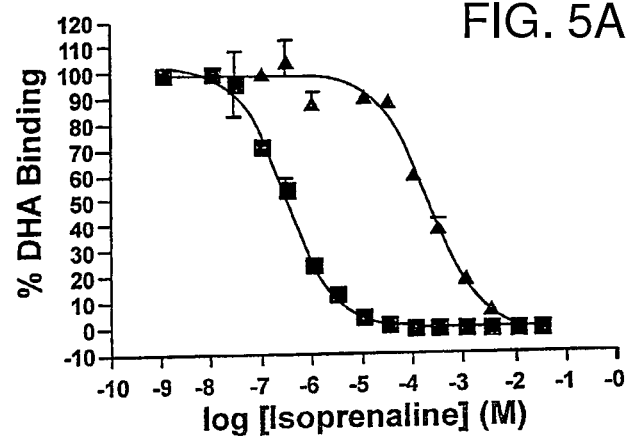
Figure 5C:
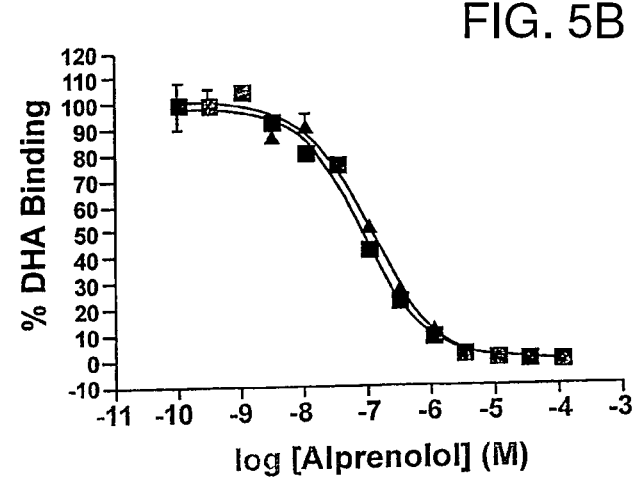
Figure 8A:
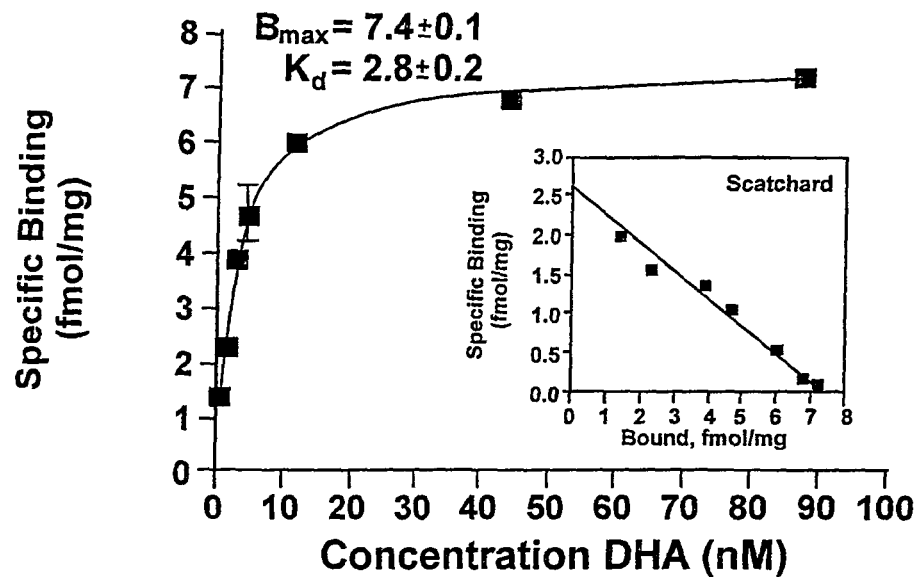
FIGS. 8A and 8B Saturation binding assays of membranes of $\beta AR_{34-424}$ and βAR-m23. Binding assays were performed as described in "Methods" using [$^3$H]-dihydroalprenolol (DHA) as radioligand; $\beta AR_{34-424}$ (a) and βAR-m23 (b). Scatchard plots are shown as insets along with the corresponding values for $B_{max}$ and $K_D$. Data points are from duplicates of two independent experiments for each protein. Data were analyzed by nonlinear regression using Prism software (GraphPad).
Figure 8B:
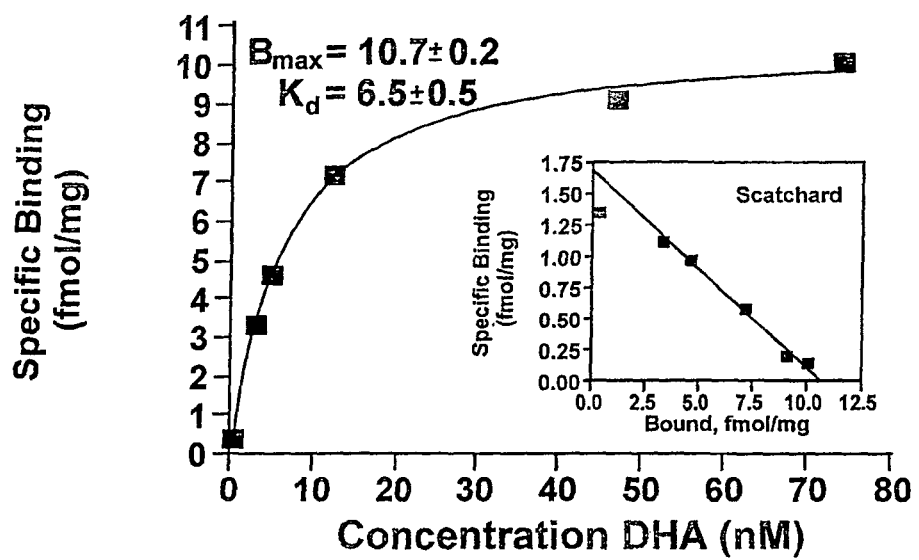

The three characteristic activities measured for βAR-m23 and βAR$_{34-424}$ to identify the effect of the six mutations were the affinity of antagonist binding, the relative efficacies of agonist binding and the ability of βAR-m23 to couple to G proteins. Saturation binding experiments to membranes using the antagonist [$^3$H]-dihydroalprenolol (FIGS. 8A and 8B) showed that the affinity of binding to βAR-m23 (K$_D$ 6.5±0.2 nM, n=2) was slightly lower than for βAR$_{34-424}$ (K$_D$ 2.8±0.1 nM, n=2), suggesting that there are no large perturbations in the structure of βARm23 in the antagonist-bound conformation. This is consistent with the observation that none of the mutations in βAR-m23 correspond with amino acids believed to be implicated in ligand binding. In contrast to antagonist binding, the efficacy of agonist binding by βAR-m23 is 3 orders of magnitude weaker than for βAR$_{34-424}$ (FIG. 5). The potency of the agonist isoprenaline is consistently lower in βAR-m23 and βAR$_{34-424}$ than for the native agonist norepinephrine, indicating that the agonist-bound conformation for the two receptors is likely to be similar. However, the large decrease in agonist efficacy in βAR-m23 compared to βAR$_{34-424}$ indicates that the 6 mutations in βAR-m23 have locked the receptor preferentially in an antagonist-bound conformation. From a crystallisation perspective, this is an added bonus to thermostabilisation, because it is essential to have a conformationally homogeneous protein population for the production of diffraction-quality crystals.

All of the thermostability assays used to derive βAR-m23 were performed on receptors solubilised in DDM. The aim of the thermostabilisation process was to produce a receptor that is ideal for crystallography, which means being stable in a variety of different detergents and not just DDM. We therefore tested the stability of βAR-m23 and βAR in a variety of different detergents, concentrating on small detergents that are preferentially used in crystallising integral membrane proteins.

Figure 6A:
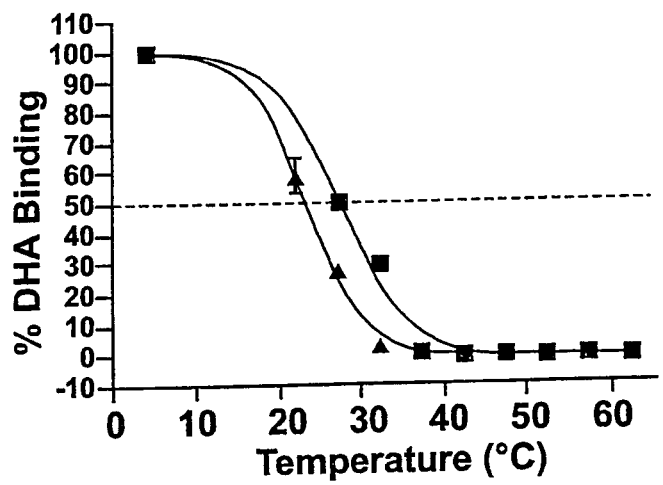
FIGS. 6A-6C Stability of βAR-m23 and $\beta AR_{34-424}$ in five different detergents. Samples of $\beta AR_{34-424}$ (a), and βAR-m23 (b) solubilized in DDM were partially purified on Ni-NTA agarose columns allowing the exchange into various different detergents: DDM (squares), DM (triangles), OG (inverted triangles), LDAO (diamonds) and NG (circles). βAR is so unstable in OG, NG and LDAO that it was not possible to measure any activity after purification at 6° C. Assays were carried out as described in the Methods and the Tm is shown at the intersection between the curves and the discontinuous line. Results are from duplicate measurements in a representative experiment performed in parallel. (c) Photomicrograph of a crystal of RAR-m23 mutant, which showed good order by X-ray diffraction.
Figure 6B:
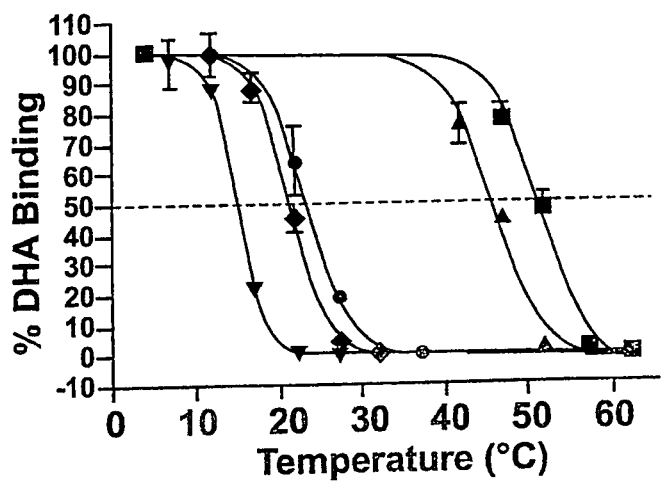
Figure 6C:
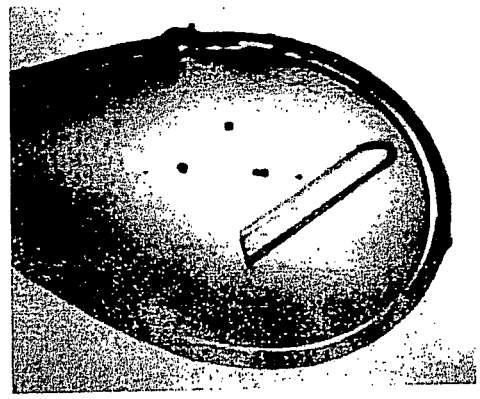

Membranes prepared from *E. coli* expressing βAR-m23 or βAR$_{34-424}$ were solubilised in DDM, bound to Ni-NTA agarose then washed with either DDM, decylmaltoside (DM), octylglucoside (OG), lauryldimethylamine oxide (LDAO) or nonylglucoside (NG). Stability assays were performed on the receptors in each of the different detergents (FIG. 6). βAR$_{34-424}$ was only stable in DDM and DM, with no active receptors eluting from the resin washed with OG, NG or LDAO. In contrast, functional βAR-m23 was still present in all detergents and the Tm could be determined. As expected, the smaller detergents were considerably more denaturing than either DDM (Tm 52° C.) or DM (Tm 48° C.), with T$_m$s of 25° C. (NG), 23° C. (LDAO) and 17° C. (OG). The difference in Tm between βAR-m23 and βAR$_{34-424}$ is about 20° C., irrespective of whether the receptors were solubilised in either DDM or DM; it is therefore not surprising that no active βAR$_{34-424}$ could be found in even NG, because the predicted Tm would be about 5° C., thus resulting in rapid inactivation of the receptor under the conditions used for purification. The selection strategy used for the generation of βAR-m23 was chosen deliberately to be based upon thermostability, because it is far simpler to apply than selecting for stability in detergents of increasing harshness. However, it is clear that increasing the thermostability of βAR$_{34-424}$ also resulted in increasing tolerance to small detergents ideal for crystallising integral membrane proteins.

Crystallisation of Mutant GPCR

Earlier attempts to crystallise several different constructs of turkey beta-adrenegic receptor failed. Despite experimenting with a variety of conditions, using both the native sequence and several truncated and loop-deleted constructs, over many years, no crystals were obtained.

However, once the stabilising mutations from βAR-m23 were transferred into the constructs, several different crystals were obtained in different detergents and different conditions.

The crystals that have been most studied so far were obtained using the purified beta-36 construct (amino acid residues 34-367 of the turkey beta receptor containing the following changes: point mutations C116L and C358A; the 6 thermostabilising point mutations in m23; replacement of amino acid residues 244-278 with the sequence ASKRK; a C terminal His6 tag) expressed in insect cells using the baculovirus expression system, after transferring the receptor into the detergent octyl-thioglucoside. The precipitant used was PEG600 or PEG1000 and the crystals obtained are elongated plates.

Experiments have also been carried out to see whether, once the crystallisation conditions had been defined using the stabilised receptor, it was possible to get crystals using the original non-stablised construct. It was possible that similar or perhaps very small crystals could have been obtained, but, in fact, the "wild type" (i.e. the starting structure from which the mutagenesis began) never gave any crystals.

The crystals are plate-shaped with space group C2 and diffract well, though the cell dimensions do vary depending on the freezing conditions used.

In general, once a GPCR has been stabilised it may be subjected to a variety of well-known techniques for structure determination. The most common technique for crystallising membrane proteins is by vapour diffusion (20, 21), usually using initially a few thousand crystallisation conditions set up using commercial robotic devices (22). However, sometimes the crystals formed by vapour diffusion are small and disordered, so additional techniques may then be employed. One technique involves the co-crystallisation (by vapour diffusion) of the membrane protein with antibodies that bind specifically to conformational epitopes on the proteins' surface (23, 24); this increases the hydrophilic surface of the protein and can form strong crystal contacts. A second alternative is to use a different crystallisation matrix that is commonly called either lipidic cubic phase or lipidic mesophase (25, 26), which has also been developed into a robotic platform (27). This has proven very successful for producing high quality crystals of proteins with only small hydrophilic surfaces e.g. bacteriorhodopsin (28). Membrane protein structures can also be determined to high-resolution by electron crystallography (29).

The evolution of βAR-m23 from βAR$_{34-424}$ by a combination of alanine scanning mutagenesis and the selection of thermostable mutants has resulted in a GPCR that is ideal for crystallography. The Tm for βAR-m23 is 21° C. higher than for βAR$_{34-424}$ and, in the presence of antagonist, βAR-m23 has a similar stability to rhodopsin. The increased Tm of βAR-m23 has resulted in an increased stability in a variety of small detergents that inactivate βAR$_{34-424}$. In addition, the selection strategy employed resulted in a receptor that is preferentially in the antagonist-bound conformation, which will also improve the chances of obtaining crystals, because the population of receptor conformations will be more homogeneous than for wild type βAR$_{34-424}$. Thus we have achieved a process of conformational stabilisation in a single selection procedure.

It is not at all clear why the particular mutations we have introduced lead to the thermostabilisation of the receptor. Equivalent positions in rhodopsin suggest that the amino acid residues mutated could be pointing into the lipid bilayer, into the centre of the receptor or at the interfaces between these two environments. Given the difficulties in trying to understand the complexities of the thermostabilisation of soluble proteins[15], it seems unlikely that membrane proteins will be any easier to comprehend; we found that there was no particular pattern in the amino acid residues in βAR that, when mutated, led to thermostability. However, since nearly 5% of the mutants produced were more stable than the native receptor, alanine scanning mutagenesis represents an efficient strategy to rapidly identify thermostable mutants.

The procedure we have used to generate βAR-m23 is equally applicable to any membrane protein that has a convenient assay for detecting activity in the detergent solubilized form. While we have selected for stability as a function of temperature as the most convenient primary parameter, the procedure can easily be extended to test primarily for stability, for example, in a harsh detergent, an extreme of pH or in the presence of chaotropic salts. Conformational stabilisation of a variety of human receptors, channels and transporters will make them far more amenable to crystallography and will also allow the improvement in resolution of membrane proteins that have already been crystallised. It is to be hoped that conformational stabilisation will allow membrane protein crystallisation to become a far more tractable problem with a greater probability of rapid success than is currently the case. This should allow routine crystallisation of human membrane proteins in the pharmaceutical industry, resulting in valuable structural insights into drug development.

Methods

Materials.

The truncated β1 adrenergic receptor from turkey (βAR$_{34-424}$)[9] was kindly provided by Dr Tony Warne (MRC Laboratory of Molecular Biology, Cambridge, UK). This βAR construct encoding residues 34-424 contains the mutation C116L to improve expression[11], and a C-terminal tag of 10 histidines for purification. 1-[4,6-propyl-$^3$H]-dihydroalprenolol ([$^3$H]-DHA) was supplied by Amersham Bioscience, (+) L-norepinephrine bitartrate salt, (−) isoprenaline hydrochloride, (−) alprenolol tartrate salt and s-propranolol hydrochloride were from Sigma.

Mutagenesis of βAR.

The βAR cDNA was ligated into pRGIII to allow the functional expression of βAR in *E. coli* as a MalE fusion protein[16]. Mutants were generated by PCR using the expression plasmid as template using the QuikChange II methodology (Stratagene). PCR reactions were transformed into XL10-Gold ultracompetent cells (Stratagene) and individual clones were fully sequenced to check that only the desired mutation was present. Different mutations were combined randomly by PCR by including all the pairs of primers that introduced the following mutations: Mut4, G67A, G068A, V230A, D322A and F327A; Mut6, R068S, Y227A, A234L, A282L and A334L; Mut7, M90V, I129V, Y227A, A282L and F338M; Mut10, R68S, M90V, V230A, F327A and A334L. The PCR mixes were transformed and the clones sequenced to determine exactly which mutations were introduced.

Protein Expression and Membrane Preparations.

Expression of βAR and the mutants was performed in XL10 cells (Stratagene). Cultures of 50 ml of 2×TY medium containing ampicillin (100 μg/ml) were grown at 37° C. with shaking until OD$_{600}$=3 and then induced with 0.4 mM IPTG. Induced cultures were incubated at 25° C. for 4 h and then cells were harvested by centrifugation at 13,000×g for 1 min (aliquots of 2 ml) and stored at −20° C. For the assays, cells were broken by freeze-thaw (five cycles), resuspended in 500 μl of buffer [20 mM Tris pH 8, 0.4 M NaCl, 1 mM EDTA and protease inhibitors (Complete™, Roche)]. After an incubation for 1 h at 4° C. with 100 μg/ml lysozyme and DNase I (Sigma), samples were solubilized with 2% DDM on ice for 30 minutes. Insoluble material was removed by centrifugation (15,000×g, 2 min, 4° C.) and the supernatant was used directly in radioligand binding assays.

For large-scale membrane preparations, 2L and 6L of *E. coli* culture of βAR and Mut23, respectively, were grown as described above. Cells were harvested by centrifugation at 5,000×g for 20 min, frozen in liquid nitrogen and stored at −80° C. Pellets were resuspended in 10 ml of 20 mM Tris pH 7.5 containing 1× protease inhibitor cocktail (Complete™ EDTA-free, Roche); 1 mg DNase I (Sigma) was added and the final volume was made to 100 ml. Cells were broken by a French press (2 passages, 20,000 psi), and centrifuged at 12,000×g for 45 min at 4° C. to remove cell debris. The supernatant (membranes) was centrifuged at 200,000×g for 30 min at 4° C.; the membrane pellet was resuspended in 15 ml of 20 mM Tris pH 7.5 and stored in 1 ml aliquots at −80° C. after flash-freezing in liquid nitrogen. The protein concentration was determined by the amido black method[17]. These samples were used in radioligand binding assays after thawing and being solubilized in 2% DDM as above.

For competition assays, as well as testing different detergents, DDM-solubilized βAR was partially purified with Ni-NTA agarose (Qiagen). 200 μl of Ni-NTA agarose was added to 2 ml of solubilized samples (10 mg/ml of membrane protein) in 20 mM Tris pH 8, 0.4 M NaCl, 20 mM imidazole pH 8 and incubated for 1 h at 4° C. After incubation, samples were centrifuged at 13,000×g for 30 sec and washed twice with 250 μl of buffer (20 mM Tris pH 8, 0.4 M NaCl, 20 mM imidazole) containing detergent (either 0.1% DDM, 0.1% DM, 0.1% LDAO, 0.3% NG or 0.7% OG).

Receptors were eluted in 2×100 μl of buffer (0.4 M NaCl, 1 mM EDTA, 250 mM imidazole pH 8, plus the relevant detergent). The $K_D$ for [$^3$H]-DHA binding to semipurified βAR$_{34-424}$ and βAR-m23 was, respectively 3.7 nM and 12.5 nM and the final concentration of [$^3$H]-DHA used in the competition assays was 3 times the $K_D$ ie 12 nM for βAR$_{34-424}$ and 40 nM for βAR-m23.

Radioligand Binding and Thermostability Assays.

Single point binding assays contained 20 mM Tris pH 8, 0.4 M NaCl, 1 mM EDTA, 0.1% DDM (or corresponding detergent) with 50 nM [$^3$H]-DHA and 20-100 μg membrane protein in a final volume of 120 μl; equilibration was for 1 h at 4° C. Thermostability was assessed by incubating the binding assay mix, with or without [$^3$H]-DHA at the specified temperature for 30 minutes; reactions were placed on ice and [$^3$H]-DHA added as necessary and equilibrated for a further hour. Receptor-bound and free radioligand were separated by gel filtration as described previously[18]. Non-specific binding was determined in the presence of 1 μM of s-propranolol. Saturation curves were obtained using a range of [$^3$H]-DHA concentration from 0.4 nM to 100 nM. Competition assays were performed using a concentration of [$^3$H]-DHA of 12 nM for βAR$_{34-424}$ and 40 nM for βAR-m23 (ie three times the $K_D$) and various concentrations of unlabeled ligands (0-100 mM). Radioactivity was counted on a Beckman LS6000 liquid scintillation counter and data were analyzed by nonlinear regression using Prism software (GraphPad).

Location of βAR-m23 Thermostable Mutations in Rhodopsin Structure.

The pdb file for the rhodopsin structure, accession code 1GZM[14], was downloaded from the Protein Data Bank website and displayed in the program PyMOLX11Hybrid (DeLano Scientific). The equivalent amino acid residues in rhodopsin for the thermostable mutations in βAR were located in the rhodopsin structure based upon an alignment among the four GPCRs with which we are most familiar, namely rhodopsin, β1 adrenergic receptor, neurotensin receptor and adenosine A$_{2a}$ receptor[19].

Example 2

Mutants of the Adenosine A$_{2a}$ Receptor (A$_{2a}$R) with Increased Thermostability 1. 315 site-directed mutants made between residues 2-316 of A$_{2a}$R.
2. All of these mutants have been assayed for thermostability using an assay measuring agonist and antagonist binding after the heating step (Ligand(−) format as described in FIG. 12).

a. 26 mutants showed improved thermostability when measured with $^3$H-NECA (agonist): G114 A, G118A, L167A, A184L, R199A, A$_{203}$L, L208A, Q210A, S213A, E219A, R220A, S223A, T224A, Q226A, K227A, H230A, L241A, P260A, S263A, L267A, L272A, T279A, N284A, Q311A, P313A, K315A.

b. 18 mutants showed improved thermostability when assayed with $^3$H-ZM241385 (antagonist): A54L, V57A, H75A, T88A, G114A, G118A, T119A, K122A, G123A, P149A, E151A, G152A, A203L, A204L, A231L, L235A, V239A.

3. Mutations have been combined to generate mutants in a putative antagonist conformation. Wildtype A$_{2a}$R has a Tm of 31° C. with ZM241385 bound.

a. Rant17 A54L+K122A+L235A Tm 48° C. (ZM241385 bound)
   b. Rant19 A54L,T88A,V239A+A204L Tm 47° C. (ZM241385 bound)
   c. Rant21 A54L,T88A,V239A+K122A Tm 49° C. (ZM241385 bound)

4. Mutations from the agonist screen have been combined, but have led to only a very low level of improvement in Tm of +2° C.

TABLE (i)

List of A2aR stabilising mutations. Mutants were expressed in *E. coli*, solubilised in 2% DDM + 10% glycerol and tested for ligand-binding, using the agonist [$^3$H]-NECA (on the right) and the antagonist [$^3$H]-ZM241385 (left). Concentrations of radioligands were 6-10-fold above their K$_D$ measured for the wild-type receptor. Expression of active receptor was evaluated by ligand binding at 4° C. Stability was assayed by heating the solubilised receptor in its apo-state at 30° C. for 30 minutes and then measuring residual binding activity. Under these conditions, wild-type activity decays to 50% (S.D. = 15%). Data obtained for expression and stability were normalised to wild-type values. Mutations included in subsequent rounds of mutagenesis were those whose expression was ≥ 30-40% and stability ≥ 130-140% compared to the wild-type. Bold lines indicate cluster of mutations.

| | Agonist | | | Agonist | |
|---|---|---|---|---|---|
| Mutation | Expression (%) | Stability (%) | Mutation | Expression (%) | Stability (%) |
| wt | 100 | 100 | wt | 100 | 100 |
| S090A | 151 | 151 | A054L | 90 | 140 |
| G114A | 62 | 143 | V057A | 44 | 144 |
| G118A | 71 | 151 | H075A | 82 | 152 |
| L167A | 41 | 174 | T088A | 67 | 230 |
| A184L | 140 | 150 | G114A | 73 | 153 |
| R199A | 73 | 202 | G118A | 84 | 148 |
| A203L | 42 | 172 | T119A | 90 | 148 |
| L208A | 276 | 215 | K122A | 52 | 153 |
| Q210A | 46 | 155 | G123A | 90 | 158 |
| S213A | 40 | 140 | P149A | 54 | 215 |
| E219A | 96 | 221 | E151A | 63 | 173 |
| R220A | 84 | 250 | G152A | 70 | 156 |
| S223A | 57 | 146 | A203L | 111 | 132 |
| T224A | 142 | 276 | A204L | 40 | 181 |
| Q226A | 119 | 217 | A231L | 90 | 148 |
| K227A | 87 | 222 | L235A | 85 | 140 |
| H230A | 57 | 154 | V239A | 91 | 134 |
| L241A | 139 | 156 | | | |
| P260A | 70 | 169 | | | |
| S263A | 60 | 158 | | | |
| L267A | 40 | 187 | | | |
| L272A | 34 | 157 | | | |
| T279A | 125 | 158 | | | |
| N284A | 64 | 151 | | | |
| Q311A | 49 | 164 | | | |
| P313A | 44 | 148 | | | |
| K315A | 64 | 186 | | | |

TABLE (ii)

Stability of best combinations. Receptors were solubilised in 1% DDM (no glycerol). A melting profile was obtained by heating the solubilised receptor at different temperatures in absence (apo-state) or presence of ligand (ligand-occupied state). Data shown are representative of at least three independent experiments. S.D. is <1° C.

| | Tm (° C.) | | | Tm (° C.) | |
|---|---|---|---|---|---|
| | − agonist | + agonist | | − antagonist | + antagonist |
| Wt | 21 | 29 | wt | 31 | 32 |
| Rag 1 (A184L/ R199A/L272A) | 26 | 34 | Rant 5 (A54L/ T88A/ V239A) | 42 | 46 |
| Rag 23 (Rag 1 + F79A/ L208A) | 22 | 38 | Rant 21 (Rant 5 + K122A) | 41 | 49 |

TABLE iii

Summary of results for competition assays of detergent-solubilised wild-type A2aR and thermo-stable mutant Rant 21.

| | K$_i$ (M) | |
|---|---|---|
| Competitor | wt | Rant 21 |
| XAC | $2.3 \times 10^{-6}$ | $2.3 \times 10^{-6}$ |
| Theophylline | $1.5 \times 10^{-3}$ | $0.9 \times 10^{-3}$ |
| NECA | $7.0 \times 10^{-6}$ | $>1 \times 10^{-1}$ |
| R-PIA | $1.6 \times 10^{-5}$ | $3.6 \times 10^{-3}$ |

Values are representative of two independent experiments. Each data point was assayed in triplicate and plotted as mean ± SD. Each solubilised receptor was incubated with ligands for one hour on ice in binding buffer (50 mM Tris pH 7.5 and 0.025% DDM) containing 400 mM NaCl. Binding of [3H]ZM241385 (10 nM) in the absence of unlabeled ligand was set to 100%. Data shown are from two independent experiments with each data point measured in triplicate. Incubation of samples with ligands was for 1 hour on ice with [$^3$H]ZM241385 at a concentration of 10 nM. K$_i$ values were calculated according to the Cheng and Prusoff equation using the non-linear regression equation of the software Prism, applying a K$_D$ for [$^3$H]ZM241385 of 12 nM for the wild-type and 15 nM for Rant 21. Rant 21 did not bind NECA sufficiently for an accurate K$_i$ determination (hence indicated as $>1 \times 10^{-1}$). The affinity of Rant21 for agonist binding is weakened 232 fold for R-PIA and at least by 1900 fold for NECA.

TABLE iv

Summary of results for saturation assays of detergent-solubilised wild-type A2aR and thermostable mutants.

| | K$_D$ (nM) | |
|---|---|---|
| Receptor | [$^3$H]NECA (agonist) | [$^3$H]ZM241385 (antagonist) |
| wt | 32 ± 1 | 12 ± 3 |
| Rag 1 | 26 ± 0.4 | 26 ± 0.5 |
| Rag 23 | 21 ± 1 | 62 ± 1 |
| Rant 21 | >450 | 15 ± 3 |

Values are representative of three independent experiments. Each data point was assayed in triplicate and plotted as mean ± SD. Data were fitted to the Michaelis-Menten equation using the non-linear regression equation of the software Prism.

TABLE v

Summary of stability of wild-type and mutant receptors in different detergents.

| | Tm (° C.) | | | |
|---|---|---|---|---|
| | Agonist-binding | | Antagonist-binding | |
| | wt | Rag 23 | wt | Rant 21 |
| 0.01% DDM | 27 | 34 | 25 | 39 |
| 0.1% DM | 23 | 29 | 10 | 28 |
| 0.3% NM | 22 | 28 | <4 | 25 |
| 0.3% NG | † | † | † | 22 |
| 0.6% OG | <9 | 16 | † | 23 |
| 0.003% LDAO | 28 | 38 | 32 | 42 |
| 0.006% FC12 | 37 | 39 | 43 | 49 |

Solubilisation of receptors and detergent exchange was performed during the IMAC step. S.D. is <1° C. It was not possible to determine the Tm for some receptor-detergent combinations, because the receptor was too unstable (†).

Example 3

Mutants of the Neurotensin Receptor (NTR) with Increased Thermostability 1. 340 site-directed mutants have been made between residues 61-400 of NTR.
2. Initially, all of these mutants were assayed for thermostability using an assay measuring $^3$H-neurotensin (agonist) binding after the heating step. 24 mutations led to a small but significant increase in thermostability: A356L, H103A, D345A, A86L, A385L, Y349A, C386A, K397A, H393A, 1116A, F358A, S108A, M181A, R392A, D113A, G209A, L205A, L72A, A120L, P399A, Y351A, V268A, T207A, A155L, S362A, F189A, N262A, L109A, W391A, T179A, S182A, M293A, L256A, F147A, D139A, S100A, K176A, L111A, A90L, N270A.
3. Mutants tested for thermostability by heating in the absence of the agonist were re-tested using a slightly different assay where the mutants were heated in the presence of $^3$H-neurotensin (Ligand(+) format in FIG. 12). Mutants with improved thermostability are: A69L, A73L, A86L, A90L, H103A, V165A, E166A, G215A, V229A, M250A, 1253A, A177L, R183A, 1260A, T279A, T294A, G306A, L308A, V309A, L310A, V313A, F342A, F358A, V360A, S362A, N370A, S373A, F380A, A385L, P389A, G390A, R395A.
4. There are also mutants that have a significantly enhanced expression level compared to the wildtype receptor and could be used to boost preceptor production levels for crystallisation: A86L, H103A, F358A, S362A, N370A, A385L, G390A. All of these also have increased thermostability.
5. Preferred combinations are
   a. Nag7m F358A+A86L+1260A+F342A Tm 51° C. (neurotensin bound)
   b. Nag7n F358A+H103A+1260A+F342A Tm 51° C. (neurotensin bound)
   Wildtype NTR has a Tm of 35° C. with neurotensin bound.

Example 4

Identification of Structural Motifs in which Stabilising GPCR Mutations Reside

The structure of the β2 adrenergic receptor has been determined (20, 21), which is 59% identical to the turkey β1 receptor, but with a distinctly different pharmacological profile (22, 23). In order to determine the structural motifs in which the stabilising mutations of the turkey β1 receptor reside, we mapped the mutations onto the human β2 structure (21).

The beta adrenergic receptors were first aligned using ClustalW in the MacVector package; thermostabilising mutations in turkey β1 were highlighted along with the corresponding residue in the human β2 sequence. The human β2 model (pdb accession code 2RH1) was visualised in Pymol and the desired amino acids were shown as space filling models by standard procedures known in the art. The structural motifs in which the stabilising mutations were located, were determined by visual inspection.

Table (vi) lists the equivalent positions in the β2 receptor corresponding to the thermostabilising mutations in βAR-m23 and the structural motifs in which they reside.

As seen from Table (vi), the mutations are positioned in a number of distinct localities. Three mutations are in loop regions that are predicted to be accessible to aqueous solvent (loop). Eight mutations are in the transmembrane α-helices and point into the lipid bilayer (lipid); three of these mutations are near the end of the helices and may be considered to be at the hydrophilic boundary layer (lipid boundary). Eight mutations are found at the interfaces between transmembrane α-helices (helix-helix interface), three of which are either within a kinked or distorted region of the helix (kink) and another two mutations occur in one helix but are adjacent to one or more other helices which contain a kink adjacent in space to the mutated residue (opposite kink). These latter mutations could affect the packing of the amino acids within the kinked region, which could result in thermostabilisation. Another mutation is in a substrate binding pocket.(pocket).

TABLE vi

Position in the human β2 structure of the amino acid residues equivalent to the thermostabilising mutations found in the turkey β1 receptor and the structural motifs in which they reside.

| | Turkey β1 | Human β2 | Description | |
|---|---|---|---|---|
| Helix 1 | I55A | I47 | 3-helix kink interface | FIG. 18 |
| Helix 1 | G67A | A59 | lipid boundary | |
| Helix 1 | R68S | K60 | lipid boundary | FIG. 25 |
| Helix 2 | V89L | V81 | kink | FIG. 19 |
| Helix 2 | M90V | M82 | kink | FIG. 20 |
| Helix 2 | G98A | G90 | pocket | |
| Helix 3 | I129V | I121 | opposite kink | FIG. 21 |
| | S151E | S143 | loop | |
| Helix 4 | V160A | V152 | lipid | |
| | Q194A | A186 | loop | |
| Helix 5 | L221V | V213 | lipid | |
| Helix 5 | Y227A | Y219 | helix-helix interface | FIG. 23 |
| Helix 5 | R229Q | R221 | lipid | |
| Helix 5 | V230A | V222 | helix-helix interface | |
| Helix 5 | A234L | A226 | helix-helix interface | |
| Helix 6 | A282L | C265 | loop | FIG. 24 |
| | D322K | K305 | lipid boundary | |
| Helix 7 | F327A | L310 | lipid | |
| Helix 7 | A334L | V317 | lipid | |
| Helix 7 | F338M | F321 | kink | FIG. 22 |

Such structural motifs, by virtue of them containing stabilising mutations, are important in determining protein stability. Therefore, targeting mutations to these motifs will facilitate the generation of stabilised mutant GPCRs. Indeed, there were several instances where more than one mutation mapped to the same structural motif. For example, the Y227A, V230A and A234L mutations in the turkey β1 adrenergic receptor all mapped to the same helical interface, the V89L and M90V mutations mapped to the same helical kink and the F327A and A334L mutations mapped to the same helical surface pointing towards the lipid bilayer (Table (vi)). Thus, when one stabilising mutation has been identified, the determination of the structural motif in which that mutation is located will enable the identification of further stabilising mutations.

Example 5

Transferability of Stabilizing Mutations Among β-Adrenergic Receptors

Summary

We have described six point mutations that stabilized the turkey β1-adrenergic receptor (AR). The mutant, β1AR-m23, reached an apparent Tm of 21° C. higher than the native protein when solubilized in dodecylmaltoside (DDM). These mutations helped to the crystallization and structure determination of a truncated version of the protein. Now we checked the transferability of these stabilizing mutations to the human β1AR and β2AR. Stability analysis revealed that human β1AR is much more unstable and lipid dependent than turkey β1AR, whereas β2AR is more stable than any of them. In both cases the mutations increased the Tm of the receptors, especially for the β1AR in the presence of detergent. Other changes in these residues showed that the original mutations of turkey β1 AR worked as well for the human βARs as for turkey, revealing the importance of the mutations in this concrete residues.

Methods

Materials.

Human β1, β2 and β3 were cloned into pcDNA3.1+. These constructions were provided by Missouri S&T cDNA Resource center. Turkey β1AR ($\beta AR_{34-424}$), and the mutated version β1 AR-m23, are described in Serrano-Vega et al (*PNAS* (2008) 105: 877). Both were cloned into pcDNA3. 1-[4,6-propyl-$^3$H]dihydroalprenolol ([$^3$H]DHA) was supplied by Amersham Bioscience.

Mutagenesis.

Human receptors were mutated by PCR using primers containing the desired mutations as described in ref. C-terminus region of human β1 was also truncated by PCR using a primer than contained a deletion after $Leu_{463}$. PCR reactions were carried out using KOD polymerase (Novagen)

Expression.

The proteins were expressed by transient transfections in HEK cells using the reagent Gene Juice (Novagen). After transfection, cells were incubated for 48 hours, and aliquots of 1 ml in a concentration of 2 million cells/ml were harvested by centrifugation and stored at −20° C. For the assays, cells were resuspended in 500 µl of buffer [75 mM Tris, pH8/12.5 mM $MgCl_2$/5 mM EDTA/protease inhibitors (Complete; Roche)] containing different amount of detergent dodecylmaltoside (DDM).

Ligand Binding and Thermostability Assays.

Binding assays were carried out incubating 40 µl of sample with 80 nM [$^3$H]DHA in a final volume of 120 µl of buffer [75 mM Tris, pH8/12.5 mM $MgCl_2$/5 mM EDTA/0.01% DDM]. Equilibration was for 1 h at 4° C. Receptor-bound and free radioligand were separated by gel filtration as described previously (ref Tony). The thermostability was calculated incubating the samples in the absence of ligand for 30 min at different temperatures, and data were analyzed by nonlinear regression using Prism software (GraphPad)

Results

Expression and Thermostability of Human β1AR and β2AR.

We have described six mutations in the turkey β1-adrenergic receptor (AR), construction β1AR-m23, that stabilised the protein when solubilised in detergent and displaced it to the antagonist bound conformation (Serrano-Vega et al, PNAS (2008) 105: 877). This thermostabilisation in a certain conformation was essential for the crystallisation of the receptor (Warne et al, Nature (2008) 454: 486). Now we studied the transferability of these mutations to others receptors in the same family. Turkey β1AR has a 76% and a 59% of identity with human β1AR and β2AR respectively (N- and C-termini removed in the alignments). Most of the thermostabilising mutations are conserved among turkey and human βARs (FIG. 29) (SEQ ID NOS: 13-16). These mutations are preferentially in the transmembrane regions, more conserved. Therefore, it was possible that the mutations that stabilised the turkey β1AR may also stabilise human β1AR and β2AR.

We first analysed the expression and the stability of the wild types. The constructions were expressed in HEK cells by transient transfections. Expression was calculated by binding assay with the radioligand 1-[4,6-propyl-$^3$H]dihydroalprenolol ([$^3$H]DHA). Expression for human β1AR was very low so the C-terminus was truncated after $Leu_{463}$ in order to increase the expression. The truncated protein β1AR-Cdel increased the expression 5 times respect the wild type (data not shown). As result, human β1AR-Cdel and β2AR had similar activity levels when assayed in membranes, lower than turkey β1AR (FIG. 30A). However, when solubilized with 2% DDM the activity of human β1AR-Cdel decayed dramatically (FIG. 30B). This destabilisation due to the detergent apparently did not affect the turkey β1AR or the human β2AR. Sensitivity to detergent was measured solubilising the samples in increasing amounts of detergents, from 0.01% to 1%, this last one still above the c.m.c although the solubilisation is not complete (FIGS. 31A-31C). Everything was carried out at 4° C. Turkey β1AR and human β2AR showed the same activity for all the conditions, less activity with 0.01% DDM possibly due to the partial solubilisation, but human β1AR-Cdel had a clear sensitivity for the detergent (this was also observed in the wild type, β1AR, data not shown).

Figure 32A:
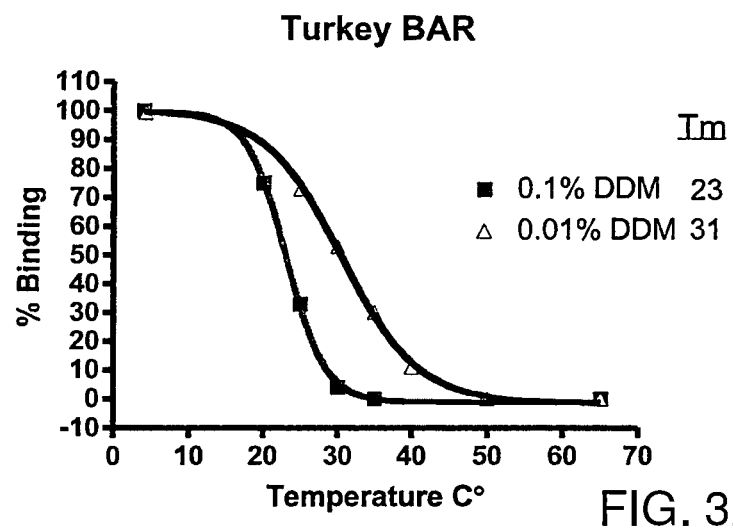
Figure 32B:
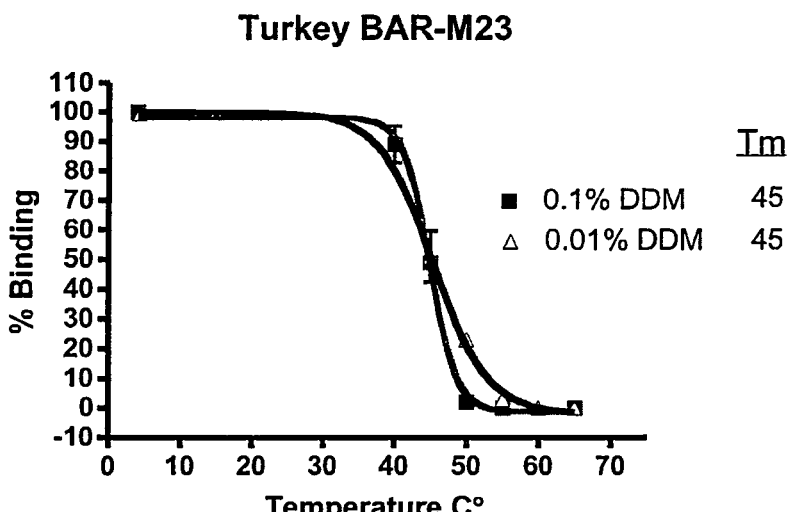
Figure 32C:
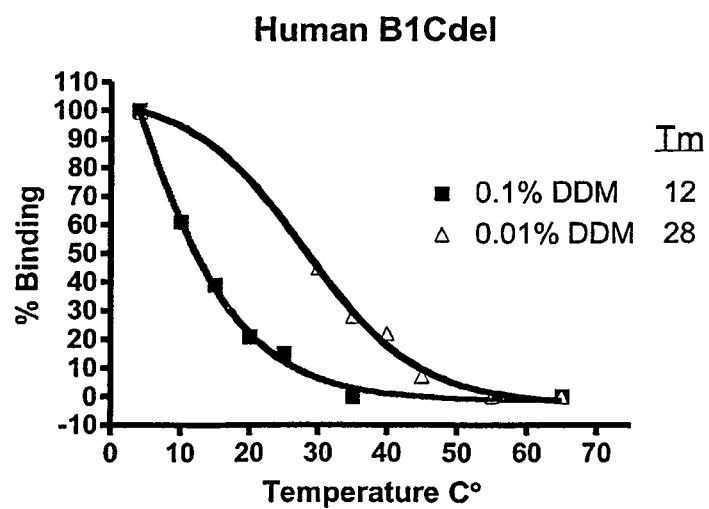
Figure 32D:
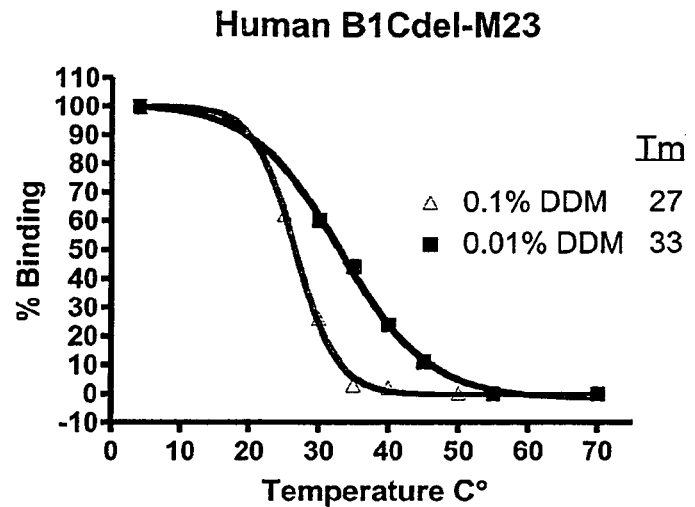
Figure 32E:
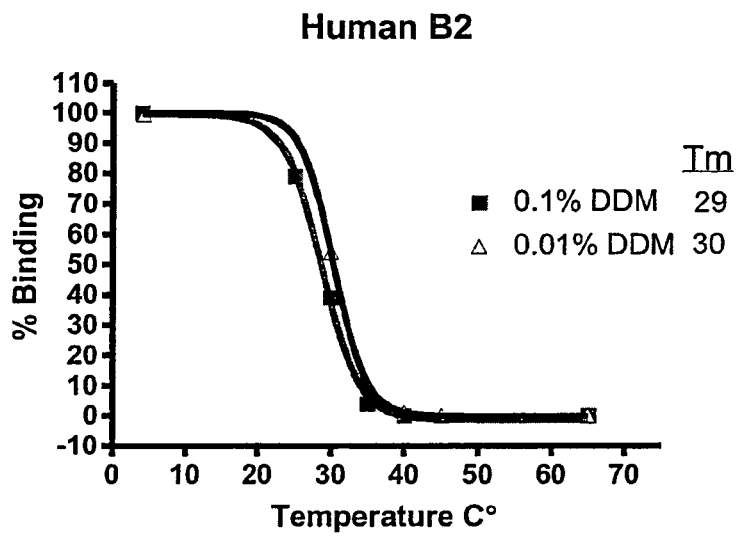
Figure 32F:
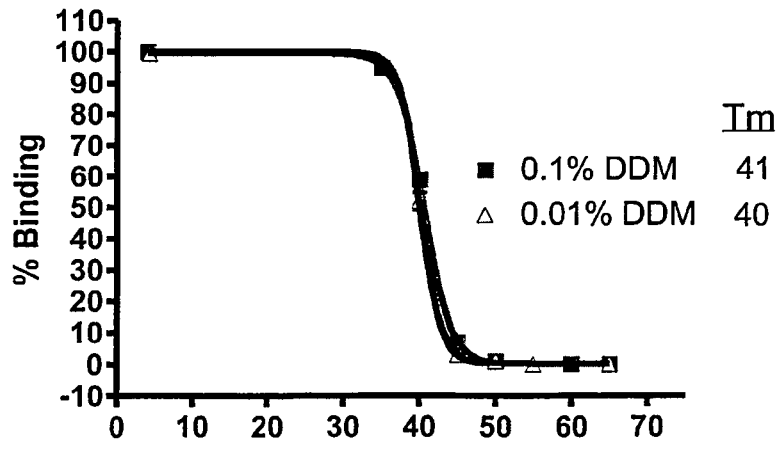

The thermostability of the receptors was checked by calculating the Tm in the presence of 0.1% or 0.01% of DDM (FIG. 32A). In the presence of a low amount of detergent the three of them presented a similar Tm, the one for human β1AR-Cdel the lowest (31° C., 28° C. and 30° C. for turkey β1AR, human β1AR-Cdel and human β2AR, respectively). However when solubilised with 0.1% of DDM, turkey β1AR and human β1AR-Cdel were more unstable, especially human β1AR-Cdel (23° C. and 12° C., respectively). This revealed than both of them are lipid dependent whereas human β2AR is as stable solubilised (29° C.) as in membranes (30° C.). Therefore, working with human β2AR is especially advantageous to purify or crystallise the receptor, and it should also facilitate stabilising other receptors, at least as much as human β2AR.

Effect of Turkey β1AR-m23 Stabilizing Mutations in Human βARs.

Human β1AR-Cdel and β2AR were mutated to incorporate the corresponding changes present in turkey β1AR-m23 (R68S, M90V, Y227A, A282L, F327A and F338M). The Tm of all the mutants carrying m23 mutations was calculated to compare the stability with and without mutations (FIGS. 31A-31C). In all cases, the Tm was increased, especially so when high amount of detergent was added (22° C., 15° C. and 12° C. increase for turkey β1AR, human β1AR-Cdel and human β2AR, respectively). In the case of turkey β3AR-m23, the mutations made the receptor more stable when solubilised. There were no differences in Tm between more or less amounts of detergent (45° C. Tm when solubilized with 0.1% or 0.01% DDM). Human β1AR-Cdel-m23 increased the stability in both conditions (high (27° C.) and low (33° C.) amount of detergent) and is still sensitive to detergent, but less than wild type. For human β2AR-m23, the Tm was 41° C. and 40° C. for 0.1% and 0.01% respectively, about 10 degrees over the wild type.

New Round of Mutagenesis to Increase the Thermostability in Human βARs.

New changes were selected for the aminoacids in human βARs corresponding to the ones involved in m23 stabilization in turkey, and the aminoacid in position I129 of turkey β1AR, that reported good results in previous experiments (see Examples 1-4). FIGS. 30C-30K summarize the results for human β1AR-Cdel-m23. It is remarkable that there were no large improvements with respect to the original mutant. The most interesting mutations were in the residue corresponding to I129 in turkey β1AR. We calculated the Tm for the most promising changes in this residue and we got 38° C. when mutated to glycine and 40° C. when mutated to alanine. The Tm for human β1AR-Cdel-m23 was 31° C. (these samples were solubilised with 0.05% DDM). A similar situation was observed for changes in human β2AR-m23 (FIGS. 30L-30T). In this case, the activity measured was more sensitive to changes than in human β1AR-m23. Only one change to alanine, in the residue corresponding to I129 of turkey, improved the stability, 5° C. over the wild type.

Example 6

Analysis of Stabilising Mutations as a Function of Alignment Position

Summary

We have undertaken computational and statistical analyses on data sets of thermostabilising mutations (Tms) from four different GPCRs: human adenosine receptor 2A (A2AA), turkey β1 adrenergic receptor (B1), rat neurotensin receptor 1 (NTR) and human muscarinic receptor (M1). The aims of this work were to identify the statistical likelihood of alignment of mutations based on sequence in order to determine whether predictive models could be constructed from the existing data that may have utility in improving the efficiency of further mutation scanning campaigns.

Experiments were performed to assess the degree of statistical significance that the Tms identified for B1, A2AA, M1 and NTR receptors are aligned. In order to do this, the sequences were aligned and numbers of alignment positions containing at least two mutations were counted. This number was compared with statistics generated from a distribution of 10,000 sequence mappings in which mutations were randomly assigned sequence positions.

The results of this study showed that alignment between all pairs of sequences (except for those involving M1) were highly significant and alignment between groups of sequences were also highly significant.

Based on these results it was further determined as to whether using a window of residues to define a match also led to statistical significant results. The majority of stabilising mutations (Tms) exist in the helical transmembrane domains such that they are possibly mapping to similar helical regions that are spatially related, although are not at identical alignment positions. As such, the number of alignment matches identified at different window sizes were determined. This data showed that statistical significance generally increases with increasing window size and the most significant window size was 9 (i.e. window=i plus or minus 4). This data supports that the co-occurrence of Tms in 'regions' is highly statistically significant.

Following the determination that Tm co-occurrence is highly significant both in terms of exact alignment and window alignment, experiments were performed to assess the ability of these metrics to identify Tms. A set of experiments were performed in which data from 3 receptors was used to predict Tm locations in a fourth receptor sequence. This analysis reveals that this approach results in a hit rate enrichment of up to 2 fold (i.e. 100%) compared with the existing random method. The method is applicable to B1, A2A and NTR receptors but not to the M1 receptor.

The method is expected to be useful in reducing the number of mutations that must be made on a new receptor, with the optimal method to use a small window size first, identify the stabilising mutations from that sequence subset and then scan further residues at increasing window size, depending on whether enough mutations have been found.

Results

Tm Position Analysis

An alignment of A2AA, β1, NTR and M1 sequences was generated using the program ClustalW (FIGS. 34A and 34B) (SEQ ID NOs 9, 1, 5, 12, 3, 17). Generally, this alignment is very similar to that in FIGS. 17A-17C (SEQ ID NO 3, 9, 12, 1, 5), with some variation in the loop regions.

Using the alignment, thermostabilising mutations (Tms) identified were mapped to sequences and the statistical significance was calculated for:

1. Co-occurrence of Tms between pairs of sequences; and
2. Co-occurrence of Tms between groups of sequences (sets of 3 or all sequences)

Statistics were facilitated by the generation of a dataset of 10,000 random Tm (thermostabilising mutant) assignments (i.e. same number per sequence as in true data) which provided a normal distribution of co-occurrence statistics (mean and standard deviation) which could be compared to the observed values. Initial analyses revealed that some of the alignment position co-occurrences of reported Tms are highly significant. Table A shows the likelihood (ρ value) of pairwise sequence co-occurrence according to a normal distribution of results from random sampling:

TABLE A

| Statistical significance of sequence aligned co-occurrence between pairs of sequences (p values) | | | |
|---|---|---|---|
| | B1 | A2AA | M1 |
| NTR | 0.022794 | 0.009444109 | 0.693669 |
| B1 | — | 2.28318E−05 | 0.999991 |
| A2AA | — | — | 0.645103 |

When multiple sequences are considered, the statistical significance of co-occurrences were recorded in Table B:

TABLE B

| Statistical significance of sequence aligned co-occurrence between groups of sequences | |
|---|---|
| Sequences | p value |
| NTR-B1-A2AA | 4.37E−07 |
| NTR-B1-A2AA-M1 | 1.67E−05 |

From this analysis it can be concluded that all Tm co-occurrences apart from those involving the M1 sequence are statistically meaningful. Similar data is obtained using the alignment from FIGS. 17A-17C (SEQ ID NO: 12).

Consideration of Residue Windows

In a helical structure residues within i to i+4 position are spatially proximal to one another. Since the majority of Tms are located in helical domains, rather than look for exact position alignment of Tms, we used a window to represent the i→i+4 positions to determine if this would provide an alternative method for matching Tms in different sequences to one another. It was considered that matching a general helix area (or turn) rather than an exact helix position may represent an important concept for predicting helix stabilisation positions. Clearly, not all of the receptor is helical but at least 80% of Tms identified by us to date are in such regions.

To test out this concept, studies were conducted in which, for a given Tm in the alignment, the number of matches to other Tms were determined within a given window from the query Tm. In addition, the average number of Tms in the window was also calculated. The results of this analysis for the alignment of the 4 sequences (B1, A2AA, M1 and NTR) are shown in Table C:

TABLE C

Numbers of Tm matches with residue window size and statistical significance

| Window Size | Total matches | p value matches | Average Tms per window match | p value average |
|---|---|---|---|---|
| 11 | 61 | 0.000378 | 2.951 | 1.8E−07 |
| 9 | 60 | 4.54E−05 | 2.533 | 3.24E−06 |
| 7 | 50 | 0.001567 | 2 | 0.00083 |
| 5 | 40 | 0.005287 | 1.5 | 0.059352 |

A window is defined as i plus or minus n, where i=the reference residue and n=residues either side (therefore i plus or minus 5 residues equates to a window of 11 amino acids).

The data revealed that as the window size increased, both the statistical significance of the observed matches increased and the statistical significance of the average number of Tms per match window increased. The number of matches were statistically significant at all window sizes.

The significance of this data is that Tms are more likely to exist closer to other Tms in aligned positions with a window size of 9 (i.e. the most statistically significant) and where a Tm is close to another Tm, it is also more likely to be closer to other Tms (average Tm density in windows of 9 and 11 is greater than 5)

Interestingly, the optimum window size of 9 correlates with the number of residues in a helix turn in either direction.

Based on these statistical results it was interesting to consider the practical implication of using the window matching method in terms of Tm prediction. A set of simple studies were thus conducted in which for each of the 4 sequences for which Tm data is available, the other 3 sequences were used to predict potential Tm positions using the window method. For example, using Tm data from NTR, B1 and A2AA the window method was applied to predict Tm positions in M1. The hit rate of the window prediction could then be calculated comparing with the known Tm data for the sequence. These results are shown in Table D.

TABLE D

Mutation prediction accuracy for four receptors based on the window method

| Target | Window Size | Length | Mutations Sites predicted | Tms Identified | Total Tms known | Ave no. Residues per Tm | Ave no. res per Tm baseline | Enrichment factor | Coverage |
|---|---|---|---|---|---|---|---|---|---|
| M1 | 3 | 460 | 132 | 1 | 5 | 132 | 92 | 0.7 | 0.2 |
|  | 5 | 460 | 182 | 2 | 5 | 91 | 92 | 1.01 | 0.4 |
|  | 7 | 460 | 215 | 2 | 5 | 107.5 | 92 | 0.86 | 0.4 |
|  | 9 | 460 | 242 | 3 | 5 | 80.67 | 92 | 1.14 | 0.6 |
|  | 11 | 460 | 264 | 4 | 5 | 66 | 92 | 1.39 | 0.8 |
| NTR | 3 | 424 | 95 | 8 | 24 | 11.88 | 17.67 | 1.49 | 0.33 |
|  | 5 | 424 | 134 | 11 | 24 | 12.18 | 17.67 | 1.45 | 0.458 |
|  | 7 | 424 | 165 | 12 | 24 | 13.75 | 17.67 | 1.28 | 0.5 |
|  | 9 | 424 | 190 | 15 | 24 | 12.67 | 17.67 | 1.39 | 0.625 |
|  | 11 | 424 | 212 | 16 | 24 | 13.25 | 17.67 | 1.33 | 0.66 |
| A2AA | 3 | 412 | 122 | 9 | 17 | 13.56 | 24.24 | 1.79 | 0.53 |
|  | 5 | 412 | 171 | 10 | 17 | 17.1 | 24.24 | 1.42 | 0.59 |
|  | 7 | 412 | 205 | 10 | 17 | 20.5 | 24.24 | 1.18 | 0.59 |
|  | 9 | 412 | 232 | 14 | 17 | 16.57 | 24.24 | 1.46 | 0.82 |
|  | 11 | 412 | 249 | 15 | 17 | 16.6 | 24.24 | 1.46 | 0.88 |
| B1 | 3 | 483 | 112 | 10 | 21 | 11.2 | 23 | 2.05 | 0.48 |
|  | 5 | 483 | 155 | 12 | 21 | 12.92 | 23 | 1.78 | 0.57 |
|  | 7 | 483 | 190 | 14 | 21 | 13.57 | 23 | 1.69 | 0.67 |
|  | 9 | 483 | 217 | 15 | 21 | 14.47 | 23 | 1.59 | 0.71 |
|  | 11 | 483 | 237 | 17 | 21 | 13.94 | 23 | 1.65 | 0.81 |

The data revealed that for all four targets the window match concept is predictive of mutation position. Enrichment factor is defined as baseline average number of residues per Tm/average number of residues per Tm screen and represents the improvement of the prediction above a random screen. Coverage is defined simply as the fraction of known Tms identified in the screen. Enrichment rates with a window size of 11 are between 39% (M1) to 65% (B1) above random. Interestingly, none of the M1 Tms align with any of the Tms for the other 3 sequences, yet the window concept does provide some predictive ability for this sequence, although only at larger window sizes. For all the receptors there is a trade off between hit coverage (numbers of Tms identified) and window size.

FIG. 35 shows the effect of window size on coverage and enrichment. The important consideration is how many Tms are required for each sequence in order to stabilise the receptor sufficiently to enable crystallisation which will dictate the required window size. FIG. 36 shows enrichment vs coverage for each of the receptors at different window sizes.

Interestingly, despite the statistical significance of the increasing window size when all sequences are considered together, a smaller window (3) shows best enrichment rates for B1, NTR and A2AA sequences. Only M1 has highest enrichment at the larger window sizes.

Example 7

3D Mapping and Statistics of Tms

Summary

In Example 6, procedures were described which determined the statistical significance of sequence alignment co-occurrence of thermostabilising mutations. In principle the analogous study can be performed by an analysis of structurally mapped Tms, with distances between the mutations quantified from 3D co-ordinates.

Therefore, we conducted studies to determine the statistical significance of Tm co-occurrence by spatial distance between Tms for existing data sets compared to a random distribution and to what degree existing sets of Tms can be used to predict the locations of Tms on another receptor. Further, we have compared the results of these studies to the sequence based predictions and have considered where the structure 'hot spots' of Tms when considering multiple Tm sets are, and how can the statistical significance of these be defined (See Example 8).

Methods

In order to conduct these studies structural models of the receptors in question were required. Two sets of homology models were built based on the available structures of β2 (models: β1, A2AA, M1, NTR) and β1 (models: A2AA, M1, NTR) using homology modelling protocols available in MOE. For the requirements of the current studies no effort was made to apply the Origami® modelling approach to predict agonist binding states of these receptors, rather to compare antagonist states for receptors in question. It was considered that structural differences between antagonist and agonist receptor states would not alter the gross statistics of distances between Tms.

Each receptor model was built using the alignment shown in FIGS. 34A and 34B (SEQ ID NOs: 9, 1, 5, 12, 3, 17). Final models were minimised using an AMBER forcefield, with an explicit solvent shell of cyclohexane for transmembrane layer and water molecules for the intracellular and extracellular domains.

Mutations were mapped to the receptor structures using an automated procedure written in MOE (Chemical Computing Group Inc) to read mutations from a text file and assign them to the structure. The set of mutations used for the receptors are described in FIG. 33 (SEQ ID NOs: 5, 1, 9).

To provide the basis for statistical analysis a set of random mutations mappings were also required. This dataset was obtained by randomly assigning the same number of mutations to each receptor structure as the number of known Tms. This was performed 1000 times, representing 67000 Tm mappings with co-ordinate data. This dataset was considered large enough to provide a representative statistical distribution from which comparisons of actual data could be made.

Results

Tm Distance Mapping

Two different measures of distance between mapped Tms were calculated. The first was simply distances between C atoms of residues. The second was the distance between any atom of two residues.

For each Tm the number of other Tms found within a given distance were recorded. For the $C\alpha$ method the distances used were 6 Å, 8 Å, 10 Å and 12 Å. For the any atom method, the distance shells used were 4 Å, 6 Å and 8 Å.

The analysis was also applied to the 1,000 random Tm mappings providing a mean and standard deviation at each radius from which the significance of the observed data can be calculated. The results for $C\alpha$ method are shown in Table E below.

TABLE E $C\alpha$ atom distances within cut-offs of Tms

| Radius | Mean | Mean random | Std_dev | p value |
|---|---|---|---|---|
| 6 Å | 1.701 | 1.1606 | 0.2025 | 0.003808 |
| 8 Å | 2.71642 | 1.8279 | 0.2401 | 0.000108 |
| 10 Å | 4.59701 | 3.2821 | 0.4014 | 0.000527 |
| 12 Å | 7.8806 | 5.3835 | 0.6159 | 2.51E−05 |

The data shows that the average numbers (Mean) of Tms found within all radii are higher than those found for the random distribution (Mean random) and that these values are statistically significant ($p<0.005$). Moreover, as the radius become larger the difference between the observed value and random distribution becomes more significant. The data determined by the any-atom criteria are shown in Table F below:

TABLE F

Any-atom from residue distances within cut-offs of Tms

| Radius | Mean | Mean random | Std_dev | p value |
|---|---|---|---|---|
| 4 Å | 4.228 | 3.0515 | 0.2803 | 1.35E−05 |
| 6 Å | 6.106 | 4.363 | 0.41 | 1.06E−05 |
| 8 Å | 9.03 | 6.4828 | 0.622 | 2.11E−05 |

The data shows that the average numbers (Mean) of Tms found within all radii measured are higher than those found for the random distribution (Mean random) and that these values are also statistically significant ($p<0.005$). As expected, more Tms are identified within a given radius compared to the analogous $C\alpha$ method as sidechain contacts are also included. The fact that any atom method p values are lower indicates that sidechain positions may be important for Tm locations and distances between them.

Tm Identification Using Distance Criteria

Based on the results obtained from Tm structure mapping that the number of Tms identified are statistically meaningful compared to a random distribution, it was considered important to assess the utility of this in its ability to predict the locations of Tms on a receptor not seen in training data. The studies were performed in a similar manner to the sequence based Tm prediction analysis described in Example 6. For each receptor out of β1, A2AA, NTR and M1, the known mutations for the other 3 were used as the basis for structural identification of candidate Tm locations. Both the Cα and any atom method were used with different radii used in each case. Both a set of models based on the turkey β1 structure (PDB code: 2vt4), and a set of models based on the human β2 structure (PDB accession code: 2rh1 were analysed, enabling the analysis of how sensitive the results are to differences in structural template.

Table G below shows Cα method prediction capabilities for the β2 based templates and Table H shows the any atom method prediction capabilities for the β2 based templates As expected, coverage of Tms for both methods increases with increasing radius. Generally the enrichments are not very high ~10-20% for NTR, A2AA and B1 structures but up to ~60% enrichment for the M1 structure. Although enrichment factors are similar depending on whether sidechains are taken into account in distance metrics, the coverage of correct predictions is generally better with the any-atom distance criteria. This implies that calculations including the sidechains enables the identification of more Tms than with the CI method, at the same enrichment factor.

Results for the same analysis performed on models built based on the turkey β1 structure are shown in the following tables.

Table I below shows CI method prediction capabilities for the β1 based templates and Table J shows the any atom method prediction capabilities for the β1 based templates

TABLE G

Structure search - contact defined by CI method, B2 template

| Target | Distance A | Length | Mutations sites predicted | Tms identified | total Tms known | Average no. residues per Tm | Av res per Tm baseline | Enrichment factor | coverage |
|---|---|---|---|---|---|---|---|---|---|
| M1 | 6 | 416 | 193 | 3 | 5 | 64.33 | 83.20 | 1.29 | 0.6 |
|  | 8 | 416 | 229 | 3 | 5 | 76.33 | 83.20 | 1.09 | 0.6 |
|  | 10 | 416 | 261 | 4 | 5 | 65.25 | 83.20 | 1.28 | 0.8 |
|  | 12 | 416 | 289 | 5 | 5 | 57.80 | 83.20 | 1.44 | 1 |
| NTR | 6 | 327 | 151 | 13 | 24 | 11.62 | 13.63 | 1.17 | 0.541667 |
|  | 8 | 327 | 201 | 18 | 24 | 11.17 | 13.63 | 1.22 | 0.75 |
|  | 10 | 327 | 250 | 20 | 24 | 12.50 | 13.63 | 1.09 | 0.833333 |
|  | 12 | 327 | 280 | 23 | 24 | 12.17 | 13.63 | 1.12 | 0.958333 |
| A2AA | 6 | 296 | 197 | 11 | 17 | 17.91 | 17.41 | 0.97 | 0.647059 |
|  | 8 | 296 | 233 | 15 | 17 | 15.53 | 17.41 | 1.12 | 0.882353 |
|  | 10 | 296 | 264 | 16 | 17 | 16.50 | 17.41 | 1.06 | 0.941176 |
|  | 12 | 296 | 274 | 16 | 17 | 17.13 | 17.41 | 1.02 | 0.941176 |
| B1 | 6 | 320 | 173 | 16 | 21 | 10.81 | 15.24 | 1.41 | 0.761905 |
|  | 8 | 320 | 206 | 16 | 21 | 12.88 | 15.24 | 1.18 | 0.761905 |
|  | 10 | 320 | 244 | 19 | 21 | 12.84 | 15.24 | 1.19 | 0.904762 |
|  | 12 | 320 | 263 | 20 | 21 | 13.15 | 15.24 | 1.16 | 0.952381 |

TABLE H

Structure search - contact defined by any-atom or residue method, B2 template

| Target | Distance A | Length | Mutations sites predicted | Tms identified | total Tms known | Average no. residues per Tm | Av res per Tm baseline | Enrichment factor | Coverage |
|---|---|---|---|---|---|---|---|---|---|
| M1 | 4 | 416 | 233 | 3 | 5 | 77.67 | 83.20 | 1.07 | 0.6 |
|  | 6 | 416 | 261 | 5 | 5 | 52.20 | 83.20 | 1.59 | 1 |
|  | 8 | 416 | 285 | 5 | 5 | 57.00 | 83.20 | 1.46 | 1 |
|  | 10 | 416 | 302 | 5 | 5 | 60.40 | 83.20 | 1.38 | 1 |
| NTR | 4 | 327 | 210 | 18 | 24 | 11.67 | 13.63 | 1.17 | 0.75 |
|  | 6 | 327 | 247 | 20 | 24 | 12.35 | 13.63 | 1.10 | 0.833333 |
|  | 8 | 327 | 277 | 23 | 24 | 12.04 | 13.63 | 1.13 | 0.958333 |
|  | 10 | 327 | 298 | 24 | 24 | 12.42 | 13.63 | 1.10 | 1 |
| A2AA | 4 | 296 | 227 | 14 | 17 | 16.21 | 17.41 | 1.07 | 0.823529 |
|  | 6 | 296 | 257 | 16 | 17 | 16.06 | 17.41 | 1.08 | 0.941176 |
|  | 8 | 296 | 274 | 16 | 17 | 17.13 | 17.41 | 1.02 | 0.941176 |
|  | 10 | 296 | 282 | 17 | 17 | 16.59 | 17.41 | 1.05 | 1 |
| B1 | 4 | 320 | 205 | 15 | 21 | 13.67 | 15.24 | 1.11 | 0.714286 |
|  | 6 | 320 | 232 | 18 | 21 | 12.89 | 15.24 | 1.18 | 0.857143 |
|  | 8 | 320 | 262 | 21 | 21 | 12.48 | 15.24 | 1.22 | 1 |
|  | 10 | 320 | 272 | 21 | 21 | 12.95 | 15.24 | 1.18 | 1 |

TABLE I

Structure search - contact defined by CI method, B1 template

| Target | Distance A | Length | Mutations sites predicted | Tms identified | total Tms known | Average no. residues per Tm | Av res per Tm baseline | Enrichment factor | coverage |
|---|---|---|---|---|---|---|---|---|---|
| M1 | 6 | 416 | 187 | 3 | 5 | 62.33 | 83.20 | 1.33 | 0.6 |
|  | 8 | 416 | 223 | 3 | 5 | 74.33 | 83.20 | 1.12 | 0.6 |
|  | 10 | 416 | 253 | 4 | 5 | 63.25 | 83.20 | 1.32 | 0.8 |
|  | 12 | 416 | 284 | 5 | 5 | 56.80 | 83.20 | 1.46 | 1 |
| NTR | 6 | 327 | 139 | 12 | 24 | 11.58 | 13.63 | 1.18 | 0.5 |
|  | 8 | 327 | 192 | 16 | 24 | 12.00 | 13.63 | 1.14 | 0.666667 |
|  | 10 | 327 | 243 | 20 | 24 | 12.15 | 13.63 | 1.12 | 0.833333 |
|  | 12 | 327 | 276 | 24 | 24 | 11.50 | 13.63 | 1.18 | 1 |
| A2AA | 6 | 296 | 192 | 12 | 17 | 16.00 | 17.41 | 1.09 | 0.705882 |
|  | 8 | 296 | 232 | 15 | 17 | 15.47 | 17.41 | 1.13 | 0.764706 |
|  | 10 | 296 | 256 | 16 | 17 | 16.00 | 17.41 | 1.09 | 0.882353 |
|  | 12 | 296 | 270 | 17 | 17 | 15.88 | 17.41 | 1.10 | 1 |
| B1 | 6 | 274 | 173 | 12 | 17 | 14.42 | 16.12 | 1.12 | 0.705882 |
|  | 8 | 274 | 210 | 13 | 17 | 16.15 | 16.12 | 1.00 | 0.764706 |
|  | 10 | 274 | 239 | 15 | 17 | 15.93 | 16.12 | 1.01 | 0.882353 |
|  | 12 | 274 | 257 | 17 | 17 | 15.12 | 16.12 | 1.07 | 1 |

TABLE J

Structure search - contact defined by any-atom or residue method, B1 template

| Target | Distance A | Length | Mutations sites predicted | Tms identified | total Tms known | Average no. residues per Tm | Av res per Tm baseline | Enrichment factor | Coverage |
|---|---|---|---|---|---|---|---|---|---|
| M1 | 4 | 416 | 223 | 3 | 5 | 74.33 | 83.20 | 1.12 | 0.6 |
|  | 6 | 416 | 251 | 5 | 5 | 50.20 | 83.20 | 1.66 | 1 |
|  | 8 | 416 | 279 | 5 | 5 | 55.80 | 83.20 | 1.49 | 1 |
|  | 10 | 416 | 293 | 5 | 5 | 58.60 | 83.20 | 1.42 | 1 |
| NTR | 4 | 327 | 188 | 15 | 24 | 12.53 | 13.63 | 1.09 | 0.625 |
|  | 6 | 327 | 229 | 19 | 24 | 12.05 | 13.63 | 1.13 | 0.791667 |
|  | 8 | 327 | 267 | 22 | 24 | 12.14 | 13.63 | 1.12 | 0.916667 |
|  | 10 | 327 | 289 | 24 | 24 | 12.04 | 13.63 | 1.13 | 1 |
| A2AA | 4 | 296 | 218 | 14 | 17 | 15.57 | 17.41 | 1.12 | 0.823529 |
|  | 6 | 296 | 246 | 16 | 17 | 15.38 | 17.41 | 1.13 | 0.941176 |
|  | 8 | 296 | 269 | 17 | 17 | 15.82 | 17.41 | 1.10 | 1 |
|  | 10 | 296 | 276 | 17 | 17 | 16.24 | 17.41 | 1.07 | 1 |
| B1 | 4 | 274 | 198 | 12 | 17 | 16.50 | 16.12 | 0.98 | 0.705882 |
|  | 6 | 274 | 230 | 15 | 17 | 15.33 | 16.12 | 1.05 | 0.882353 |
|  | 8 | 274 | 255 | 17 | 17 | 15.00 | 16.12 | 1.07 | 1 |
|  | 10 | 274 | 269 | 17 | 17 | 15.82 | 16.12 | 1.02 | 1 |

The results are very similar to those for the β2 template, with similar enrichments seen for all four receptors and higher coverages at given enrichment factors generally seen for the any atom method.

Interestingly, using either template and either distance criteria, enrichments are consistently higher for the M1 receptor. This is in contrast to the sequence method where enrichment rates are much lower for this receptor. This indicates that some of the M1 mutations are possibly structurally related to other Tms in other receptors, although statistically there are not enough of them to be confident of this.

Another conclusion is that enrichment rates are higher for the sequence scanning method (with the exception of M1) compared to the structure scanning approach, although coverages are higher for the structure based approach. It is perhaps expected that given the extra set of intra-helical relationships revealed in 3D between mapped Tms that the coverage may be higher with this method, but perhaps unexpected that a sequence only analysis would provide higher enrichments.

The following graphs plot enrichment factors vs coverage values for structure based and sequence based analyses FIG. 37 shows the relationships between enrichment and coverage for both the Cα and any-atom method for the β1 template based work. Generally, the any-atom method afforded better coverage at similar enrichment rates as the CI method.

A comparison of sequence based vs structure based Tm identification is shown in FIG. 38 and is a composite of FIGS. 37 and 36.

These data show that structure based and sequence based Tm prediction methods provide different profiles of coverage vs enrichment capabilities. Depending on the requirements as to whether greater coverage or greater enrichment is desirable one method may be selected over the other. The exception is for M1 receptor for which the structure based approach performs better both in terms of enrichment and coverage.

Example 8

Tm Cluster Analysis

Summary

The Tm structure analysis described in the previous Section shows that Tms are statistically closer together on average than expected according to a random distribution and that this usefully translates to the ability to identify Tms in a receptor based on Tms identified in other receptors. Whereas this analysis has been based on averages and sets of Tms together, an interesting analysis can be performed on identifying the significance of specific clusters of Tms within the dataset. Identification of such clusters may result in the understanding of the structural importance of particular Tms. In addition, these clusters may be used to target specific regions of a receptor for Tm scanning, based upon statistics of occurrences of sets of knowns.

Methods

The random distributions of Tms calculated for the structural mapping studies were used to derive statistics on the significance of clusters of Tms in overlaid structures of [3], A2AA, NTR and M1 receptors (based on the β1 structure). From the distribution of random mappings, the mean numbers and standard deviations of clusters at each radius using the Cα method was calculated and was assumed to fit a normal distribution. The significance of each cluster identified at different radii from the real Tm mappings was then calculated and statistically significant clusters saved for analysis. Table K summarises these clusters. The clusters identified at 6 Å have the lowest significance (ρ=0.054).

As such, this data suggests that an improved structural based Tm screen could be afforded by selecting a centre of all important clusters and using this as the radius centre for a super cluster which would maximise the enrichment of the screen.

For example, a sphere of radius 15 Å placed at the centre of the major clusters would cover 459 residues (from a total of 1359) from the four receptors but would predict 39 out of 67 thermostabilising mutations. As such this represents an enrichment factor of 1.72 and coverage of 0.58 in Tm prediction. It is suggested that this represents a good balance of enrichment and coverage since approximately only one third of the sequence is covered. As a method, this cluster of clusters approach would require thermostability data for ~130 residues to be collected from which we would expect to identify ⅔ of possible all mutations. This is an improvement on the structure screening data shown in Example 7 and relies on the fact that within the Tm sets that there are statistically significant clusters which can be targeted towards the intracellular portion of the GPCR. This cluster is illustrated in the following FIG. 41.

TABLE K

Statistically significant clusters

| Radius | No | Size | Significance | Residues (Ballesteros and Weinstein number in bold) |
|---|---|---|---|---|
| 10 Å | 1 | 11 | 0.000127 | NTR:VAL160 3.43, NTR:MET250 5.51, NTR:ASN257 5.58, NTR:VAL309 6.36, NTR:LEU310 6.37, NTR:VAL313 6.40, NTR:ALA316 6.43, B1:ILE129 3.40, B1:TYR227 5.58, A2AA:LEU235 6.38, A2AA:VAL239 6.41 |
| 8 Å | 2 | 7 | 0.0017 | NTR:ASN257 5.58, B1:TYR227 5.58, B1:ARG229 5.60, B1:ALA234 5.65, A2AA:ALA203 5.64, A2AA:ALA204 5.65, NTR:ILE260 5.61 |
|  | 3 | 7 | 0.0017 | NTR:GLY306 6.33, NTR:LEU310 6.37, NTR:VAL313 6.40, NTR:SER373, A2AA:ALA231 6.34, A2AA:LEU235 6.38, NTR:VAL309 6.36 |
|  | 4 | 7 | 0.0017 | NTR:PHE358 7.42, NTR:VAL360 7.44, B1:ILE55 1.46, B1:MET90 2.53, B1:ALA334 7.44, B1:PHE338 7.48, NTR:SER362 7.46 |
|  | 5 | 7 | 0.0017 | NTR:ASN257 5.58, B1:TYR227 5.58, B1:ARG229 5.60, B1:ALA234 5.65, A2AA:ALA203 5.64, A2AA:ALA204 5.65, B1:VAL230 5.61 |
| 6 Å | 6 | 6 | 0.054 | NTR:ASN257 5.58, B1:TYR227 5.58, B1:ARG229 5.60, A2AA:ALA203 5.64, NTR:ILE260 5.61 |
|  | 7 | 6 | 0.054 | NTR:GLY306 6.33, NTR:LEU310 6.37, A2AA:ALA231 6.34, A2AA:LEU235 6.38, NTR:VAL309 6.36 |
|  | 8 | 6 | 0.054 | NTR:LEU310 6.37, NTR:ALA316 6.43, A2AA:LEU235 5.66, A2AA:VAL239 6.41, NTR:VAL313 6.40 |
|  | 9 | 6 | 0.054 | NTR:VAL360 7.44, B1:ILE55 1.46, B1:ALA334 7.44, B1:PHE338 7.48, NTR:SER362 7.46 |
|  | 10 | 6 | 0.054 | NTR:ASN257 5.58, NTR:ILE260 5.61, B1TYR227 5.58, B1:VAL230 5.61, B1:ARG229 5.60 |
|  | 11 | 6 | 0.054 | NTR:ASN257 5.58, B1:TYR227 5.58, B1:ARG229 5.60, A2AA:ALA203 5.64, B1:VAL230 5.61 |
|  | 12 | 6 | 0.054 | B1:VAL160, A2AA:THR119 4.40, A2AA:GLY123 4.44, ACM1_HUMAN:MET145 4.45, A2AA:LYS122 4.43 |
|  | 13 | 6 | 0.054 | NTR:ILE260 5.61, B1:VAL230 5.61, B1:ALA234 5.65, A2AA:ALA204 5.65, A2AA:ALA203 5.64 |

The results show that out of 67 Tms mapping to the four receptors only 26 map to statistically significant clusters (at 8 Å and 10 Å). Out of these clusters 1, 2, 3 and 5 share some of the same residues with cluster 4 being structurally distinct. As such only 2 areas of the GPCRs contain statistically significant clusters of Tms. The only residues in the clusters at 6 Å that are found outside of the clusters at 8 or 10 Å are found in cluster 12, which map to TM4 (see FIGS. 39A-39M, including clusters 6-13).

The clusters mostly map to the bottom of TM5, TM6 and mid TM7, with another located on the intracellular end of TM4 (a 6 Å cluster). Interestingly, almost all of these residues are located towards the intracellular portion of the receptor. Another interesting aspect is that almost all the clusters, with the exception of the largest cluster (cluster 1) and cluster 4 which map to two transmembrane helices, are all located on the same helix. This explains why the sequence based method works well when compared to the structure method—there are 1-2 turn sections of helices 4, 5, 6 and 7 which dominate the existing TM data (when viewed in terms of statistical clustering).

The structural and functional role of these cluster residues is interesting and may provide an explanation of why mutations at these positions stabilise the receptor.

REFERENCES

1. S. H. White (2004) *Protein Sci* 13, 1948-1949.
2. C. G. Tate (2001) *FEBS Lett* 504, 94-98.
3. R. Grisshammer, C. G. Tate (1995) *Q Rev Biophys* 28, 315-422.
4. J. U. Bowie (2001) *Curr Opin Struct Biol* 11, 397-402.
5. F. W. Lau, S, Nauli, Y. Zhou, J. U. Bowie (1999) *J Mol Biol* 290, 559-564.
6. Y. Zhou, J. U. Bowie (2000) *J Biol Chem* 275, 6975-6979.
7. S. Faham, D. Yang, E. Bare, S. Yohannan, J. P. Whitelegge, J. U. Bowie (2004) *J Mol Biol* 335, 297-305.
8. Y. Yarden, H. Rodriguez, S. K. Wong, D. R. Brandt, D. C. May, J. Burnier, R. N. Harkins, E. Y. Chen, J. Ramachandran, A. Ullrich, et al (1986) *Proc. Natl. Acad. Sci. USA* 83, 6795-6799.

9. T. Warne, J. Chirnside, G. F. Schertler (2003) *Biochim Biophys Acta* 1610, 133-140.
10. E. M. Parker, E. M. Ross (1991) *J Biol Chem* 266, 9987-9996.
11. E. M. Parker, K. Kameyama, T. Higashijima, E. M. Ross (1991) *J Biol Chem* 266, 519-527.
12. W. J. Degrip (1982) *Methods in Enzymology* 81, 256-265.
13. K. Palczewski, T. Kumasaka, T. Hori, C. A. Behnke, H. Motoshima, B. A. Fox, I. Le Trong, D. C. Teller, T. Okada, R. E. Stenkamp, et al (2000) *Science* 289, 739-745.
14. J. Li, P. C. Edwards, M. Burghammer, C. Villa, G. F. Schertler (2004) *J Mol Biol* 343, 1409-1438.
15. R. Jaenicke, G. Bohm (1998) *Current Opinion in Structural Biology* 8, 738-748.
16. J. Tucker, R. Grisshammer (1996) *Biochem J* 317 (Pt 3), 891-899.
17. W. Schaffner, C. Weissmann (1973) *Anal. Biochem.* 56, 502-514.
18. C. G. Tate (1998) *Methods Enzymol* 296, 443-455.
19. H. M. Weiss, R. Grisshammer (2002) *Eur J Biochem* 269, 82-92.
20. Rasmussen, S. G., Choi, H. J., Rosenbaum, D. M., Kobilka, T. S., Thian, F. S., Edwards, P. C., Burghammer, M., Ratnala, V. R., Sanishvili, R., Fischetti, R. F., Schertler, G. F., Weis, W. I. and Kobilka, B. K. (2007) *Nature* 15, 383-387.
21. Cherezov, V., Rosenbaum, D. M., Hanson, M. A., Rasmussen, S. G., Thian, F. S., Kobilka, T. S., Choi, H. J., Kuhn, P., Weis, W. I., Kobilka, B. K. and Stevens, R. C. (2007) *Science* 318:1258-1265.
22. Minneman, K. P., Weiland, G. A. and Molinoff, P. B. (1980) *Mol Pharmacol* 17:1-7.
23. Parker, E. M., Swigart, P., Nunnally, M. H., Perkins, J. P. and Ross, E. M. (1995) *J Biol Chem* 270:6482-6487.

---

The invention claimed is:

1. A method of producing a mutant GPCR with increased stability in a particular conformation under denaturing conditions relative to its parent GPCR in the same particular conformation under denaturing conditions, the method comprising:
   (a) identifying in the amino acid sequence of one or more mutants of a first parent GPCR with increased stability in a particular conformation under denaturing conditions relative to the first parent GPCR in the same particular conformation under denaturing conditions, the position or positions at which the one or more mutants have at least one different amino acid residue compared to the first parent GPCR, and
   (b) making one or more mutations in the amino acid sequence that defines a second GPCR at the corresponding position or positions, to provide one or more mutants of a second parent GPCR with increased stability in a particular conformation under denaturing conditions relative to the second parent GPCR in the same particular conformation under denaturing conditions, or
   making one or more mutations in the amino acid sequence that defines a second GPCR within a window or windows of i plus or minus 5 residues where i is the corresponding position or positions, to provide one or more mutants of a second parent GPCR with increased stability in a particular conformation under denaturing conditions relative to the second parent GPCR in the same particular conformation under denaturing conditions, or
   making one or more mutations in the amino acid sequence that defines a second GPCR within a distance of 12 Å from the Cα atom of, or within a distance of 8 Å from any atom of, the amino acid residue i, where i is the corresponding position or positions, to provide one or more mutants of a second parent GPCR with increased stability in a particular conformation under denaturing conditions relative to the second parent GPCR in the same particular conformation under denaturing conditions.

2. A method of producing a mutant GPCR with increased stability in a particular conformation under denaturing conditions relative to its parent GPCR in the same particular conformation under denaturing conditions, the method comprising:
   a) providing one or more mutants of a first parent GPCR with increased stability in a particular conformation under denaturing conditions relative to the first parent GPCR in the same particular conformation under denaturing conditions
   b) identifying in a structural membrane protein model the structural motif or motifs in which the one or more mutants have at least one different amino acid residue compared to the first parent GPCR, and
   c) making one or more mutations in the amino acid sequence that defines a corresponding structural motif or motifs in a second parent GPCR, to provide one or more mutants of a second parent GPCR with increased stability in a particular conformation under denaturing conditions relative to the second parent GPCR in the same particular conformation under denaturing conditions.

3. A method according to claim 1, wherein the one or more mutants of the first parent GPCR in step (a) are obtainable by a method comprising:
   (i) providing one or more mutants of a first parent GPCR,
   (ii) selecting a ligand, the ligand being one which binds to the parent GPCR when the GPCR is residing in a particular conformation,
   (iii) determining whether the or each mutant GPCR when residing in a particular conformation has increased conformational stability with respect to binding the selected ligand compared to the stability of the first parent GPCR when residing in the same particular conformation with respect to binding that ligand, and
   (iv) selecting those mutants that have an increased conformational stability compared to the first parent GPCR with respect to binding the selected ligand.

4. A method according to claim 3, wherein the particular conformation in which the GPCR resides in step (iii) corresponds to the class of ligand selected in step (ii).

5. A method according to claim 4, wherein the selected ligand is from the agonist class of ligands and the particular conformation is an agonist conformation, or the selected ligand is from the antagonist class of ligands and the particular conformation is an antagonist conformation.

6. A method according to claim 5, wherein the selected ligand is from the agonist class of ligands and the particular conformation in which the GPCR resides in step (iii) is the agonist conformation.

7. A method according to claim 3, wherein the binding affinity of the one or more mutants of the first GPCR is substantially the same or greater than the binding affinity of the parent for the selected ligand.

8. A method according to claim 3, wherein steps (i)-(iv) are repeated for one or more rounds, with the selected mutants of the first GPCR having increased conformational stability in step (iv) representing the parent GPCR in a subsequent round of the method.

9. A method according to claim 3 wherein the ligand is any one of a full agonist, a partial agonist, an inverse agonist, an antagonist.

10. A method according to claim 3 wherein in step (ii) two or more ligands are selected, the presence of each causes the GPCR to reside in the same particular conformation.

11. A method according to claim 3 wherein a mutant GPCR in step (iv) is selected which has reduced ability to bind a ligand of a different class to the ligand selected in step (ii) compared to its parent.

12. A method according to claim 1, wherein the one or more mutants of the first parent GPCR in step (a) contain a plurality of mutations compared to the first parent GPCR.

13. A method according to claim 1, wherein the one or more mutants of the first parent GPCR in step (a) have increased stability to any one or more of heat, a detergent, a chaotropic agent and an extreme of pH.

14. A method according to claim 1 wherein the first parent GPCR is any one of a β-adrenergic receptor, an adenosine receptor and a neurotensin receptor.

15. A method according to claim 1, further comprising:
   (I) selecting a ligand, the ligand being one which binds to the second parent GPCR when the GPCR is residing in a particular conformation
   (II) determining whether the or each mutant of the second parent GPCR when residing in a particular conformation has increased conformational stability with respect to binding the selected ligand compared to the stability of the second parent GPCR when residing in the same particular conformation with respect to binding that ligand, and
   (III) selecting those mutants that have an increased conformational stability compared to the second parent GPCR with respect to binding the selected ligand.

16. A method according to claim 15, wherein the particular conformation in which the GPCR resides in step (II) corresponds to the class of ligand selected in step (I).

* * * * *

UNITED STATES PATENT AND TRADEMARK OFFICE
CERTIFICATE OF CORRECTION

PATENT NO. : 8,748,182 B2
APPLICATION NO. : 12/746674
DATED : June 10, 2014
INVENTOR(S) : Heal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 325 days.

Signed and Sealed this
Fourth Day of August, 2015

Michelle K. Lee
*Director of the United States Patent and Trademark Office*

SEQUENCE LISTING

<160> NUMBER OF SEQ ID NOS: 17

<210> SEQ ID NO 1
<211> LENGTH: 483
<212> TYPE: PRT
<213> ORGANISM: Meleagris gallopavo

<400> SEQUENCE: 1

```
Met Gly Asp Gly Trp Leu Pro Pro Asp Cys Gly Pro His Asn Arg Ser
1               5                   10                  15

Gly Gly Gly Gly Ala Thr Ala Ala Pro Thr Gly Ser Arg Gln Val Ser
            20                  25                  30

Ala Glu Leu Leu Ser Gln Gln Trp Glu Ala Gly Met Ser Leu Leu Met
        35                  40                  45

Ala Leu Val Val Leu Leu Ile Val Ala Gly Asn Val Leu Val Ile Ala
    50                  55                  60

Ala Ile Gly Arg Thr Gln Arg Leu Gln Thr Leu Thr Asn Leu Phe Ile
65                  70                  75                  80

Thr Ser Leu Ala Cys Ala Asp Leu Val Met Gly Leu Leu Val Val Pro
                85                  90                  95

Phe Gly Ala Thr Leu Val Val Arg Gly Thr Trp Leu Trp Gly Ser Phe
            100                 105                 110

Leu Cys Glu Cys Trp Thr Ser Leu Asp Val Leu Cys Val Thr Ala Ser
        115                 120                 125

Ile Glu Thr Leu Cys Val Ile Ala Ile Asp Arg Tyr Leu Ala Ile Thr
    130                 135                 140

Ser Pro Phe Arg Tyr Gln Ser Leu Met Thr Arg Ala Arg Ala Lys Val
145                 150                 155                 160

Ile Ile Cys Thr Val Trp Ala Ile Ser Ala Leu Val Ser Phe Leu Pro
                165                 170                 175

Ile Met Met His Trp Trp Arg Asp Glu Asp Pro Gln Ala Leu Lys Cys
            180                 185                 190

Tyr Gln Asp Pro Gly Cys Cys Asp Phe Val Thr Asn Arg Ala Tyr Ala
        195                 200                 205

Ile Ala Ser Ser Ile Ile Ser Phe Tyr Ile Pro Leu Leu Ile Met Ile
    210                 215                 220

Phe Val Tyr Leu Arg Val Tyr Arg Glu Ala Lys Glu Gln Ile Arg Lys
225                 230                 235                 240
```

```
Ile Asp Arg Cys Glu Gly Arg Phe Tyr Gly Ser Gln Glu Gln Pro Gln
            245                 250                 255

Pro Pro Pro Leu Pro Gln His Gln Pro Ile Leu Gly Asn Gly Arg Ala
        260                 265                 270

Ser Lys Arg Lys Thr Ser Arg Val Met Ala Met Arg Glu His Lys Ala
        275                 280                 285

Leu Lys Thr Leu Gly Ile Ile Met Gly Val Phe Thr Leu Cys Trp Leu
        290                 295                 300

Pro Phe Phe Leu Val Asn Ile Val Asn Val Phe Asn Arg Asp Leu Val
305                 310                 315                 320

Pro Asp Trp Leu Phe Val Phe Phe Asn Trp Leu Gly Tyr Ala Asn Ser
                325                 330                 335

Ala Phe Asn Pro Ile Ile Tyr Cys Arg Ser Pro Asp Phe Arg Lys Ala
                340                 345                 350

Phe Lys Arg Leu Leu Cys Phe Pro Arg Lys Ala Asp Arg Arg Leu His
                355                 360                 365

Ala Gly Gly Gln Pro Ala Pro Leu Pro Gly Gly Phe Ile Ser Thr Leu
                370                 375                 380

Gly Ser Pro Glu His Ser Pro Gly Gly Thr Trp Ser Asp Cys Asn Gly
385                 390                 395                 400

Gly Thr Arg Gly Gly Ser Glu Ser Ser Leu Glu Glu Arg His Ser Lys
                405                 410                 415

Thr Ser Arg Ser Glu Ser Lys Met Glu Arg Glu Lys Asn Ile Leu Ala
                420                 425                 430

Thr Thr Arg Phe Tyr Cys Thr Phe Leu Gly Asn Gly Asp Lys Ala Val
                435                 440                 445

Phe Cys Thr Val Leu Arg Ile Val Lys Leu Phe Glu Asp Ala Thr Cys
450                 455                 460

Thr Cys Pro His Thr His Lys Leu Lys Met Lys Trp Arg Phe Lys Gln
465                 470                 475                 480

His Gln Ala

<210> SEQ ID NO 2
<211> LENGTH: 477
<212> TYPE: PRT
<213> ORGANISM: Homo sapiens

<400> SEQUENCE: 2

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
                20                  25                  30

Leu Val Pro Ala Ser Pro Pro Ala Ser Leu Leu Pro Pro Ala Ser Glu
            35                  40                  45

Ser Pro Glu Pro Leu Ser Gln Gln Trp Thr Ala Gly Met Gly Leu Leu
        50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
                100                 105                 110

Pro Phe Gly Ala Thr Ile Val Val Trp Gly Arg Trp Glu Tyr Gly Ser
            115                 120                 125
```

```
Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
    370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
    450                 455                 460

Glu Pro Cys Arg Pro Gly Phe Ala Ser Glu Ser Lys Val
465                 470                 475

<210> SEQ ID NO 3
<211> LENGTH: 413
<212> TYPE: PRT
<213> ORGANISM: Homo sapiens

<400> SEQUENCE: 3

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30
```

Val Val Gly Met Gly Ile Val Met Ser Leu Ile Val Leu Ala Ile Val
 35                  40                  45

Phe Gly Asn Val Leu Val Ile Thr Ala Ile Ala Lys Phe Glu Arg Leu
 50                  55                  60

Gln Thr Val Thr Asn Tyr Phe Ile Thr Ser Leu Ala Cys Ala Asp Leu
 65                  70                  75                  80

Val Met Gly Leu Ala Val Val Pro Phe Gly Ala Ala His Ile Leu Met
             85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
            115                 120                 125

Val Asp Arg Tyr Phe Ala Ile Thr Ser Pro Phe Lys Tyr Gln Ser Leu
130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
            195                 200                 205

Tyr Val Pro Leu Val Ile Met Val Phe Val Tyr Ser Arg Val Phe Gln
            210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
            290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
            370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 4
<211> LENGTH: 408
<212> TYPE: PRT
<213> ORGANISM: Homo sapiens

<400> SEQUENCE: 4

```
Met Ala Pro Trp Pro His Glu Asn Ser Ser Leu Ala Pro Trp Pro Asp
1               5                   10                  15
Leu Pro Thr Leu Ala Pro Asn Thr Ala Asn Thr Ser Gly Leu Pro Gly
            20                  25                  30
Val Pro Trp Glu Ala Ala Leu Ala Gly Ala Leu Leu Ala Leu Ala Val
        35                  40                  45
Leu Ala Thr Val Gly Gly Asn Leu Leu Val Ile Val Ala Ile Ala Trp
    50                  55                  60
Thr Pro Arg Leu Gln Thr Met Thr Asn Val Phe Val Thr Ser Leu Ala
65                  70                  75                  80
Ala Ala Asp Leu Val Met Gly Leu Leu Val Val Pro Pro Ala Ala Thr
                85                  90                  95
Leu Ala Leu Thr Gly His Trp Pro Leu Gly Ala Thr Gly Cys Glu Leu
            100                 105                 110
Trp Thr Ser Val Asp Val Leu Cys Val Thr Ala Ser Ile Glu Thr Leu
        115                 120                 125
Cys Ala Leu Ala Val Asp Arg Tyr Leu Ala Val Thr Asn Pro Leu Arg
    130                 135                 140
Tyr Gly Ala Leu Val Thr Lys Arg Cys Ala Arg Thr Ala Val Val Leu
145                 150                 155                 160
Val Trp Val Val Ser Ala Ala Val Ser Phe Ala Pro Ile Met Ser Gln
                165                 170                 175
Trp Trp Arg Val Gly Ala Asp Ala Glu Ala Gln Arg Cys His Ser Asn
            180                 185                 190
Pro Arg Cys Cys Ala Phe Ala Ser Asn Met Pro Tyr Val Leu Leu Ser
        195                 200                 205
Ser Ser Val Ser Phe Tyr Leu Pro Leu Leu Val Met Leu Phe Val Tyr
    210                 215                 220
Ala Arg Val Phe Val Val Ala Thr Arg Gln Leu Arg Leu Leu Arg Gly
225                 230                 235                 240
Glu Leu Gly Arg Phe Pro Pro Glu Glu Ser Pro Pro Ala Pro Ser Arg
                245                 250                 255
Ser Leu Ala Pro Ala Pro Val Gly Thr Cys Ala Pro Pro Glu Gly Val
            260                 265                 270
Pro Ala Cys Gly Arg Arg Pro Ala Arg Leu Leu Pro Leu Arg Glu His
        275                 280                 285
Arg Ala Leu Cys Thr Leu Gly Leu Ile Met Gly Thr Phe Thr Leu Cys
    290                 295                 300
Trp Leu Pro Phe Phe Leu Ala Asn Val Leu Arg Ala Leu Gly Gly Pro
305                 310                 315                 320
Ser Leu Val Pro Gly Pro Ala Phe Leu Ala Leu Asn Trp Leu Gly Tyr
                325                 330                 335
Ala Asn Ser Ala Phe Asn Pro Leu Ile Tyr Cys Arg Ser Pro Asp Phe
            340                 345                 350
Arg Ser Ala Phe Arg Arg Leu Leu Cys Arg Cys Gly Arg Arg Leu Pro
        355                 360                 365
Pro Glu Pro Cys Ala Ala Ala Arg Pro Ala Leu Phe Pro Ser Gly Val
    370                 375                 380
Pro Ala Ala Arg Ser Ser Pro Ala Gln Pro Arg Leu Cys Gln Arg Leu
385                 390                 395                 400
Asp Gly Ala Ser Trp Gly Val Ser
                405
```

```
<210> SEQ ID NO 5
<211> LENGTH: 412
<212> TYPE: PRT
<213> ORGANISM: Homo sapiens

<400> SEQUENCE: 5
```

| Met | Pro | Ile | Met | Gly | Ser | Ser | Val | Tyr | Ile | Thr | Val | Glu | Leu | Ala | Ile |
|---|---|---|---|---|---|---|---|---|---|---|---|---|---|---|---|
| 1 | | | | 5 | | | | | 10 | | | | | 15 | |

| Ala | Val | Leu | Ala | Ile | Leu | Gly | Asn | Val | Leu | Val | Cys | Trp | Ala | Val | Trp |
|---|---|---|---|---|---|---|---|---|---|---|---|---|---|---|---|
| | | | 20 | | | | | 25 | | | | | 30 | | |

| Leu | Asn | Ser | Asn | Leu | Gln | Asn | Val | Thr | Asn | Tyr | Phe | Val | Val | Ser | Leu |
|---|---|---|---|---|---|---|---|---|---|---|---|---|---|---|---|
| | | | 35 | | | | | 40 | | | | | 45 | | |

| Ala | Ala | Ala | Asp | Ile | Ala | Val | Gly | Val | Leu | Ala | Ile | Pro | Phe | Ala | Ile |
|---|---|---|---|---|---|---|---|---|---|---|---|---|---|---|---|
| | 50 | | | | | 55 | | | | | 60 | | | | |

| Thr | Ile | Ser | Thr | Gly | Phe | Cys | Ala | Ala | Cys | His | Gly | Cys | Leu | Phe | Ile |
|---|---|---|---|---|---|---|---|---|---|---|---|---|---|---|---|
| 65 | | | | | 70 | | | | | 75 | | | | | 80 |

| Ala | Cys | Phe | Val | Leu | Val | Leu | Thr | Gln | Ser | Ser | Ile | Phe | Ser | Leu | Leu |
|---|---|---|---|---|---|---|---|---|---|---|---|---|---|---|---|
| | | | | 85 | | | | | 90 | | | | | 95 | |

| Ala | Ile | Ala | Ile | Asp | Arg | Tyr | Ile | Ala | Ile | Arg | Ile | Pro | Leu | Arg | Tyr |
|---|---|---|---|---|---|---|---|---|---|---|---|---|---|---|---|
| | | | 100 | | | | | 105 | | | | | 110 | | |

| Asn | Gly | Leu | Val | Thr | Gly | Thr | Arg | Ala | Lys | Gly | Ile | Ile | Ala | Ile | Cys |
|---|---|---|---|---|---|---|---|---|---|---|---|---|---|---|---|
| | | | 115 | | | | | 120 | | | | | 125 | | |

| Trp | Val | Leu | Ser | Phe | Ala | Ile | Gly | Leu | Thr | Pro | Met | Leu | Gly | Trp | Asn |
|---|---|---|---|---|---|---|---|---|---|---|---|---|---|---|---|
| 130 | | | | | 135 | | | | | 140 | | | | | |

| Asn | Cys | Gly | Gln | Pro | Lys | Glu | Gly | Lys | Asn | His | Ser | Gln | Gly | Cys | Gly |
|---|---|---|---|---|---|---|---|---|---|---|---|---|---|---|---|
| 145 | | | | | 150 | | | | | 155 | | | | | 160 |

| Glu | Gly | Gln | Val | Ala | Cys | Leu | Phe | Glu | Asp | Val | Val | Pro | Met | Asn | Tyr |
|---|---|---|---|---|---|---|---|---|---|---|---|---|---|---|---|
| | | | | 165 | | | | | 170 | | | | | 175 | |

| Met | Val | Tyr | Phe | Asn | Phe | Phe | Ala | Cys | Val | Leu | Val | Pro | Leu | Leu | Leu |
|---|---|---|---|---|---|---|---|---|---|---|---|---|---|---|---|
| | | | 180 | | | | | 185 | | | | | 190 | | |

| Met | Leu | Gly | Val | Tyr | Leu | Arg | Ile | Phe | Leu | Ala | Ala | Arg | Arg | Gln | Leu |
|---|---|---|---|---|---|---|---|---|---|---|---|---|---|---|---|
| | | | 195 | | | | | 200 | | | | | 205 | | |

| Lys | Gln | Met | Glu | Ser | Gln | Pro | Leu | Pro | Gly | Glu | Arg | Ala | Arg | Ser | Thr |
|---|---|---|---|---|---|---|---|---|---|---|---|---|---|---|---|
| | 210 | | | | | 215 | | | | | 220 | | | | |

| Leu | Gln | Lys | Glu | Val | His | Ala | Ala | Lys | Ser | Leu | Ala | Ile | Ile | Val | Gly |
|---|---|---|---|---|---|---|---|---|---|---|---|---|---|---|---|
| 225 | | | | | 230 | | | | | 235 | | | | | 240 |

| Leu | Phe | Ala | Leu | Cys | Trp | Leu | Pro | Leu | His | Ile | Ile | Asn | Cys | Phe | Thr |
|---|---|---|---|---|---|---|---|---|---|---|---|---|---|---|---|
| | | | | 245 | | | | | 250 | | | | | 255 | |

| Phe | Phe | Cys | Pro | Asp | Cys | Ser | His | Ala | Pro | Leu | Trp | Leu | Met | Tyr | Leu |
|---|---|---|---|---|---|---|---|---|---|---|---|---|---|---|---|
| | | | 260 | | | | | 265 | | | | | 270 | | |

| Ala | Ile | Val | Leu | Ser | His | Thr | Asn | Ser | Val | Val | Asn | Pro | Phe | Ile | Tyr |
|---|---|---|---|---|---|---|---|---|---|---|---|---|---|---|---|
| | | | 275 | | | | | 280 | | | | | 285 | | |

| Ala | Tyr | Arg | Ile | Arg | Glu | Phe | Arg | Gln | Thr | Phe | Arg | Lys | Ile | Ile | Arg |
|---|---|---|---|---|---|---|---|---|---|---|---|---|---|---|---|
| | 290 | | | | | 295 | | | | | 300 | | | | |

| Ser | His | Val | Leu | Arg | Gln | Gln | Glu | Pro | Phe | Lys | Ala | Ala | Gly | Thr | Ser |
|---|---|---|---|---|---|---|---|---|---|---|---|---|---|---|---|
| 305 | | | | | 310 | | | | | 315 | | | | | 320 |

| Ala | Arg | Val | Leu | Ala | Ala | His | Gly | Ser | Asp | Gly | Glu | Gln | Val | Ser | Leu |
|---|---|---|---|---|---|---|---|---|---|---|---|---|---|---|---|
| | | | | 325 | | | | | 330 | | | | | 335 | |

| Arg | Leu | Asn | Gly | His | Pro | Pro | Gly | Val | Trp | Ala | Asn | Gly | Ser | Ala | Pro |
|---|---|---|---|---|---|---|---|---|---|---|---|---|---|---|---|
| | | | 340 | | | | | 345 | | | | | 350 | | |

| His | Pro | Glu | Arg | Arg | Pro | Asn | Gly | Tyr | Ala | Leu | Gly | Leu | Val | Ser | Gly |
|---|---|---|---|---|---|---|---|---|---|---|---|---|---|---|---|
| | | | 355 | | | | | 360 | | | | | 365 | | |

| Gly | Ser | Ala | Gln | Glu | Ser | Gln | Gly | Asn | Thr | Gly | Leu | Pro | Asp | Val | Glu |
|---|---|---|---|---|---|---|---|---|---|---|---|---|---|---|---|
| | 370 | | | | | 375 | | | | | 380 | | | | |

```
Leu Leu Ser His Glu Leu Lys Gly Val Cys Pro Glu Pro Gly Leu
385                 390                 395                 400

Asp Asp Pro Leu Ala Gln Asp Gly Ala Gly Val Ser
            405                 410

<210> SEQ ID NO 6
<211> LENGTH: 332
<212> TYPE: PRT
<213> ORGANISM: Homo sapiens

<400> SEQUENCE: 6

Met Leu Leu Glu Thr Gln Asp Ala Leu Tyr Val Ala Leu Glu Leu Val
1               5                   10                  15

Ile Ala Ala Leu Ser Val Ala Gly Asn Val Leu Val Cys Ala Ala Val
            20                  25                  30

Gly Thr Ala Asn Thr Leu Gln Thr Pro Thr Asn Tyr Phe Leu Val Ser
            35                  40                  45

Leu Ala Ala Ala Asp Val Ala Val Gly Leu Phe Ala Ile Pro Phe Ala
            50                  55                  60

Ile Thr Ile Ser Leu Gly Phe Cys Thr Asp Phe Tyr Gly Cys Leu Phe
65                  70                  75                  80

Leu Ala Cys Phe Val Leu Val Leu Thr Gln Ser Ser Ile Phe Ser Leu
                85                  90                  95

Leu Ala Val Ala Val Asp Arg Tyr Leu Ala Ile Cys Val Pro Leu Arg
            100                 105                 110

Tyr Lys Ser Leu Val Thr Gly Thr Arg Ala Arg Gly Val Ile Ala Val
            115                 120                 125

Leu Trp Val Leu Ala Phe Gly Ile Gly Leu Thr Pro Phe Leu Gly Trp
130                 135                 140

Asn Ser Lys Asp Ser Ala Thr Asn Asn Cys Thr Glu Pro Trp Asp Gly
145                 150                 155                 160

Thr Thr Asn Glu Ser Cys Cys Leu Val Lys Cys Leu Phe Glu Asn Val
                165                 170                 175

Val Pro Met Ser Tyr Met Val Tyr Phe Asn Phe Phe Gly Cys Val Leu
            180                 185                 190

Pro Pro Leu Leu Ile Met Leu Val Ile Tyr Ile Lys Ile Phe Leu Val
            195                 200                 205

Ala Cys Arg Gln Leu Gln Arg Thr Glu Leu Met Asp His Ser Arg Thr
210                 215                 220

Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
                245                 250                 255

Thr Leu Phe Gln Pro Ala Gln Gly Lys Asn Lys Pro Lys Trp Ala Met
            260                 265                 270

Asn Met Ala Ile Leu Leu Ser His Ala Asn Ser Val Val Asn Pro Ile
            275                 280                 285

Val Tyr Ala Tyr Arg Asn Arg Asp Phe Arg Tyr Thr Phe His Lys Ile
            290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
            325                 330
```

<210> SEQ ID NO 7
<211> LENGTH: 318
<212> TYPE: PRT
<213> ORGANISM: Homo sapiens

<400> SEQUENCE: 7

```
Met Pro Asn Asn Ser Thr Ala Leu Ser Leu Ala Asn Val Thr Tyr Ile
1               5                   10                  15

Thr Met Glu Ile Phe Ile Gly Leu Cys Ala Ile Val Gly Asn Val Leu
            20                  25                  30

Val Ile Cys Val Val Lys Leu Asn Pro Ser Leu Gln Thr Thr Thr Phe
        35                  40                  45

Tyr Phe Ile Val Ser Leu Ala Leu Ala Asp Ile Ala Val Gly Val Leu
    50                  55                  60

Val Met Pro Leu Ala Ile Val Val Ser Leu Gly Ile Thr Ile His Phe
65                  70                  75                  80

Tyr Ser Cys Leu Phe Met Thr Cys Leu Leu Leu Ile Phe Thr His Ala
                85                  90                  95

Ser Ile Met Ser Leu Leu Ala Ile Ala Val Asp Arg Tyr Leu Arg Val
            100                 105                 110

Lys Leu Thr Val Arg Tyr Lys Arg Val Thr Thr His Arg Arg Ile Trp
        115                 120                 125

Leu Ala Leu Gly Leu Cys Trp Leu Val Ser Phe Leu Val Gly Leu Thr
    130                 135                 140

Pro Met Phe Gly Trp Asn Met Lys Leu Thr Ser Glu Tyr His Arg Asn
145                 150                 155                 160

Val Thr Phe Leu Ser Cys Gln Phe Val Ser Val Met Arg Met Asp Tyr
                165                 170                 175

Met Val Tyr Phe Ser Phe Leu Thr Trp Ile Phe Ile Pro Leu Val Val
            180                 185                 190

Met Cys Ala Ile Tyr Leu Asp Ile Phe Tyr Ile Ile Arg Asn Lys Leu
        195                 200                 205

Ser Leu Asn Leu Ser Asn Ser Lys Glu Thr Gly Ala Phe Tyr Gly Arg
    210                 215                 220

Glu Phe Lys Thr Ala Lys Ser Leu Phe Leu Val Leu Phe Leu Phe Ala
225                 230                 235                 240

Leu Ser Trp Leu Pro Leu Ser Ile Ile Asn Cys Ile Ile Tyr Phe Asn
                245                 250                 255

Gly Glu Val Pro Gln Leu Val Leu Tyr Met Gly Ile Leu Leu Ser His
            260                 265                 270

Ala Asn Ser Met Met Asn Pro Ile Val Tyr Ala Tyr Lys Ile Lys Lys
        275                 280                 285

Phe Lys Glu Thr Tyr Leu Leu Ile Leu Lys Ala Cys Val Cys His
    290                 295                 300

Pro Ser Asp Ser Leu Asp Thr Ser Ile Glu Lys Asn Ser Glu
305                 310                 315
```

<210> SEQ ID NO 8
<211> LENGTH: 326
<212> TYPE: PRT
<213> ORGANISM: Homo sapiens

<400> SEQUENCE: 8

```
Met Pro Pro Ser Ile Ser Ala Phe Gln Ala Ala Tyr Ile Gly Ile Glu
1               5                   10                  15

Val Leu Ile Ala Leu Val Ser Val Pro Gly Asn Val Leu Val Ile Trp
            20                  25                  30
```

```
Ala Val Lys Val Asn Gln Ala Leu Arg Asp Ala Thr Phe Cys Phe Ile
         35                  40                  45

Val Ser Leu Ala Val Ala Asp Val Ala Val Gly Ala Leu Val Ile Pro
 50                  55                  60

Leu Ala Ile Leu Ile Asn Ile Gly Pro Gln Thr Tyr Phe His Thr Cys
 65                  70                  75                  80

Leu Met Val Ala Cys Pro Val Leu Ile Leu Thr Gln Ser Ser Ile Leu
                 85                  90                  95

Ala Leu Leu Ala Ile Ala Val Asp Arg Tyr Leu Arg Val Lys Ile Pro
                100                 105                 110

Leu Arg Tyr Lys Met Val Val Thr Pro Arg Arg Ala Val Ala Ile
        115                 120                 125

Ala Gly Cys Trp Ile Leu Ser Phe Val Val Gly Leu Thr Pro Met Phe
        130                 135                 140

Gly Trp Asn Asn Leu Ser Ala Val Glu Arg Ala Trp Ala Ala Asn Gly
145                 150                 155                 160

Ser Met Gly Glu Pro Val Ile Lys Cys Glu Phe Glu Lys Val Ile Ser
                165                 170                 175

Met Glu Tyr Met Val Tyr Phe Asn Phe Phe Val Trp Val Leu Pro Pro
        180                 185                 190

Leu Leu Leu Met Val Leu Ile Tyr Leu Glu Val Phe Tyr Leu Ile Arg
        195                 200                 205

Lys Gln Leu Asn Lys Lys Val Ser Ala Ser Ser Gly Asp Pro Gln Lys
210                 215                 220

Tyr Tyr Gly Lys Glu Leu Lys Ile Ala Lys Ser Leu Ala Leu Ile Leu
225                 230                 235                 240

Phe Leu Phe Ala Leu Ser Trp Leu Pro Leu His Ile Leu Asn Cys Ile
                245                 250                 255

Thr Leu Phe Cys Pro Ser Cys His Lys Pro Ser Ile Leu Thr Tyr Ile
        260                 265                 270

Ala Ile Phe Leu Thr His Gly Asn Ser Ala Met Asn Pro Ile Val Tyr
        275                 280                 285

Ala Phe Arg Ile Gln Lys Phe Arg Val Thr Phe Leu Lys Ile Trp Asn
        290                 295                 300

Asp His Phe Arg Cys Gln Pro Ala Pro Pro Ile Asp Glu Asp Leu Pro
305                 310                 315                 320

Glu Glu Arg Pro Asp Asp
                325

<210> SEQ ID NO 9
<211> LENGTH: 424
<212> TYPE: PRT
<213> ORGANISM: Rattus norvegicus

<400> SEQUENCE: 9

Met His Leu Asn Ser Ser Val Pro Gln Gly Thr Pro Gly Glu Pro Asp
 1               5                  10                  15

Ala Gln Pro Phe Ser Gly Pro Gln Ser Glu Met Glu Ala Thr Phe Leu
                20                  25                  30

Ala Leu Ser Leu Ser Asn Gly Ser Gly Asn Thr Ser Glu Ser Asp Thr
        35                  40                  45

Ala Gly Pro Asn Ser Asp Leu Asp Val Asn Thr Asp Ile Tyr Ser Lys
 50                  55                  60

Val Leu Val Thr Ala Ile Tyr Leu Ala Leu Phe Val Val Gly Thr Val
 65                  70                  75                  80
```

Gly Asn Ser Val Thr Ala Phe Thr Leu Ala Arg Lys Lys Ser Leu Gln
                    85                  90                  95

Ser Leu Gln Ser Thr Val His Tyr His Leu Gly Ser Leu Ala Leu Ser
                100                 105                 110

Asp Leu Leu Ile Leu Leu Leu Ala Met Pro Val Glu Leu Tyr Asn Phe
                115                 120                 125

Ile Trp Val His His Pro Trp Ala Phe Gly Asp Ala Gly Cys Arg Gly
            130                 135                 140

Tyr Tyr Phe Leu Arg Asp Ala Cys Thr Tyr Ala Thr Ala Leu Asn Val
145                 150                 155                 160

Ala Ser Leu Ser Val Glu Arg Tyr Leu Ala Ile Cys His Pro Phe Lys
                165                 170                 175

Ala Lys Thr Leu Met Ser Arg Ser Arg Thr Lys Lys Phe Ile Ser Ala
                180                 185                 190

Ile Trp Leu Ala Ser Ala Leu Leu Ala Ile Pro Met Leu Phe Thr Met
            195                 200                 205

Gly Leu Gln Asn Arg Ser Gly Asp Gly Thr His Pro Gly Gly Leu Val
            210                 215                 220

Cys Thr Pro Ile Val Asp Thr Ala Thr Val Lys Val Val Ile Gln Val
225                 230                 235                 240

Asn Thr Phe Met Ser Phe Leu Phe Pro Met Leu Val Ile Ser Ile Leu
                245                 250                 255

Asn Thr Val Ile Ala Asn Lys Leu Thr Val Met Val His Gln Ala Ala
                260                 265                 270

Glu Gln Gly Arg Val Cys Thr Val Gly Thr His Asn Gly Leu Glu His
            275                 280                 285

Ser Thr Phe Asn Met Thr Ile Glu Pro Gly Arg Val Gln Ala Leu Arg
290                 295                 300

His Gly Val Leu Val Leu Arg Ala Val Val Ile Ala Phe Val Val Cys
305                 310                 315                 320

Trp Leu Pro Tyr His Val Arg Arg Leu Met Phe Cys Tyr Ile Ser Asp
                325                 330                 335

Glu Gln Trp Thr Thr Phe Leu Phe Asp Phe Tyr His Tyr Phe Tyr Met
            340                 345                 350

Leu Thr Asn Ala Leu Phe Tyr Val Ser Ser Ala Ile Asn Pro Ile Leu
                355                 360                 365

Tyr Asn Leu Val Ser Ala Asn Phe Arg Gln Val Phe Leu Ser Thr Leu
            370                 375                 380

Ala Cys Leu Cys Pro Gly Trp Arg His Arg Arg Lys Lys Arg Pro Thr
385                 390                 395                 400

Phe Ser Arg Lys Pro Asn Ser Met Ser Ser Asn His Ala Phe Ser Thr
                405                 410                 415

Ser Ala Thr Arg Glu Thr Leu Tyr
            420

<210> SEQ ID NO 10
<211> LENGTH: 418
<212> TYPE: PRT
<213> ORGANISM: Homo sapiens

<400> SEQUENCE: 10

Met Arg Leu Asn Ser Ser Ala Pro Gly Thr Pro Gly Thr Pro Ala Ala
1               5                   10                  15

Asp Pro Phe Gln Arg Ala Gln Ala Gly Leu Glu Glu Ala Leu Leu Ala
                20                  25                  30

Pro Gly Phe Gly Asn Ala Ser Gly Asn Ala Ser Glu Arg Val Leu Ala
        35                  40                  45

Ala Pro Ser Ser Glu Leu Asp Val Asn Thr Asp Ile Tyr Ser Lys Val
 50                  55                  60

Leu Val Thr Ala Val Tyr Leu Ala Leu Phe Val Val Gly Thr Val Gly
 65                  70                  75                  80

Asn Thr Val Thr Ala Phe Thr Leu Ala Arg Lys Lys Ser Leu Gln Ser
                 85                  90                  95

Leu Gln Ser Thr Val His Tyr His Leu Gly Ser Leu Ala Leu Ser Asp
                100                 105                 110

Leu Leu Thr Leu Leu Leu Ala Met Pro Val Glu Leu Tyr Asn Phe Ile
             115                 120                 125

Trp Val His His Pro Trp Ala Phe Gly Asp Ala Gly Cys Arg Gly Tyr
     130                 135                 140

Tyr Phe Leu Arg Asp Ala Cys Thr Tyr Ala Thr Ala Leu Asn Val Ala
145                 150                 155                 160

Ser Leu Ser Val Glu Arg Tyr Leu Ala Ile Cys His Pro Phe Lys Ala
                165                 170                 175

Lys Thr Leu Met Ser Arg Ser Arg Thr Lys Lys Phe Ile Ser Ala Ile
            180                 185                 190

Trp Leu Ala Ser Ala Leu Leu Ala Val Pro Met Leu Phe Thr Met Gly
        195                 200                 205

Glu Gln Asn Arg Ser Ala Asp Gly Gln His Ala Gly Gly Leu Val Cys
210                 215                 220

Thr Pro Thr Ile His Thr Ala Thr Val Lys Val Val Ile Gln Val Asn
225                 230                 235                 240

Thr Phe Met Ser Phe Ile Phe Pro Met Val Val Ile Ser Val Leu Asn
                245                 250                 255

Thr Ile Ile Ala Asn Lys Leu Thr Val Met Val Arg Gln Ala Ala Glu
            260                 265                 270

Gln Gly Gln Val Cys Thr Val Gly Gly Glu His Ser Thr Phe Ser Met
        275                 280                 285

Ala Ile Glu Pro Gly Arg Val Gln Ala Leu Arg His Gly Val Arg Val
290                 295                 300

Leu Arg Ala Val Val Ile Ala Phe Val Val Cys Trp Leu Pro Tyr His
305                 310                 315                 320

Val Arg Arg Leu Met Phe Cys Tyr Ile Ser Asp Glu Gln Trp Thr Pro
                325                 330                 335

Phe Leu Tyr Asp Phe Tyr His Tyr Phe Tyr Met Val Thr Asn Ala Leu
            340                 345                 350

Phe Tyr Val Ser Ser Thr Ile Asn Pro Ile Leu Tyr Asn Leu Val Ser
        355                 360                 365

Ala Asn Phe Arg His Ile Phe Leu Ala Thr Leu Ala Cys Leu Cys Pro
370                 375                 380

Val Trp Arg Arg Arg Lys Arg Pro Ala Phe Ser Arg Lys Ala Asp
385                 390                 395                 400

Ser Val Ser Ser Asn His Thr Leu Ser Ser Asn Ala Thr Arg Glu Thr
                405                 410                 415

Leu Tyr

<210> SEQ ID NO 11
<211> LENGTH: 409
<212> TYPE: PRT
<213> ORGANISM: Homo sapiens

```
<400> SEQUENCE: 11

Met Glu Thr Ser Ser Pro Arg Pro Pro Arg Pro Ser Ser Asn Pro Gly
1               5                   10                  15

Leu Ser Leu Asp Ala Arg Leu Gly Val Asp Thr Arg Leu Trp Ala Lys
            20                  25                  30

Val Leu Phe Thr Ala Leu Tyr Ala Leu Ile Trp Ala Leu Gly Ala Ala
        35                  40                  45

Gly Asn Ala Leu Ser Val His Val Leu Lys Ala Arg Ala Gly Arg
50                  55                  60

Ala Gly Arg Leu Arg His His Val Leu Ser Leu Ala Leu Ala Gly Leu
65                  70                  75                  80

Leu Leu Leu Leu Val Gly Val Pro Val Glu Leu Tyr Ser Phe Val Trp
                85                  90                  95

Phe His Tyr Pro Trp Val Phe Gly Asp Leu Gly Cys Arg Gly Tyr Tyr
            100                 105                 110

Phe Val His Glu Leu Cys Ala Tyr Ala Thr Val Leu Ser Val Ala Gly
        115                 120                 125

Leu Ser Ala Glu Arg Cys Leu Ala Val Cys Gln Pro Leu Arg Ala Arg
130                 135                 140

Ser Leu Leu Thr Pro Arg Arg Thr Arg Trp Leu Val Ala Leu Ser Trp
145                 150                 155                 160

Ala Ala Ser Leu Gly Leu Ala Leu Pro Met Ala Val Ile Met Gly Gln
                165                 170                 175

Lys His Glu Leu Glu Thr Ala Asp Gly Glu Pro Glu Pro Ala Ser Arg
            180                 185                 190

Val Cys Thr Val Leu Val Ser Arg Thr Ala Leu Gln Val Phe Ile Gln
        195                 200                 205

Val Asn Val Leu Val Ser Phe Val Leu Pro Leu Ala Leu Thr Ala Phe
210                 215                 220

Leu Asn Gly Val Thr Val Ser His Leu Leu Ala Leu Cys Ser Gln Val
225                 230                 235                 240

Pro Ser Thr Ser Thr Pro Gly Ser Ser Thr Pro Ser Arg Leu Glu Leu
                245                 250                 255

Leu Ser Glu Glu Gly Leu Leu Ser Phe Ile Val Trp Lys Lys Thr Phe
            260                 265                 270

Ile Gln Gly Gly Gln Val Ser Leu Val Arg His Lys Asp Val Arg Arg
        275                 280                 285

Ile Arg Ser Leu Gln Arg Ser Val Gln Val Leu Arg Ala Ile Val Val
290                 295                 300

Met Tyr Val Ile Cys Trp Leu Pro Tyr His Ala Arg Arg Leu Met Tyr
305                 310                 315                 320

Cys Tyr Val Pro Asp Asp Ala Trp Thr Asp Pro Leu Tyr Asn Phe Tyr
                325                 330                 335

His Tyr Phe Tyr Met Val Thr Asn Thr Leu Phe Tyr Val Ser Ser Ala
            340                 345                 350

Val Thr Pro Leu Leu Tyr Asn Ala Val Ser Ser Ser Phe Arg Lys Leu
        355                 360                 365

Phe Leu Glu Ala Val Ser Ser Leu Cys Gly His His Pro Met Lys
370                 375                 380

Arg Leu Pro Pro Lys Pro Gln Ser Pro Thr Leu Met Asp Thr Ala Ser
385                 390                 395                 400

Gly Phe Gly Asp Pro Pro Glu Thr Arg
                405
```

```
<210> SEQ ID NO 12
<211> LENGTH: 460
<212> TYPE: PRT
<213> ORGANISM: Homo sapiens

<400> SEQUENCE: 12

Met Asn Thr Ser Ala Pro Ala Val Ser Pro Asn Ile Thr Val Leu
1               5                   10                  15

Ala Pro Gly Lys Gly Pro Trp Gln Val Ala Phe Ile Gly Ile Thr Thr
                20                  25                  30

Gly Leu Leu Ser Leu Ala Thr Val Thr Gly Asn Leu Leu Val Leu Ile
                35                  40                  45

Ser Phe Lys Val Asn Thr Glu Leu Lys Thr Val Asn Asn Tyr Phe Leu
50                  55                  60

Leu Ser Leu Ala Cys Ala Asp Leu Ile Ile Gly Thr Phe Ser Met Asn
65                  70                  75                  80

Leu Tyr Thr Thr Tyr Leu Leu Met Gly His Trp Ala Leu Gly Thr Leu
                85                  90                  95

Ala Cys Asp Leu Trp Leu Ala Leu Asp Tyr Val Ala Ser Asn Ala Ser
                100                 105                 110

Val Met Asn Leu Leu Leu Ile Ser Phe Asp Arg Tyr Phe Ser Val Thr
                115                 120                 125

Arg Pro Leu Ser Tyr Arg Ala Lys Arg Thr Pro Arg Arg Ala Ala Leu
130                 135                 140

Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Val Leu Ala Gly
                165                 170                 175

Gln Cys Tyr Ile Gln Phe Leu Ser Gln Pro Ile Ile Thr Phe Gly Thr
                180                 185                 190

Ala Met Ala Ala Phe Tyr Leu Pro Val Thr Val Met Cys Thr Leu Tyr
                195                 200                 205

Trp Arg Ile Tyr Arg Glu Thr Glu Asn Arg Ala Arg Glu Leu Ala Ala
210                 215                 220

Leu Gln Gly Ser Glu Thr Pro Gly Lys Gly Gly Gly Ser Ser Ser Ser
225                 230                 235                 240

Ser Glu Arg Ser Gln Pro Gly Ala Glu Gly Ser Pro Glu Thr Pro Pro
                245                 250                 255

Gly Arg Cys Cys Arg Cys Cys Arg Ala Pro Arg Leu Leu Gln Ala Tyr
                260                 265                 270

Ser Trp Lys Glu Glu Glu Glu Asp Glu Gly Ser Met Glu Ser Leu
                275                 280                 285

Thr Ser Ser Glu Gly Glu Glu Pro Gly Ser Glu Val Val Ile Lys Met
290                 295                 300

Pro Met Val Asp Pro Glu Ala Gln Ala Pro Thr Lys Gln Pro Pro Arg
305                 310                 315                 320

Ser Ser Pro Asn Thr Val Lys Arg Pro Thr Lys Lys Gly Arg Asp Arg
                325                 330                 335

Ala Gly Lys Gly Gln Lys Pro Arg Gly Lys Glu Gln Leu Ala Lys Arg
                340                 345                 350

Lys Thr Phe Ser Leu Val Lys Glu Lys Lys Ala Ala Arg Thr Leu Ser
                355                 360                 365

Ala Ile Leu Leu Ala Phe Ile Leu Thr Trp Thr Pro Tyr Asn Ile Met
370                 375                 380
```

```
Val Leu Val Ser Thr Phe Cys Lys Asp Cys Val Pro Glu Thr Leu Trp
385                 390                 395                 400

Glu Leu Gly Tyr Trp Leu Cys Tyr Val Asn Ser Thr Ile Asn Pro Met
            405                 410                 415

Cys Tyr Ala Leu Cys Asn Lys Ala Phe Arg Asp Thr Phe Arg Leu Leu
        420                 425                 430

Leu Leu Cys Arg Trp Asp Lys Arg Trp Arg Lys Ile Pro Lys Arg
    435                 440                 445

Pro Gly Ser Val His Arg Thr Pro Ser Arg Gln Cys
450                 455                 460

<210> SEQ ID NO 13
<211> LENGTH: 329
<212> TYPE: PRT
<213> ORGANISM: Meleagris gallopavo

<400> SEQUENCE: 13

Gln Val Ser Ala Glu Leu Leu Ser Gln Gln Trp Glu Ala Gly Met Ser
1               5                   10                  15

Leu Leu Met Ala Leu Val Val Leu Ile Val Ala Gly Asn Val Leu
            20                  25                  30

Val Ile Ala Ala Ile Gly Arg Thr Gln Arg Leu Gln Thr Leu Thr Asn
        35                  40                  45

Leu Phe Ile Thr Ser Leu Ala Cys Ala Asp Leu Val Met Gly Leu Leu
    50                  55                  60

Val Val Pro Phe Gly Ala Thr Leu Val Val Arg Gly Thr Trp Leu Trp
65                  70                  75                  80

Gly Ser Phe Leu Cys Glu Cys Trp Thr Ser Leu Asp Val Leu Cys Val
                85                  90                  95

Thr Ala Ser Ile Glu Thr Leu Cys Val Ile Ala Ile Asp Arg Tyr Leu
            100                 105                 110

Ala Ile Thr Ser Pro Phe Arg Tyr Gln Ser Leu Met Thr Arg Ala Arg
        115                 120                 125

Ala Lys Val Ile Ile Cys Thr Val Trp Ala Ile Ser Ala Leu Val Ser
130                 135                 140

Phe Leu Pro Ile Met Met His Trp Trp Arg Asp Glu Asp Pro Gln Ala
145                 150                 155                 160

Leu Lys Cys Tyr Gln Asp Pro Gly Cys Cys Asp Phe Val Thr Asn Arg
                165                 170                 175

Ala Tyr Ala Ile Ala Ser Ser Ile Ser Phe Tyr Ile Pro Leu Leu
            180                 185                 190

Ile Met Ile Phe Val Tyr Leu Arg Val Tyr Arg Glu Ala Lys Glu Gln
        195                 200                 205

Ile Arg Lys Ile Asp Arg Cys Glu Gly Arg Phe Tyr Gly Ser Gln Glu
210                 215                 220

Gln Pro Gln Pro Pro Pro Leu Pro Gln His Gln Pro Ile Leu Gly Asn
225                 230                 235                 240

Gly Arg Ala Ser Lys Arg Lys Thr Ser Arg Val Met Ala Met Arg Glu
                245                 250                 255

His Lys Ala Leu Lys Thr Leu Gly Ile Ile Met Gly Val Phe Thr Leu
            260                 265                 270

Cys Trp Leu Pro Phe Phe Leu Val Asn Ile Val Asn Val Phe Asn Arg
        275                 280                 285

Asp Leu Val Pro Asp Trp Leu Phe Val Phe Phe Asn Trp Leu Gly Tyr
290                 295                 300
```

```
Ala Asn Ser Ala Phe Asn Pro Ile Ile Tyr Cys Arg Ser Pro Asp Phe
305                 310                 315                 320

Arg Lys Ala Phe Lys Arg Leu Leu Cys
                325
```

<210> SEQ ID NO 14
<211> LENGTH: 348
<212> TYPE: PRT
<213> ORGANISM: Homo sapiens

<400> SEQUENCE: 14

```
Pro Ala Ser Glu Ser Pro Glu Pro Leu Ser Gln Gln Trp Thr Ala Gly
1               5                   10                  15

Met Gly Leu Leu Met Ala Leu Ile Val Leu Leu Ile Val Ala Gly Asn
            20                  25                  30

Val Leu Val Ile Val Ala Ile Ala Lys Thr Pro Arg Leu Gln Thr Leu
        35                  40                  45

Thr Asn Leu Phe Ile Met Ser Leu Ala Ser Ala Asp Leu Val Met Gly
    50                  55                  60

Leu Leu Val Val Pro Phe Gly Ala Thr Ile Val Val Trp Gly Arg Trp
65                  70                  75                  80

Glu Tyr Gly Ser Phe Phe Cys Glu Leu Trp Thr Ser Val Asp Val Leu
                85                  90                  95

Cys Val Thr Ala Ser Ile Glu Thr Leu Cys Val Ile Ala Leu Asp Arg
            100                 105                 110

Tyr Leu Ala Ile Thr Ser Pro Phe Arg Tyr Gln Ser Leu Leu Thr Arg
        115                 120                 125

Ala Arg Ala Arg Gly Leu Val Cys Thr Val Trp Ala Ile Ser Ala Leu
    130                 135                 140

Val Ser Phe Leu Pro Ile Leu Met His Trp Trp Arg Ala Glu Ser Asp
145                 150                 155                 160

Glu Ala Arg Arg Cys Tyr Asn Asp Pro Lys Cys Cys Asp Phe Val Thr
                165                 170                 175

Asn Arg Ala Tyr Ala Ile Ala Ser Ser Val Val Ser Phe Tyr Val Pro
            180                 185                 190

Leu Cys Ile Met Ala Phe Val Tyr Leu Arg Val Phe Arg Glu Ala Gln
        195                 200                 205

Lys Gln Val Lys Lys Ile Asp Ser Cys Glu Arg Arg Phe Leu Gly Gly
    210                 215                 220

Pro Ala Arg Pro Pro Ser Pro Ser Pro Ser Pro Val Pro Ala Pro Ala
225                 230                 235                 240

Pro Pro Pro Gly Pro Pro Arg Pro Ala Ala Ala Ala Thr Ala Pro
                245                 250                 255

Leu Ala Asn Gly Arg Ala Gly Lys Arg Arg Pro Ser Arg Leu Val Ala
            260                 265                 270

Leu Arg Glu Gln Lys Ala Leu Lys Thr Leu Gly Ile Ile Met Gly Val
        275                 280                 285

Phe Thr Leu Cys Trp Leu Pro Phe Phe Leu Ala Asn Val Val Lys Ala
    290                 295                 300

Phe His Arg Glu Leu Val Pro Asp Arg Leu Phe Val Phe Phe Asn Trp
305                 310                 315                 320

Leu Gly Tyr Ala Asn Ser Ala Phe Asn Pro Ile Ile Tyr Cys Arg Ser
                325                 330                 335

Pro Asp Phe Arg Lys Ala Phe Gln Gly Leu Leu Cys
            340                 345
```

<210> SEQ ID NO 15
<211> LENGTH: 320
<212> TYPE: PRT
<213> ORGANISM: Homo sapiens

<400> SEQUENCE: 15

His Asp Val Thr Gln Gln Arg Asp Glu Val Trp Val Gly Met Gly
1               5                   10                  15

Ile Val Met Ser Leu Ile Val Leu Ala Ile Val Phe Gly Asn Val Leu
            20                  25                  30

Val Ile Thr Ala Ile Ala Lys Phe Glu Arg Leu Gln Thr Val Thr Asn
        35                  40                  45

Tyr Phe Ile Thr Ser Leu Ala Cys Ala Asp Leu Val Met Gly Leu Ala
    50                  55                  60

Val Val Pro Phe Gly Ala Ala His Ile Leu Met Lys Met Trp Thr Phe
65                  70                  75                  80

Gly Asn Phe Trp Cys Glu Phe Trp Thr Ser Ile Asp Val Leu Cys Val
                85                  90                  95

Thr Ala Ser Ile Glu Thr Leu Cys Val Ile Ala Val Asp Arg Tyr Phe
            100                 105                 110

Ala Ile Thr Ser Pro Phe Lys Tyr Gln Ser Leu Leu Thr Lys Asn Lys
        115                 120                 125

Ala Arg Val Ile Ile Leu Met Val Trp Ile Val Ser Gly Leu Thr Ser
130                 135                 140

Phe Leu Pro Ile Gln Met His Trp Tyr Arg Ala Thr His Gln Glu Ala
145                 150                 155                 160

Ile Asn Cys Tyr Ala Asn Glu Thr Cys Cys Asp Phe Phe Thr Asn Gln
                165                 170                 175

Ala Tyr Ala Ile Ala Ser Ser Ile Val Ser Phe Tyr Val Pro Leu Val
            180                 185                 190

Ile Met Val Phe Val Tyr Ser Arg Val Phe Gln Glu Ala Lys Arg Gln
        195                 200                 205

Leu Gln Lys Ile Asp Lys Ser Glu Gly Arg Phe His Val Gln Asn Leu
210                 215                 220

Ser Gln Val Glu Gln Asp Gly Arg Thr Gly His Gly Leu Arg Arg Ser
225                 230                 235                 240

Ser Lys Phe Cys Leu Lys Glu His Lys Ala Leu Lys Thr Leu Gly Ile
                245                 250                 255

Ile Met Gly Thr Phe Thr Leu Cys Trp Leu Pro Phe Phe Ile Val Asn
            260                 265                 270

Ile Val His Val Ile Gln Asp Asn Leu Ile Arg Lys Glu Val Tyr Ile
        275                 280                 285

Leu Leu Asn Trp Ile Gly Tyr Val Asn Ser Gly Phe Asn Pro Leu Ile
290                 295                 300

Tyr Cys Arg Ser Pro Asp Phe Arg Ile Ala Phe Gln Glu Leu Leu Cys
305                 310                 315                 320

<210> SEQ ID NO 16
<211> LENGTH: 338
<212> TYPE: PRT
<213> ORGANISM: Homo sapiens

<400> SEQUENCE: 16

Thr Ala Asn Thr Ser Gly Leu Pro Gly Val Pro Trp Glu Ala Ala Leu
1               5                   10                  15

Ala Gly Ala Leu Leu Ala Leu Ala Val Leu Ala Thr Val Gly Gly Asn
            20                  25                  30

-continued

Leu Leu Val Ile Val Ala Ile Ala Trp Thr Pro Arg Leu Gln Thr Met
        35                  40                  45

Thr Asn Val Phe Val Thr Ser Leu Ala Ala Ala Asp Leu Val Met Gly
    50                  55                  60

Leu Leu Val Val Pro Pro Ala Thr Leu Ala Leu Thr Gly His Trp
65                  70                  75                  80

Pro Leu Gly Ala Thr Gly Cys Glu Leu Trp Thr Ser Val Asp Val Leu
                85                  90                  95

Cys Val Thr Ala Ser Ile Glu Thr Leu Cys Ala Leu Ala Val Asp Arg
                100                 105                 110

Tyr Leu Ala Val Thr Asn Pro Leu Arg Tyr Gly Ala Leu Val Thr Lys
            115                 120                 125

Arg Cys Ala Arg Thr Ala Val Val Leu Val Trp Val Val Ser Ala Ala
130                 135                 140

Val Ser Phe Ala Pro Ile Met Ser Gln Trp Trp Arg Val Gly Ala Asp
145                 150                 155                 160

Ala Glu Ala Gln Arg Cys His Ser Asn Pro Arg Cys Cys Ala Phe Ala
                165                 170                 175

Ser Asn Met Pro Tyr Val Leu Leu Ser Ser Val Ser Phe Tyr Leu
            180                 185                 190

Pro Leu Leu Val Met Leu Phe Val Tyr Ala Arg Val Phe Val Val Ala
        195                 200                 205

Thr Arg Gln Leu Arg Leu Leu Arg Gly Glu Leu Gly Arg Phe Pro Pro
210                 215                 220

Glu Glu Ser Pro Pro Ala Pro Ser Arg Ser Leu Ala Pro Ala Pro Val
225                 230                 235                 240

Gly Thr Cys Ala Pro Pro Glu Gly Val Pro Ala Cys Gly Arg Arg Pro
                245                 250                 255

Ala Arg Leu Leu Pro Leu Arg Glu His Arg Ala Leu Cys Thr Leu Gly
            260                 265                 270

Leu Ile Met Gly Thr Phe Thr Leu Cys Trp Leu Pro Phe Phe Leu Ala
        275                 280                 285

Asn Val Leu Arg Ala Leu Gly Gly Pro Ser Leu Val Pro Gly Pro Ala
290                 295                 300

Phe Leu Ala Leu Asn Trp Leu Gly Tyr Ala Asn Ser Ala Phe Asn Pro
305                 310                 315                 320

Leu Ile Tyr Cys Arg Ser Pro Asp Phe Arg Ser Ala Phe Arg Arg Leu
                325                 330                 335

Leu Cys

<210> SEQ ID NO 17
<211> LENGTH: 348
<212> TYPE: PRT
<213> ORGANISM: Homo sapiens

<400> SEQUENCE: 17

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
    50                  55                  60

-continued

```
His Lys Lys Leu Arg Thr Pro Leu Asn Tyr Ile Leu Leu Asn Leu Ala
 65              70              75               80

Val Ala Asp Leu Phe Met Val Leu Gly Gly Phe Thr Ser Thr Leu Tyr
             85              90                  95

Thr Ser Leu His Gly Tyr Phe Val Phe Gly Pro Thr Gly Cys Asn Leu
            100             105             110

Glu Gly Phe Phe Ala Thr Leu Gly Gly Glu Ile Ala Leu Trp Ser Leu
            115             120             125

Val Val Leu Ala Ile Glu Arg Tyr Val Val Val Cys Lys Pro Met Ser
        130             135             140

Asn Phe Arg Phe Gly Glu Asn His Ala Ile Met Gly Val Ala Phe Thr
145             150             155                         160

Trp Val Met Ala Leu Ala Cys Ala Ala Pro Pro Leu Ala Gly Trp Ser
                165             170             175

Arg Tyr Ile Pro Glu Gly Leu Gln Cys Ser Cys Gly Ile Asp Tyr Tyr
            180             185             190

Thr Leu Lys Pro Glu Val Asn Asn Glu Ser Phe Val Ile Tyr Met Phe
        195             200             205

Val Val His Phe Thr Ile Pro Met Ile Ile Ile Phe Phe Cys Tyr Gly
        210             215             220

Gln Leu Val Phe Thr Val Lys Glu Ala Ala Ala Gln Gln Gln Glu Ser
225             230             235             240

Ala Thr Thr Gln Lys Ala Glu Lys Glu Val Thr Arg Met Val Ile Ile
            245             250             255

Met Val Ile Ala Phe Leu Ile Cys Trp Val Pro Tyr Ala Ser Val Ala
            260             265             270

Phe Tyr Ile Phe Thr His Gln Gly Ser Asn Phe Gly Pro Ile Phe Met
            275             280             285

Thr Ile Pro Ala Phe Phe Ala Lys Ser Ala Ala Ile Tyr Asn Pro Val
        290             295             300

Ile Tyr Ile Met Met Asn Lys Gln Phe Arg Asn Cys Met Leu Thr Thr
305             310             315                         320

Ile Cys Cys Gly Lys Asn Pro Leu Gly Asp Asp Glu Ala Ser Ala Thr
            325             330             335

Val Ser Lys Thr Glu Thr Ser Gln Val Ala Pro Ala
            340             345
```